US009586988B2

(12) United States Patent
Miao et al.

(10) Patent No.: US 9,586,988 B2
(45) Date of Patent: Mar. 7, 2017

(54) COMPOSITIONS CONTAINING, METHODS INVOLVING, AND USES OF NON-NATURAL AMINO ACIDS AND POLYPEPTIDES

(71) Applicant: AMBRX, INC., La Jolla, CA (US)

(72) Inventors: Zhenwei Miao, San Diego, CA (US); Junjie Liu, San Diego, CA (US); Thea Norman, San Diego, CA (US)

(73) Assignee: AMBRX, INC., La Jolla, CA (US)

( * ) Notice: Subject to any disclaimer, the term of this patent is extended or adjusted under 35 U.S.C. 154(b) by 42 days.

(21) Appl. No.: 13/974,987

(22) Filed: Aug. 23, 2013

(65) Prior Publication Data
US 2014/0100357 A1  Apr. 10, 2014

Related U.S. Application Data

(60) Division of application No. 11/925,732, filed on Oct. 26, 2007, now Pat. No. 8,557,781, which is a continuation of application No. PCT/US2006/047822, filed on Dec. 13, 2006.

(60) Provisional application No. 60/743,041, filed on Dec. 14, 2005, provisional application No. 60/743,040, filed on Dec. 14, 2005.

(51) Int. Cl.
A61K 38/05 (2006.01)
C07K 2/00 (2006.01)
C07K 1/00 (2006.01)
C07C 229/42 (2006.01)

(52) U.S. Cl.
CPC .............. C07K 2/00 (2013.01); C07C 229/42 (2013.01); C07K 1/006 (2013.01)

(58) Field of Classification Search
None
See application file for complete search history.

(56) References Cited

U.S. PATENT DOCUMENTS

| | | | |
|---|---|---|---|
| 3,859,273 A | 1/1975 | Beregi et al. | |
| 4,680,311 A | 7/1987 | Watanabe et al. | |
| 5,364,840 A | 11/1994 | Basava et al. | |
| 5,484,771 A | 1/1996 | Beaulieu et al. | |
| 5,705,522 A * | 1/1998 | Hamedi-Sangsari | C07D 207/46 435/69.2 |
| 6,337,191 B1 | 1/2002 | Swartz | |
| 6,344,483 B1 | 2/2002 | Hallinan et al. | |
| 6,448,281 B1 | 9/2002 | Beaulieu | |
| 6,449,281 B1 | 9/2002 | Smith | |
| 6,455,550 B1 | 9/2002 | Chen et al. | |
| 6,492,421 B1 | 12/2002 | Thorsett et al. | |
| 6,583,139 B1 | 6/2003 | Thorsett et al. | |
| 6,586,402 B1 | 7/2003 | Delansorne et al. | |
| 6,608,183 B1 | 8/2003 | Cox | |
| 6,608,196 B2 | 8/2003 | Wang | |
| 6,900,218 B2 | 5/2005 | Wang | |
| 7,056,942 B2 | 6/2006 | Hildesheim et al. | |
| 7,332,571 B2 | 2/2008 | Miao et al. | |
| 7,385,028 B2 | 6/2008 | Miao et al. | |
| 7,468,458 B2 | 12/2008 | Tian et al. | |
| 7,638,491 B2 | 12/2009 | Miao et al. | |
| 7,696,312 B2 | 4/2010 | Miao et al. | |
| 7,888,533 B2 | 2/2011 | Tian et al. | |
| 8,153,758 B2 | 4/2012 | Miao et al. | |
| 8,399,614 B2 | 3/2013 | Miao et al. | |
| 8,557,781 B2 | 10/2013 | Miao et al. | |
| 2002/0065418 A1 | 5/2002 | Beaulieu | |
| 2002/0081660 A1 | 6/2002 | Swartz | |
| 2003/0072746 A1 | 4/2003 | Miller | |
| 2003/0082575 A1 | 5/2003 | Schultz et al. | |
| 2003/0108885 A1 | 6/2003 | Schultz et al. | |
| 2006/0217289 A1 | 9/2006 | Miao et al. | |
| 2008/0118464 A1 | 5/2008 | Miao et al. | |
| 2008/0139793 A1 | 6/2008 | Tian et al. | |
| 2008/0153979 A1 | 6/2008 | Miao et al. | |

(Continued)

FOREIGN PATENT DOCUMENTS

| | | |
|---|---|---|
| CA | 2110543 | 6/1994 |
| EP | 0605963 | 7/1994 |

(Continued)

OTHER PUBLICATIONS

Dorman et. al. Synthesis of Highly titrated 4-Benzoyl-L-phenylalanine, a Photoreactivable Amino Acid, J. Org. Chem., vol. 60, No. 7, 1995, 2292-2297.*
Alpha Interferon, GenBank Accession No. AAA37889, pp. 1-2. Accessed Jan. 16, 2009.
Anderson et al. Exploring the Limits of Codon and Anticodon Size, Chem. and Biol. 9:237-244 (2002).
Arnold et al. Optically Active Aromatic Amino Acids. Part VI. Synthesis and Properties of [Leu5]-enkephaline Analogues Containing O-methyl-L-Tyrosine1 with Ring Substitution at Position 3, J. Peptide Sci. 6:280-289 (2000).
Auerbach et al. Angiogenesis assays: Problems and pitfalls, Cancer and Metastasis Reviews 19:167-172 (2000).
Bain, J.D. et al. Biosynthetic site-specific incorporation of a non-natural amino acid into a polypeptide, J. Am. Chem. Soc. 111:8013-8014 (1989).

(Continued)

Primary Examiner — Jeanette Lieb
(74) Attorney, Agent, or Firm — Wilson, Sonsini, Goodrich & Rosati

(57) ABSTRACT

Disclosed herein are non-natural amino acids and polypeptides that include at least one non-natural amino acid, and methods for making such non-natural amino acids and polypeptides. The non-natural amino acids, by themselves or as a part of a polypeptide, can include a wide range of possible functionalities, but typical have at least one aromatic amine group. Also disclosed herein are non-natural amino acid polypeptides that are further modified post-translationally, methods for effecting such modifications, and methods for purifying such polypeptides. Typically, the modified non-natural amino acid polypeptides include at least one alkylated amine group. Further disclosed are methods for using such non-natural amino acid polypeptides and modified non-natural amino acid polypeptides, including therapeutic, diagnostic, and other biotechnology uses.

4 Claims, 40 Drawing Sheets

(56) References Cited

U.S. PATENT DOCUMENTS

| | | | |
|---|---|---|---|
| 2008/0154058 A1 | 6/2008 | Tian et al. |
| 2008/0177027 A1 | 7/2008 | Miao et al. |
| 2008/0177038 A1 | 7/2008 | Miao et al. |
| 2008/0182968 A1 | 7/2008 | Miao et al. |
| 2008/0182969 A1 | 7/2008 | Miao et al. |
| 2008/0187491 A1 | 8/2008 | Miao et al. |
| 2008/0194459 A1 | 8/2008 | Miao et al. |
| 2008/0213840 A1 | 9/2008 | Miao et al. |
| 2008/0268518 A1 | 10/2008 | Miao et al. |
| 2008/0268519 A1 | 10/2008 | Miao et al. |
| 2009/0111147 A1 | 4/2009 | Miao et al. |
| 2009/0123968 A1 | 5/2009 | Miao et al. |
| 2012/0315686 A1 | 12/2012 | Miao et al. |
| 2014/0100357 A1 | 4/2014 | Miao et al. |

FOREIGN PATENT DOCUMENTS

| | | |
|---|---|---|
| EP | 1481965 A1 | 12/2004 |
| FR | 2181768 | 12/1973 |
| WO | WO-90-05785 | 5/1990 |
| WO | WO 96/01901 A1 | 1/1996 |
| WO | WO-96-41813 | 12/1996 |
| WO | WO-00-55353 | 9/2000 |
| WO | WO-03-044056 | 5/2003 |
| WO | WO-2004-035743 A2 | 4/2004 |
| WO | WO-2004-094593 A2 | 11/2004 |
| WO | WO-2005-035551 A2 | 4/2005 |
| WO | WO-2006-069246 A2 | 6/2006 |
| WO | WO-2007-056448 A2 | 5/2007 |
| WO | WO-2007-056448 A3 | 5/2007 |
| WO | WO-2007-070659 A2 | 6/2007 |
| WO | WO-2007-070659 A3 | 6/2007 |
| WO | WO-2007-079130 A2 | 7/2007 |
| WO | WO-2007-079130 A3 | 7/2007 |

OTHER PUBLICATIONS

Basu et al. Catalytic transfer reduction of conjugated alkenes and an imine using polymer-supported formates, Tetrahedron Ltrs. 44:8931-8934 (2003).
Berendsen. A Glimpse of the Holy Grail?, Science 282:642-643 (1998).
Bergel et al. 19. Cyto-active amino-acids and peptides. Part V. Derivatives of p-amino-and p-mercapto-phenylalanine. Journal of the Chemical Society 90-97 (1995).
Beta Interferon, GenBank Accession No. NP_002167, pp. 1-3. Accessed Jan. 16, 2009.
Boles et al. Nat. Struct. Biol. 1:5:283-284 (1994).
Bradley et al. Limits of Cooperativity in a Structurally modular protein: Response of the Notice Ankyrin Domain to Analogous Alanine Substitutions in Each Repeat, J. Mol. Biol. 324:3;73-386 (2002).
Brannigan et al. Protein engineering 20 years on, Nature 3:964-970 (2002).
Brunner. New Photolabeling and crosslinking methods, Ann. Rev. Biochem. vol. 62, pp. 483-514 (1993).
Buckel. Recombinant Protein Drugs: Milestones in Drug Therapy, Bitkhauser Verlag, eds. 2001, Preface and pp. 191-197.
Budisa et al. Toward the experimental codon reassignment in vivo: protein building with an expanded amino acid repertoire, FASEB J. 13:41-51 (1999).
Budisa et al. High-level biosynthetic substitution of methionine in proteins by its analogs 2-aminohexanoic acid, selenmethionine, telluromethionine and ethionine in Escherichia coli, Eur. J. Biochem. 230:788-796 (1995).
Carrasco et al. A Versatile Set of Aminooxy Amino Acids for the Synthesis of Neoglycopeptides, J. Org. Chem. 68:8853-8858 (2003).
Chin et al. An Expanded Eukaryotic Genetic Code, Science 301:964-967 (2003).
Chin et al. In Vivo Photocrosslinking with Unnatural Amino Acids Mutagenesis, ChemBioChem 11:1135-1137 (2002).
Chin et al. Addition of a photocrosslinking amino acid to the genetic code of Escherichia coli, PNAS USA 99:11020-11024 (2002).
Chin et al. Addition of p-Azido-$_L$-phenylalanine to the Genetic Code of Escherichia coli, JACS 124:9026-9027 (2002).
Clinical Aspects of Cancer from Merck Manual, pp. 1-4. Accessed Feb. 20, 2008.
Cordes et al. Nucleophilic Catalysis of Semicarbazone Formation by Anilines, J. Am. Chem. Soc. 1962, 84, pp. 826-831.
Corey et al. Generation of a hybrid sequence-specific single-stranded deoxyribonuclease, Science, vol. 238, pp. 1401-1403 (1987).
Cornish et al. Probing Protein Structure and Function with an Expanded Genetic Code, Angew. Chem. Int. Ed. Engl. 34:621 (1995).
Cornish et al. Site-Specific Protein Modification Using a Ketone Handle, J. Am. Chem. Soc. 118:8150-8151 (1996).
Crick et al. General nature of the genetic code for proteins, Nature 192(4809):1227-1232(1961).
Definition of derivative and analog from http://cancerweb.ncl.ac. 7uk/cgi-bin/omd?query=derivative, pp. 1-5. Accessed Jul. 7, 2005.
Definition of moiety from http://dictionary.reference.com/browse/moiety, pp. 1-3. Accessed Aug. 26, 2010.
Dementia including Alzheimer's Disease from the Merck Manual, Accessed Apr. 30, 2007.
Dennis et al. Albumin Binding as a Genral Strategy for Improving the Pharmacokinetics of Proteins, J. Biol. Chem. 277:38:35035-35043 (2002).
Designing Custom Peptides, SIGMA, accessed Dec. 16, 2004.
Diseases from the Merck Manual, Accessed Apr. 30, 2007.
Disorders from the Merck Manual, Accessed Apr. 30, 2007.
Doring et al. Enlarging the Amino Acid Set of Escherichia coli by Infiltration of the Valine Coding Pathway, Science 292:501-504 (2001).
Dougherty. Unnatural Amino Acids as Probes of Protein Structure and Function, Curr. Op. Chem. Biol. 4:645-652 (2000).
Duewel et al. Incorporation of trifluoromethionine into a phage lysozyme: implications and a new marker for use in protein 19F NMR. Biochemistry 36:3404-3416 (1997).
Ellman et al, Biosynthetic method for introducing unnatural amino acidssite-specifically into proteins, Methods in Enz. 202:301-336 (1992).
Ellman et al, Site-specific incorporation of novel backbone structures into proteins, Science 255:197-200 (1992).
England et al. Backbone mutations in transmembrane domains of a ligand-gated ion channel: implications for the mechanism of gating. Cell 96:89-98 (1999).
EP 05855215 Supplemental Search Report dated Jan. 12, 2009.
EP 06837144.2 Search Report mailed Oct. 12, 2009.
EP 06848566.3 Supplemental European Search Report dated Jul. 22, 2009.
Farquhar et al. Syntheses of C14-mustard-labelled and C14-Leucine-labelled asaley. J. Labelled Compounds and Radiopharmaceuticals. 1908; XVII (2): 159-170.
Forster et al. Programming peptidomimetic syntheses by translating genetic codes designed de novo. PNAS USA 100:11:6353-6357 (2003).
Frankel et al. Encodamers: unnatural peptide oligomers encoded in RNA. Chem. & Biol. 10:1043-1050 (2003).
Furter. Expansion of the genetic code: site-directed p-fluoro-phenylalanine incorporation in Escherichia coli. Protein Sci. 7:419-426 (1998).
Gaertner et al, Site-Specific Attachment of Functionalized Poly(ethylene glycol) to the Amino Terminus of Proteins, Bioconj Chem 7:38-44 (1996).
Gallivan et al. Site-specific incorporation of biotinylated amino acids to identify surface-exposed residues in integral membrane proteins. Chem. Biol. 4:10:739-749 (1997).
Gao. Inhibition of Grb2 SH2 Domain Binding by Non-Phosphate-Containing Ligands. 2.4-(20Malonyl)phenylalanine as a Potent Phosphotyrosyl Mimetic, J. Med. Chem. 43:911-920 (2000).
GenBank Accession No. CAA26095 (erythropoietin) (2006).
GenBank Accession No. CAA34902 (epidermal growth factor) (2006).

(56) References Cited

OTHER PUBLICATIONS

GenBank Accession No. CAA41788 (Fibroblast Growth Factor) (2006).
Geoghegan et al. Site-directed conjugation of nonpeptide groups to peptides and proteins via periodate oxidation of a 2-amino alcohol. Application to modification at N-terminal serine. J. Bioconjug. Chem. 3:138-146 (1992).
Goodman et al. Conformational Aspects of Polypeptide Structure. XXII. Aromatic Side-Chain Effects from Poly-L-p-aminophenylalanine and Derivatives, Biochemistry 1967, 6:1533-1540.
Guckian et al. Highly Precise Shape Mimicry by a Difluorotoluene Deoxynucleoside, a Replication-Competent Substitute for Thymidine. Angew. Chem. Int. Ed. Engl. 36:24:2825-2828 (1998).
Gura., Systems for Identifying New Drugs Are Often Faulty, Cancer Models, Science 278:1041-1042 (1997).
Hamano-Takaku et al. A mutant *Escherichia coli* tyrosyl-tRNA synthetase utilizes the unnatural amino acid azatyrosine more efficiently than tyrosine. J. Biol. Chem. 275, No. 51:40324-40328 (2000).
Han, Targeted Prodrug Design to Optimize Drug Delivery, AAPS Pharmsci 2(1):1-11 (2000).
Hang et al. Chemoselective approaches to glycoprotein assembly. Acc. Chem. Res. 34:9:727-736 (2001).
Harris. Laboratory Synthesis of Polyethylene Glycol Derivatives, JMS-Rev. Macromol. Chem. Phys. C25(3):325-373 (1985).
Hartman. A Convenient Synthesis of 4-Aminomethyl-L-Phenylalanine, Synth. Comm. 21(20):2103-2107 (1991).
Hendrickson et al. Selenomethionyl proteins produced for analysis by multiwavelength anomalous diffraction (MAD): a vehicle for direct determination of three-dimensional structure. EMBO J. 9:5:1665-1672 (1990).
Hirao et al. An unnatural base pair for incorporating amino acid analogues into protein, Nature Biotech. 20:177-182 (2002).
Hofmann et al. Studies on polypeptides. XXXVI. The effect of pyrazole-imidazole replacements on the S-protein activating potency of an S-peptide fragment, J. Am. Chem., 88(24):5914-5919 (1966).
Hohsaka et al. Efficient Incorporation of Nonnatural Amino Acids with Large Aromatic Groups into Streptavidin in In Vitro Protein Synthesizing Systems. J. Am. Chem. Soc. 121:34-40 (1999).
Hohsaka et al. Incorporation of Two Different Nonnatural Amino Acids Independently into a Single Protein through Extension of the Genetic Code. J. Am. Chem. Soc. 121:12194-12195 (1999).
Human Growth Hormone, GenBank Accession No. AAA72260, p. 1. Accessed Jan. 16, 2009.
Ibba et al. Relaxing the substrate specificity of an aminoacyl-tRNA synthetase allows in vitro and in vivo synthesis of proteins containing unnatural amino acids. FEBS Lett. 364:272-275 (1995).
Ibba et al. Substrate specificity is determined by amino acid binding pocket size in *Escherichia coli* phenylalanyl-tRNA synthetase. Biochemistry 33:7107-7112 (1994).
Introduction to Cancer from Merck Manual, p. 1. Accessed Mar. 5, 2008.
Jackson et al. A Designed Peptide Ligase for Total Synthesis of Ribonuclease A with Unnatural Catalytic Residues, Science, 266:243-247 (1994).
Jain. Barriers to Drug Delivery in Solid Tumors, Scientific American, Jul. 1994, 58-65.
Jencks. General Acid-Base Catalysis of Complex Reactions in Water, Chem. Rev. 72(6):705-718 (1972).
Jencks. Studies on the Mechanism of Oxime and Semicarbazone Formation. J. Am. Chem. Soc. 81:475-481 (1959).
Jullian et al. Synthesis of New Photoactivatable Phenylalanine Analogues and Their Incorporation into a Model Peptide— Phenylseleno Derivatives as Precursors of alpha, beta-Unsaturated Ketones in Peptide Synthesis, Eur. J. Org. Chem. 1677-1684 (2002).
Kaiser et al. Chemical mutation of enzyme active sites, Science 226:505-511 (1984).
Kaiser et al. The chemical modification of enzymatic specificity, Ann. Rev. Biochem. 54:565-595 (1985).
Kaiser. Synthetic approaches to biologically active peptides and proteins including enzymes, Acc. Chem. Res. 22(2):47-54 (1989).
Kiick et al. Incorporation of azides into recombinant proteins for chemoselective modification by the Staudinger ligtation, PNAS 99:19-24 (2002).
Kiick et al. Protein Engineering by In Vivo Incorporation of Non-Natural Amico Acids: control of Incorporation of Methionine Analogues by Methionyl-tRNA Synthetase. Tetrahedron 56:9487-9493 (2000).
Kim et al. Prolonging Cell-Free Protein synthesis with a Novel ATP Regeneration System. Biotech Bioeng. 66:3:180-188 (1999).
Kim et al. Prolonging Cell-Free Protein Synthesis by Selective Reagent Additions. Biotech. Progress 16:385-390 (2000).
Kim et al. Regeneration of Adenosine Triphosphate from Glycolytic Intermediates for Cell-Free Protein Synthesis. Biotech.Bioeng. 74:4:309-316(2001).
Kim et al. Oxalate improves protein synthesis by enhancing ATP supply in a cell-free system derived from *Escherichia coli*. Biotech. Lett. 22:1537-1542 (2000).
Kinoshita et al. Studies on Antibiotics and Related Substances. XXIX. Synthesis of 2-Acetamido-5-oxo-6-heptenoic Acid and 2-Acetamido-4-oxo-5-hexenoic Acid, Bull. of Chem. Soc. Japan 40:926-931 (1967).
Kobayashi et al. Structural basis for orthogonal tRNA specificities of tyrosyl-tRNA synthetases for genetic code expansion. Nature Struct. Biol. 10(6):425-432 (2003).
Kool. Synthetically modified DNAs as substrates for polymerases. Curr. Op. Chem. Biol. 4:602-608 (2000).
Krieg et al. Photocrosslinking of the signal sequence of nascent preprolactin of the 54-kilodalton polypeptide of the signal recognition particle, PNAS 83:8604-8608 (1986).
Kumar et al. Solid Phase Synthesis and Evaluation of Tyr-Tic-Phe-Phe(p-NHCOCH2Br)([Phe(p-bromoacetamide)4]TIPP), a Potent Affinity Label of delta Opioid Receptors, J. Med. Chem. 2002, 45:3820-3823.
Kurtzhals et al. Albumin binding of insulins acylated with fatty acids: characterization of the ligand-protein interaction and correlation between binding affinity and timing of the insulin effect in vivo. Biochem. J. 312:725-731 (1995).
Leelasvatanakij et al. A solid-phase synthetic strategy for the preparation of peptide-based affinity labels: synthesis of dynorphin A analogs, J Peptide Res 56:80-87 (2000).
Ligouri et al. N,O-Heterocycles. Part 18. Regiochemistry and Site Selectivity of N-Alkylhydroxylamine Addition to 2,3-Diphenylcyclopropenone, J. Chem. Soc. Perkin Trans. 1:961-965 (1987).
Liu et al. Progress toward the evolution of an organism with an expanded genetic code, PNAS USA 96:4780-4785 (1999).
Liu et al. A method for the generation of glycoprotein mimetics. J. Am. Chem. Soc. 125:1702-1703 (2003).
Lu et al. Probing ion permeation and gating in a K+ channel with backbone mutations in the selectivity filter. Nat. Neurosci. 4:3:239-246 (2001).
Ma et al. In vitro protein engineering using synthetic tRNA(Ala) with different anticodons. Biochemistry 32:7939-7945 (1993).
Maeda et al. Synthesis and Evaluation of N,N-Dialkyl Enkephalin-Based Affinity Labels for delta Opioid Receptors, J. Med. Chem. 2000, 43:3941-3948.
Magliery. Expanding the Genetic Code: Selection of Efficient Suppressors of Four-Base Codons and Identification of Shifty Four-base Codons with a Library Approach in *Eschericia coli*, J. Mol. Biol. 307:755-769 (2001).
Mahal et al. Engineering chemical reactivity on cell surfaces through oligosaccharide biosynthesis. Science 276:1125-1128 (1997).
Makrides et al. Extended in vivo half-life of human soluble complement receptor type 1 fused to a serum albumin-binding receptor. J. Pharmacol. Exp. Ther. 277:1:534-542 (1996).
March. Advanced Organic Chemistry, Reactions, Mechanisms, and Structure John Wiley & Sons, New York, 4th ed., 1992; pp. 904-907.

(56) References Cited

OTHER PUBLICATIONS

Mattson. Pathways towards and away from Alzheimer's disease, Nature 430:631-639 (2004).
McMinn et al. Efforts toward Expansion of the Genetic Alphabet: DNA Polymerase Recognition of a Highly Stable, Self-Paring Hydrophobic Base. J. Am. Chem. Soc. 121:11585-11586 (1999).
Meggers et al. Structure of a copper-mediated base pair in DNA. J. Am. Chem. Soc.122:10714-10715 (2000).
Mehl et al. Generation of a Bacterium with a 21 Amino Acid Genetic Code, JACS 125:935-939 (2003).
Mendel et al. Site-directed mutagenesis with an expanded genetic code. Ann. Rev. Biophys. Biomol. Struct. 24:435-462 (1995).
Miller et al. Flash decaging of tyrosine sidechains in an ion channel. Neuron 20:619-624 (1998).
Minks et al. Noninvasive tracing of recombinant proteins with "fluorophenylalanine-fingers". Anal. Biochem. 284:29-34(2000).
Moore et al. Quadruplet Condons: Implications for Code Expansion and the Specification of Translation Step Size. J. Mol. Biol. 298:195-205 (2000).
Nakatsuka et al. Peptide segment coupling catalyzed by the semisynthetic enzyme thiosubtilisin, J. Am. Chem. Soc., 109:3808-3810 (1987).
Neet et al. Properties of thiol-subtilisin, J. Biol. Chem. 243(24):6392-6401 (1968).
Ngo et al. Computational complexity, protein structure prediction and the Levinthal Paradox, from The Protein Folding Problem and Tertiary Structure Prediction, K. Merc. Jr. and S. LeGrand, eds., 1994, pp. 491-495.
Noren et al. A general method for site-specific incorporation of unnatural amino acids into proteins. Science 244:182-188 (1989).
Nowak et al. Nicotinic receptor binding site probed with unnatural amino acid incorporation in intact cells. Science 268:439-42 (1995).
Offord. Protein engineering by chemical means? Protein Eng., 1(3):151-157 (1987).
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Patnaik et al. E. coli-based in vitro transcription/translation: in vivo-specific synthesis rates and high yields in a batch system. Biotechniques 24:5:862-868 (1998).
PCT/US05/46618 Search Report dated Jul. 22, 2008.
PCT/US06/043472 Search Report dated Feb. 6, 2008.
PCT/US06/47822 Search Report and Written Opinion dated Oct. 2, 2008.
PCT/US06/49397 IPER mailed Feb. 18, 2011.
Pei et al. Discovery and SAR of Novel, Potent and Selective Protein Tyrosine Phosphatase 1B Inhibitors, Bioorg. Med. Chem. Lett. 2003, 13:3129-3132.
Piccirilli et al. Enzymatic incorporation of a new base pair into DNA and RNA extends the genetic alphabet. Nature 343:33-37 (1990).
Polgar. A new enzyme containing a synthetically formed active site. Thil-subtilisin, J. Am. Chem. Soc. 88(13):3153-3154 (1966).
Pollack et al. Introduction of nucleophiles and spectroscopic probes into antibody combining sites, Science 242:1038-1040 (1988).
Primrose. Principles of Gene Manipulation and Genomics, Blackwell Publishing 2006, Ch. 8, http://www.blackwellpublishing.com/contents.asp?ref=9781405135443&site=1.
Pyne et al. Diastereoselective Addition of α-Alkoxyalkyl Radicals to Chiral 4-Methyleneoxazolidin-5-ones, Tetrahedron 54:5709-5720 (1998).
Ranganathan. Protein Engineering: Design of Single-Residue-Anchored Metal-Uptake Systems, Inorg. Chem. 38:1019-1023 (1999).
Roberts et al. RNA-peptide fusions for the in vitro selection of peptides and proteins. PNAS USA 94:12297-12302 (1997).
Rodriguez et al. A Strategy for the Chemoselective Synthesis of O-linked Glycopeptides with Native Sugar-Peptide Linkages, J. Am. Chem. Soc. 119:9905-9906 (1997).
Rosenthal. L-canaline: a potent antimetabolite and anti-cancer agent from leguminous plants. Life Sci. 60(19):1635-1641 (1997).
Rudinger. Characteristics of the amino acids as components of a peptide hormone sequence, Peptide Hormones, 1976 J.A. Parsons, MA Edition, National Institutes for Medical Research.
Santoro et al. An efficient system for the evolution of aminoacyl-tRNA synthetase specificity, Nature Biotech. 20:1044-1048 (2002).
Sayers et al. 5'3' Exonuclease in phosphorothioate-based oligo-nucleotide-directed mutagenesis, Nucleic Acids Res. 16(3):791-802 (1988).
Schinzel et al. The phosphate recognition site of *Escherichia coli* maltodextrin phosphorylase, Federation of Eur. Biochem. Soc., Jul. 1991, 286(1,2):125-128).
Schnolzer et al. Constructing proteins by dovetailing unprotected synthetic peptides: backbone-engineered HIV protease, Science, 256:221-225 (1992).
Sela et al. Poly-p-amino-DL-phenylalanine, J. Am. Chem. Soc. 1954, 76:129-133.
Sequence of fibroblast growth factor (*Homo sapien*) from NCBI GenBank, p. 1. Accessed Oct. 28, 2010.
Sequence of interferon (*Homo sapien*) fromNCBI GenBank, p. 1. Accessed Oct. 28, 2010.
Sham et al. Novel Non-Basic Bioisostere of Histidine synthesized from L-Aspartic Acid, J Chem Soc, Chem Comm. 23:1792-1793 (1987).
Shao et al. Unprotected Peptides as Building Blocks for the Synthesis of Peptide Dendrimers with Oxime, Hydrazone, and Thiazolidine Linkages. J. Am. Chem. Soc. 117:14:3893-3899 (1995).
Sharma et al. Efficient introduction of aryl bromide functionality into proteins in vivo. FEBS Lett. 467:37-40 (2000).
Short Stature from http://www.emedicine.com/PED/topic2087.htm. pp. 1-21. Accessed Nov. 30, 2008.
Sjolander et al. The serum albumin-binding region of streptococcal protein G: a bacterial fusion partner with carrier-related properties. J. Immunol. Methods 201:115-123 (1997).
Skinner et al. Potential Anticancer Agents. XXXVIII. Alkylating Agents Related to Phenylalanine Mustard. II, J. Org. Chem. 1960, 25:1756-1759.
Skolnick et al. From genes to protein structure and function: novel applications of computational approaches in the genomic era, Trends Biotech. 18:34-39 (2000).
Sriram et al. Experimental Allergic Encephalomyelitis: A Misleading Model of Multiple Sclerosis, Annals Neurology 58:939-945 (2005).
Steinman et al. How to successfully Apply Animal Studies in Experimental Allergic Encephalomyelitis to Research on Multiple Sclerosis, Annals Neurology 60:12-21 (2006).
Stemmer. DNA shuffling by random fragmentation and reassembly: In vitro recombination for molecular evolution, PNAS USA 91:10747-10751(1994).
Stemmer. Rapid evolution of a protein in vitro by DNA shuffling, Nature 370(4):389-391 (1994).
STIC search pp. 174-178.
Structure search result of WO/9601901, performed on May 22, 2013.
Stuber et al. Preparation and Evaluation of PEG-Bound Thrombin Inhibitors Based on 4-Amidinophenylalanine, Peptide Res. 8(2):78-85 (1995).
Switzer et al. Enzymatic Incorporation of a New base Pair into DNA and RNA. J. Am. Chem. Soc. 111:8322-8323 (1989).
Tae et al. Efforts toward expansion of the genetic alphabet: replication of DNA with three base pairs. J. Am. Chem. Soc. 123:7439-7440 (2001).
Tang et al. Fluorinated Coiled-Coil Proteins Prepared In Vivo Display Enhanced Thermal and Chemical Stability This work was supported by a grant from the U.S. Army Research Office. Y. Tang is supported by a Whitaker Graduate Research Fellowship. We thank Dr. Gary Hathaway for performing matrix-assisted laser desorption/ionization analyses. Angew. Chem. Int. Ed. Engl. 40:8:1494-1496 (2001).

(56) References Cited

OTHER PUBLICATIONS

Tilley. et al. Imide and Lactam Derivatives of N-Benzylpyroglutamyl-L-phenylalanine as VCAM/VLA-4 Antagonits, Bioorg. Med. Chem. Lett. 2001, 11:1-4.
Tomlinson, Ankyrin repeats generate high-affinity protein binders with biophysical properties that may favr therapeutic applications, Nature Biotech 22(5):521-522 (2004).
Turcatti et al. Probing the structure and function of the tachykinin neurokinin-2 receptor through biosynthetic incorporation of fluorescent amino acids at specific sites. J. Biol.Chem. 271:33:19991-19998 (1996).
U.S. Appl. No. 11/873,347 Office Action mailed Apr. 22, 2010.
U.S. Appl. No. 11/875,741 Office Action mailed Aug. 10, 2010.
U.S. Appl. No. 11/925,662 Office Action mailed Aug. 24, 2010.
U.S. Appl. No. 11/925,699 Office Action mailed Aug. 26, 2010.
U.S. Appl. No. 11/925,732 Notice of Allowance mailed Jun. 14, 2013.
U.S. Appl. No. 11/925,732 Office Action mailed Apr. 2, 2009.
U.S. Appl. No. 11/925,732 Office Action mailed Oct. 20, 2009.
U.S. Appl. No. 11/925,735 Office Action mailed Sep. 20, 2012.
U.S. Appl. No. 11/925,735 Office Action mailed Sep. 27, 2011.
U.S. Appl. No. 11/925,735 Office Action mailed Dec. 1, 2010.
U.S. Appl. No. 11/925,735 Office Action mailed Jun. 17, 2010.
U.S. Appl. No. 11/925,740 Office Action mailed May 18, 2011.
U.S. Appl. No. 11/925,740 Office Action mailed Aug. 22, 2011.
U.S. Appl. No. 11/925,740 Office Action mailed Sep. 9, 2010.
U.S. Appl. No. 11/952,960 Office Action mailed Oct. 29, 2010.
U.S. Appl. No. 11/952,975 Office Action mailed Nov. 3, 2010.
U.S. Appl. No. 13/467,870 Notice of Allowance dated Jun. 16, 2014.
U.S. Appl. No. 13/467,870 Office Action mailed Dec. 5, 2013.
U.S. Appl. No. 13/467,870 Office Action mailed May 29, 2013.
Uno. Stereoselective Antibody-Catalyzed Oxime Formation, J. Am. Chem. Soc. 116:1145-1146 (1994).
Van Hest et al. Efficient introduction of alkene functionality into proteins in vivo. FEBS Lett. 428:68-70 (1998).
Van Hest et al. Efficient Incorporation of Unsaturated Methionine Analogues into Proteins in Vivo. J. Am. Chem. Soc. 122:1282-1288 (2000).
Vippangunta et al. Crystalline Solids, Adv Drug Del Rev 48:3-26 (2001).
Voet et al. Biochemistry, Second Edition, 1995, 235-241.
Wang et al. Expanding the genetic code, Chem. Comm. 1:1-11 (2002).
Wang et al. Expanding the Genetic Code of *Escherichia coli*, Science 292:498-500 (2001).
Wang et al. Addition of the keto functional group to the genetic code of *Escherichia coli*, PNAS USA 100:56-61 (2003).
West et al. Novel Cyclic Tripeptides and Substituted Aromatic Amino Acids via Ruthenium-Activated SNAr Reactions, Org. Lett. 1999, 1:1819-1822.
Willans et al. Ligand-free palladium catalyzed Heck reaction of methyl 2-acetamido acrylate and aryl bromides as key step in the synthesis of enantiopure substituted phenylalanines, J. Organometallic Chem. 687:494-497 (2003).
Wong. Chemical crosslinking and the stabilization of proteins and enzymes, Enzyme Microb. Technol. 14:866-874 (1992).
Yokomatsu, T. et al. Stereocontrolled Synthesis of Hydroxymethylene Phosphonate Analogues of Phosphorylated Tyrosine and Their Conversion to Monofluoromethylene Phosphonate Analogues, Tetrahedron 1996, 52, 11725-11738.
Zalipsky. Functionalized Poly(ethylene glycol) for Preparation of Biologically Relevant Conjugates, Bioconjugate Chem. 6:150-165 (1995).
Zhang et al. A New Strategy for the Site-Specific Modification of Proteins in Vivo, Biochem. 42(22):6735-6746 (2003).

\* cited by examiner

General Structure   Examples

General Structure  Examples

A. Synthesis of 3-chloro-4-amino-phenylalanine

B. Synthesis of 3-iodo-4-amino-phenylalanine

A. Synthesis of 3-methoxy-4-amino-phenylalanine

B. Synthesis of 3-fluoro-4-amino-phenylalanine

A. Synthesis of N-methyl-p-amino-phenylalanine

B. Synthesis of N-ethyl-p-amino-phenylalanine

Formation of Polypeptides with Aromatic Amine-Containing Non-Natural Amino Acids by Post-Translational Reduction of the Masked Precursors, Followed by Reductive Alkylations with Aldehyde-Containing Reagents Reductive Alkylations of Mono-alkylated Aromatic Amine-Containing Non-Natural Amino Acid Peptides General Structure      Examples Formation of Polypeptides with Aldehyde-Containing Non-Natural Amino Acids by Post-Translational Deprotections of Masked Aldehyde Precursors, Followed by Reductive Aminations with Aromatic Amine-Containing Reagents

Reductive alkylation of non-natural amino acid peptide

Reductive amination of non-natural amino acid peptide

Reductive alkylations of reduced urotension-II (UT-II-SH) with
propionaldehyde (a) and benzaldehyde (b)

pAF = L-para-Amino-phenylalanine

Reductive alkylations of urotension-II (UT-II) with propionaldehyde (a) and benzaldehyde (b), respectively.

UT-II: H₂N–Glu–Thr–Pro–Asp–Cys–pAF–Trp–Lys–Tyr–Cys–Val–COOH
                          |                              |
                          S——————————————S pAF = L-para-Amino-phenylalanine

Reductive alkylations of peptide XT-8 with propionaldehyde (a) and benzaldehyde (b), isobutaldehyde (c) and pivalaldehyde (d)

pAF = L-Amino-phenylalanine

MS found:
1061.40 (XT-8);
1103.45 (I);
1151.52 (II);
1117.13 (III);
1131.16 (IV).

Reductive alkylations of peptide SXT-9 with propionaldehyde (a) and benzaldehyde (b), isobutaldehyde (c) and pivalaldehyde (d).

pAF = L-para-Amino-phenylalanine

MS found:
1186.47 (SXT-9);
1228.58 (I);
1276.59 (II);
1242.20 (III);
1256.30 (IV).

Reductive alkylations of peptide HXT-9 with propionaldehyde (a) and benzaldehyde (b), isobutaldehyde (c) and pivalaldehyde (d)

pAF = L-para-Amino-phenylalanine

Reductive alkylations of peptide WXT-9 with propionaldehyde (a), benzaldehyde (b), and isobutaldehyde (c)

pAF = L-para-Amino-phenylalanine

MS found:
1285.53 (WXT-9);
1327.64 (I);
1375.65 (II);
1341.44 (III).

Reductive alkylations of peptide NXT-9 with propionaldehyde (a) and benzaldehyde (b)

pAF = L-para-Amino-phenylalanine

MS found:
1213.45 (NXT-9);
1255.63 (I);
1303.52 (II).

Reductive alkylations of peptide RXT-10 with propionaldehyde (a) and benzaldehyde (b)

pAF = L-para-Amino-phenylalanine

MS found:
1369.57 (RXT-10);
1411.69 (I);
1459.58 (II).

Reductive alkylations of peptide AXT-11 with propionaldehyde (a) and benzaldehyde (b)

pAF = L-para-Amino-phenylalanine

Reductive alkylations of peptide AXT-11 with various aldehydes (a-c).

pAF = L-para-Amino-phenylalanine

Reductive alkylations of peptide AXT-11 with various heteroaromatic aldehydes (d-g).

pAF = L-para-Amino-phenylalanine

Competitive reactions of peptide AXT-11 with aldehyde and 1,3-diketone (I-III).

Competitive reactions of peptide NXT-9 with aldehyde and 1,2-diketone (I-III).

Reduction of peptide MXT-9-N3 to MXT-9NH2 (I), followed by reductive alkylations with propionaldehyde (II) and benzaldehyde (III)

Peptide PEGylations

PEG Aldehydes used for PEGylations

Linear PEG aldehydes:

Branched PEG aldehydes derived from glycerol:

A) Protein PEGylations — hGH

B) Protein PEGylations — IFNa hGH Y35pAF2 PEGylation

PEG to protein ratio is 1:1.
NaCNBH$_3$ is 5:1.
pH = 4.0.
hGH is at 350uM.

1. H6-hGH Y35pAF2
2. H6-hGH Y35pAF2 + 20K PEG, 4°C
3. H6-hGH Y35pAF2 + 30K PEG, 4°C
4. H6-hGH Y35pAF2 + 40K, 4°C
5. H6-hGH Y35pAF2 + 20K PEG, RT
6. H6-hGH Y35pAF2 + 30K PEG, RT
7. H6-hGH Y35pAF2 + 40K, RT
8. Met-hGH Y35pAF1
9. Met-hGH Y35pAF1 + 40K, 4°C
10. Met-hGH Y35pAF1 + 40K, 4°C
11. H6-hGH Y35pAF2
12. H6-hGH Y35pAF2 + 40K, 4°C

4hr/6hr incubation

3hr incubation

SEQUENCE LISTING

<160> NUMBER OF SEQ ID NOS: 31

<210> SEQ ID NO 1
<211> LENGTH: 77
<212> TYPE: DNA
<213> ORGANISM: Artificial Sequence
<220> FEATURE:
<223> OTHER INFORMATION: Synthetic polynucleotide

<400> SEQUENCE: 1
ccggcggtag ttcagcaggg cagaacggcg gactctaaat ccgcatggcg ctggttcaaa    60
tccggcccgc cggacca    77

<210> SEQ ID NO 2
<211> LENGTH: 88
<212> TYPE: DNA
<213> ORGANISM: Artificial Sequence
<220> FEATURE:
<223> OTHER INFORMATION: Synthetic polynucleotide

<400> SEQUENCE: 2
cccagggtag ccaagctcgg ccaacggcga cggactctaa atccgttctc gtaggagttc    60
gagggttcga atcccttccc tgggacca    88

<210> SEQ ID NO 3
<211> LENGTH: 89
<212> TYPE: DNA
<213> ORGANISM: Artificial Sequence
<220> FEATURE:
<223> OTHER INFORMATION: Synthetic polynucleotide

<400> SEQUENCE: 3
gcgagggtag ccaagctcgg ccaacggcga cggacttcct aatccgttct cgtaggagtt    60
cgagggttcg aatccctccc ctcgcacca    89

<210> SEQ ID NO 4
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 4

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

```
His Met Leu Ala Arg Glu Leu Leu Pro Lys Lys Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 5
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 5

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220
```

```
Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Lys Phe Gly Gly Asp Leu Thr Val Asn Ser Tyr Glu Glu
        260                 265                 270

Leu Glu Ser Leu Phe Lys Asn Lys Glu Leu His Pro Met Asp Leu Lys
            275                 280                 285

Asn Ala Val Ala Glu Leu Ile Lys Ile Leu Glu Pro Ile Arg Lys
        290                 295                 300

Arg Leu
305

<210> SEQ ID NO 6
<211> LENGTH: 304
<212> TYPE: PRT
<213> ORGANISM: Artificial Sequence
<220> FEATURE:
<223> OTHER INFORMATION: Synthetic polypeptide

<400> SEQUENCE: 6

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ala Ala Ile
                20                  25                  30

Gly Phe Glu Pro Ser Gly Lys Ile His Leu Gly His Tyr Leu Gln Ile
            35                  40                  45

Lys Lys Met Ile Asp Leu Gln Asn Ala Gly Phe Asp Ile Ile Ile Leu
    50                  55                  60

Leu Ala Asp Leu His Ala Tyr Leu Asn Gln Lys Gly Glu Leu Asp Glu
65                  70                  75                  80

Ile Arg Lys Ile Gly Asp Tyr Asn Lys Lys Val Phe Glu Ala Met Gly
                85                  90                  95

Leu Lys Ala Lys Tyr Val Tyr Gly Ser Pro Phe Gln Leu Asp Lys Asp
                100                 105                 110

Tyr Thr Leu Asn Val Tyr Arg Leu Ala Leu Lys Thr Thr Leu Lys Arg
            115                 120                 125

Ala Arg Arg Ser Met Glu Leu Ile Ala Arg Glu Asp Glu Asn Pro Lys
    130                 135                 140

Val Ala Glu Val Ile Tyr Pro Ile Met Gln Val Asn Ala Ile Tyr Leu
145                 150                 155                 160

Ala Val Asp Val Ala Val Gly Gly Met Glu Gln Arg Lys Ile His Met
                165                 170                 175

Leu Ala Arg Glu Leu Leu Pro Lys Lys Val Val Cys Ile His Asn Pro
                180                 185                 190

Val Leu Thr Gly Leu Asp Gly Glu Gly Lys Met Ser Ser Ser Lys Gly
            195                 200                 205

Asn Phe Ile Ala Val Asp Asp Ser Pro Glu Glu Ile Arg Ala Lys Ile
    210                 215                 220

Lys Lys Ala Tyr Cys Pro Ala Gly Val Val Glu Gly Asn Pro Ile Met
225                 230                 235                 240

Glu Ile Ala Lys Tyr Phe Leu Glu Tyr Pro Leu Thr Ile Lys Arg Pro
                245                 250                 255

Glu Lys Phe Gly Gly Asp Leu Thr Val Asn Ser Tyr Glu Glu Leu Glu
            260                 265                 270
```

```
Ser Leu Phe Lys Asn Lys Glu Leu His Pro Met Asp Leu Lys Asn Ala
        275                 280                 285

Val Ala Glu Glu Leu Ile Lys Ile Leu Glu Pro Ile Arg Lys Arg Leu
290                 295                 300

<210> SEQ ID NO 7
<211> LENGTH: 305
<212> TYPE: PRT
<213> ORGANISM: Artificial Sequence
<220> FEATURE:
<223> OTHER INFORMATION: Synthetic polypeptide

<400> SEQUENCE: 7

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
290                 295                 300

Leu
305

<210> SEQ ID NO 8
```

<211> LENGTH: 305
<212> TYPE: PRT
<213> ORGANISM: Artificial Sequence
<220> FEATURE:
<223> OTHER INFORMATION: Synthetic polypeptide

<400> SEQUENCE: 8

| Met | Asp | Glu | Phe | Glu | Met | Ile | Lys | Arg | Asn | Thr | Ser | Glu | Ile | Ile | Ser |
|---|---|---|---|---|---|---|---|---|---|---|---|---|---|---|---|
| 1 | | | | 5 | | | | | 10 | | | | | 15 | |

| Glu | Glu | Glu | Leu | Arg | Glu | Val | Leu | Lys | Lys | Asp | Glu | Lys | Ser | Ala | Ala |
|---|---|---|---|---|---|---|---|---|---|---|---|---|---|---|---|
| | | | 20 | | | | | 25 | | | | | 30 | | |

| Ile | Gly | Phe | Glu | Pro | Ser | Gly | Lys | Ile | His | Leu | Gly | His | Tyr | Leu | Gln |
|---|---|---|---|---|---|---|---|---|---|---|---|---|---|---|---|
| | | | 35 | | | | | 40 | | | | | 45 | | |

| Ile | Lys | Lys | Met | Ile | Asp | Leu | Gln | Asn | Ala | Gly | Phe | Asp | Ile | Ile | Ile |
|---|---|---|---|---|---|---|---|---|---|---|---|---|---|---|---|
| | 50 | | | | | 55 | | | | | 60 | | | | |

| Leu | Leu | Ala | Asp | Leu | His | Ala | Tyr | Leu | Asn | Gln | Lys | Gly | Glu | Leu | Asp |
|---|---|---|---|---|---|---|---|---|---|---|---|---|---|---|---|
| 65 | | | | | 70 | | | | | 75 | | | | | 80 |

| Glu | Ile | Arg | Lys | Ile | Gly | Asp | Tyr | Asn | Lys | Lys | Val | Phe | Glu | Ala | Met |
|---|---|---|---|---|---|---|---|---|---|---|---|---|---|---|---|
| | | | | 85 | | | | | 90 | | | | | 95 | |

| Gly | Leu | Lys | Ala | Lys | Tyr | Val | Tyr | Gly | Ser | Lys | Phe | Gln | Leu | Asp | Lys |
|---|---|---|---|---|---|---|---|---|---|---|---|---|---|---|---|
| | | | 100 | | | | | 105 | | | | | 110 | | |

| Asp | Tyr | Thr | Leu | Asn | Val | Tyr | Arg | Leu | Ala | Leu | Lys | Thr | Thr | Leu | Lys |
|---|---|---|---|---|---|---|---|---|---|---|---|---|---|---|---|
| | | | 115 | | | | | 120 | | | | | 125 | | |

| Arg | Ala | Arg | Arg | Ser | Met | Glu | Leu | Ile | Ala | Arg | Glu | Asp | Glu | Asn | Pro |
|---|---|---|---|---|---|---|---|---|---|---|---|---|---|---|---|
| | 130 | | | | | 135 | | | | | 140 | | | | |

| Lys | Val | Ala | Glu | Val | Ile | Tyr | Pro | Ile | Met | Gln | Val | Asn | Ala | Ile | Tyr |
|---|---|---|---|---|---|---|---|---|---|---|---|---|---|---|---|
| 145 | | | | | 150 | | | | | 155 | | | | | 160 |

| Leu | Ala | Val | Asp | Val | Ala | Val | Gly | Gly | Met | Glu | Gln | Arg | Lys | Ile | His |
|---|---|---|---|---|---|---|---|---|---|---|---|---|---|---|---|
| | | | | 165 | | | | | 170 | | | | | 175 | |

| Met | Leu | Ala | Arg | Glu | Leu | Leu | Pro | Lys | Lys | Val | Val | Cys | Ile | His | Asn |
|---|---|---|---|---|---|---|---|---|---|---|---|---|---|---|---|
| | | | 180 | | | | | 185 | | | | | 190 | | |

| Pro | Val | Leu | Thr | Gly | Leu | Asp | Gly | Glu | Gly | Lys | Met | Ser | Ser | Ser | Lys |
|---|---|---|---|---|---|---|---|---|---|---|---|---|---|---|---|
| | | | 195 | | | | | 200 | | | | | 205 | | |

| Gly | Asn | Phe | Ile | Ala | Val | Asp | Asp | Ser | Pro | Glu | Glu | Ile | Arg | Ala | Lys |
|---|---|---|---|---|---|---|---|---|---|---|---|---|---|---|---|
| | 210 | | | | | 215 | | | | | 220 | | | | |

| Ile | Lys | Lys | Ala | Tyr | Cys | Pro | Ala | Gly | Val | Val | Glu | Gly | Asn | Pro | Ile |
|---|---|---|---|---|---|---|---|---|---|---|---|---|---|---|---|
| 225 | | | | | 230 | | | | | 235 | | | | | 240 |

| Met | Glu | Ile | Ala | Lys | Tyr | Phe | Leu | Glu | Tyr | Pro | Leu | Thr | Ile | Lys | Arg |
|---|---|---|---|---|---|---|---|---|---|---|---|---|---|---|---|
| | | | | 245 | | | | | 250 | | | | | 255 | |

| Pro | Glu | Lys | Phe | Gly | Gly | Asp | Leu | Thr | Val | Asn | Ser | Tyr | Glu | Glu | Leu |
|---|---|---|---|---|---|---|---|---|---|---|---|---|---|---|---|
| | | | 260 | | | | | 265 | | | | | 270 | | |

| Glu | Ser | Leu | Phe | Lys | Asn | Lys | Glu | Leu | His | Pro | Met | Asp | Leu | Lys | Asn |
|---|---|---|---|---|---|---|---|---|---|---|---|---|---|---|---|
| | | | 275 | | | | | 280 | | | | | 285 | | |

| Ala | Val | Ala | Glu | Glu | Leu | Ile | Lys | Ile | Leu | Glu | Pro | Ile | Arg | Lys | Arg |
|---|---|---|---|---|---|---|---|---|---|---|---|---|---|---|---|
| | 290 | | | | | 295 | | | | | 300 | | | | |

| Leu |
|---|
| 305 |

<210> SEQ ID NO 9
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 9

Met Asp Glu Phe Glu Met Ile Lys Arg Asn Thr Ser Glu Ile Ile Ser

```
                1               5                   10                  15
        Glu Glu Glu Leu Arg Glu Val Leu Lys Lys Asp Glu Lys Ser Ala Thr
                        20                  25                  30

Ile Gly Phe Glu Pro Ser Gly Lys Ile His Leu Gly His Tyr Leu Gln
                        35                  40                  45

Ile Lys Lys Met Ile Asp Leu Gln Asn Ala Gly Phe Asp Ile Ile Ile
                        50                  55                  60

Leu Leu Ala Asp Leu His Ala Tyr Leu Asn Gln Lys Gly Glu Leu Asp
        65                      70                  75                  80

Glu Ile Arg Lys Ile Gly Asp Tyr Asn Lys Lys Val Phe Glu Ala Met
                        85                  90                  95

Gly Leu Lys Ala Lys Tyr Val Tyr Gly Ser Asn Phe Gln Leu Asp Lys
                        100                 105                 110

Asp Tyr Thr Leu Asn Val Tyr Arg Leu Ala Leu Lys Thr Thr Leu Lys
                        115                 120                 125

Arg Ala Arg Arg Ser Met Glu Leu Ile Ala Arg Glu Asp Glu Asn Pro
                        130                 135                 140

Lys Val Ala Glu Val Ile Tyr Pro Ile Met Gln Val Asn Pro Leu His
        145                     150                 155                 160

Tyr Gln Gly Val Asp Val Ala Val Gly Gly Met Glu Gln Arg Lys Ile
                        165                 170                 175

His Met Leu Ala Arg Glu Leu Leu Pro Lys Lys Val Val Cys Ile His
                        180                 185                 190

Asn Pro Val Leu Thr Gly Leu Asp Gly Glu Gly Lys Met Ser Ser Ser
                        195                 200                 205

Lys Gly Asn Phe Ile Ala Val Asp Asp Ser Pro Glu Glu Ile Arg Ala
                        210                 215                 220

Lys Ile Lys Lys Ala Tyr Cys Pro Ala Gly Val Val Glu Gly Asn Pro
        225                     230                 235                 240

Ile Met Glu Ile Ala Lys Tyr Phe Leu Glu Tyr Pro Leu Thr Ile Lys
                        245                 250                 255

Arg Pro Glu Lys Phe Gly Gly Asp Leu Thr Val Asn Ser Tyr Glu Glu
                        260                 265                 270

Leu Glu Ser Leu Phe Lys Asn Lys Glu Leu His Pro Met Asp Leu Lys
                        275                 280                 285

Asn Ala Val Ala Glu Glu Leu Ile Lys Ile Leu Glu Pro Ile Arg Lys
                        290                 295                 300

Arg Leu
        305

<210> SEQ ID NO 10
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
                20                  25                  30

Ile Gly Phe Glu Pro Ser Gly Lys Ile His Leu Gly His Tyr Leu Gln
                35                  40                  45

Ile Lys Lys Met Ile Asp Leu Gln Asn Ala Gly Phe Asp Ile Ile Ile
```

```
Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
             85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 11
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 11

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
             85                  90                  95

Gly Leu Lys Ala Lys Tyr Val Tyr Gly Ser Thr Phe Gln Leu Asp Lys
```

```
            100                 105                 110
Asp Tyr Thr Leu Asn Val Tyr Arg Leu Ala Leu Lys Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
                195                 200                 205

Lys Gly Asn Phe Ile Ala Val Asp Asp Ser Pro Glu Glu Ile Arg Ala
                210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
                275                 280                 285

Asn Ala Val Ala Glu Glu Leu Ile Lys Ile Leu Glu Pro Ile Arg Lys
                290                 295                 300

Arg Leu
305

<210> SEQ ID NO 12
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 12

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
                100                 105                 110

Asp Tyr Thr Leu Asn Val Tyr Arg Leu Ala Leu Lys Thr Leu Lys
                115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Ser His
```

```
                145                 150                 155                 160
Tyr Gln Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
                180                 185                 190
Asn Pro Val Leu Thr Gly Leu Asp Gly Glu Gly Lys Met Ser Ser Ser
                195                 200                 205
Lys Gly Asn Phe Ile Ala Val Asp Asp Ser Pro Glu Glu Ile Arg Ala
                210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
                260                 265                 270
Leu Glu Ser Leu Phe Lys Asn Lys Glu Leu His Pro Met Asp Leu Lys
                275                 280                 285
Asn Ala Val Ala Glu Glu Leu Ile Lys Ile Leu Glu Pro Ile Arg Lys
                290                 295                 300
Arg Leu
305

<210> SEQ ID NO 13
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 13

Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Leu
                20                  25                  30
Ile Gly Phe Glu Pro Ser Gly Lys Ile His Leu Gly His Tyr Leu Gln
                35                  40                  45
Ile Lys Lys Met Ile Asp Leu Gln Asn Ala Gly Phe Asp Ile Ile Ile
                50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Glu Phe Gln Leu Asp Lys
                100                 105                 110
Asp Tyr Thr Leu Asn Val Tyr Arg Leu Ala Leu Lys Thr Thr Leu Lys
                115                 120                 125
Arg Ala Arg Arg Ser Met Glu Leu Ile Ala Arg Glu Asp Glu Asn Pro
                130                 135                 140
Lys Val Ala Glu Val Ile Tyr Pro Ile Met Gln Val Asn Gly Cys His
145                 150                 155                 160
Tyr Arg Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
                180                 185                 190
Asn Pro Val Leu Thr Gly Leu Asp Gly Glu Gly Lys Met Ser Ser Ser
```

```
                195                 200                 205
Lys Gly Asn Phe Ile Ala Val Asp Asp Ser Pro Glu Ile Arg Ala
        210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
            260                 265                 270
Leu Glu Ser Leu Phe Lys Asn Lys Glu Leu His Pro Met Asp Leu Lys
            275                 280                 285
Asn Ala Val Ala Glu Glu Leu Ile Lys Ile Leu Glu Pro Ile Arg Lys
            290                 295                 300
Arg Leu
305

<210> SEQ ID NO 14
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 14

Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Leu
            20                  25                  30
Ile Gly Phe Glu Pro Ser Gly Lys Ile His Leu Gly His Tyr Leu Gln
        35                  40                  45
Ile Lys Lys Met Ile Asp Leu Gln Asn Ala Gly Phe Asp Ile Ile Ile
    50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Glu Phe Gln Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Gly Thr His
145                 150                 155                 160
Tyr Arg Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
            180                 185                 190
Asn Pro Val Leu Thr Gly Leu Asp Gly Glu Gly Lys Met Ser Ser Ser
            195                 200                 205
Lys Gly Asn Phe Ile Ala Val Asp Asp Ser Pro Glu Ile Arg Ala
        210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
```

245                 250                 255
Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 15
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 15

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly His His
145                 150                 155                 160

Tyr Leu Gly Val Asp Val Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys 290                 295                 300

Arg Leu
305

<210> SEQ ID NO 16
<211> LENGTH: 306
<212> TYPE: PRT
<213> ORGANISM: Artificial Sequence
<220> FEATURE:
<223> OTHER INFORMATION: Synthetic polypeptide

<400> SEQUENCE: 16

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 17
<211> LENGTH: 306
<212> TYPE: PRT

<213> ORGANISM: Artificial Sequence
<220> FEATURE:
<223> OTHER INFORMATION: Synthetic polypeptide

<400> SEQUENCE: 17

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: L-para-amino-phenylalanine

<400> SEQUENCE: 18

Glu Thr Pro Asp Cys Phe Trp Lys Tyr Cys Val
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (5)..(10)
<223> OTHER INFORMATION: disulfide bridge between amino acid positions 5
      and 10
<220> FEATURE:
<221> NAME/KEY: MOD_RES
<222> LOCATION: (6)..(6)
<223> OTHER INFORMATION: L-para-amino-phenylalanine

<400> SEQUENCE: 19

Glu Thr Pro Asp Cys Phe Trp Lys Tyr Cys Val
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: L-para-amino-phenylalanine
<220> FEATURE:
<221> NAME/KEY: DISULFID
<222> LOCATION: (2)..(7)
<223> OTHER INFORMATION: disulfide bridge between amino acid positions 2
      and 7
<220> FEATURE:
<221> NAME/KEY: MOD_RES
<222> LOCATION: (4)..(4)
<223> OTHER INFORMATION: dTrp

<400> SEQUENCE: 20

Phe Cys Tyr Trp Lys Val Cys Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: L-para-amino-phenylalanine
<220> FEATURE:
<221> NAME/KEY: DISULFID
<222> LOCATION: (3)..(8)
<223> OTHER INFORMATION: disulfide bridge between amino acid positions 3
      and 8

<400> SEQUENCE: 21

Ser Phe Cys Tyr His Lys Trp Cys Thr
1               5

<210> SEQ ID NO 22
<211> LENGTH: 9
<212> TYPE: PRT
<213> ORGANISM: Artificial Sequence

```
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: L-para-amino-phenylalanine
<220> FEATURE:
<221> NAME/KEY: DISULFID
<222> LOCATION: (3)..(8)
<223> OTHER INFORMATION: disulfide bridge between amino acid positions 3
      and 8

<400> SEQUENCE: 22

His Phe Cys Tyr His Lys Trp Cys Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: L-para-amino-phenylalanine
<220> FEATURE:
<221> NAME/KEY: DISULFID
<222> LOCATION: (3)..(8)
<223> OTHER INFORMATION: disulfide bridge between amino acid positions 3
      and 8

<400> SEQUENCE: 23

Trp Phe Cys Tyr His Lys Trp Cys Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: L-para-amino-phenylalanine
<220> FEATURE:
<221> NAME/KEY: DISULFID
<222> LOCATION: (3)..(8)
<223> OTHER INFORMATION: disulfide bridge between amino acid positions 3
      and 8

<400> SEQUENCE: 24

Asn Phe Cys Tyr His Lys Trp Cys Thr
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: L-para-amino-phenylalanine
<220> FEATURE:
<221> NAME/KEY: DISULFID
<222> LOCATION: (4)..(9)
<223> OTHER INFORMATION: disulfide bridge between amino acid positions 4
      and 9

<400> SEQUENCE: 25
```

```
Arg Asn Phe Cys Tyr His Lys Trp Cys Thr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: L-para-amino-phenylalanine
<220> FEATURE:
<221> NAME/KEY: DISULFID
<222> LOCATION: (5)..(10)
<223> OTHER INFORMATION: disulfide bridge between amino acid positions 5
      and 10

<400> SEQUENCE: 26

Ala Arg Asn Phe Cys Tyr His Lys Trp Cys Thr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: variable amino acid
<220> FEATURE:
<221> NAME/KEY: DISULFID
<222> LOCATION: (4)..(9)
<223> OTHER INFORMATION: disulfide bridge between amino acid positions 4
      and 9

<400> SEQUENCE: 27

Ala Arg Xaa Cys Tyr His Lys Trp Cys Thr
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: variable amino acid
<220> FEATURE:
<221> NAME/KEY: DISULFID
<222> LOCATION: (3)..(8)
<223> OTHER INFORMATION: disulfide bridge between amino acid positions 3
      and 8

<400> SEQUENCE: 28

Asn Xaa Cys Tyr His Lys Trp Cys Thr
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (2)..(2)
<223> OTHER INFORMATION: variable amino acid
<220> FEATURE:
<221> NAME/KEY: DISULFID
<222> LOCATION: (3)..(8)
<223> OTHER INFORMATION: disulfide bridge between amino acid positions 3
      and 8
<220> FEATURE:
<221> NAME/KEY: MOD_RES
<222> LOCATION: (5)..(5)
<223> OTHER INFORMATION: dTrp

<400> SEQUENCE: 29

Met Xaa Cys Tyr Trp Lys Val Cys Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: dTrp

<400> SEQUENCE: 30

Cys Tyr Trp Lys Val Cys Thr
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (3)..(8)
<223> OTHER INFORMATION: disulfide bridge between amino acid positions 3
      and 8
<220> FEATURE:
<221> NAME/KEY: MOD_RES
<222> LOCATION: (5)..(5)
<223> OTHER INFORMATION: dTrp

<400> SEQUENCE: 31

Met Phe Cys Tyr Trp Lys Val Cys Thr
1               5
```

COMPOSITIONS CONTAINING, METHODS INVOLVING, AND USES OF NON-NATURAL AMINO ACIDS AND POLYPEPTIDES

RELATED APPLICATIONS

This is a divisional of U.S. application Ser. No. 11/925,732, filed Oct. 26, 2007, which is a continuation of application no. PCT/US2006/047822, filed Dec. 13, 2006; which claims benefit of U.S. Provisional Application No. 60/743,041, filed Dec. 14, 2005 and U.S. Provisional Application No. 60/743,040, filed Dec. 14, 2005, all of which are entitled "Compositions Containing, Methods Involving, and Uses of Non-natural Amino Acids and Polypeptides", and are incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 20, 2013, is named 31362-711-402SEQ.txt and is 44,574 bytes in size.

FIELD OF THE INVENTION

Described herein are methods and compositions for making and using non-natural amino acid agents.

BACKGROUND OF THE INVENTION

The ability to incorporate non-genetically encoded amino acids (i.e., "non-natural amino acids") into proteins permits the introduction of chemical functional groups that could provide valuable alternatives to the naturally-occurring functional groups, such as the epsilon —$NH_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages with functional groups that can be incorporated onto non-natural amino acids.

Methods are now available to selectively introduce chemical functional groups that are not found in proteins, that are chemically inert to all of the functional groups found in the 20 common, genetically-encoded amino acids and that may be used to react efficiently and selectively with reagents comprising certain functional groups to form stable covalent linkages.

SUMMARY OF THE INVENTION

Described herein are methods, compositions, techniques and strategies for making, purifying, characterizing, and using non-natural amino acids, non-natural amino acid polypeptides and modified non-natural amino acid polypeptides. In one aspect are methods, compositions, techniques and strategies for derivatizing a non-natural amino acid and/or a non-natural amino acid polypeptide. In one embodiment, such methods, compositions, techniques and strategies involved chemical derivatization, in other embodiments, biological derivatization, in other embodiments, physical derivatization, in other embodiments a combination of derivatizations. In further or additional embodiments, such derivatizations are regioselective. In further or additional embodiments, such derivatizations are regiospecific. In further or additional embodiments, such derivations are stoichiometric, near stoichiometric or stoichiometric-like in both the non-natural amino acid containing reagent and the derivatizing reagent. In further or additional embodiments are provided methods which allow the stoichiometric, near stoichiometric or stoichiometric-like incorporation of a desired group onto a non-natural amino acid polypeptide. In further or additional embodiments are provided strategies, reaction mixtures, synthetic conditions which allow the stoichiometric, near stoichiometric or stoichiometric-like incorporation of a desired group onto a non-natural amino acid polypeptide. In further or additional embodiments, such derivatizations are rapid at ambient temperature. In further or additional embodiments, such derivatizations occur in aqueous solutions. In further or additional embodiments, such derivatizations occur at a pH between about 4 and about 10. In further or additional embodiments, such derivatizations occur at a pH between about 4 and about 7. In further or additional embodiments, such derivatizations occur at a pH between about 4 and about 5. In further or additional embodiments, such derivatizations occur at a pH of about 5. In further or additional embodiments, such derivatizations occur at a pH of about 4.

In one aspect are non-natural amino acids for the chemical derivatization of peptides and proteins based upon the reactivity of an aromatic amine group. In further or additional embodiments, at least one of the aforementioned non-natural amino acids is incorporated into a polypeptide, that is, such embodiments are non-natural amino acid polypeptides. In further or additional embodiments, the non-natural amino acids are functionalized on their sidechains such that their reaction with a derivatizing molecule generates an amine linkage. In further or additional embodiments, the non-natural amino acids are selected from amino acids having aromatic amine sidechains. In further or additional embodiments, the non-natural amino acids comprise a masked sidechain, including a masked aromatic amine group.

In further or additional embodiments, the non-natural amino acids comprise aromatic amine sidechains where the aromatic amine is selected from an aryl amine or a heteroaryl amine. In a further or additional embodiment, the non-natural amino acids resemble a natural amino acid in structure but contain aromatic amine groups. In another or further embodiment the non-natural amino acids resemble phenylalanine or tyrosine (aromatic amino acids). In one embodiment, the non-natural amino acids have properties that are distinct from those of the natural amino acids. In one embodiment, such distinct properties are the chemical reactivity of the sidechain; in a further embodiment this distinct chemical reactivity permits the sidechain of the non-natural amino acid to undergo a reaction while being a unit of a polypeptide even though the sidechains of the naturally-occurring amino acid units in the same polypeptide do not undergo the aforementioned reaction. In a further embodiment, the sidechain of the non-natural amino acid has a chemistry orthogonal to those of the naturally-occurring amino acids. In a further embodiment, the sidechain of the non-natural amino acid comprises a nucleophile-containing moiety; in a further embodiment, the nucleophile-containing moiety on the sidechain of the non-natural amino acid can undergo a reaction to generate an amine derivatized protein. In a further embodiment, the sidechain of the non-natural amino acid comprises an electrophile-containing moiety; in a further embodiment, the electrophile-containing moiety on the sidechain of the non-natural amino acid can undergo nucleophilic attack to generate an amine derivatized protein. In any of the aforementioned embodiments in this paragraph, the non-natural amino acid may exist as a separate molecule or may be incorporated into a polypeptide of any length; if the latter, then the polypeptide may further incorporate naturally-occurring or non-natural amino acids.

In another aspect are carbonyl-substituted molecules such as, by way of example, aldehydes, and ketones, for the production of derivatized non-natural amino acid polypeptides based upon an amine linkage. In a further embodiment are aldehyde-substituted molecules used to derivatize aromatic amine-containing non-natural amino acid polypeptides via the formation of an amine linkage between the derivatizing molecule and the aromatic amine-containing non-natural amino acid polypeptide. In further or additional embodiments, the aldehyde-substituted molecules comprise a group selected from: a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter, an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof. In further or additional embodiments, the aldehyde-substituted molecules are aldehyde-substituted polyethylene glycol (PEG) molecules. In a further embodiment, the sidechain of the non-natural amino acid has a chemistry orthogonal to those of the naturally-occurring amino acids that allows the non-natural amino acid to react selectively with the aldehyde-substituted molecules. In a further embodiment, the sidechain of the non-natural amino acid comprises an aromatic amine-containing moiety that reacts selectively with the aldehyde-containing molecule; in a further embodiment, the aromatic amine-containing moiety on the sidechain of the non-natural amino acid can undergo reaction to generate an alkylated amine-derivatized protein. In a further aspect related to the embodiments described in this paragraph are the modified non-natural amino acid polypeptides that result from the reaction of the derivatizing molecule with the non-natural amino acid polypeptides. Further embodiments include any further modifications of the already modified non-natural amino acid polypeptides.

In another aspect are aromatic amine-substituted molecules such as, by way of example, aryl amines and heteroaryl amines, for the production of derivatized non-natural amino acid polypeptides based upon an amine linkage. In a further embodiment are aromatic amine-substituted molecules used to derivatize aldehyde-containing non-natural amino acid polypeptides via the formation of an amine linkage between the derivatizing molecule and the aldehyde-containing non-natural amino acid polypeptide. In further or additional embodiments, the aromatic amine-substituted molecules comprise a group selected from: a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof. In further or additional embodiments, the aromatic amine-substituted molecules are aromatic amine-substituted polyethylene glycol (PEG) molecules. In a further embodiment, the sidechain of the non-natural amino acid has a chemistry orthogonal to those of the naturally-occurring amino acids that allows the non-natural amino acid to react selectively with the aromatic amine-substituted molecules. In a further embodiment, the sidechain of the non-natural amino acid comprises an aldehyde-containing moiety that reacts selectively with the aromatic amine-containing molecule; in a further embodiment, the aldehyde-containing moiety on the sidechain of the non-natural amino acid can undergo reaction to generate an alkylated amine-derivatized protein. In a further aspect related to the embodiments described in this paragraph are the modified non-natural amino acid polypeptides that result from the reaction of the derivatizing molecule with the non-natural amino acid polypeptides. Further embodiments include any further modifications of the already modified non-natural amino acid polypeptides.

In another aspect are mono-, bi- and multi-functional linkers for the generation of derivatized non-natural amino acid polypeptides based upon an amine linkage. In one embodiment are molecular linkers (bi- and multi-functional) that can be used to connect aromatic amine-containing non-natural amino acid polypeptides to other molecules. In another embodiment the aromatic amine-containing non-natural amino acid polypeptides comprise an aryl amine or a heteroaryl amine sidechain. In an embodiment utilizing an aromatic amine-containing non-natural amino acid polypeptide, the molecular linker contains an aldehyde group at one of its termini. In further or additional embodiments, the aldehyde-substituted linker molecules are aldehyde-substituted polyethylene glycol (PEG) linker molecules. In further embodiments, the phrase "other molecules" includes, by way of example only, proteins, other polymers and small molecules. In further or additional embodiments, the aldehyde-containing molecular linkers comprise the same or equivalent groups on all termini so that upon reaction with an aromatic amine-containing non-natural amino acid polypeptide, the resulting product is the homo-multimerization of the aromatic amine-containing non-natural amino acid polypeptide. In further embodiments, the homo-multimerization is a homo-dimerization. In further or additional embodiments, the molecular linkers comprise at least one aldehyde group and a different group on all termini so that upon reaction with an aromatic amine-containing non-natural amino acid polypeptide, the resulting product is the hetero-multimerization of the aromatic amine-containing non-natural amino acid polypeptide. In further embodiments, the hetero-multimerization is a hetero-dimerization. In a further embodiment, the sidechain of the non-natural amino acid has a chemistry orthogonal to those of the naturally-occurring amino acids that allows the non-natural amino acid to react selectively with the aldehyde-substituted linker molecules. In a further aspect related to the embodiments described in this paragraph are the linked modified or unmodified non-natural amino acid polypeptides that result from the reaction of the linker molecule with the non-natural amino acid polypeptides. Further embodiments include any further modifications of the already linked modified or unmodified non-natural amino acid polypeptides.

In one aspect are methods to derivatize proteins via the reaction of aromatic amines and aldehyde reactants to alkylated amine-derivatized protein. Included within this aspect are methods for the derivatization of proteins based upon the reductive alkylation of aromatic amine- and aldehyde-containing reactants to generate alkylated amine-derivatized protein adduct. In additional or further embodiments are methods to derivatize aromatic amine-containing proteins with aldehyde-functionalized polyethylene glycol (PEG) molecules. In yet additional or further aspects, the aldehyde-substituted molecule can include proteins, other polymers (non-branched and branched), and small molecules.

In another aspect are methods for the chemical synthesis of aldehyde-substituted molecules for the derivatization of aromatic amine-substituted proteins. In one embodiment, the aldehyde-substituted molecule can comprise peptides, other polymers (non-branched and branched) and small molecules. In one embodiment are methods for the preparation of aldehyde-substituted molecules suitable for the derivatization of aromatic amine-containing non-natural amino acid polypeptides. In a further or additional embodiment, the non-natural amino acids, including, but not limited to, aromatic amine-containing non natural amino acids, are incorporated site-specifically during the in vivo translation of proteins. In further or alternative embodiments, the non-natural amino acids, including, but not limited to, aromatic amine-containing non natural amino acids, are incorporated site-specifically by ribosomal translation. In further or alternative embodiments, the non-natural amino acids, including, but not limited to, aromatic amine-containing non natural amino acids, are incorporated site-specifically during the in vitro translation. In a further or additional embodiment, the aldehyde-substituted molecules allow for the site-specific derivatization of aromatic amine-containing non-natural amino acids via reductive alkylation of the aromatic amine moiety to form an alkylated amine-derivatized polypeptide in a site-specific fashion. In a further or additional embodiment, the method for the preparation of aldehyde-substituted molecules provides access to a wide variety of site-specifically derivatized polypeptides. In a further or additional embodiment are methods for synthesizing aldehyde-functionalized polyethylene glycol (PEG) molecules.

In another aspect are methods for the chemical derivatization of aromatic amine-substituted non-natural amino acid polypeptides using an aldehyde-containing bi-functional linker. In one embodiment are methods for attaching an aldehyde-substituted linker to an aromatic amine-substituted protein via a reductive alkylation reaction to generate an amine linkage. In further or additional embodiments, the aromatic amine-substituted non-natural amino acid is an aryl amine or a heteroaryl amine-substituted non-natural amino acid. In further or additional embodiments, the non-natural amino acid polypeptides are derivatized site-specifically and/or with precise control of three-dimensional structure, using an aldehyde-containing bi-functional linker. In one embodiment, such methods are used to attach molecular linkers (mono- bi- and multi-functional) to aromatic amine-containing non-natural amino acid polypeptides, wherein at least one of the linker termini contains an aldehyde group which can link to the aromatic amine-containing non-natural amino acid polypeptides via an amine linkage. In a further or additional embodiment, these linkers are used to connect the aromatic amine-containing non-natural amino acid polypeptides to other molecules, including by way of example, proteins, other polymers (branched and non-branched) and small molecules.

In some embodiments, the non-natural amino acid polypeptide is linked to a water soluble polymer. In some embodiments, the water soluble polymer comprises a polyethylene glycol moiety. In some embodiments, the poly (ethylene glycol) molecule is a bifunctional polymer. In some embodiments, the bifunctional polymer is linked to a second polypeptide. In some embodiments, the second polypeptide is identical to the first polypeptide, in other embodiments; the second polypeptide is a different polypeptide. In some embodiments, the non-natural amino acid polypeptide comprises at least two amino acids linked to a water soluble polymer comprising a polyethylene glycol moiety.

In some embodiments, the non-natural amino acid polypeptide comprises a substitution, addition or deletion that increases affinity of the non-natural amino acid polypeptide for a receptor. In some embodiments, the non-natural amino acid polypeptide comprises a substitution, addition, or deletion that increases the stability of the non-natural amino acid polypeptide. In some embodiments, the non-natural amino acid polypeptide comprises a substitution, addition, or deletion that increases the aqueous solubility of the non-natural amino acid polypeptide. In some embodiments, the non-natural amino acid polypeptide comprises a substitution, addition, or deletion that increases the solubility of the non-natural amino acid polypeptide produced in a host cell. In some embodiments, the non-natural amino acid polypeptide comprises a substitution, addition, or deletion that modulates protease resistance, serum half-life, immunogenicity, and/or expression relative to the amino-acid polypeptide without the substitution, addition or deletion.

In some embodiments, the non-natural amino acid polypeptide is an agonist, partial agonist, antagonist, partial antagonist, or inverse agonist. In some embodiments, the agonist, partial agonist, antagonist, partial antagonist, or inverse agonist comprises a non-natural amino acid linked to a water soluble polymer. In some embodiments, the water polymer comprises a polyethylene glycol moiety. In some embodiments, the polypeptide comprising a non-natural amino acid linked to a water soluble polymer, for example, may prevent dimerization of the corresponding receptor. In some embodiments, the polypeptide comprising a non-natural amino acid linked to a water soluble polymer modulates binding of the polypeptide to a binding partner, ligand or receptor. In some embodiments, the polypeptide comprising a non-natural amino acid linked to a water soluble polymer modulates one or more properties or activities of the polypeptide.

In some embodiments, the selector codon is selected from the group consisting of an amber codon, ochre codon, opal codon, a unique codon, a rare codon, an unnatural codon, a five-base codon, and a four-base codon.

In further or additional embodiments, the non-natural aromatic amine amino acid polypeptides and/or modified non-natural aromatic amine amino acid polypeptides described herein have at least one of the following characteristics: (1) the amine moiety of the aromatic amine is a primary amine; (2) the amine moiety of the aromatic amine is a secondary amine; (3) the aromatic moiety of the aromatic amine is a heteroaromatic moiety; (4) the aromatic moiety of the aromatic amine is an aryl moiety; (5) the aromatic amine reacts with aldehyde functionalized groups; (6) is coupled to a water soluble polymer; (7) is PEGylated; (8) has increased therapeutic half-life relative to the corresponding polypeptide without the non-natural aromatic amine amino acid; (9) has increased serum half-life relative to the corresponding polypeptide without the non-natural aromatic amine amino acid; (10) has increased circulation time relative to the corresponding polypeptide without the non-natural aromatic amine amino acid; (11) has increased water solubility relative to the corresponding polypeptide without the non-natural aromatic amine amino acid; (12) has enhanced bioavailability relative to the corresponding polypeptide without the non-natural aromatic amine amino acid; (13) has modulated immunogenicity relative to the corresponding polypeptide without the non-natural aromatic amine amino acid; (14) has modulated biological activity relative to the corresponding polypeptide without the non-natural aromatic amine amino acid; (15) is part of a pharmaceutical composition; (16) is obtained from cell culture; (17) is chemically synthesized; (18) is used in library screening methods; (19) is used with arrays; (20) is used with protein arrays; (21) is used for gene expression analysis; (22) is coupled to at least one agent; (23) is coupled to a label; (24) is coupled to a dye; (25) is coupled to a polymer; (26) is coupled to a cytotoxic compound; (27) is coupled to a drug; (28) is coupled to a second protein or polypeptide or polypeptide analog; (29) is coupled to an antibody or antibody fragment; (30) is coupled to a carbohydrate; (31) is coupled to a polynucleotide; (32) is coupled to an antisense polynucleotide; (33) is coupled to a saccharide, (34) is coupled to a fluorophore, (35) is coupled to a chemically cleavable group; (36) is coupled to a photocleavable group; (37) is coupled to an energy transfer agent; (38) is coupled to a radionucleotide; (39) may be post-translationally modified; (40) may be post-translationally modified by reductive alkylation; (41) may be post-translationally modified by reductive alkylation in a pH range between about 4 to about 10; (42) may be site-specifically derivatized by post-translational reductive alkylation; (43) may be rapidly post-translationally modified by reductive alkylation at room temperature, (44) may be post-translationally modified by reductive alkylation in aqueous conditions; (45) may be post-translationally modified by reductive alkylation with stoichiometric reaction conditions; (46) may be post-translationally modified by reductive alkylation with near-stoichiometric reaction conditions; (47) may be post-translationally modified by reductive alkylation with stoichiometric-like reaction conditions; (48) is used to treat a mammal suffering from a disease, disorder or condition; (49) is used to treat a human suffering from a disease, disorder or condition; (50) is used to diagnose a mammal suffering from a disease, disorder or condition; (51) is used to diagnose a human suffering from a disease, disorder or condition; (52) is part of a sustained-release compositions; (53) the amine moiety is formed by post-translational reduction of a masked amine moiety; (54) the amine moiety is formed by post-translational reduction of an imine moiety; (55) the amine moiety is formed by post-translational reduction of an azide moiety; (56) the amine moiety is formed by post-translational reduction of a hydrazine moiety; (57) the amine moiety is formed by post-translational reduction of a nitro moiety, (58) is coupled to a pro-drug; (59) is obtained from cell lysate; (60) is ribosomally translated; (61) may be post-translationally modified by reductive alkylation in a pH range between about 4 to about 7; (62) may be post-translationally modified by reductive alkylation in a pH range between about 4 to about 5; (63) may be post-translationally modified by reductive alkylation at a pH of about 5; (64) may be post-translationally modified by reductive alkylation at a pH of about 4; (65) reacts rapidly in reductive alkylation reactions; (66) reacts in less than about 10 hours in reductive alkylation reactions; (67) reacts in less than about 8 hours in reductive alkylation reactions; (68) reacts in less than about 6 hours in reductive alkylation reactions; (68) reacts in less than about 4 hours in reductive alkylation reactions; (69) reacts in less than about 2 hours in reductive alkylation reactions; (70) reacts in less than about 1 hour in reductive alkylation reactions, or (71) reacts in less than about 30 minutes in reductive alkylation reactions.

In further or alternative embodiments the non-natural aromatic amine amino acid polypeptides and/or modified non-natural aromatic amine amino acid polypeptides described herein have at least two of the aforementioned characteristics. In further or alternative embodiments the non-natural aromatic amine amino acid polypeptides and/or modified non-natural aromatic amine amino acid polypeptides described herein have at least three of the aforementioned characteristics. In further or alternative embodiments the non-natural aromatic amine amino acid polypeptides and/or modified non-natural aromatic amine amino acid polypeptides described herein have at least four of the aforementioned characteristics. In further or alternative embodiments the non-natural aromatic amine amino acid polypeptides and/or modified non-natural aromatic amine amino acid polypeptides described herein have at least five of the aforementioned characteristics.

In further or additional embodiments, the non-natural aldehyde-based amino acid polypeptides and/or modified non-natural aldehyde-based amino acid polypeptides described herein have at least one of the following characteristics: (1) contains a protected or masked aldehyde moiety; (2) contains a deprotected or unmasked aldehyde moiety (3) contains a deprotected or unmasked aldehyde moiety which can react with an aromatic amine; (4) contains a deprotected or unmasked aldehyde moiety which can react with a heteroaromatic amine; (5) contains a deprotected or unmasked aldehyde moiety which can react with an aromatic amine or a heteroaromatic amine by reductive amination; (6) is coupled to a water soluble polymer; (7) is PEGylated; (8) has increased therapeutic half-life relative to the corresponding polypeptide without the non-natural aldehyde-based amino acid; (9) has increased serum half-life relative to the corresponding polypeptide without the non-natural aldehyde-based amino acid; (10) has increased circulation time relative to the corresponding polypeptide without the non-natural aldehyde-based amino acid; (11) has increased water solubility relative to the corresponding polypeptide without the non-natural aldehyde-based amino acid; (12) has enhanced bioavailability relative to the corresponding polypeptide without the non-natural aldehyde-based amino acid; (13) has modulated immunogenicity relative to the corresponding polypeptide without the non-natural aldehyde-based amino acid; (14) has modulated biological activity relative to the corresponding polypeptide without the non-natural aldehyde-based amino acid; (15) is part of a pharmaceutical composition; (16) is obtained from cell culture; (17) is chemically synthesized; (18) is used in library screening methods; (19) is used with arrays; (20) is used with protein arrays; (21) is used for gene expression analysis; (22) can be coupled to an agent via reductive amination; (23) is coupled to a label; (24) is coupled to a dye; (25) is coupled to a polymer; (26) is coupled to a cytotoxic compound; (27) is coupled to a drug; (28) is coupled to a second protein or polypeptide or polypeptide analog; (29) is coupled to an antibody or antibody fragment; (30) is coupled to a carbohydrate; (31) is coupled to a polynucleotide; (32) is coupled to an antisense polynucleotide; (33) is coupled to a saccharide, (34) is coupled to a fluorophore, (35) is coupled to a chemically cleavable group; (36) is coupled to a photocleavable group; (37) is coupled to an energy transfer agent; (38) is coupled to a radionucleotide; (39) may be post translationally modified; (40) may be post-translationally modified by reductive amination; (41) may be post-translationally modified by reductive amination in a pH range between about 4 to about 10; (42) may be site-specifically derivatized by post-translation reductive amination; (43) may be rapidly post-translationally modified by reductive amination at room temperature, (44) may be post-translationally modified by reductive amination in aqueous conditions; (45) may be post-translationally modified by reductive amination with stoichiometric reaction conditions; (46) may be post-translationally modified by reductive amination with near-stoichiometric reaction conditions; (47) may be post-translationally modified by reductive amination with stoichiometric-like reaction conditions; (48) is used treat a mammal suffering from a disease, disorder or condition; (49) is used treat a human suffering from a disease, disorder or condition; (50) is used diagnose a mammal suffering from a disease, disorder or condition; (51) is used diagnose a human suffering from a disease, disorder or condition; (52) is part of a sustained-release compositions; (53) is coupled to a pro-drug; (54) is obtained from cell lysate; (55) is ribosomally translated; (56) may be post-translationally modified by reductive amination in a pH range between about 4 to about 7; (57) may be post-translationally modified by reductive amination in a pH range between about 4 to about 5; (58) may be post-translationally modified by reductive amination at a pH of about 5; (59) may be post-translationally modified by reductive amination at a pH of about 4; (60) reacts rapidly in reductive amination reactions; (61) reacts in less than about 10 hours in reductive amination reactions; (62) reacts in less than about 8 hours in reductive amination reactions; (63) reacts in less than about 6 hours in reductive amination reactions; (68) reacts in less than about 4 hours in reductive amination reactions; (64) reacts in less than about 2 hours in reductive amination reactions; (65) reacts in less than about 1 hour in reductive amination reactions, or (66) reacts in less than about 30 minutes in reductive amination reactions.

In further or alternative embodiments the non-natural aldehyde-based amino acid polypeptides and/or modified non-natural aldehyde-based amino acid polypeptides described herein have at least two of the aforementioned characteristics. In further or alternative embodiments the non-natural aldehyde-based amino acid polypeptides and modified non-natural aldehyde-based amino acid polypeptides described herein have at least three of the aforementioned characteristics. In further or alternative embodiments the non-natural aldehyde-based amino acid polypeptides and/or modified non-natural aldehyde-based amino acid polypeptides described herein have at least four of the aforementioned characteristics. In further or alternative embodiments the non-natural aldehyde-based amino acid polypeptides and/or modified non-natural aldehyde-based amino acid polypeptides described herein have at least five of the aforementioned characteristics.

Also described herein are methods of making a non-natural amino acid polypeptide linked to a water soluble polymer. In some embodiments, the method comprises contacting an isolated polypeptide comprising a non-natural amino acid with a water soluble polymer comprising a moiety that reacts with the non-natural amino acid. In some embodiments, the non-natural amino acid incorporated into is reactive toward a water soluble polymer that is otherwise unreactive toward any of the 20 common amino acids. In some embodiments, the water polymer comprises a polyethylene glycol moiety. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the polyethylene glycol molecule is a branched polymer. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

Also described herein are compositions comprising a polypeptide comprising at least one of the non-natural amino acids described herein and a pharmaceutically acceptable carrier. In some embodiments, the non-natural amino acid is linked to a water soluble polymer. Also described herein are pharmaceutical compositions comprising a pharmaceutically acceptable carrier and a polypeptide, wherein at least one amino acid is substituted by a non-natural amino acid. In some embodiments, the non-natural amino acid comprises a saccharide moiety. In some embodiments, the water soluble polymer is linked to the polypeptide via a saccharide moiety.

Also described herein are cells comprising a polynucleotide encoding the polypeptide comprising a selector codon. In some embodiments, the cells comprise an orthogonal RNA synthetase and/or an orthogonal tRNA for substituting a non-natural amino acid into the polypeptide. In some embodiments the cells are in a cell culture, whereas in other embodiments the cells of part of a multicellular organism, including amphibians, reptiles, birds, and mammals. In any of the cell embodiments, further embodiments include expression of the polynucleotide to produce the non-natural amino acid polypeptide. In some embodiments, the non-natural amino acid polypeptide is produced in vitro. In some embodiments, the non-natural amino acid polypeptide is produced in cell lysate. In some embodiments, the non-natural amino acid polypeptide is produced by ribosomal translation.

Also described herein are methods of making a polypeptide comprising a non-natural amino acid. In some embodiments, the methods comprise culturing cells comprising a polynucleotide or polynucleotides encoding a polypeptide, an orthogonal RNA synthetase and/or an orthogonal tRNA under conditions to permit expression of the polypeptide; and purifying the polypeptide from the cells and/or culture medium.

Also described herein are libraries of the non-natural amino acids described herein or libraries of the non-natural amino acid polypeptides described herein, or libraries of the modified non-natural amino acid polypeptides described herein, or combination libraries thereof. Also described herein are arrays containing at least one non-natural amino acid, at least one non-natural amino acid polypeptide, and/or at least one modified non-natural amino acid. Also described herein are arrays containing at least one polynucleotide encoding a polypeptide comprising a selector codon. The arrays described herein may be used to screen for the production of the non-natural amino acid polypeptides in an organism (either by detecting transcription of the polynucleotide encoding the polypeptide or by detecting the translation of the polypeptide).

Also described herein are methods for screening libraries described herein for a desired activity, or for using the arrays described herein to screen the libraries described herein, or for other libraries of compounds and/or polypeptides and/or polynucleotides for a desired activity. Also described herein is the use of such activity data from library screening to develop and discover new therapeutic agents, as well as the therapeutic agents themselves.

Also described herein are methods of increasing therapeutic half-life, serum half-life or circulation time of a polypeptide. In some embodiments, the methods comprise substituting at least one non-natural amino acid for any one or more amino acids in a naturally occurring polypeptide and/or linking the polypeptide to a water soluble polymer.

Also described herein are methods of treating a patient, in need of such treatment, with an effective amount of a pharmaceutical composition which comprises a polypeptide comprising a non-natural amino acid and a pharmaceutically acceptable carrier. In some embodiments, the non-natural amino acid is linked to a water soluble polymer.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the inventions described herein, the preferred methods, devices and materials are now described.

All publications and patents mentioned herein are incorporated herein by reference in their entirety for the purpose of describing and disclosing, for example, the constructs and methodologies that are described in the publications, which might be used in connection with the presently described inventions. The publications discussed herein are provided solely for their disclosure prior to the filing date of the present application. Nothing herein is to be construed as an admission that the inventors described herein are not entitled to antedate such disclosure by virtue of prior invention or for any other reason.

The term "affinity label," as used herein, refers to a label which reversibly or irreversibly binds another molecule, either to modify it, destroy it, or form a compound with it. By way of example, affinity labels include enzymes and their substrates, or antibodies and their antigens.

The terms "alkoxy," "alkylamino" and "alkylthio" are used in their conventional sense, and refer to alkyl groups linked to molecules via an oxygen atom, an amino group, a sulfur atom, respectively.

The term "alkyl," by itself or as part of another molecule, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl", "haloalkyl" and "homoalkyl".

The term "alkylene" by itself or as part of another molecule means a divalent radical derived from an alkane, as exemplified by (—CH$_2$—)$_n$, wherein n may be 1 to about 24. By way of example only, such groups include, but are not limited to, groups having 10 or fewer carbon atoms such as the structures —CH$_2$CH$_2$— and —CH$_2$CH$_2$CH$_2$CH$_2$—. A "lower alkyl" or "lower alkylene" is a shorter chain alkyl or alkylene group, generally having eight or fewer carbon atoms. The term "alkylene," unless otherwise noted, is also meant to include those groups described below as "heteroalkylene."

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, by way of example, an a carbon that is bound to a hydrogen, a carboxyl group, an amino group, and an R group. Such analogs may have modified R groups (by way of example, norleucine) or may have modified peptide backbones, while still retaining the same basic chemical structure as a naturally occurring amino acid. Non-limiting examples of amino acid analogs include homoserine, norleucine, methionine sulfoxide, methionine methyl sulfonium.

Amino acids may be referred to herein by either their name, their commonly known three letter symbols or by the one-letter symbols recommended by the IUPAC-IUB Biochemical Nomenclature Commission. Additionally, nucleotides, may be referred to by their commonly accepted single-letter codes.

An "amino terminus modification group" refers to any molecule that can be attached to a terminal amine group. By way of example, such terminal amine groups may be at the end of polymeric molecules, wherein such polymeric molecules include, but are not limited to, polypeptides, polynucleotides, and polysaccharides. Terminus modification groups include but are not limited to, various water soluble polymers, peptides or proteins. By way of example only, terminus modification groups include polyethylene glycol or serum albumin. Terminus modification groups may be used to modify therapeutic characteristics of the polymeric molecule, including but not limited to increasing the serum half-life of peptides.

By "antibody fragment" is meant any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab)$_2$, single chain Fv (scFv), diabodies, triabodies, tetrabodies, bifunctional hybrid antibodies, CDR1, CDR2, CDR3, combinations of CDR's, variable regions, framework regions, constant regions, heavy chains, light chains, and variable regions, and alternative scaffold non-antibody molecules, bispecific antibodies, and the like (Maynard & Georgiou, 2000, *Annu. Rev. Biomed. Eng.* 2:339-76; Hudson, 1998, *Curr. Opin. Biotechnol.* 9:395-402). Another functional substructure is a single chain Fv (scFv), comprised of the variable regions of the immunoglobulin heavy and light chain, covalently connected by a peptide linker (S-z Hu et al., 1996, *Cancer Research,* 56, 3055-3061). These small (Mr 25,000) proteins generally retain specificity and affinity for antigen in a single polypeptide and can provide a convenient building block for larger, antigen-specific molecules. Unless specifically noted otherwise, statements and claims that use the term "antibody" or "antibodies" specifically includes "antibody fragment" and "antibody fragments."

The term "aromatic amine," as used herein, refers to an aryl moiety which contains an amino moiety. Such amino moieties may include, but are not limited to primary amines, secondary amines, tertiary amines, masked amines, or protected amines. Such tertiary amines, masked amines, or protected amines may be converted to primary amine or secondary amine moieties. Additionally, the amine moiety may include an amine-like moiety which has similar chemical characteristics as amine moieties, including but not limited to chemical reactivity.

The term "aromatic" or "aryl", as used herein, refers to a closed ring structure which has at least one ring having a conjugated pi electron system and includes both carbocyclic aryl and heterocyclic aryl (or "heteroaryl" or "heteroaromatic") groups. The carbocyclic or heterocyclic aromatic group may contain from 5 to 20 ring atoms. The term includes monocyclic rings linked covalently or fused-ring polycyclic (i.e., rings which share adjacent pairs of carbon atoms) groups. An aromatic group can be unsubstituted or substituted. Non-limiting examples of "aromatic" or "aryl", groups include phenyl, 1-naphthyl, 2-naphthyl, 4-biphenyl, anthracenyl, and phenanthracenyl. Substituents for each of the above noted aryl and heteroaryl ring systems are selected from the group of acceptable substituents described below.

For brevity, the term "aromatic" or "aryl" when used in combination with other terms (including but not limited to, aryloxy, arylthioxy, aralkyl) includes both aryl and heteroaryl rings as defined above. Thus, the term "aralkyl" or "alkaryl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by a heteroatom, by way of example only, by an oxygen atom. Examples of such aryl groups include, but are not limited to, phenoxymethyl, 2-pyridyloxymethyl, 3-(1-naphthyloxy) propyl, and the like.

A "bifunctional polymer", also referred to as a "bifunctional linker", refers to a polymer comprising two functional groups that are capable of reacting specifically with other moieties to form covalent or non-covalent linkages. Such moieties may include, but are not limited to, the side groups on natural or non-natural amino acids or peptides which contain such natural or non-natural amino acids. By way of example only, a bifunctional linker may have a functional group reactive with a group on a first peptide, and another functional group which is reactive with a group on a second peptide, whereby forming a conjugate that includes the first peptide, the bifunctional linker and the second peptide. Many procedures and linker molecules for attachment of various compounds to peptides are known. See, e.g., European Patent Application No. 188,256; U.S. Pat. Nos. 4,671, 958, 4,659,839, 4,414,148, 4,699,784; 4,680,338; and U.S. Pat. No. 4,569,789 which are incorporated by reference herein in their entirety. A "multi-functional polymer" also referred to as a "multi-functional linker", refers to a polymer comprising two or more functional groups that are capable of reacting with other moieties. Such moieties may include, but are not limited to, the side groups on natural or non-natural amino acids or peptides which contain such natural or non-natural amino acids (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to a compound and molecules it binds to or the compound.

The term "bioavailability," as used herein, refers to the rate and extent to which a substance or its active moiety is delivered from a pharmaceutical form and becomes available at the site of action or in the general circulation.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the methods and compositions described herein include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

The term "biomaterial," as used herein, refers to a biologically-derived material, including but not limited to material obtained from bioreactors and/or from recombinant methods and techniques.

The term "biophysical probe," as used herein, refers to probes which can detect or monitor structural changes in molecules. Such molecules include, but are not limited to, proteins and the "biophysical probe" may be used to detect or monitor interaction of proteins with other macromolecules. Examples of biophysical probes include, but are not limited to, spin-labels, a fluorophores, and photoactivatable groups.

The term "biotin analogue," or also referred to as "biotin mimic", as used herein, is any molecule, other than biotin, which bind with high affinity to avidin and/or streptavidin.

The term "carboxy terminus modification group" refers to any molecule that can be attached to a terminal carboxy group. By way of example, such terminal carboxy groups may be at the end of polymeric molecules, wherein such polymeric molecules include, but are not limited to, polypeptides, polynucleotides, and polysaccharides. Terminus modification groups include but are not limited to, various water soluble polymers, peptides or proteins. By way of example only, terminus modification groups include polyethylene glycol or serum albumin. Terminus modification groups may be used to modify therapeutic characteristics of the polymeric molecule, including but not limited to increasing the serum half-life of peptides.

The term "chemically cleavable group," also referred to as "chemically labile", as used herein, refers to a group which breaks or cleaves upon exposure to acid, base, oxidizing agents, reducing agents, chemical initiators, or radical initiators.

The term "chemiluminescent group," as used herein, refers to a group which emits light as a result of a chemical reaction without the addition of heat. By way of example only, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "cofactor," as used herein, refers to an atom or molecule essential for the action of a large molecule. Cofactors include, but are not limited to, inorganic ions, coenzymes, proteins, or some other factor necessary for the activity of enzymes. Examples include, heme in hemoglobin, magnesium in chlorophyll, and metal ions for proteins.

"Cofolding," as used herein, refers to refolding processes, reactions, or methods which employ at least two molecules which interact with each other and result in the transformation of unfolded or improperly folded molecules to properly folded molecules. By way of example only, "cofolding," employ at least two polypeptides which interact with each other and result in the transformation of unfolded or improperly folded polypeptides to native, properly folded polypeptides. Such polypeptides may contain natural amino acids and/or at least one non-natural amino acid.

A "comparison window," as used herein, refers a segment of any one of contiguous positions used to compare a sequence to a reference sequence of the same number of contiguous positions after the two sequences are optimally aligned. Such contiguous positions include, but are not limited to a group consisting of from about 20 to about 600 sequential units, including about 50 to about 200 sequential units, and about 100 to about 150 sequential units. By way of example only, such sequences include polypeptides and polypeptides containing non-natural amino acids, with the sequential units including, but are not limited to natural and non-natural amino acids. In addition, by way of example only, such sequences include polynucleotides with nucleotides being the corresponding sequential units. Methods of alignment of sequences for comparison are well-known in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

By way of example, an algorithm which may be used to determine percent sequence identity and sequence similarity are the BLAST and BLAST 2.0 algorithms, which are described in Altschul et al. (1997) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences)

uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) *Proc. Natl. Acad. Sci. USA* 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more or less than about 0.01, or less than about 0.001.

The term "conservatively modified variants" applies to both natural and non-natural amino acid and natural and non-natural nucleic acid sequences, and combinations thereof. With respect to particular nucleic acid sequences, "conservatively modified variants" refers to those natural and non-natural nucleic acids which encode identical or essentially identical natural and non-natural amino acid sequences, or where the natural and non-natural nucleic acid does not encode a natural and non-natural amino acid sequence, to essentially identical sequences. By way of example, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Thus by way of example every natural or non-natural nucleic acid sequence herein which encodes a natural or non-natural polypeptide also describes every possible silent variation of the natural or non-natural nucleic acid. One of ordinary skill in the art will recognize that each codon in a natural or non-natural nucleic acid (except AUG, which is ordinarily the only codon for methionine, and TGG, which is ordinarily the only codon for tryptophan) can be modified to yield a functionally identical molecule. Accordingly, each silent variation of a natural and non-natural nucleic acid which encodes a natural and non-natural polypeptide is implicit in each described sequence.

As to amino acid sequences, individual substitutions, deletions or additions to a nucleic acid, peptide, polypeptide, or protein sequence which alters, adds or deletes a single natural and non-natural amino acid or a small percentage of natural and non-natural amino acids in the encoded sequence is a "conservatively modified variant" where the alteration results in the deletion of an amino acid, addition of an amino acid, or substitution of a natural and non-natural amino acid with a chemically similar amino acid. Conservative substitution tables providing functionally similar natural amino acids are well known in the art. Such conservatively modified variants are in addition to and do not exclude polymorphic variants, interspecies homologs, and alleles of the methods and compositions described herein.

Conservative substitution tables providing functionally similar amino acids are known to those of ordinary skill in the art. The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins: Structures and Molecular Properties* (W H Freeman & Co.; 2nd edition (December 1993))

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. The heteroatom may include, but is not limited to, oxygen, nitrogen or sulfur. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses multicyclic structures, including but not limited to, bicyclic and tricyclic ring structures. Similarly, the term "heterocycloalkylene" by itself or as part of another molecule means a divalent radical derived from heterocycloalkyl, and the term "cycloalkylene" by itself or as part of another molecule means a divalent radical derived from cycloalkyl.

The term "cyclodextrin," as used herein, refers to cyclic carbohydrates consisting of at least six to eight glucose molecules in a ring formation. The outer part of the ring contains water soluble groups; at the center of the ring is a relatively nonpolar cavity able to accommodate small molecules.

The term "cytotoxic," as used herein, refers to a compound which harms cells.

"Denaturing agent" or "denaturant," as used herein, refers to any compound or material which will cause a reversible unfolding of a polymer. By way of example only, "denaturing agent" or "denaturants," may cause a reversible unfolding of a protein. The strength of a denaturing agent or denaturant will be determined both by the properties and the concentration of the particular denaturing agent or denaturant. By way of example, denaturing agents or denaturants include, but are not limited to, chaotropes, detergents, organic, water miscible solvents, phospholipids, or a combination thereof. Non-limiting examples of chaotropes include, but are not limited to, urea, guanidine, and sodium thiocyanate. Non-limiting examples of detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N→2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Non-limiting examples of organic, water miscible solvents include, but are not limited to, acetonitrile, lower alkanols (especially $C_2$-$C_4$ alkanols such as ethanol or isopropanol), or lower alkandiols ($C_2$-$C_4$ alkandiols such as ethylene-glycol) may be used as denaturants. Non-limiting examples of phospholipids include, but are not limited to, naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

The term "detectable label," as used herein, refers to a label which may be observable using analytical techniques including, but not limited to, fluorescence, chemiluminescence, electron-spin resonance, ultraviolet/visible absorbance spectroscopy, mass spectrometry, nuclear magnetic resonance, magnetic resonance, and electrochemical methods.

The term "dicarbonyl," as used herein refers to a group containing at least two moieties selected from the group consisting of —C(O)—, —S(O)—, —S(O)$_2$—, and —C(S)—, including, but not limited to, 1,2-dicarbonyl groups, a 1,3-dicarbonyl groups, and 1,4-dicarbonyl groups, and groups containing a least one ketone group, and/or at least one aldehyde groups, and/or at least one ester group, and/or at least one carboxylic acid group, and/or at least one thioester group. Such dicarbonyl groups include diketones, ketoaldehydes, ketoacids, ketoesters, and ketothioesters. In addition, such groups may be part of linear, branched, or cyclic molecules.

The term "drug," as used herein, refers to any substance used in the prevention, diagnosis, alleviation, treatment, or cure of a disease or condition.

The term "dye," as used herein, refers to a soluble, coloring substance which contains a chromophore.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. By way of example, an agent or a compound being administered includes, but is not limited to, a natural amino acid polypeptide, non-natural amino acid polypeptide, modified natural amino acid polypeptide, or modified non-amino acid polypeptide. Compositions containing such natural amino acid polypeptides, non-natural amino acid polypeptides, modified natural amino acid polypeptides, or modified non-natural amino acid polypeptides can be administered for prophylactic, enhancing, and/or therapeutic treatments. An appropriate "effective" amount in any individual case may be determined using techniques, such as a dose escalation study.

The term "electron dense group," as used herein, refers to a group which scatters electrons when irradiated with an electron beam. Such groups include, but are not limited to, ammonium molybdate, bismuth subnitrate cadmium iodide, 99%, carbohydrazide, ferric chloride hexahydrate, hexamethylene tetramine, 98.5%, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which can either donate or accept energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

As used herein, the term "eukaryote" refers to organisms belonging to the phylogenetic domain Eucarya, including but not limited to animals (including but not limited to, mammals, insects, reptiles, birds, etc.), ciliates, plants (including but not limited to, monocots, dicots, and algae), fungi, yeasts, flagellates, microsporidia, and protists.

The term "fatty acid," as used herein, refers to carboxylic acids with about $C_6$ or longer hydrocarbon side chain.

The term "fluorophore," as used herein, refers to a molecule which upon excitation emits photons and is thereby fluorescent.

The terms "functional group", "active moiety", "activating group", "leaving group", "reactive site", "chemically reactive group" and "chemically reactive moiety," as used herein, refer to portions or units of a molecule at which chemical reactions occur. The terms are somewhat synonymous in the chemical arts and are used herein to indicate the portions of molecules that perform some function or activity and are reactive with other molecules.

The term "halogen" includes fluorine, chlorine, iodine, and bromine.

The term "haloacyl," as used herein, refers to acyl groups which contain halogen moieties, including, but not limited to, —C(O)CH$_3$, —C(O)CF$_3$, —C(O)CH$_2$OCH$_3$, and the like.

The term "haloalkyl," as used herein, refers to alkyl groups which contain halogen moieties, including, but not limited to, —CF$_3$ and —CH$_2$CF$_3$ and the like.

The term "heteroalkyl," as used herein, refers to straight or branched chain, or cyclic hydrocarbon radicals, or combinations thereof, consisting of an alkyl group and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—

CH$_3$. In addition, up to two heteroatoms may be consecutive, such as, by way of example, —CH$_2$—NH—OCH$_3$ and —CH$_2$—O—Si(CH$_3$)$_3$.

The term "heteroalkylene," as used herein, refers to a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, the same or different heteroatoms can also occupy either or both of the chain termini (including but not limited to, alkyleneoxy, alkylenedioxy, alkylene amino, alkylenediamino, aminooxyalkylene, and the like). Still further, for alkylene and heteroalkylene linking groups, no orientation of the linking group is implied by the direction in which the formula of the linking group is written. By way of example, the formula —C(O)$_2$R'— represents both —C(O)$_2$R'— and —R'C(O)$_2$—.

The term "heteroaryl" or "heteroaromatic," as used herein, refers to aryl groups which contain at least one heteroatom selected from N, O, and S; wherein the nitrogen and sulfur atoms may be optionally oxidized, and the nitrogen atom(s) may be optionally quaternized. Heteroaryl groups may be substituted or unsubstituted. A heteroaryl group may be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "homoalkyl," as used herein refers to alkyl groups which are hydrocarbon groups.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using a comparison algorithm or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "intercalating agent," also referred to as "intercalating group," as used herein, refers to a chemical that can insert into the intramolecular space of a molecule or the intermolecular space between molecules. By way of example only an intercalating agent or group may be a molecule which inserts into the stacked bases of the DNA double helix.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. Purity and homogeneity may be determined using analytical chemistry techniques including, but not limited to, polyacrylamide gel electrophoresis or high performance liquid chromatography. In addition, when a component of interest is isolated and is the predominant species present in a preparation, the component is described herein as substantially purified. The term "purified," as used herein, may refer to a component of interest which is at least 85% pure, at least 90% pure, at least 95% pure, at least 99% or greater pure. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

The term "label," as used herein, refers to a substance which is incorporated into a compound and is readily detected, whereby its physical distribution may be detected and/or monitored.

The term "linkage," as used herein to refer to bonds or chemical moiety formed from a chemical reaction between the functional group of a linker and another molecule. Such bonds may include, but are not limited to, covalent linkages and non-covalent bonds, while such chemical moieties may include, but are not limited to, esters, carbonates, imines phosphate esters, hydrazones, acetals, orthoesters, peptide linkages, and oligonucleotide linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages means that the linkages are degradable in water or in aqueous solutions, including for example, blood. Enzymatically unstable or degradable linkages means that the linkage can be degraded by one or more enzymes. By way of example only, PEG and related polymers may include degradable linkages in the polymer backbone or in the linker group between the polymer backbone and one or more of the terminal functional groups of the polymer molecule. Such degradable linkages include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The terms "medium" or "media," as used herein, refer to any culture medium used to grow and harvest cells and/or products expressed and/or secreted by such cells. Such "medium" or "media" include, but are not limited to, solution, solid, semi-solid, or rigid supports that may support or contain any host cell, including, by way of example, bacterial host cells, yeast host cells, insect host cells, plant host cells, eukaryotic host cells, mammalian host cells, CHO cells, prokaryotic host cells, *E. coli*, or *Pseudomonas* host cells, and cell contents. Such "medium" or "media" includes, but is not limited to, medium or media in which the host cell has been grown into which a polypeptide has been secreted, including medium either before or after a proliferation step. Such "medium" or "media" also includes, but is not limited to, buffers or reagents that contain host cell lysates, by way of example a polypeptide produced intracellularly and the host cells are lysed or disrupted to release the polypeptide.

The term "metabolite," as used herein, refers to a derivative of a natural amino acid polypeptide, a non-natural amino acid polypeptide, a modified natural amino acid polypeptide, or a modified non-natural amino acid polypeptide that is formed when the natural amino acid polypeptide, non-natural amino acid polypeptide, modified natural amino acid polypeptide, or modified non-natural amino acid polypeptide is metabolized. The term "active metabolite" refers to a biologically active derivative of a natural amino acid polypeptide, a non-natural amino acid polypeptide, a modified natural amino acid polypeptide, or a modified non-natural amino acid polypeptide that is formed when the natural amino acid polypeptide, non-natural amino acid polypeptide, modified natural amino acid polypeptide, or modified non-natural amino acid polypeptide is metabolized.

The term "metabolized," as used herein, refers to the sum of the processes by which a particular substance is changed by an organism. Such processes include, but are not limited to, hydrolysis reactions and reactions catalyzed by enzymes. Further information on metabolism may be obtained from The Pharmacological Basis of Therapeutics, 9th Edition, McGraw-Hill (1996). By way of example only, metabolites of natural amino acid polypeptides, non-natural amino acid polypeptides, modified natural amino acid polypeptides, or modified non-natural amino acid polypeptides may be identified either by administration of the natural amino acid polypeptides, non-natural amino acid polypeptides, modified natural amino acid polypeptides, or modified non-natural amino acid polypeptides to a host and analysis of tissue samples from the host, or by incubation of natural amino acid polypeptides, non-natural amino acid polypeptides, modified natural amino acid polypeptides, or modified non-natural amino acid polypeptides with hepatic cells in vitro and analysis of the resulting compounds.

The term "metal chelator," as used herein, refers to a molecule which forms a metal complex with metal ions. By way of example, such molecules may form two or more coordination bonds with a central metal ion and may form ring structures.

The term "metal-containing moiety," as used herein, refers to a group which contains a metal ion, atom or particle. Such moieties include, but are not limited to, cisplatin, chelated metals ions (such as nickel, iron, and platinum), and metal nanoparticles (such as nickel, iron, and platinum).

The term "moiety incorporating a heavy atom," as used herein, refers to a group which incorporates an ion of atom which is usually heavier than carbon. Such ions or atoms include, but are not limited to, silicon, tungsten, gold, lead, and uranium.

The term "modified," as used herein refers to the presence of a change to a natural amino acid, a non-natural amino acid, a natural amino acid polypeptide or a non-natural amino acid polypeptide. Such changes, or modifications, may be obtained by post synthesis modifications of natural amino acids, non-natural amino acids, natural amino acid polypeptides or non-natural amino acid polypeptides, or by post-translational modification of natural amino acids, non-natural amino acids, natural amino acid polypeptides or non-natural amino acid polypeptides. The form "(modified)" means that the natural amino acid, non-natural amino acid, natural amino acid polypeptide or non-natural amino acid polypeptide being discussed are optionally modified, that is, he natural amino acid, non-natural amino acid, natural amino acid polypeptide or non-natural amino acid polypeptide under discussion can be modified or unmodified.

As used herein, the term "modulated serum half-life" refers to positive or negative changes in the circulating half-life of a modified biologically active molecule relative to its non-modified form. By way of example, the modified biologically active molecules include, but are not limited to, natural amino acid, non-natural amino acid, natural amino acid polypeptide or non-natural amino acid polypeptide. By way of example, serum half-life is measured by taking blood samples at various time points after administration of the biologically active molecule or modified biologically active molecule, and determining the concentration of that molecule in each sample. Correlation of the serum concentration with time allows calculation of the serum half-life. By way of example, modulated serum half-life may be an increased in serum half-life, which may enable an improved dosing regimens or avoid toxic effects. Such increases in serum may be at least about two fold, at least about three-fold, at least about five-fold, or at least about ten-fold.

The term "modulated therapeutic half-life," as used herein, refers to positive or negative change in the half-life of the therapeutically effective amount of a modified biologically active molecule, relative to its non-modified form. By way of example, the modified biologically active molecules include, but are not limited to, natural amino acid, non-natural amino acid, natural amino acid polypeptide or non-natural amino acid polypeptide. By way of example, therapeutic half-life is measured by measuring pharmacokinetic and/or pharmacodynamic properties of the molecule at various time points after administration. Increased therapeutic half-life may enable a particular beneficial dosing regimen, a particular beneficial total dose, or avoids an undesired effect. By way of example, the increased therapeutic half-life may result from increased potency, increased or decreased binding of the modified molecule to its target, an increase or decrease in another parameter or mechanism of action of the non-modified molecule, or an increased or decreased breakdown of the molecules by enzymes such as, by way of example only, proteases.

The term "nanoparticle," as used herein, refers to a particle which has a particle size between about 500 nm to about 1 nm.

The term "near-stoichiometric," as used herein, refers to the ratio of the moles of compounds participating in a chemical reaction being about 0.75 to about 1.5 relative to the number of hydrogens on the aromatic amine side chain of the non-natural amino acid polypeptide. By way of example, a primary aromatic amine has 2 hydrogens, whereas a secondary amine has one hydrogen.

As used herein, the term "non-eukaryote" refers to non-eukaryotic organisms. By way of example, a non-eukaryotic organism may belong to the Eubacteria, (which includes but is not limited to, *Escherichia coli, Thermus thermophilus*, or *Bacillus stearothermophilus, Pseudomonas fluorescens, Pseudomonas aeruginosa, Pseudomonas putida*), phylogenetic domain, or the Archaea, which includes, but is not limited to, *Methanococcus jannaschii, Methanobacterium thermoautotrophicum, Archaeoglobus fulgidus, Pyrococcus furiosus, Pyrococcus horikoshii, Aeuropyrum pernix*, or *Halobacterium* such as *Haloferax volcanii* and *Halobacterium* species NRC-1, or phylogenetic domain.

A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

The term "nucleic acid," as used herein, refers to deoxyribonucleotides, deoxyribonucleosides, ribonucleosides or ribonucleotides and polymers thereof in either single- or double-stranded form. By way of example only, such nucleic acids and nucleic acid polymers include, but are not limited to, (i) analogues of natural nucleotides which have similar binding properties as a reference nucleic acid and are metabolized in a manner similar to naturally occurring nucleotides; (ii) oligonucleotide analogs including, but are not limited to, PNA (peptidonucleic acid), analogs of DNA used in antisense technology (phosphorothioates, phosphoroamidates, and the like); (iii) conservatively modified variants thereof (including but not limited to, degenerate codon substitutions) and complementary sequences and sequence explicitly indicated. By way of example, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "oxidizing agent," as used herein, refers to a compound or material which is capable of removing an electron from a compound being oxidized. By way of example oxidizing agents include, but are not limited to, oxidized glutathione, cystine, cystamine, oxidized dithiothreitol, oxidized erythreitol, and oxygen. A wide variety of oxidizing agents are suitable for use in the methods and compositions described herein.

The term "photoaffinity label," as used herein, refers to a label with a group, which, upon exposure to light, forms a linkage with a molecule for which the label has an affinity. By way of example only, such a linkage may be covalent or non-covalent.

The term "photocaged moiety," as used herein, refers to a group which, upon illumination at certain wavelengths, covalently or non-covalently binds other ions or molecules.

The term "photocleavable group," as used herein, refers to a group which breaks upon exposure to light.

The term "photocrosslinker," as used herein, refers to a compound comprising two or more functional groups which, upon exposure to light, are reactive and form a covalent or non-covalent linkage with two or more monomeric or polymeric molecules.

The term "photoisomerizable moiety," as used herein, refers to a group wherein upon illumination with light changes from one isomeric form to another.

The term "polyalkylene glycol," as used herein, refers to linear or branched polymeric polyether polyols. Such polyalkylene glycols, including, but are not limited to, polyethylene glycol, polypropylene glycol, polybutylene glycol, and derivatives thereof. Other exemplary embodiments are listed, for example, in commercial supplier catalogs, such as Shearwater Corporation's catalog "Polyethylene Glycol and Derivatives for Biomedical Applications" (2001). By way of example only, such polymeric polyether polyols have average molecular weights between about 0.1 kDa to about 100 kDa. By way of example, such polymeric polyether polyols include, but are not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da.

In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the poly(ethylene glycol) molecule is a branched polymer. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

The term "polymer," as used herein, refers to a molecule composed of repeated subunits. Such molecules include, but are not limited to, polypeptides, polynucleotides, or polysaccharides or polyalkylene glycols.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. Additionally, such "polypeptides," "peptides" and "proteins" include amino acid chains of any length, including full length proteins, wherein the amino acid residues are linked by covalent peptide bonds.

The term "post-translationally modified" refers to any modification of a natural or non-natural amino acid which occurs after such an amino acid has been translationally incorporated into a polypeptide chain. Such modifications include, but are not limited to, co-translational in vivo modifications, co-translational in vitro modifications (such as in a cell-free translation system), post-translational in vivo modifications, and post-translational in vitro modifications.

The term "prodrug," as used herein, refers to an agent that is converted into the parent drug in vivo or in vitro. The benefits of such prodrugs include, but are not limited to, (i) ease of administration compared with the parent drug; (ii) the prodrug may be bioavailable by oral administration whereas the parent is not; and (iii) the prodrug may also have improved solubility in pharmaceutical compositions compared with the parent drug. A pro-drug includes a pharmacologically inactive, or reduced-activity, derivative of an active drug. Prodrugs may be designed to modulate the amount of a drug or biologically active molecule that reaches a desired site of action through the manipulation of the properties of a drug, such as physiochemical, biopharmaceutical, or pharmacokinetic properties. Prodrugs are converted into active drug within the body through enzymatic or non-enzymatic reactions. Prodrugs may provide improved physiochemical properties such as better solubility, enhanced delivery characteristics, such as specifically targeting a particular cell, tissue, organ or ligand, and improved therapeutic value of the drug.

The term "prophylactically effective amount," as used herein, refers that amount of a composition containing at least one non-natural amino acid polypeptide or at least one modified non-natural amino acid polypeptide prophylactically applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "protected," as used herein, refers to the presence of a "protecting group" or moiety that prevents reaction of the chemically reactive functional group under certain reaction conditions. The protecting group will vary depending on the type of chemically reactive group being protected. By way of example only, (i) if the chemically reactive group is an amine or a hydrazide, the protecting group may be selected from tert-butyloxycarbonyl (t-Boc) and 9-fluorenylmethoxycarbonyl (Fmoc); (ii) if the chemically reactive group is a thiol, the protecting group may be orthopyridyldisulfide; and (iii) if the chemically reactive group is a carboxylic acid, such as butanoic or propionic acid, or a hydroxyl group, the protecting group may be benzyl or an alkyl group such as methyl, ethyl, or tert-butyl.

By way of example only, blocking/protecting groups may also be selected from:

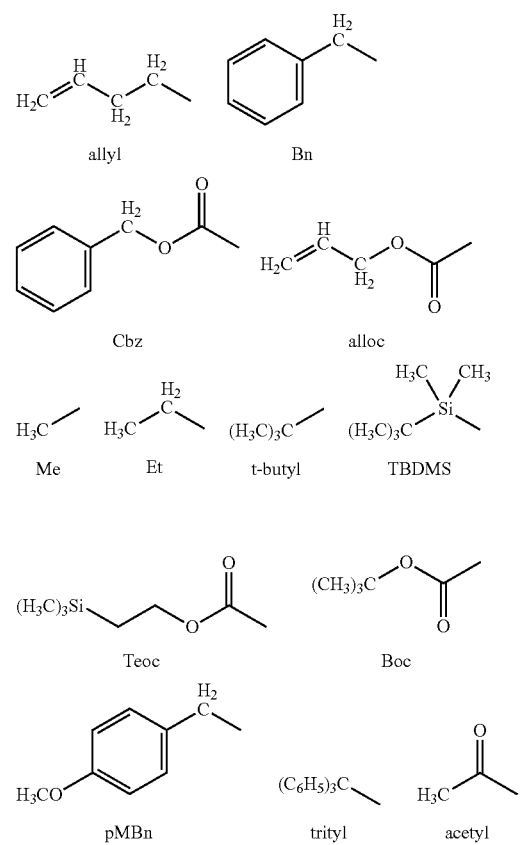

-continued

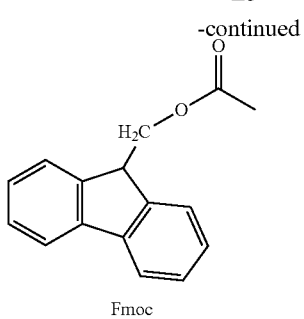

Fmoc

Additionally, protecting groups include, but are not limited to, including photolabile groups such as Nvoc and MeNvoc and other protecting groups known in the art. Other protecting groups are described in Greene and Wuts, Protective Groups in Organic Synthesis, 3rd Ed., John Wiley & Sons, New York, N.Y., 1999, which is incorporated herein by reference in its entirety.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "reactive compound," as used herein, refers to a compound which under appropriate conditions is reactive toward another atom, molecule or compound.

The term "recombinant host cell," also referred to as "host cell," refers to a cell which includes an exogenous polynucleotide, wherein the methods used to insert the exogenous polynucleotide into a cell include, but are not limited to, direct uptake, transduction, f-mating, or other methods known in the art to create recombinant host cells. By way of example only, such exogenous polynucleotide may be a nonintegrated vector, including but not limited to a plasmid, or may be integrated into the host genome.

The term "redox-active agent," as used herein, refers to a molecule which oxidizes or reduces another molecule, whereby the redox active agent becomes reduced or oxidized. Examples of redox active agent include, but are not limited to, ferrocene, quinones, $Ru^{2+/3+}$ complexes, $Co^{2+/3+}$ complexes, and $Os^{2+/3+}$ complexes.

The term "reducing agent," as used herein, refers to a compound or material which is capable of adding an electron to a compound being reduced. By way of example reducing agents include, but are not limited to, dithiothreitol (DTT), 2-mercaptoethanol, dithioerythritol, cysteine, cysteamine (2-aminoethanethiol), and reduced glutathione. Such reducing agents may be used, by way of example only, to maintain sulfhydryl groups in the reduced state and to reduce intra- or intermolecular disulfide bonds.

"Refolding," as used herein describes any process, reaction or method which transforms an improperly folded or unfolded state to a native or properly folded conformation. By way of example only, refolding transforms disulfide bond containing polypeptides from an improperly folded or unfolded state to a native or properly folded conformation with respect to disulfide bonds. Such disulfide bond containing polypeptides may be natural amino acid polypeptides or non-natural amino acid polypeptides.

The term "resin," as used herein, refers to high molecular weight, insoluble polymer beads. By way of example only, such beads may be used as supports for solid phase peptide synthesis, or sites for attachment of molecules prior to purification.

The term "saccharide," as used herein, refers to a series of carbohydrates including but not limited to sugars, monosaccharides, oligosaccharides, and polysaccharides.

The phrase "selectively hybridizes to" or "specifically hybridizes to," as used herein, refers to the binding, duplexing, or hybridizing of a molecule to a particular nucleotide sequence under stringent hybridization conditions when that sequence is present in a complex mixture including but not limited to, total cellular or library DNA or RNA.

The term "spin label," as used herein, refers to molecules which contain an atom or a group of atoms exhibiting an unpaired electron spin (i.e. a stable paramagnetic group) that can be detected by electron spin resonance spectroscopy and can be attached to another molecule. Such spin-label molecules include, but are not limited to, nitoryl radicals and nitroxides, and may be single spin-labels or double spin-labels.

The term "stoichiometric," as used herein, refers to the ratio of the moles of compounds participating in a chemical reaction being about 0.9 to about 1.1 relative to the number of hydrogen's on the aromatic amine side chain of the non-natural amino acid polypeptide. By way of example, a primary aromatic amine has 2 hydrogen's, whereas a secondary amine has one hydrogen.

The term "stoichiometric-like," as used herein, refers to a chemical reaction which becomes stoichiometric or near-stoichiometric upon changes in reaction conditions or in the presence of additives. Such changes in reaction conditions include, but are not limited to, an increase in temperature or change in pH. Such additives include, but are not limited to, accelerants.

The phrase "stringent hybridization conditions" refers to hybridization of sequences of DNA, RNA, PNA or other nucleic acid mimics, or combinations thereof, under conditions of low ionic strength and high temperature. By way of example, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. By way of example, longer sequences hybridize specifically at higher temperatures. Stringent hybridization conditions include, but are not limited to, (i) about 5-10° C. lower than the thermal melting point ($T_m$) for the specific sequence at a defined ionic strength and pH; (ii) the salt concentration is about 0.01 M to about 1.0 M at about pH 7.0 to about pH 8.3 and the temperature is at least about 30° C. for short probes (including but not limited to, 10 to 50 nucleotides) and at least about 60° C. for long probes (including but not limited to, greater than 50 nucleotides); (iii) the addition of destabilizing agents including, but not limited to, formamide, (iv) 50% formamide, 5×SSC, and 1% SDS, incubating at 42° C., or 5×SSC, 1% SDS, incubating at 65° C., with wash in 0.2×SSC, and 0.1% SDS at 65° C. for between about 5 minutes to about 120 minutes. By way of example only, detection of selective or specific hybridization, includes, but is not limited to, a positive signal at least two times background. An extensive guide to the hybridization of nucleic acids is found in Tijssen, *Laboratory Techniques in Biochemistry and Molecular Biology—Hybridization with Nucleic Probes*, "Overview of principles of hybridization and the strategy of nucleic acid assays" (1993).

The term "subject" as used herein, refers to an animal which is the object of treatment, observation or experiment. By way of example only, a subject may be, but is not limited to, a mammal including, but not limited to, a human.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater. By way of example only, a natural amino acid polypeptide or a non-natural amino acid polypeptide may be purified from a native cell, or host cell in the case of recombinantly produced natural amino acid polypeptides or non-natural amino acid polypeptides. By way of example a preparation of a natural amino acid polypeptide or a non-natural amino acid polypeptide may be "substantially purified" when the preparation contains less than about 30%, less than about 25%, less than about 20%, less than about 15%, less than about 10%, less than about 5%, less than about 4%, less than about 3%, less than about 2%, or less than about 1% (by dry weight) of contaminating material. By way of example when a natural amino acid polypeptide or a non-natural amino acid polypeptide is recombinantly produced by host cells, the natural amino acid polypeptide or non-natural amino acid polypeptide may be present at about 30%, about 25%, about 20%, about 15%, about 10%, about 5%, about 4%, about 3%, about 2%, or about 1% or less of the dry weight of the cells. By way of example when a natural amino acid polypeptide or a non-natural amino acid polypeptide is recombinantly produced by host cells, the natural amino acid polypeptide or non-natural amino acid polypeptide may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. By way of example, "substantially purified" natural amino acid polypeptides or non-natural amino acid polypeptides may have a purity level of about 30%, about 35%, about 40%, about 45%, about 50%, about 55%, about 60%, about 65%, about 70%, about 75%, about 80%, about 85%, about 90%, about 95%, about 99% or greater as determined by appropriate methods, including, but not limited to, SDS/PAGE analysis, RP-HPLC, SEC, and capillary electrophoresis.

The term "substituents" also referred to as "non-interfering substituents" "refers to groups which may be used to replace another group on a molecule. Such groups include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$-$C_{10}$ alkyl), —C(O)—($C_1$-$C_{10}$ alkyl), $C_2$-$C_{10}$ alkthioalkyl, —C(O)O—($C_1$-$C_{10}$ alkyl), —OH, —$SO_2$, =S, —COOH, —$NR_2$, carbonyl, —C(O)—($C_1$-$C_{10}$ alkyl)-$CF_3$, —C(O)—$CF_3$, —C(O)$NR_2$, —($C_1$-$C_{10}$ aryl)-S—($C_6$-$C_{10}$ aryl), —C(O)—($C_6$-$C_{10}$ aryl), —$(CH_2)_m$—O—$(CH_2)_m$—O—($C_1$-$C_{10}$ alkyl) wherein each m is from 1 to 8, —C(O)$NR_2$, —C(S)$NR_2$, —$SO_2NR_2$, —NRC(O)$NR_2$, —NRC(S)$NR_2$, salts thereof, and the like. Each R group in the preceding list includes, but is not limited to, H, alkyl or substituted alkyl, aryl or substituted aryl, or alkaryl. Where substituent groups are specified by their conventional chemical formulas, written from left to right, they equally encompass the chemically identical substituents that would result from writing the structure from right to left, for example, —$CH_2O$— is equivalent to —$OCH_2$—.

By way of example only, substituents for alkyl and heteroalkyl radicals (including those groups referred to as alkylene, alkenyl, heteroalkylene, heteroalkenyl, alkynyl, cycloalkyl, heterocycloalkyl, cycloalkenyl, and heterocycloalkenyl) includes, but is not limited to: —OR, =O, =NR, =N—OR, —$NR_2$, —SR, -halogen, —$SiR_3$, —OC(O)R, —C(O)R, —$CO_2R$, —$CONR_2$, —OC(O)$NR_2$, —NRC(O)R, —NR—C(O)$NR_2$, —NR(O)$_2$R, —NR—C($NR_2$)=NR, —S(O)R, —S(O)$_2$R, —S(O)$_2NR_2$, —$NRSO_2R$, —CN and —$NO_2$. Each R group in the preceding list includes, but is not limited to, hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or aralkyl groups. When two R groups are attached to the same nitrogen atom, they can be combined with the nitrogen atom to form a 5-, 6-, or 7-membered ring. For example, —$NR_2$ is meant to include, but not be limited to, 1-pyrrolidinyl and 4-morpholinyl.

By way of example, substituents for aryl and heteroaryl groups include, but are not limited to, —OR, =O, =NR, =N—OR, —$NR_2$, —SR, -halogen, —$SiR_3$, —OC(O)R, —C(O)R, —$CO_2R$, —$CONR_2$, —OC(O)$NR_2$, —NRC(O)R, —NR—C(O)$NR_2$, —NR(O)$_2$R, —NR—C($NR_2$)=NR, —S(O)R, —S(O)$_2$R, —S(O)$_2NR_2$, —$NRSO_2R$, —CN, —$NO_2$, —R, —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where each R group in the preceding list includes, but is not limited to, hydrogen, alkyl, heteroalkyl, aryl and heteroaryl.

The term "therapeutically effective amount," as used herein, refers to the amount of a composition containing at least one non-natural amino acid polypeptide and/or at least one modified non-natural amino acid polypeptide administered to a patient already suffering from a disease, condition or disorder, sufficient to cure or at least partially arrest, or relieve to some extent one or more of the symptoms of the disease, disorder or condition being treated. The effectiveness of such compositions depend conditions including, but not limited to, the severity and course of the disease, disorder or condition, previous therapy, the patient's health status and response to the drugs, and the judgment of the treating physician. By way of example only, therapeutically effective amounts may be determined by routine experimentation, including but not limited to a dose escalation clinical trial.

The term "thioalkoxy," as used herein, refers to sulfur containing alkyl groups linked to molecules via an oxygen atom.

The term "thermal melting point" or $T_m$ is the temperature (under defined ionic strength, pH, and nucleic concentration) at which 50% of probes complementary to a target hybridize to the target sequence at equilibrium.

The term "toxic moiety," as used herein, refers to a compound which can cause harm or death.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the term "water soluble polymer" refers to any polymer that is soluble in aqueous solvents. Such water soluble polymers include, but are not limited to, polyethylene glycol, polyethylene glycol propionaldehyde, mono $C_1$-$C_{10}$ alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, serum albumin, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. By way of example, linkage of such water soluble polymers to a natural amino acid polypeptide or a non-natural polypeptide can result in changes including, but not limited to, increased or modulated serum half-life, increased or modulated therapeutic half-life relative to the unmodified form, modulated immunogenicity, modulated physical association characteristics including, but not limited to, aggregation and multimer formation, altered receptor binding, altered binding to one or more binding partners, and altered receptor dimerization or multimerization. In addition, such water soluble polymers may or may not have their own biological activity.

Unless otherwise indicated, conventional methods of mass spectroscopy, NMR, HPLC, protein chemistry, biochemistry, recombinant DNA techniques and pharmacology, within the skill of the art are employed.

Compounds, (including, but not limited to non-natural amino acids, non-natural amino acid polypeptides and modified non-natural amino acid polypeptides, and reagents for producing the aforementioned compounds) presented herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

Some of the compounds herein (including, but not limited to non-natural amino acids, non-natural amino acid polypeptides and modified non-natural amino acid polypeptides, and reagents for producing the aforementioned compounds) have asymmetric carbon atoms and can therefore exist as enantiomers or diastereomers. Diasteromeric mixtures can be separated into their individual diastereomers on the basis of their physical chemical differences by methods known, for example, by chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

In additional or further embodiments, the compounds described herein (including, but not limited to non-natural amino acids, non-natural amino acid polypeptides and modified non-natural amino acid polypeptides, and reagents for producing the aforementioned compounds) are used in the form of pro-drugs. In additional or further embodiments, the compounds described herein ((including, but not limited to non-natural amino acids, non-natural amino acid polypeptides and modified non-natural amino acid polypeptides, and reagents for producing the aforementioned compounds) are metabolized upon administration to an organism in need to produce a metabolite that is then used to produce a desired effect, including a desired therapeutic effect. In further or additional embodiments are active metabolites of non-natural amino acids and modified or unmodified non-natural amino acid polypeptides.

The methods and formulations described herein include the use of N-oxides, crystalline forms (also known as polymorphs), or pharmaceutically acceptable salts of non-natural amino acids, non-natural amino acid polypeptides and modified non-natural amino acid polypeptides. In certain embodiments, non-natural amino acids, non-natural amino acid polypeptides and modified non-natural amino acid polypeptides may exist as tautomers. All tautomers are included within the scope of the non-natural amino acids, non-natural amino acid polypeptides and modified non-natural amino acid polypeptides presented herein. In addition, the non-natural amino acids, non-natural amino acid polypeptides and modified non-natural amino acid polypeptides described herein can exist in unsolvated as well as solvated forms with pharmaceutically acceptable solvents such as water, ethanol, and the like. The solvated forms of the non-natural amino acids, non-natural amino acid polypeptides and modified non-natural amino acid polypeptides presented herein are also considered to be disclosed herein.

Some of the compounds herein (including, but not limited to non-natural amino acids, non-natural amino acid polypeptides and modified non-natural amino acid polypeptides and reagents for producing the aforementioned compounds) may exist in several tautomeric forms. All such tautomeric forms are considered as part of the compositions described herein. Also, for example all enol-keto forms of any compounds (including, but not limited to non-natural amino acids, non-natural amino acid polypeptides and modified non-natural amino acid polypeptides and reagents for producing the aforementioned compounds) herein are considered as part of the compositions described herein.

Some of the compounds herein (including, but not limited to non-natural amino acids, non-natural amino acid polypeptides and modified non-natural amino acid polypeptides and reagents for producing either of the aforementioned compounds) are acidic and may form a salt with a pharmaceutically acceptable cation. Some of the compounds herein (including, but not limited to non-natural amino acids, non-natural amino acid polypeptides and modified non-natural amino acid polypeptides and reagents for producing the aforementioned compounds) can be basic and accordingly, may form a salt with a pharmaceutically acceptable anion. All such salts, including di-salts are within the scope of the compositions described herein and they can be prepared by conventional methods. For example, salts can be prepared by contacting the acidic and basic entities, in either an aqueous, non-aqueous or partially aqueous medium. The salts are recovered by using at least one of the following techniques: filtration, precipitation with a non-solvent followed by filtration, evaporation of the solvent, or, in the case of aqueous solutions, lyophilization.

Salts, for example, include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

BRIEF DESCRIPTION OF THE FIGURES

A better understanding of the features and advantages of the present methods and compositions may be obtained by reference to the following detailed description that sets forth illustrative embodiments, in which the principles of our methods, compositions, devices and apparatuses are utilized, and the accompanying drawings of which.

DETAILED DESCRIPTION OF THE INVENTION

I. Introduction

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Saccharomyces cerevisiae* (*S. cerevisiae*) (e.g., J. Chin et al., *Science* 301: 964-7 (2003)), which has enabled the incorporation of non-natural amino acids to proteins in vivo. A number of new amino acids with novel chemical, physical or biological properties, including photoaffinity labels and photoisomerizable amino acids, photocrosslinking amino acids (See, e.g., Chin, J. W., et al. (2002) Proc. Natl. Acad. Sci. U.S.A. 99:11020-11024; and, Chin, J. W., et al., (2002) J. Am. Chem. Soc. 124:9026-9027), heavy atom containing amino acids, keto amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027 (incorporated by reference in its entirety); J. W. Chin, & P. G. Schultz, (2002), *ChemBioChem* 3(11): 1135-1137 (incorporated by reference in its entirety); J. W. Chin, et al., (2002), *PNAS United States of America* 99:11020-11024 (incorporated by reference in its entirety); and, L. Wang, & P. G. Schultz, (2002), *Chem. Comm.*, 1:1-11 (incorporated by reference in its entirety). These studies have demonstrated that it is possible to selectively and routinely introduce chemical functional groups that are not found in proteins, that are chemically inert to all of the functional groups found in the 20 common, genetically-encoded amino acids and that may be used to react efficiently and selectively to form stable covalent linkages.

II. Overview

Figure 1:
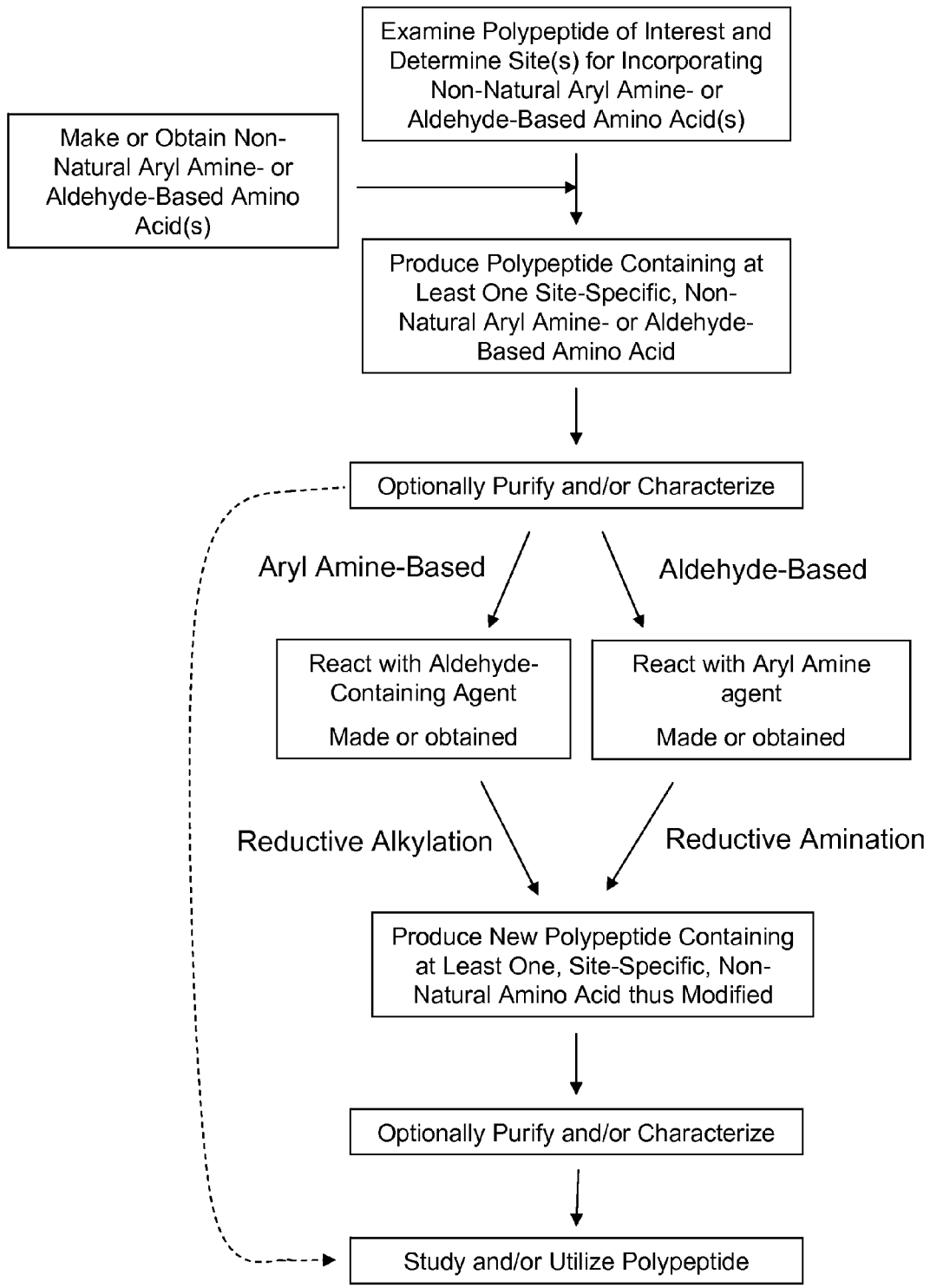
FIG. 1 illustrates a non-limiting aspect of methods for selecting and designing a polypeptide to be modified using the methods, compositions and techniques described herein.
Figure 2:
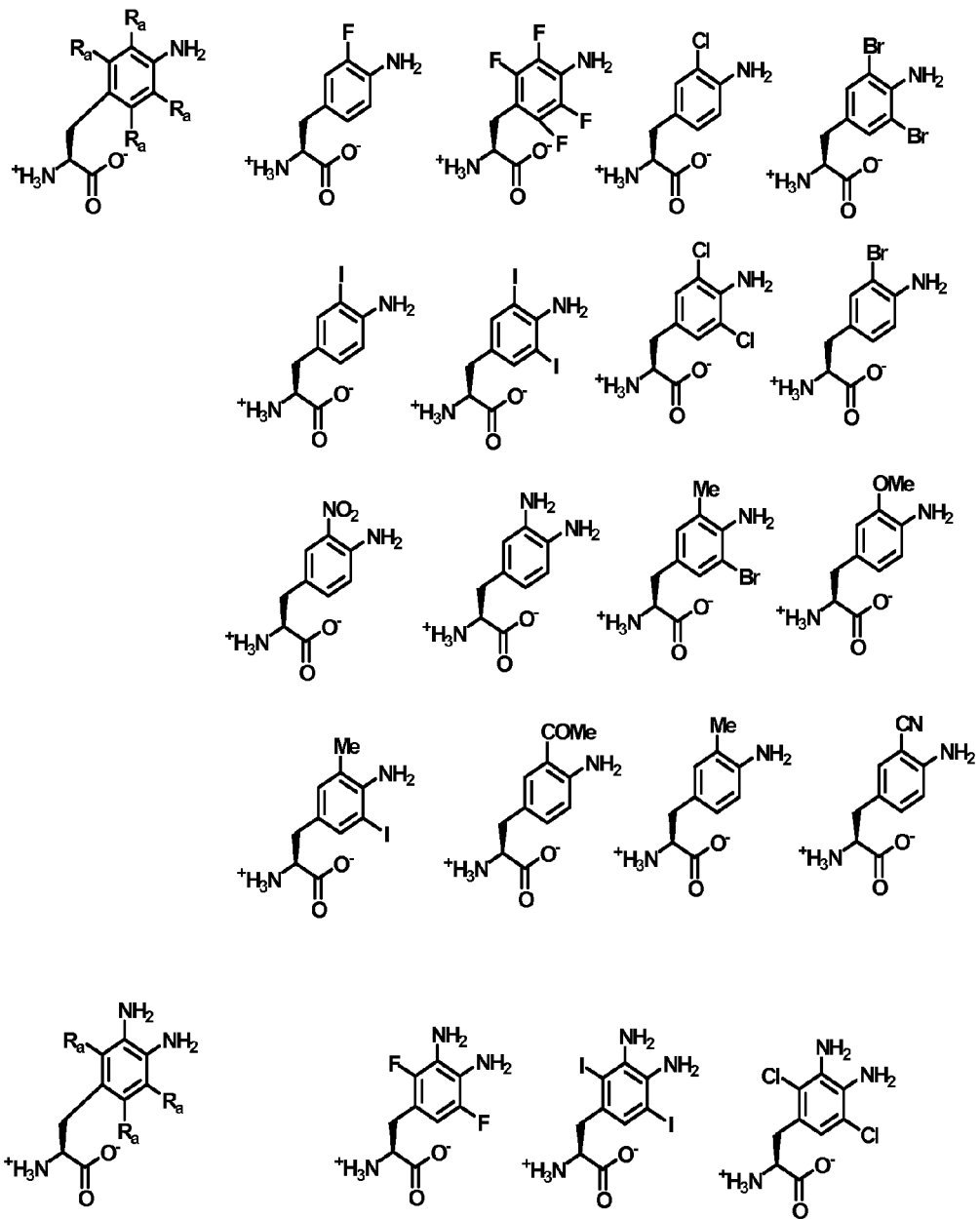
FIG. 2 presents illustrative, non-limiting examples of the types of non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.
Figure 3:
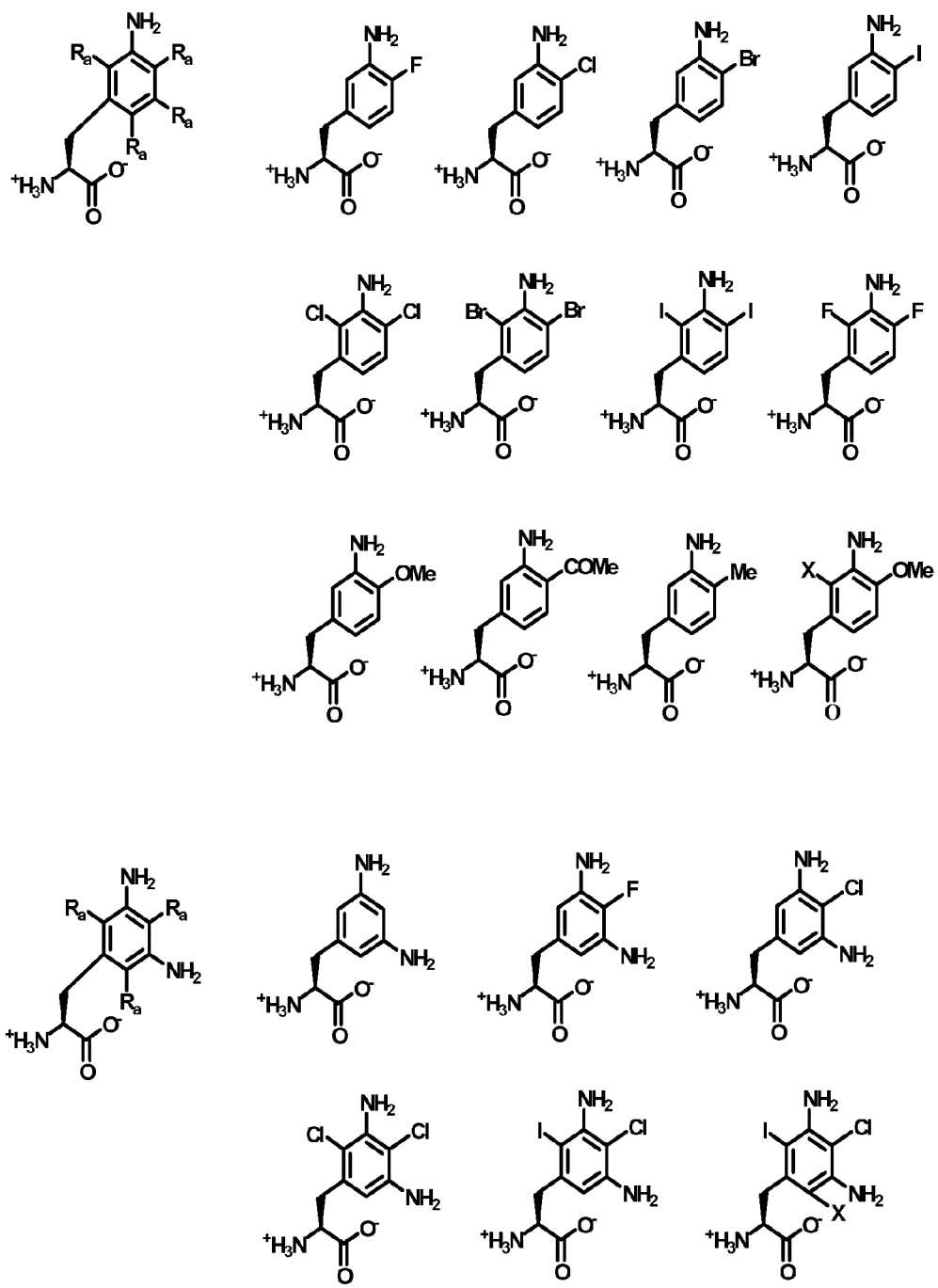
FIG. 3 presents illustrative, non-limiting examples of the types of non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein. For FIG. 3 only, X represents a halogen.
Figure 4:
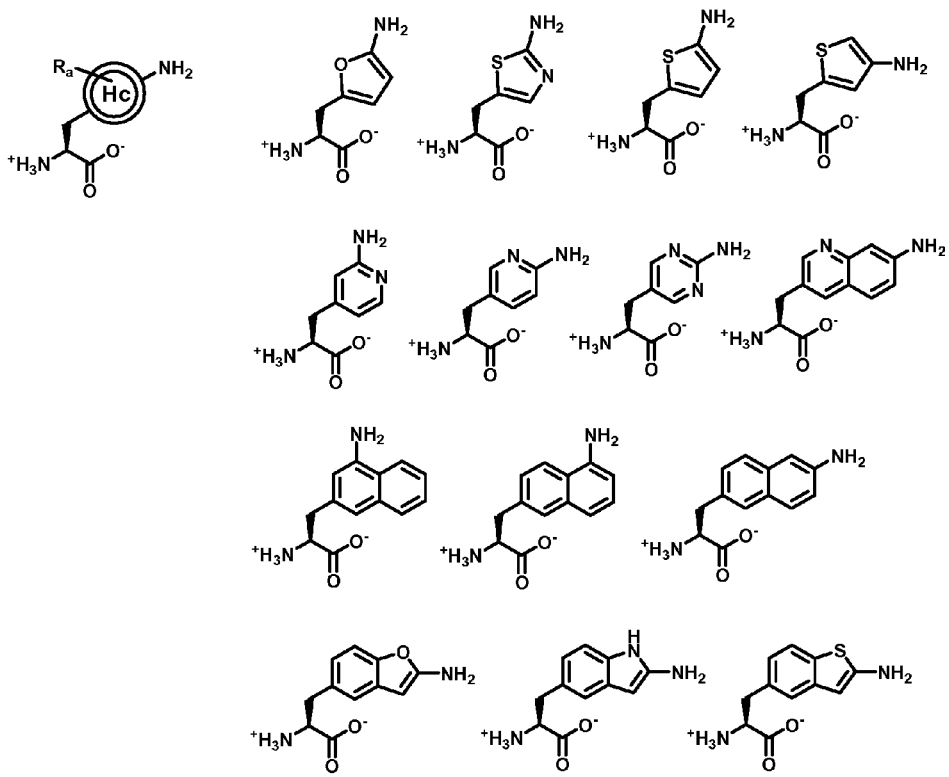
FIG. 4 presents illustrative, non-limiting examples of the types of non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.
Figure 5:
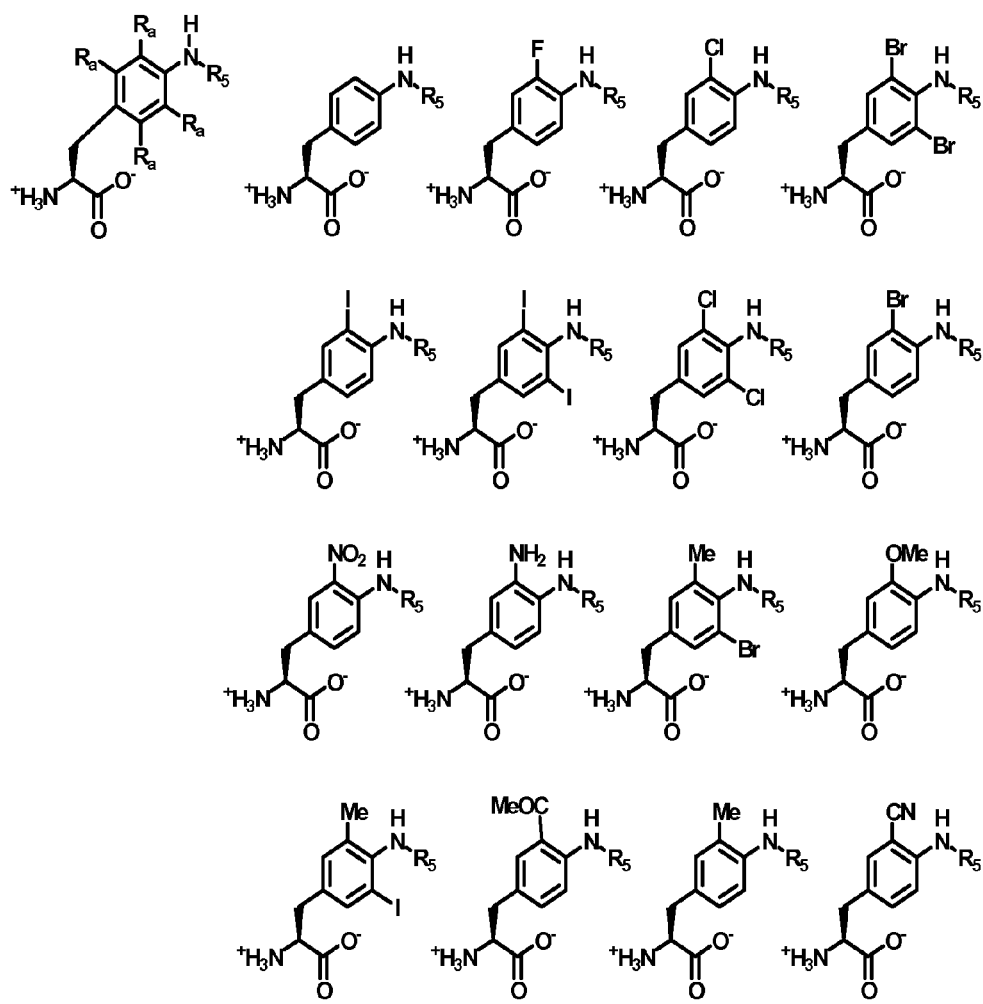
FIG. 5 presents illustrative, non-limiting examples of the types of non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.
Figure 6:
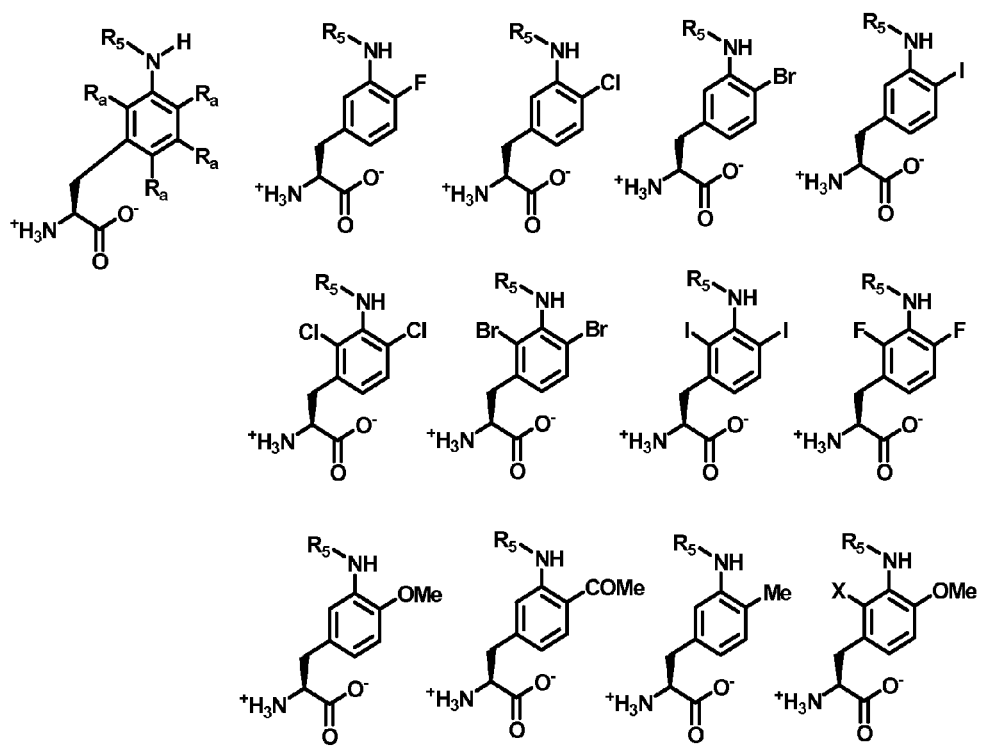
FIG. 6 presents illustrative, non-limiting examples of the types of non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein. For FIG. 6 only, X represents a halogen.
Figure 7:
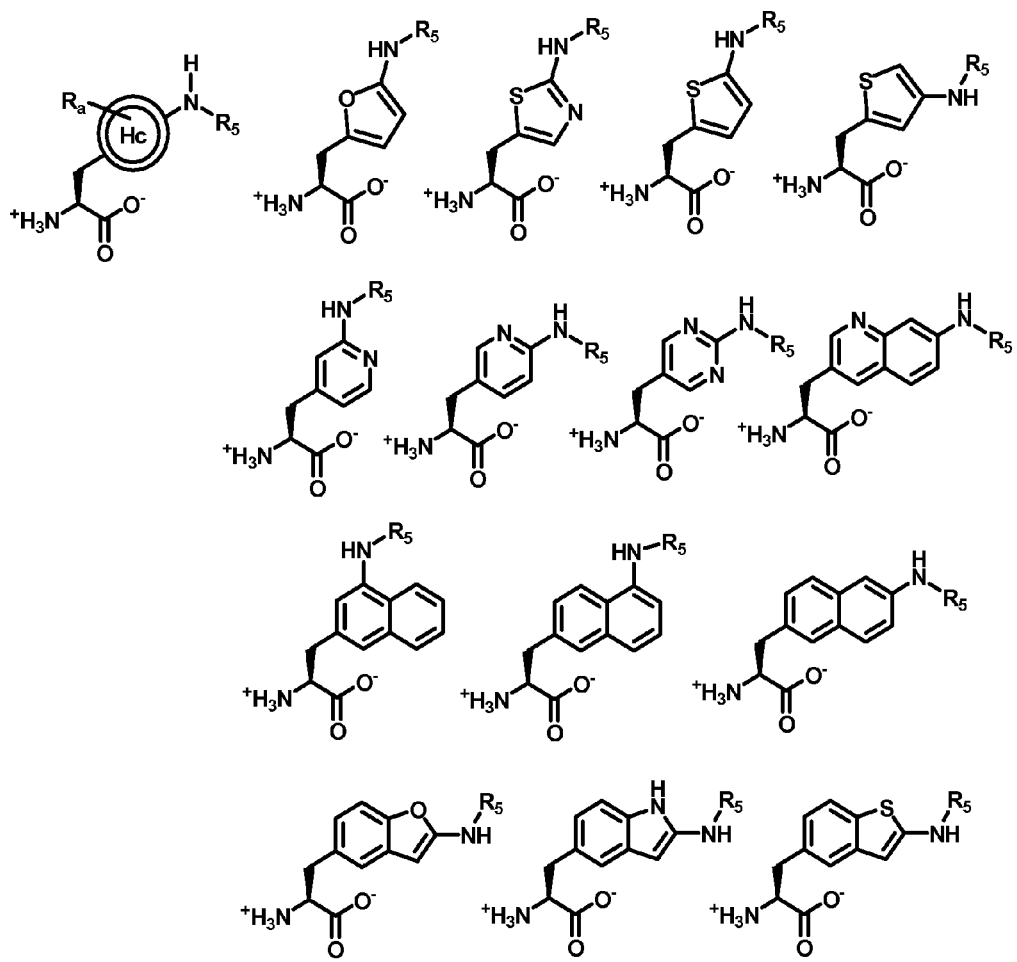
FIG. 7 presents illustrative, non-limiting examples of the types of non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.

FIG. 1 presents an overview of the compositions, methods and techniques that are described herein. At one level, described herein are the tools (methods, compositions, techniques) for creating and using a polypeptide comprising at least one non-natural amino acid or modified non-natural amino acid with an aromatic amine or a heteroaromatic amine. The heteroaromatic group includes, but is not limited to, furans, pyrroles, thiophenes, pyridines, quinolines, iso- quinolines, imidazole, thiazoles, pyrimidines, pyridazines, pyrazines, benzothiazoles, thiazolopyridines, oxazoles, benzoxazoles, oxazolopyridines, thiazolopyrimidines, oxazolopyrimidines, benzoxazines, and benzothiazines. Such non-natural amino acids may contain further functionality, including but not limited to, a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof.

As shown in FIG. 1, in one aspect are methods for selecting and designing a polypeptide to be modified using the methods, compositions and techniques described herein. The new polypeptide may be designed de novo, including by way of example only, as part of high-throughput screening process (in which case numerous polypeptides may be designed, synthesized, characterized and/or tested) or based on the interests of the researcher. The new polypeptide may also be designed based on the structure of a known or partially characterized polypeptide. By way of example only, the Growth Hormone Gene Superfamily (see infra) has been the subject of intense study by the scientific community; a new polypeptide may be designed based on the structure of a member or members of this gene superfamily. The principles for selecting which amino acid(s) to substitute and/or modify are described separately herein. The choice of which modification to employ is also described herein, and can be used to meet the need of the experimenter or end user. Such needs may include, but are not limited to, manipulating the therapeutic effectiveness of the polypeptide, improving the safety profile of the polypeptide, adjusting the pharmacokinetics, pharmacologics and/or pharmacodynamics of the polypeptide, such as, by way of example only, increasing water solubility, bioavailability, increasing serum half-life, increasing therapeutic half-life, modulating immunogenicity, modulating biological activity, or extending the circulation time. In addition, such modifications include, by way of example only, providing additional functionality to the polypeptide, incorporating a tag, label or detectable signal into the polypeptide, easing the isolation properties of the polypeptide, and any combination of the aforementioned modifications.

Also described herein are non-natural amino acids that have or can be modified to contain an aromatic amine or a heteroaromatic amine. The heteroaromatic group includes, but is not limited to, furans, pyrroles, thiophenes, pyridines, quinolines, isoquinolines, imidazole, thiazoles, pyrimidines, pyridazines, pyrazines, benzothiazoles, thiazolopyridines, oxazoles, benzoxazoles, oxazolopyridines, thiazolopyrimidines, oxazolopyrimidines, benzoxazines, and benzothiazines. Included with this aspect are methods for producing, purifying, characterizing and using such non-natural amino acids. In another aspect described herein are methods, strategies and techniques for incorporating at least one such non-natural amino acids into a polypeptide. Also included with this aspect are methods for producing, purifying, characterizing and using such polypeptides containing at least one such non-natural amino acids. Also included with this aspect are compositions of and methods for producing, purifying, characterizing and using oligonucleotides (including DNA and RNA) that can be used to produce, at least in part, a polypeptide containing at least one non-natural amino acid. Also included with this aspect are compositions of and methods for producing, purifying, characterizing and using cells that can express such oligonucleotides that can be used to produce, at least in part, a polypeptide containing at least one non-natural amino acid.

Thus, polypeptides comprising at least one non-natural amino acid or modified non-natural amino acid with an aromatic amine or a heteroaromatic amine are provided and described herein. The heteroaromatic group includes, but is not limited to, furans, pyrroles, thiophenes, pyridines, quinolines, isoquinolines, imidazole, thiazoles, pyrimidines, pyridazines, pyrazines, benzothiazoles, thiazolopyridines, oxazoles, benzoxazoles, oxazolopyridines, thiazolopyrimidines, oxazolopyrimidines, benzoxazines, and benzothiazines. In certain embodiments, polypeptides with at least one non-natural amino acid or modified non-natural amino acid with an aromatic amine or a heteroaromatic amine include at least one post-translational modification at some position on the polypeptide. In such embodiments, the heterocycle modified non-natural amino acids may include, but are not limited to, furans, pyrroles, thiophenes, pyridines, quinolines, isoquinolines, imidazole, thiazoles, pyrimidines, pyridazines, pyrazines, benzothiazoles, thiazolopyridines, oxazoles, benzoxazoles, oxazolopyridines, thiazolopyrimidines, oxazolopyrimidines, benzoxazines, and benzothiazines. In some embodiments the post-translational modification occurs via the cellular machinery (e.g., glycosylation, acetylation, acylation, lipid modification, palmitoylation, palmitate addition, phosphorylation, glycolipid-linkage modification, and the like), in many instances, such cellular-machinery-based post-translational modifications occur at the naturally occurring amino acid sites on the polypeptide, however, in certain embodiments, the cellular-machinery-based post-translational modifications occur on the non-natural amino acid site(s) on the polypeptide.

In other embodiments the post-translational modification does not utilize cellular machinery, but the functionality is instead provided by attachment of a molecule (including but not limited to, a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof) comprising a second reactive group to the at least one non-natural amino acid comprising a first reactive group (including but not limited to, non-natural amino acid containing an aromatic amine or a heteroaromatic amine functional group) utilizing reductive alkylation methodology. In certain embodiments, such second reactive groups may be carbonyl containing groups, including, but not limited to, aldehydes and ketones. In certain embodiments, the post-translational modification is made in vivo in a eukaryotic cell or in a non-eukaryotic cell. In certain embodiments, the post-translational modification is made in vitro. Also included with this aspect are methods for producing, purifying, characterizing and using such polypeptides containing at least one such post-translationally modified non-natural amino acids.

Also included within the scope of the methods, compositions, strategies and techniques described herein are reagents capable of reacting with a non-natural amino acid (containing either an aromatic amine group, a heteroaromatic amine group, or protected forms thereof) that is part of a polypeptide so as to produce any of the aforementioned post-translational modifications. In general, the resulting post-translationally modified non-natural amino acid will contain at least one reductively aminated aldehyde or ketone, which may undergo further modification reactions. Also included with this aspect are methods for producing, purifying, characterizing and using such reagents that are capable of any such post-translational modifications of such non-natural amino acid(s).

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of such post-translational modifications include, but are not limited to, glycosylation, acetylation, acylation, lipid modification, palmitoylation, palmitate addition, phosphorylation, glycolipid-linkage modification, and the like. In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon. In certain embodiments, a protein or polypeptide can comprise a secretion or localization sequence, an epitope tag, a FLAG tag, a polyhistidine tag, a GST fusion, and/or the like. Also included with this aspect are methods for producing, purifying, characterizing and using such polypeptides containing at least one such post-translational modification. In other embodiments, the glycosylated non-natural amino acid polypeptide is produced in a non-glycosylated form. Such a non-glycosylated form of a glycosylated non-natural amino acid may be produced by methods that include chemical or enzymatic removal of oligosaccharide groups from an isolated or substantially purified or unpurified glycosylated non-natural amino acid polypeptide; production of the non-natural amino acid in a host that does not glycosylate such a non-natural amino acid polypeptide (such a host including, prokaryotes or eukaryotes engineered or mutated to not glycosylate such a polypeptide), the introduction of a glycosylation inhibitor into the cell culture medium in which such a non-natural amino acid polypeptide is being produced by a eukaryote that normally would glycosylate such a polypeptide, or a combination of any such methods. Also described herein are such non-glycosylated forms of normally-glycosylated non-natural amino acid polypeptides (by normally-glycosylated is meant a polypeptide that would be glycosylated when produced under conditions in which naturally-occurring polypeptides are glycosylated). Of course, such non-glycosylated forms of normally-glycosylated non-natural amino acid polypeptides may be in an unpurified form, a substantially purified form, or in an isolated form.

In certain embodiments, the protein includes at least one post-translational modification that is made in vitro, wherein the post-translational modification is stoichiometric, stoichiometric-like, or near-stoichiometric. Examples of such post-translational modifications include, but are not limited to, reductive alkylations of aromatic amine groups or heteroaromatic amine groups with carbonyl containing reagents using a reducing agent. In certain embodiments, such post-translational modifications include, but are not limited to, reductive alkylations of aromatic amine groups or heteroaromatic amine groups with aldehyde containing reagents using a reducing agent. In certain embodiments, such post-translational modifications include, but are not limited to, reductive alkylations of aromatic amine groups or heteroaromatic amine groups with aldehyde containing reagents using sodium cyanoborohydride reducing agent.

The non-natural amino acid containing polypeptide can contain at least one, at least two, at least three, at least four, at least five, at least six, at least seven, at least eight, at least nine, or ten or more non-natural amino acids containing an aromatic amine, heteroaromatic amine, or protected forms thereof. The non-natural amino acids can be the same or different, for example, there can be 1, 2, 3, 4, 5, 6, 7, 8, 9, 10, 11, 12, 13, 14, 15, 16, 17, 18, 19, 20, or more different sites in the protein that comprise 1, 2, 3, 4, 5, 6, 7, 8, 9, 10, 11, 12, 13, 14, 15, 16, 17, 18, 19, 20, or more different non-natural amino acids. In certain embodiments, at least one, but fewer than all, of a particular amino acid present in a naturally occurring version of the protein is substituted with a non-natural amino acid. The non-natural amino acid polypeptide may also contain one or more non-natural amino acids that are not non-natural amino acids containing an aromatic amine, heteroaromatic amine, or protected forms thereof.

The methods and compositions provided and described herein include polypeptides comprising at least one non-natural amino acid containing an aromatic amine, heteroaromatic amine, or protected forms thereof. Introduction of at least one such non-natural amino acid into a polypeptide can allow for the application of conjugation chemistries that involve specific chemical reactions, including, but not limited to, with one or more non-natural amino acids while not reacting with the commonly occurring 20 amino acids. Such specific chemical reactions involving such incorporated the amino acid side chains includes, but is not limited to, reductive alkylation chemistry methodologies suitable for the particular functional groups or substituents present. Once incorporated, the amino acid side chains can then be modified by utilizing chemistry methodologies known to those of ordinary skill in the art to be suitable for the particular functional groups or substituents present in the naturally encoded amino acid.

The non-natural amino acid methods and compositions described herein provides conjugates of substances having a wide variety of functional groups, substituents or moieties, with other substances including but not limited to a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof.

In another aspect of the compositions, methods, techniques and strategies described herein are methods for studying or using any of the aforementioned modified or unmodified non-natural amino acid polypeptides. Included within this aspect, by way of example only, are therapeutic, diagnostic, assay-based, industrial, cosmetic, plant biology, environmental, energy-production, and/or military uses which would benefit from a polypeptide comprising a modified or unmodified non-natural amino acid polypeptide or protein.

III. Location of Non-Natural Amino Acids in Polypeptides

The methods and compositions described herein include incorporation of one or more non-natural amino acids into a polypeptide. One or more non-natural amino acids may be incorporated at one or more particular position which does not disrupt activity of the polypeptide. This can be achieved by making "conservative" substitutions, including but not limited to, substituting hydrophobic amino acids with non-natural or natural hydrophobic amino acids, bulky amino acids for non-natural or natural bulky amino acids, hydrophilic amino acids for non-natural or natural hydrophilic amino acids and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be for producing a non-natural amino acid polypeptide (which may be further modified or remain unmodified) having any desired property or activity, including but not limited to agonists, super-agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using point mutation analysis, alanine scanning or homolog scanning methods known in the art. Residues other than those identified as critical to biological activity by alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to simply make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

The structure and activity of naturally-occurring mutants of a polypeptide that contain deletions can also be examined to determine regions of the protein that are likely to be tolerant of substitution with a non-natural amino acid. Once residues that are likely to be intolerant to substitution with non-natural amino acids have been eliminated, the impact of proposed substitutions at each of the remaining positions can be examined from the three-dimensional structure of the relevant polypeptide, and any associated ligands or binding proteins. X-ray crystallographic and NMR structures of many polypeptides are available in the Protein Data Bank (PDB, www.rcsb.org), a centralized database containing three-dimensional structural data of large molecules of proteins and nucleic acids. In addition, models may be made investigating the secondary and tertiary structure of polypeptides, if three-dimensional structural data is not available. Thus, the identity of amino acid positions that can be substituted with non-natural amino acids can be readily obtained.

Exemplary sites of incorporation of a non-natural amino acid include, but are not limited to, those that are excluded from potential receptor binding regions or regions for binding to binding proteins or ligands, may be fully or partially solvent exposed, have minimal or no hydrogen-bonding interactions with nearby residues, may be minimally exposed to nearby reactive residues, and may be in regions that are highly flexible as predicted by the three-dimensional crystal structure of a particular polypeptide with its associated receptor, ligand or binding proteins.

A wide variety of non-natural amino acids can be substituted for, or incorporated into, a given position in a polypeptide. In general, a particular non-natural amino acid is selected for incorporation based on an examination of the three dimensional crystal structure of a polypeptide with its associated ligand, receptor and/or binding proteins, a preference for conservative substitutions (i.e., aryl-based non-natural amino acids, such as p-acetylphenylalanine or O-propargyltyrosine substituting for Phe, Tyr or Trp), and the specific conjugation chemistry that one desires to introduce into the polypeptide protein.

In one embodiment, the method further includes incorporating into the protein the non-natural amino acid, where the non-natural amino acid comprises a first reactive group; and contacting the protein with a molecule (including but not limited to a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof) that comprises a second reactive group. In certain embodiments, the first reactive group is an amine moiety on an aromatic amine and the second reactive group is an aldehyde, wherein the amine group is reductively alkylated upon contact with the aldehyde in the presence of a reducing agent, such as sodium cyanborohydride. In other embodiments, the first reactive group is an amine moiety on a heteroaromatic amine and the second reactive group is an aldehyde, wherein the amine group is reductively alkylated upon contact with the aldehyde in the presence of a reducing agent, such as sodium cyanborohydride.

In some cases, the non-natural amino acid substitution(s) or incorporation(s) will be combined with other additions, substitutions, or deletions within the polypeptide to affect other biological traits. In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility (including but not limited to, when expressed in E. coli or other host cells) of the polypeptide. In some embodiments sites are selected for substitution with a naturally encoded or non-natural amino acid in addition to another site for incorporation of a non-natural amino acid for the purpose of increasing the polypeptide solubility following expression in E. coli or other recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification transport thru tissues or cell membranes, prod-rug release or activation, size reduction, or other traits of the polypeptide.

IV. Growth Hormone Supergene Family as Exemplar

The methods, compositions, strategies and techniques described herein are not limited to a particular type, class or family of polypeptides or proteins. Indeed, virtually any polypeptides may be designed or modified to include at least one modified or unmodified non-natural amino acids described herein. By way of example only, the polypeptide can be homologous to a therapeutic protein selected from the group consisting of: alpha-1 antitrypsin, angiostatin, antihemolytic factor, antibody, antibody fragment, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, any interferon-like molecule or member of the IFN family, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropia, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

Thus, the following description of the growth hormone (GH) supergene family is provided for illustrative purposes and by way of example only, and not as a limit on the scope of the methods, compositions, strategies and techniques described herein. Further, reference to GH polypeptides in this application is intended to use the generic term as an example of any member of the GH supergene family. Thus, it is understood that the modifications and chemistries described herein with reference to GH polypeptides or protein can be equally applied to any member of the GH supergene family, including those specifically listed herein.

The following proteins include those encoded by genes of the growth hormone (GH) supergene family (Bazan, F., *Immunology Today* 11: 350-354 (1990); Bazan, J. F. *Science* 257: 410-413 (1992); Mott, H. R. and Campbell, I. D., *Current Opinion in Structural Biology* 5: 114-121 (1995); Silvennoinen, O. and Ihle, J. N., SIGNALLING BY THE HEMATOPOIETIC CYTOKINE RECEPTORS (1996)): growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor, leukemia inhibitory factor, alpha interferon, beta interferon, epsilon interferon, gamma interferon, omega interferon, tau interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features allow new members of the gene family to be readily identified and the non-natural amino acid methods and compositions described herein similarly applied.

Structures of a number of cytokines, including G-CSF (Zink et al., FEBS Lett. 314:435 (1992); Zink et al., Biochemistry 33:8453 (1994); Hill et al., Proc. Natl. Acad. Sci. USA 90:5167 (1993)), GM-CSF (Diederichs, K., et al. *Science* 154: 1779-1782 (1991); Walter et al., *J. Mol. Biol.* 224:1075-1085 (1992)), IL-2 (Bazan, J. F. and McKay, D. B. *Science* 257: 410-413 (1992)), IL-4 (Redfield et al., Biochemistry 30: 11029-11035 (1991); Powers et al., *Science* 256:1673-1677 (1992)), and IL-5 (Milburn et al., *Nature* 363: 172-176 (1993)) have been determined by X-ray diffraction and NMR studies and show striking conservation with the GH structure, despite a lack of significant primary sequence homology. IFN is considered to be a member of this family based upon modeling and other studies (Lee et al., J. Interferon Cytokine Res. 15:341 (1995); Murgolo et al., Proteins 17:62 (1993); Radhakrishnan et al., Structure 4:1453 (1996); Klaus et al., *J. Mol. Biol.* 274:661 (1997)). A large number of additional cytokines and growth factors including ciliary neurotrophic factor (CNTF), leukemia inhibitory factor (LIF), thrombopoietin (TPO), oncostatin M, macrophage colony stimulating factor (M-CSF), IL-3, IL-6, IL-7, IL-9, IL-12, IL-13, IL-15, and granulocyte-colony stimulating factor (G-CSF), as well as the IFN's such as alpha, beta, omega, tau, epsilon, and gamma interferon belong to this family (reviewed in Mott and Campbell, *Current Opinion in Structural Biology* 5: 114-121 (1995); Silvennoinen and Ihle (1996) SIGNALLING BY THE HEMATOPOIETIC CYTOKINE RECEPTORS). All of the above cytokines and growth factors are now considered to comprise one large gene family.

In addition to sharing similar secondary and tertiary structures, members of this family share the property that they must oligomerize cell surface receptors to activate intracellular signaling pathways. Some GH family members, including but not limited to; GH and EPO, bind a single type of receptor and cause it to form homodimers. Other family members, including but not limited to, IL-2, IL4. and IL-6, bind more than one type of receptor and cause the receptors to form heterodimers or higher order aggregates (Davis et al., (1993) Science 260: 1805-1808; Paonessa et al., 1995) EMBO J. 14: 1942-1951; Mott and Campbell, *Current Opinion in Structural Biology* 5: 114-121 (1995)). Mutagenesis studies have shown that, like GH, these other cytokines and growth factors contain multiple receptor binding sites, typically two, and bind their cognate receptors sequentially (Mott and Campbell, *Current Opinion in Structural Biology* 5: 114-121 (1995); Matthews et al., (1996) *Proc. Natl. Acad. Sci. USA* 93: 9471-9476). Like GH, the primary receptor binding sites for these other family members occur primarily in the four alpha helices and the A-B loop. The specific amino acids in the helical bundles that participate in receptor binding differ amongst the family members. Most of the cell surface receptors that interact with members of the GH supergene family are structurally related and comprise a second large multi-gene family. See, e.g. U.S. Pat. No. 6,608,183, which is herein incorporated by reference in its entirety.

A general conclusion reached from mutational studies of various members of the GH supergene family is that the loops joining the alpha helices generally tend to not be involved in receptor binding. In particular the short B-C loop appears to be non-essential for receptor binding in most, if not all, family members. For this reason, the B-C loop may be substituted with non-natural amino acids as described herein in members of the GH supergene family. The A-B loop, the C-D loop (and D-E loop of interferon/IL-10-like members of the GH superfamily) may also be substituted with a non-natural amino acid Amino acids proximal to helix A and distal to the final helix also tend not to be involved in receptor binding and also may be sites for introducing non-natural amino acids. In some embodiments, a non-natural amino acid is substituted at any position within a loop structure including but not limited to the first 1, 2, 3, 4, 5, 6, 7, or more amino acids of the A-B, B-C, C-D or D-E loop. In some embodiments, a non-natural amino acid is substituted within the last 1, 2, 3, 4, 5, 6, 7, or more amino acids of the A-B, B-C, C-D or D-E loop.

Certain members of the GH family, including but not limited to, EPO, IL-2, IL-3, IL-4, IL-6, GM-CSF, TPO, IL-10, IL-12 p35, IL-13, IL-15 and beta interferon contain N-linked and/or O-linked sugars. The glycosylation sites in the proteins occur almost exclusively in the loop regions and not in the alpha helical bundles. Because the loop regions generally are not involved in receptor binding and because they are sites for the covalent attachment of sugar groups, they may be useful sites for introducing non-natural amino acid substitutions into the proteins Amino acids that comprise the N- and O-linked glycosylation sites in the proteins may be sites for non-natural amino acid substitutions because these amino acids are surface-exposed. Therefore, the natural protein can tolerate bulky sugar groups attached to the proteins at these sites and the glycosylation sites tend to be located away from the receptor binding sites.

Additional members of the GH gene family are likely to be discovered in the future. New members of the GH supergene family can be identified through computer-aided secondary and tertiary structure analyses of the predicted protein sequences, and by selection techniques designed to identify molecules that bind to a particular target. Members of the GH supergene family typically possess four or five amphipathic helices joined by non-helical amino acids (the loop regions). The proteins may contain a hydrophobic signal sequence at their N-terminus to promote secretion from the cell. Such later discovered members of the GH supergene family also are included within the methods and compositions described herein.

V. Non-Natural Amino Acids

A very wide variety of non-natural amino acids are suitable for use in the methods and compositions described herein as long as they have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an aromatic amine or heteroaromatic amine, or a functional group that can be transformed into an aromatic amine or heteroaromatic amine, by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 10, or where the reactive site on the non-natural amino acid is an nucleophilic site. Illustrative, non-limiting examples of amino acids that satisfy these four properties for non-natural amino acids that can be used with the compositions and methods described herein are presented throughout the Figures and the text herein. Any number of non-natural amino acids can be introduced into the polypeptide. Non-natural amino acids may also include a protected or masked aromatic amine or heteroaromatic amine, whereby upon deprotection or unmasking, the protected or masked aromatic amine or heteroaromatic amine are transformed into an aromatic amine or heteroaromatic amine.

Non-natural amino acids of interest that may be suitable for use in the methods and compositions described herein include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an amine linkage, and the like. Examples of such amino acids also include saccharides that are not commonly found in naturally-occurring proteins such as 2-deoxy-glucose, 2-deoxygalactose and the like.

The chemical moieties via non-natural amino acids that can be incorporated into proteins offer a variety of advantages and manipulations of the protein. For example, a heavy atom non-natural amino acid, for example, can be useful for phasing x-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylaz- ides (including but not limited to, phenylazide) side chains), for example, allow for efficient in vivo and in vitro photo-crosslinking of protein. Examples of photoreactive non-natural amino acids include, but are not limited to, p-azidophenylalanine and p-benzoyl-phenylalanine. The protein with the photoreactive non-natural amino acids can then be crosslinked at will by excitation of the photoreactive group-providing temporal control. In one example, the methyl group of a non-natural amino can be substituted with an isotopically labeled, including but not limited to, methyl group, as a probe of local structure and dynamics, including but not limited to, with the use of nuclear magnetic resonance and vibrational spectroscopy.

A. Structure and Synthesis of Non-Natural Amino Acids: Alkylated Aromatic Amine Groups Non-natural amino acids with nucleophilic reactive groups, such as, by way of example only, an aromatic amine group (including secondary and tertiary amine groups), a masked aromatic amine group (which can be readily converted into a aromatic amine group), or a protected aromatic amine group (which has reactivity similar to an aromatic amine group upon deprotection) allow for a variety of reactions to link molecules via various reactions, including but not limited to, reductive alkylation reactions with aldehyde containing reagents. Such aromatic amine containing non-natural amino acids include amino acids having the structure of Formula (A):

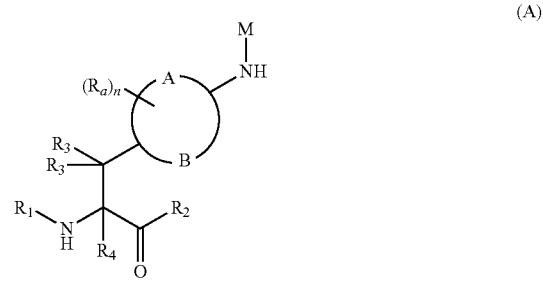

(A)

wherein:

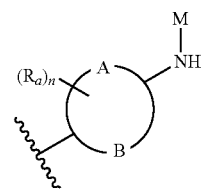

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently $CR_a$, or N;

B is independently $CR_a$, N, O, or S;

each $R_a$ is independently selected from the group consisting of H, halogen, alkyl, $-NO_2$, $-CN$, substituted alkyl, $-N(R')_2$, $-C(O)_kR'$, $-C(O)N(R')_2$, $-OR'$, and $-S(O)_k R'$, where k is 1, 2, or 3; and n is 0, 1, 2, 3, 4, 5, or 6;

$R_1$ is H, an amino protecting group, resin, amino acid, polypeptide, or polynucleotide; and $R_2$ is OH, an ester protecting group, resin, amino acid, polypeptide, or polynucleotide;

each of R₃ and R₄ is independently H, halogen, lower alkyl, or substituted lower alkyl, or R₃ and R₄ or two R₃ groups optionally form a cycloalkyl or a heterocycloalkyl;

M is H or —CH₂R₅; or the M-N=C(R₅) moiety may form a 4 to 7 membered ring structure;

R₅ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")₂, —C(O)NHCH(R")₂, -(alkylene or substituted alkylene)-N(R")₂, -(alkenylene or substituted alkenylene)-N(R")₂, -(alkylene or substituted alkylene)-(aryl or substituted aryl), -(alkenylene or substituted alkenylene)-(aryl or substituted aryl), -(alkylene or substituted alkylene)-ON(R")₂, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or R₅ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)ₖ— where k is 1, 2, or 3, —S(O)ₖ(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S(O)ₖ-(alkylene or substituted alkylene)-S—, -(alkylene or substituted alkylene)-S—S—, —S(O)ₖN(R')—, —N(R')C(O)N(R')—, —N(R')C(S)N(R')—, —N(R')S(O)ₖN(R')—, —N(R')—N=, —C(R')=N—, —C(R')=N—N(R')—, —C(R')=N—N=, —C(R')₂—N=N—, and —C(R')₂—N(R')—N(R')—;

or two R₅ groups optionally form a cycloalkyl or a heterocycloalkyl;

or R₅ and any Rₐ optionally form a cycloalkyl or a heterocycloalkyl; and each R' is independently H, alkyl, or substituted alkyl.

Such non-natural amino acids may also be in the form of a salt, or may be incorporated into a non-natural amino acid polypeptide, polymer, polysaccharide, or a polynucleotide and optionally reductively alkylated.

The structure

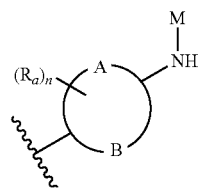

(as presented in all examples herein) does not present the relative orientations of "A," "B," "NH-M" and "Rₐ"; rather these four features of this structure may be oriented in any chemically-sound manner (along with other features of this structure), as illustrated by example herein.

Non-natural amino acids containing an aromatic amine moiety having the structure of Formula (A) include non-natural amino acids having the structure of Formula (I), Formula (II), Formula (III), Formula (IV), and Formula (V):

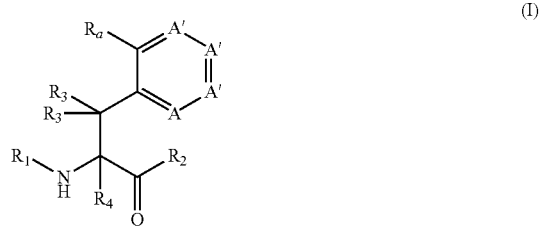

(I)

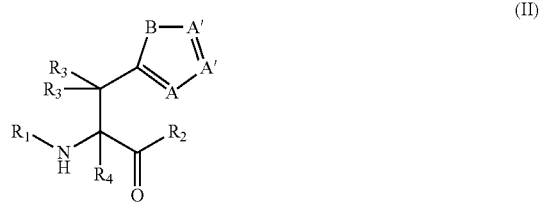

(II)

-continued

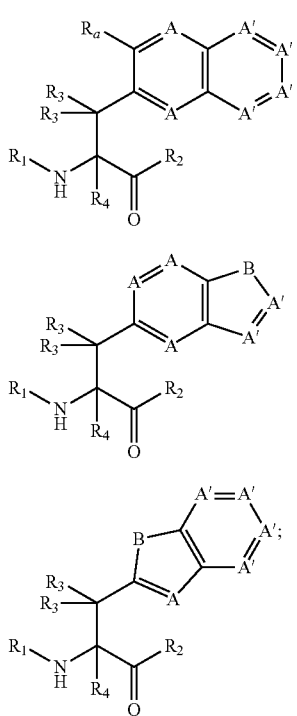

wherein, each A' is independently selected from $CR_a$, N, or

and up to two A' may be

with the remaining A' selected from $CR_a$, or N.

Such non-natural amino acids may also be in the form of a salt, or may be incorporated into a non-natural amino acid polypeptide, polymer, polysaccharide, or a polynucleotide and optionally reductively alkylated.

Non-limiting examples of non-natural amino acids containing an aromatic amine moiety having the structure of Formula (A) include non-natural amino acids having the structure of Formula (VI), and Formula (VII),

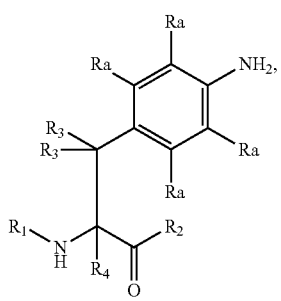

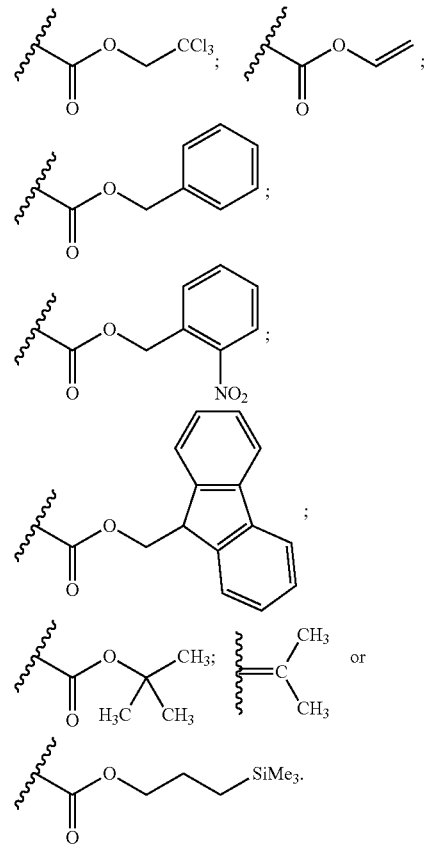

wherein; G is an amine protecting group, including, but not limited to,

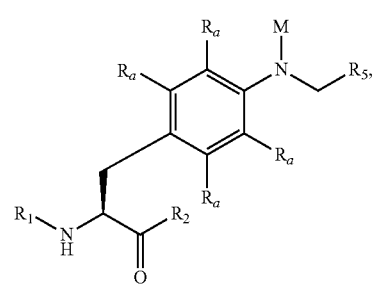

Such non-natural amino acids may be in the form of a salt, or may be incorporated into a non-natural amino acid polypeptide, polymer, polysaccharide, or a polynucleotide and optionally reductively alkylated.

Non-natural amino acids containing an aromatic amine moiety have the following structures:

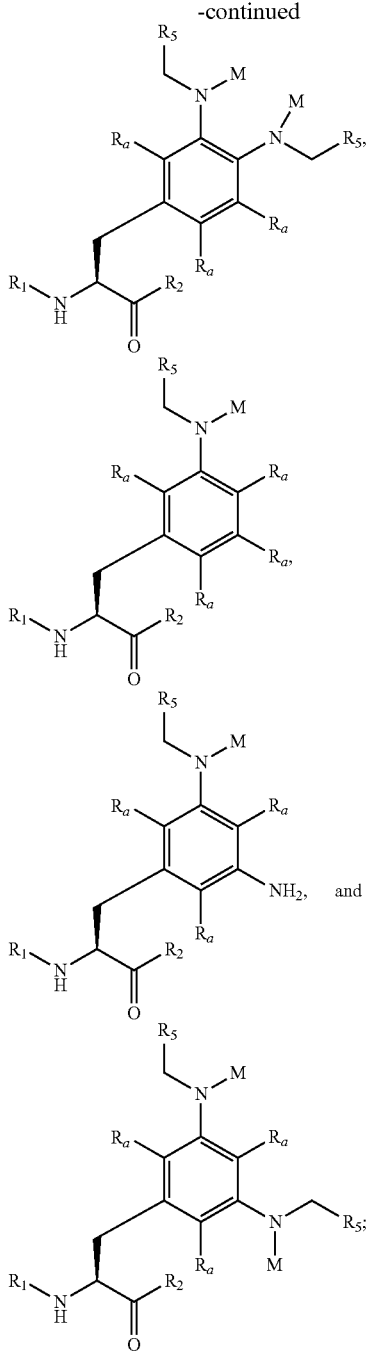

wherein each $R_a$ is independently selected from the group consisting of H, halogen, alkyl, —NO₂, —CN, substituted alkyl, —N(R')₂, —C(O)$_k$R', —C(O)N(R')₂, —OR', and —S(O)$_k$R', where k is 1, 2, or 3;

M is H or —CH₂R₅; or the M-N—C(R₅) moiety may form a 4 to 7 membered ring structure;

R₁ is H, an amino protecting group, resin, amino acid, polypeptide, or polynucleotide;

R₂ is OH, an ester protecting group, resin, amino acid, polypeptide, or polynucleotide;

R₅ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")₂, —C(O)NHCH(R")₂, -(alkylene or substituted alkylene)-N(R")₂, -(alkenylene or substituted alkenylene)-N(R")₂, -(alkylene or substituted alkylene)-(aryl or substituted aryl), -(alkenylene or substituted alkenylene)-(aryl or substituted aryl), -(alkylene or substituted alkylene)-ON(R")₂, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or R₅ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—;

or R$_5$ and any R$_a$ optionally form a cycloalkyl or a heterocycloalkyl; and each R' is independently H, alkyl, or substituted alkyl. Such non-natural amino acids may also be in the form of a salt, or may be incorporated into a non-natural amino acid polypeptide, polymer, polysaccharide, or a polynucleotide.

Other non-limiting examples of non-natural amino acids containing an aromatic amine moiety having the structure of Formula (A) are shown in FIGS. 2-10. Such non-natural amino acids may also be in the form of a salt, or may be incorporated into a non-natural amino acid polypeptide, polymer, polysaccharide, or a polynucleotide.

Figure 11:
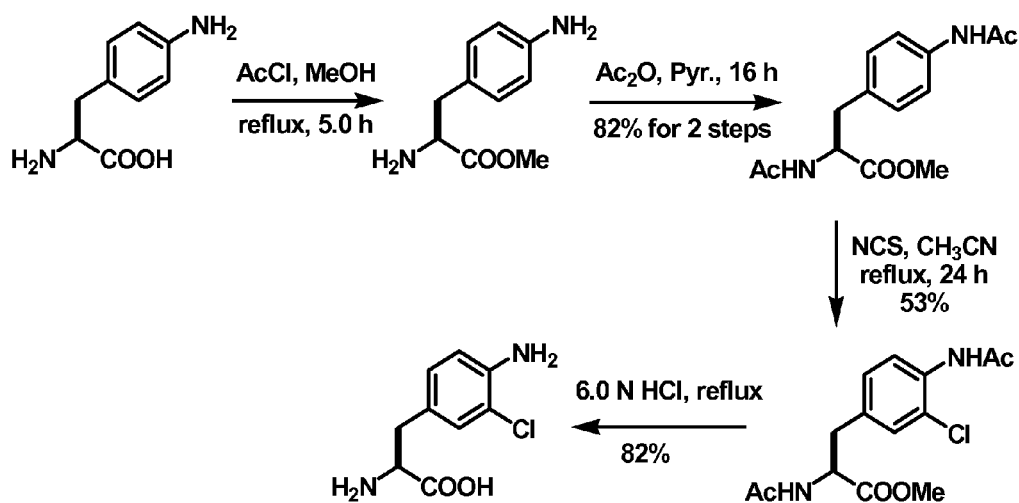
FIG. 11 presents an illustrative, non-limiting example of the synthetic methodology used to make the non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.
Figure 11:
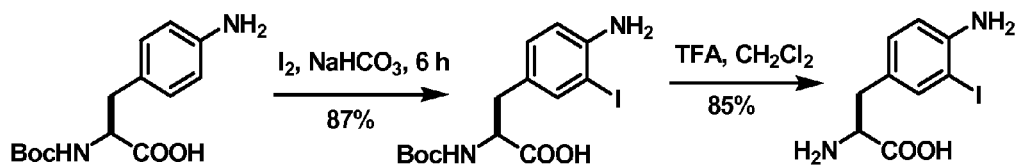
Figure 12:
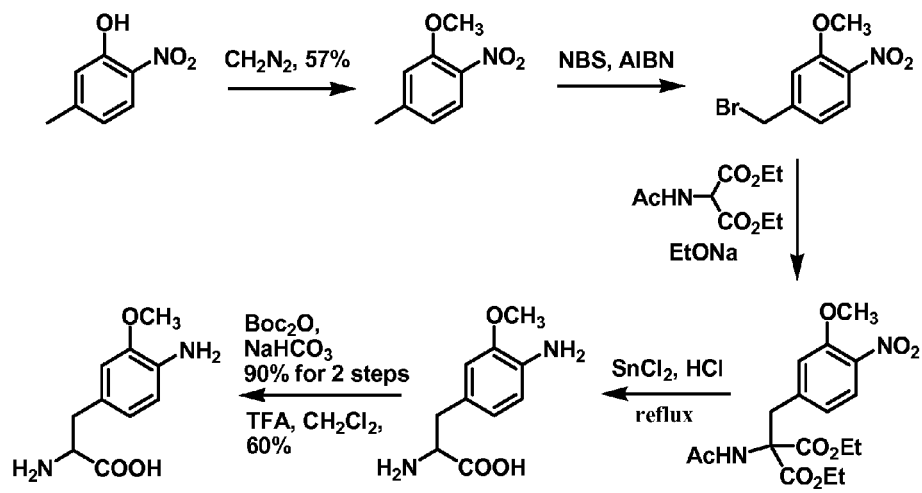
FIG. 12 presents an illustrative, non-limiting example of the synthetic methodology used to make the non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.
Figure 12:
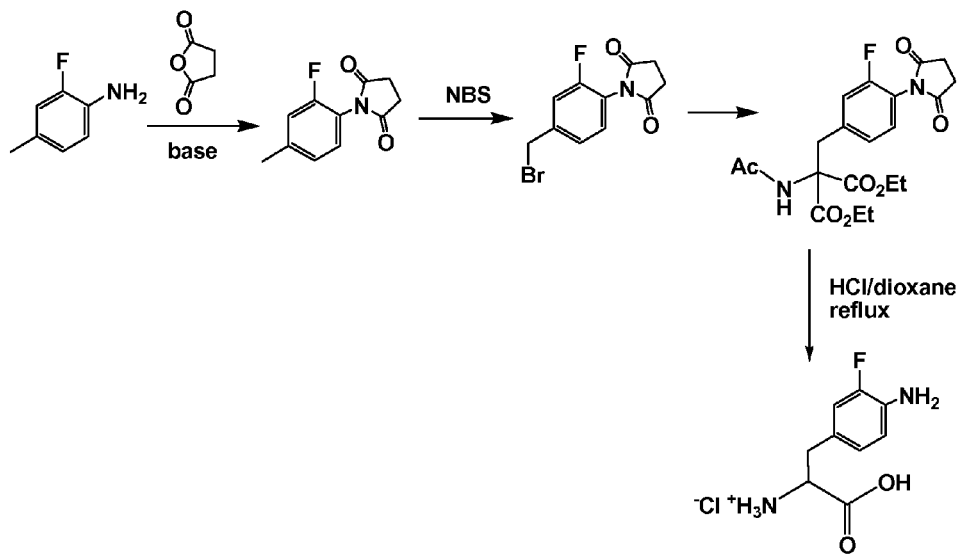
Figure 13:
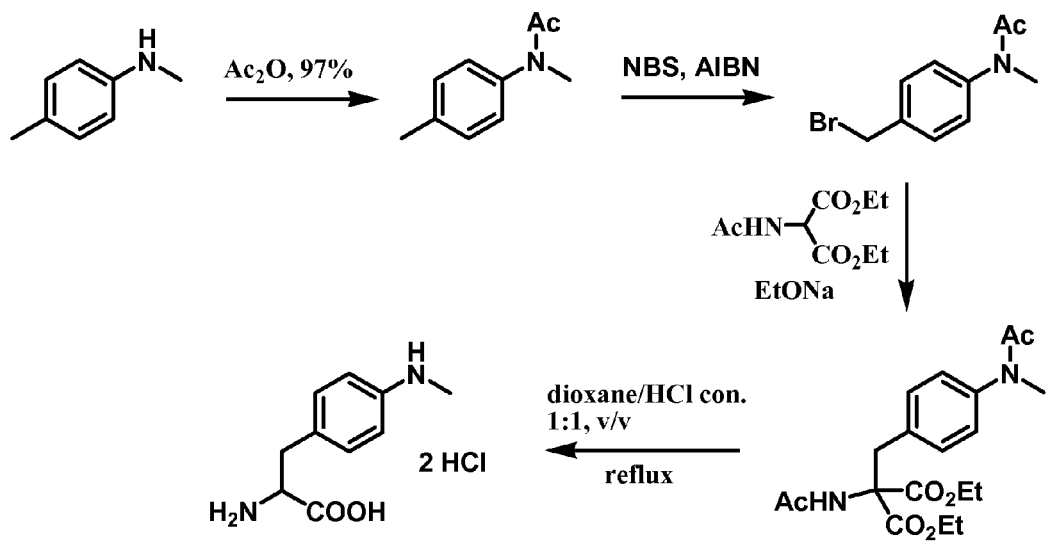
FIG. 13 presents an illustrative, non-limiting example of the synthetic methodology used to make the non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.
Figure 13:
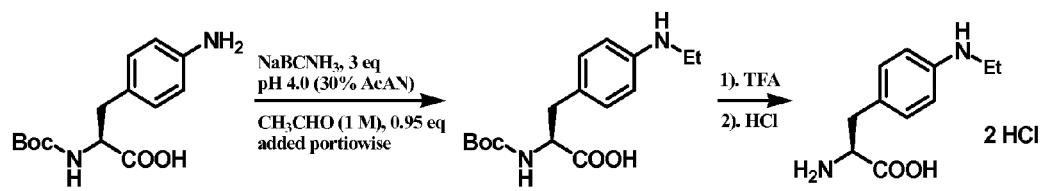

Non-limiting examples of syntheses of compounds of Formula (A) are shown in FIGS. 11-13. Such examples show the syntheses of non-natural amino acids containing aromatic amine moieties, wherein the amine moiety created is a primary or secondary amine. Such non-natural amino acids may be in the form of a salt, or may be incorporated into a non-natural amino acid polypeptide, polymer, polysaccharide, or a polynucleotide and optionally reductively alkylated.

Figure 14:
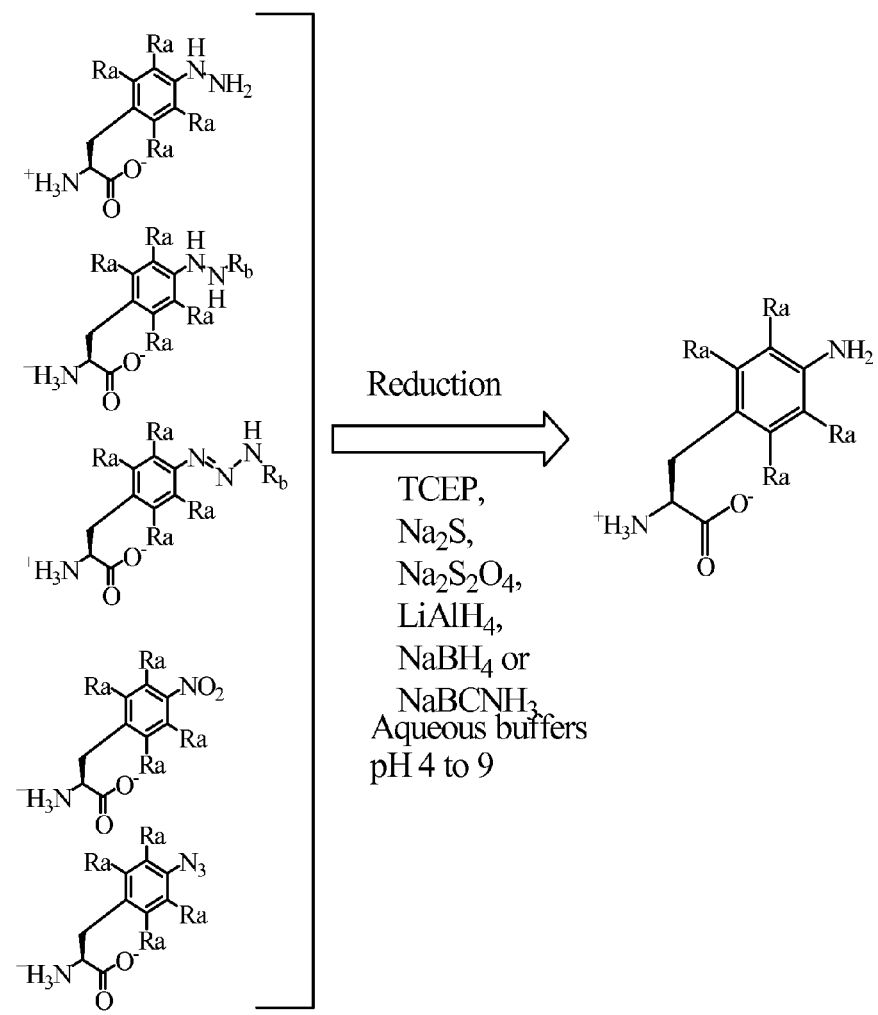
FIG. 14 presents illustrative, non-limiting examples of non-natural amino acids described herein which contain masked and/or protected amine moieties which can be converted to unmasked and/or deprotected amine moieties. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.
Figure 14:
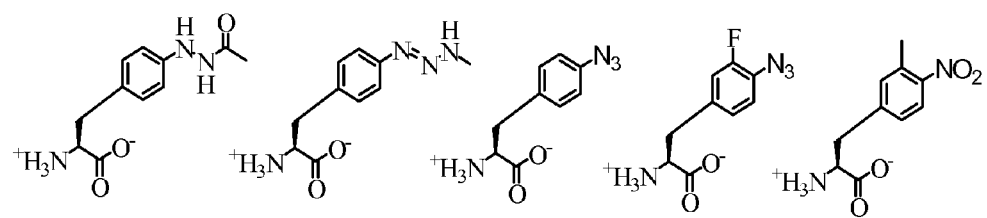

A non-limiting formation of an aromatic amine-containing non-natural amino acid having the structure of Formula (A) is shown in FIG. 14, wherein by way of example only, non-natural amino acids of Formula (A) may be formed by reduction of protected or masked amine moieties on the aromatic moiety of a non-natural amino acid. Such protected or masked amine moieties include, but are not limited to, imines, hydrazines, nitro, or azide substituents. The reducing agents used to reduce such protected or masked amine moieties include, but are not limited to, TCEP, Na$_2$S, Na$_2$S$_2$O$_4$, LiAlH$_4$, NaBH$_4$ or NaBCNH$_3$. Such non-natural amino acids containing the protected or masked amine moieties on an aromatic moiety have the structure of Formula (B),

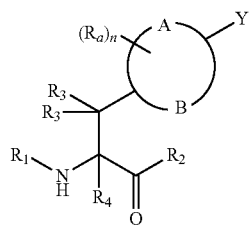

(B)

wherein:

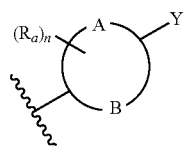

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently CR$_a$, or N;

B is independently CR$_a$, N, O, or S;

each R$_a$ is independently selected from the group consisting of H, halogen, alkyl, —NO$_2$, —CN, substituted alkyl, —N(R')$_2$, —C(O)$_k$R', —C(O)N(R')$_2$, —OR', and —S(O)$_k$R', where k is 1, 2, or 3; and n is 0, 1, 2, 3, 4, 5, or 6;

R$_1$ is H, an amino protecting group, resin, amino acid, polypeptide, or polynucleotide; and R$_2$ is OH, an ester protecting group, resin, amino acid, polypeptide, or polynucleotide;

each of R$_3$ and R$_4$ is independently H, halogen, lower alkyl, or substituted lower alkyl, or R$_3$ and R$_4$ or two R$_3$ groups optionally form a cycloalkyl or a heterocycloalkyl;

Y is —NH—NH$_2$, —NH—NHR', —CR'═NR', —NO$_2$, or —N$_3$, and each R' is independently H, alkyl, or substituted alkyl.

Such protected non-natural amino acids may be in the form of a salt, or may be incorporated into a non-natural amino acid polypeptide, polymer, polysaccharide, or polynucleotide.

The structure

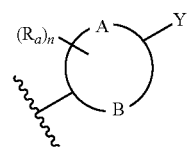

(as presented in all examples herein) does not present the relative orientations of "A," "B," "Y" and "R$_a$"; rather these four features of this structure may be oriented in any chemically-sound manner (along with other features of this structure), as illustrated by example herein.

Non-natural amino acids containing an aromatic amine moiety having the structure of Formula (B) include non-natural amino acids having the structures of Formula (VIII), Formula (IX), Formula (X), and Formula (XI),

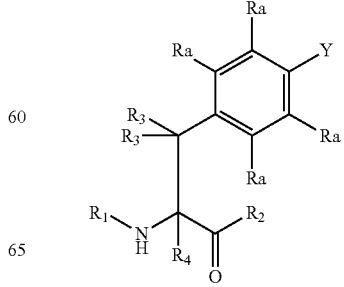

(VIII)

-continued

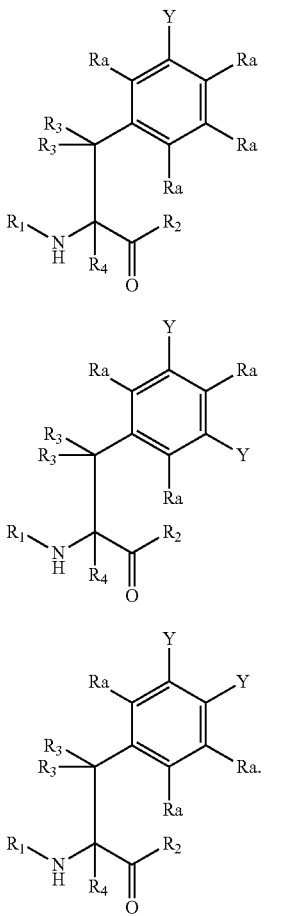

(IX)

(X)

(XI)

Such protected non-natural amino acids may be in the form of a salt, or may be incorporated into a non-natural amino acid polypeptide, polymer, polysaccharide, or polynucleotide. Such non-natural amino acids may also be translationally incorporated into a non-natural amino acid polypeptide and then post-translationally modified by reduction to form non-natural amino acids having the structure of Formula (A) as part of the non-natural amino acid polypeptide. In addition, non-natural amino acids having the structure of Formula (B) may also be incorporated into a polymer, polysaccharide, polynucleotide or chemically synthesized polypeptide, and are then reduced to form non-natural amino acids having the structure of Formula (A) as part of the polymer, polysaccharide, polynucleotide or chemically synthesized polypeptide. Such incorporated non-natural amino acids having the structure of Formula (A) may then be optionally reductively alkylated.

Figure 15:
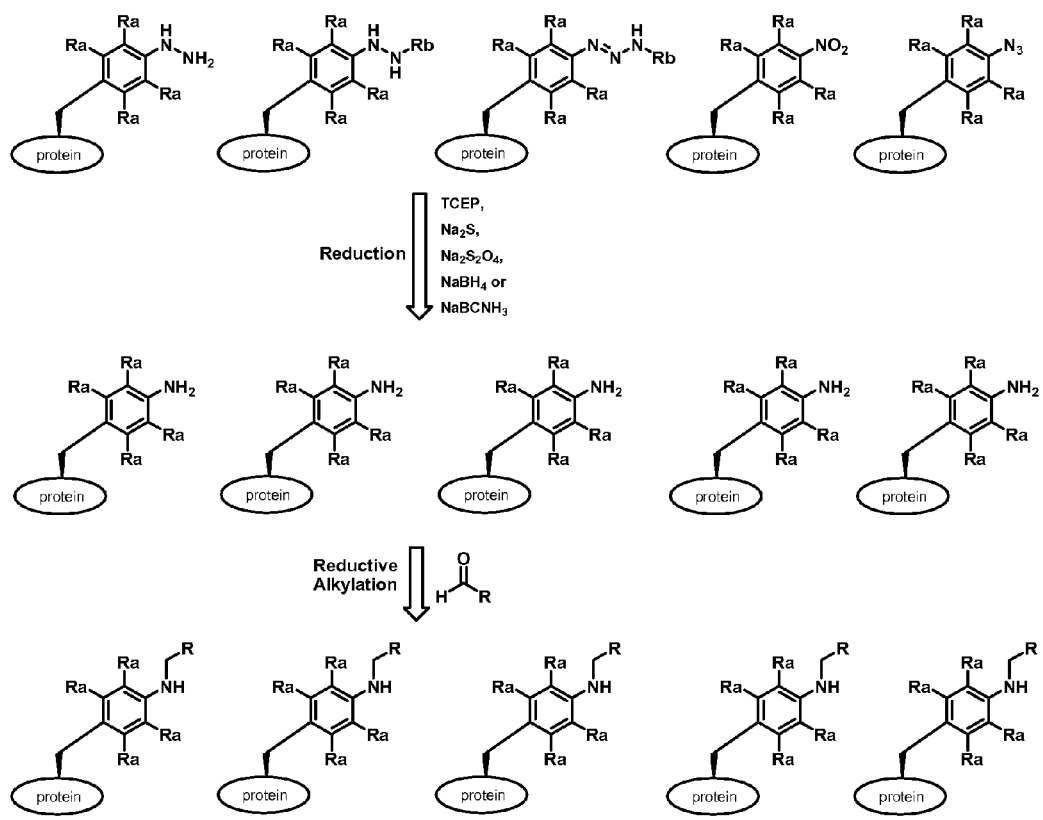
FIG. 15 presents illustrative, non-limiting examples of non-natural amino acids described herein which contain masked and/or protected amine side chains for reductive amination with an aldehyde-containing reagent. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.

Other non-limiting examples of such non-natural amino acids containing protected or masked amine moieties are shown in FIG. 15

B. Structure and Synthesis of Non-Natural Amino Acids: Alkylated Aromatic Amine Groups Non-natural amino acids with nucleophilic reactive groups, such as, by way of example only, an aromatic amine group (including secondary and tertiary amine groups), a masked aromatic amine group (which can be readily converted into a aromatic amine group), or a protected aromatic amine group (which has reactivity similar to a aromatic amine group upon deprotection) allow for a variety of reactions to link molecules via various reactions, including but not limited to, reductive alkylation reactions with aldehyde containing reagents. Such alkylated non-natural amino acids include amino acids having the structure of Formula (C):

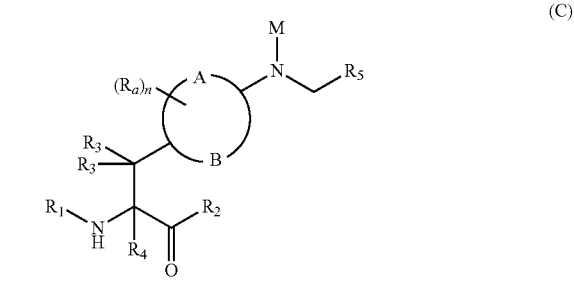

(C)

wherein:

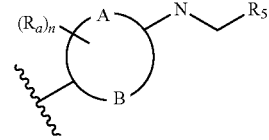

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently $CR_a$, or N;

B is independently $CR_a$, N, O, or S;

each $R_a$ is independently selected from the group consisting of H, halogen, alkyl, —$NO_2$, —CN, substituted alkyl, —$N(R')_2$, —$C(O)_kR'$, —$C(O)N(R')_2$, —OR', and —$S(O)_k$ R', where k is 1, 2, or 3; and n is 0, 1, 2, 3, 4, 5, or 6;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

M is H or —$CH_2R_5$; or the M-N—$C(R_5)$ moiety may form a 4 to 7 membered ring structure;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O) R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or R$_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—;

or two R$_5$ groups optionally form a cycloalkyl or a heterocycloalkyl;

or R$_5$ and any R$_a$ optionally form a cycloalkyl or a heterocycloalkyl; and each R' is independently H, alkyl, or substituted alkyl.

Such non-natural amino acids may also be in the form of a salt, or may be incorporated into a non-natural amino acid polypeptide, polymer, polysaccharide, or a polynucleotide and optionally reductively alkylated.

The structure

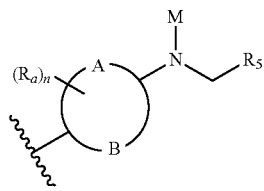

(as presented in all examples herein) does not present the relative orientations of "A," "B," "N(M)CH$_2$R$_5$" and "R$_a$"; rather these four features of this structure may be oriented in any chemically-sound manner (along with other features of this structure), as illustrated by example herein.

Non-natural amino acids containing an aromatic amine moiety having the structure of Formula (C) include non-natural amino acids having the structure of Formula (XII), Formula (XIII), Formula (XIV), Formula (XV), and Formula (XVI):

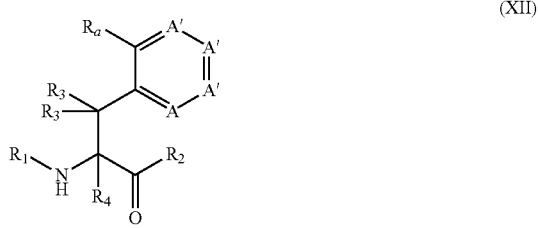

(XII)

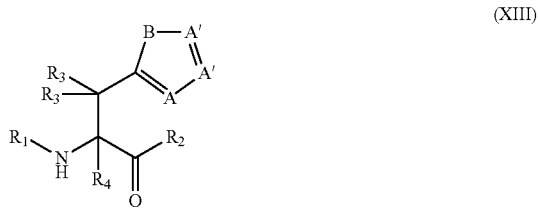

(XIII)

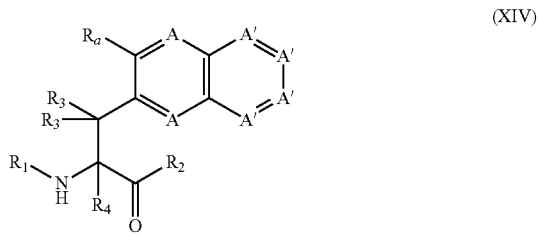

(XIV)

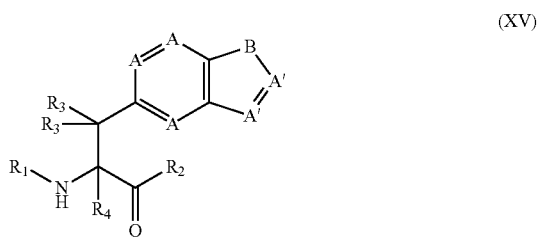

(XV)

-continued

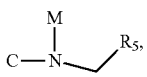
(XVI)

wherein, each A' is independently selected from $CR_a$, N, or

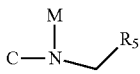

and up to two A' may be

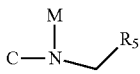

with the remaining A' selected from $CR_a$, or N.

Such non-natural amino acids may also be in the form of a salt, or may be incorporated into a non-natural amino acid polypeptide, polymer, polysaccharide, or a polynucleotide and optionally reductively alkylated.

Figure 8:
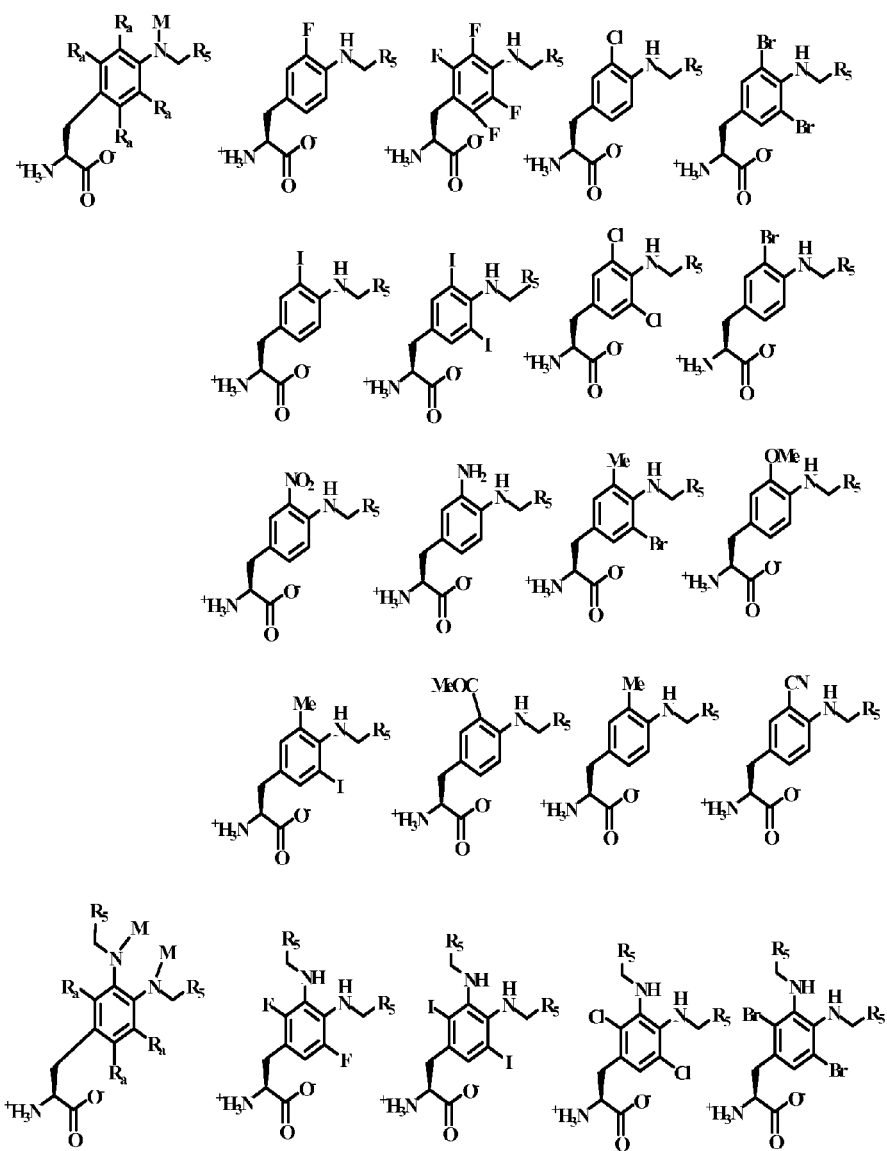
FIG. 8 presents illustrative, non-limiting examples of the types of non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.
Figure 9:
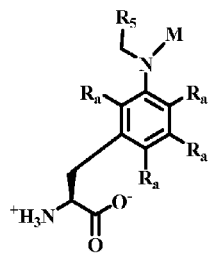
FIG. 9 presents illustrative, non-limiting examples of the types of non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein. For FIG. 9 only, X represents a halogen.
Figure 9:
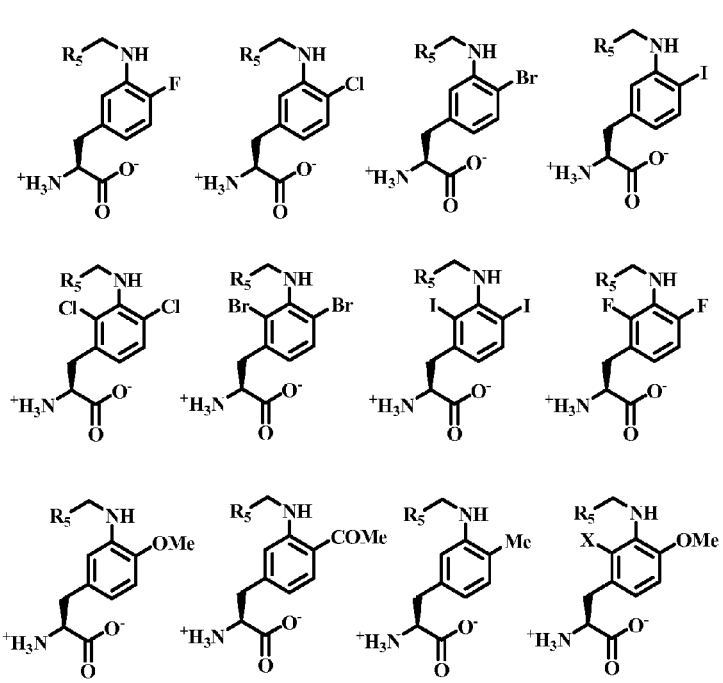
Figure 9:
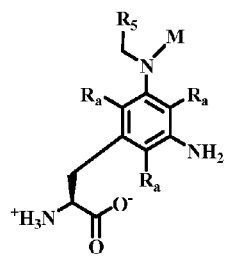
Figure 9:
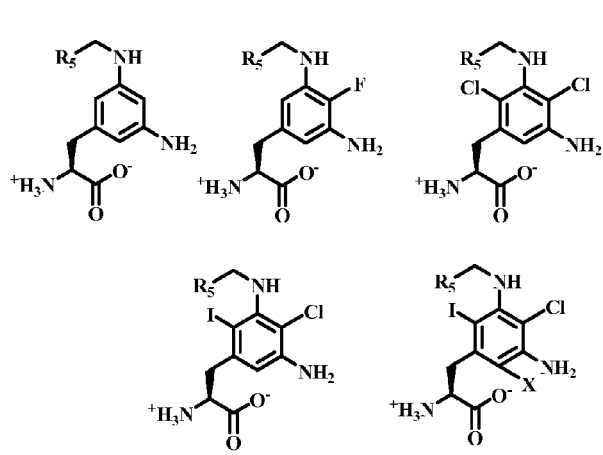
Figure 10:
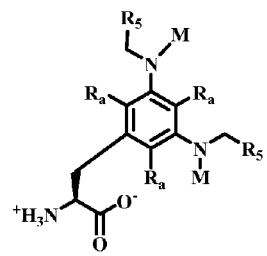
FIG. 10 presents illustrative, non-limiting examples of the types of non-natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.
Figure 10:
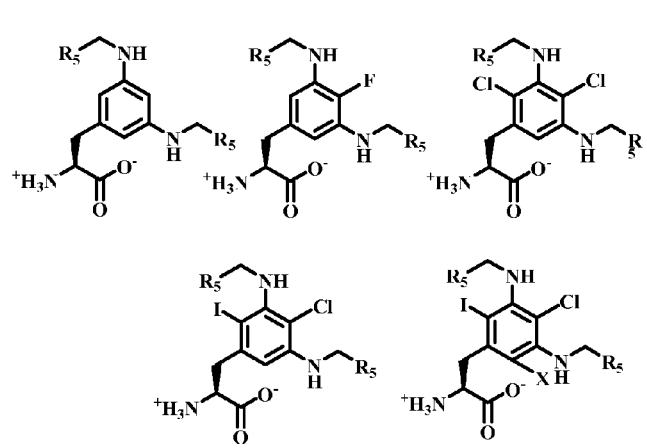
Figure 10:
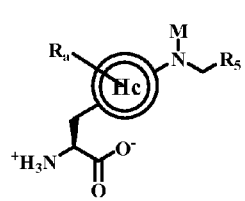
Figure 10:
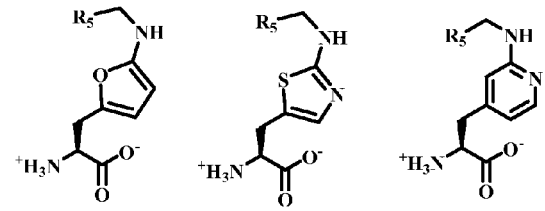
Figure 10:
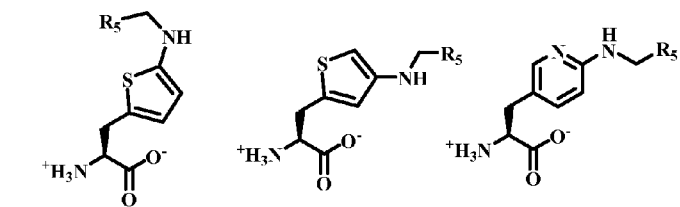
Figure 10:
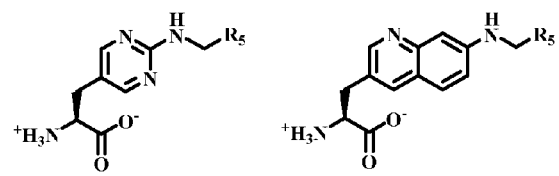

Other non-limiting examples of non-natural amino acids containing an aromatic amine moiety having the structure of Formula (C) are shown in FIGS. 8-10. Such non-natural amino acids may also be in the form of a salt, or may be incorporated into a non-natural amino acid polypeptide, polymer, polysaccharide, or a polynucleotide and optionally reductively alkylated.

Compounds of Formula (C) may be formed by the reductive alkylation of compounds of Formula (A) with carbonyl containing reagents such as, by way of example, ketones, esters, thioesters, and aldehydes. By way of example, such aldehyde containing reagents may have the structure corresponding to

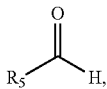

wherein;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or $R_5$ is L-X, where, X is a selected from the group consisting of: a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$ (alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—; each R' is independently H, alkyl, or substituted alkyl.

Other non-natural amino acids having the structure of Formula (B) are non-limiting examples described herein:

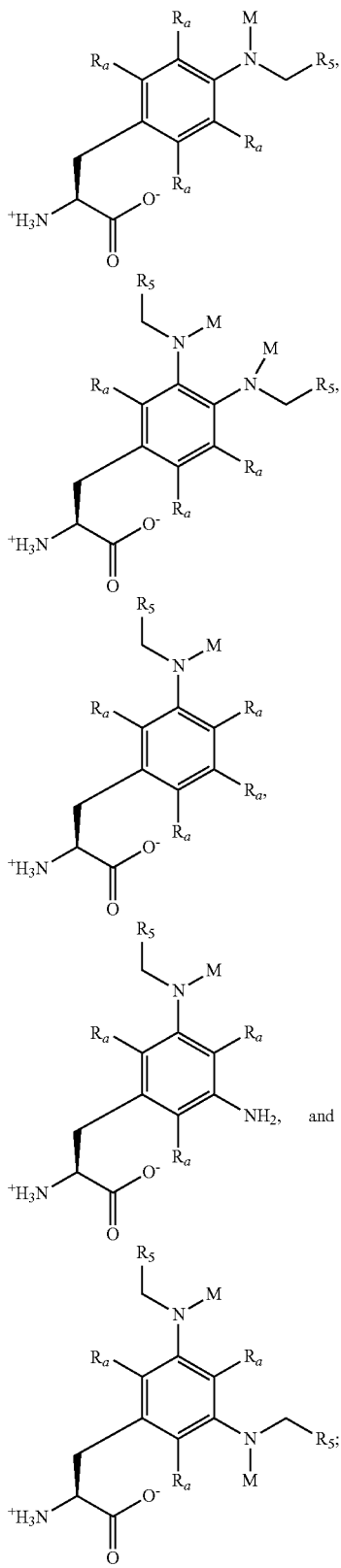

wherein each $R_a$ is independently selected from the group consisting of H, halogen, alkyl, —$NO_2$, —CN, substituted alkyl, —$N(R')_2$, —$C(O)_kR'$, —$C(O)N(R')_2$, —OR', and —$S(O)_kR'$, where k is 1, 2, or 3;

M is H or —$CH_2R_5$; or the M-N—$C(R_5)$ moiety may form a 4 to 7 membered ring structure;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —$C(O)N(R")_2$, —$C(O)NHCH(R")_2$, -(alkylene or substituted alkylene)-$N(R")_2$, -(alkenylene or substituted alkenylene)-$N(R")_2$, -(alkylene or substituted alkylene)-(aryl or substituted aryl), -(alkenylene or substituted alkenylene)-(aryl or substituted aryl), -(alkylene or substituted alkylene)-$ON(R")_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or $R_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—;

or R$_5$ and any R$_a$ optionally form a cycloalkyl or a heterocycloalkyl; and each R' is independently H, alkyl, or substituted alkyl.

The following non-natural amino acids having the structure of Formula (C) are non-limiting examples of alkylated non-natural amino acids described herein:

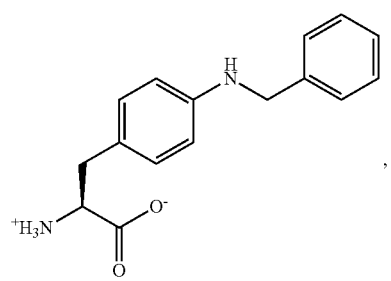

,

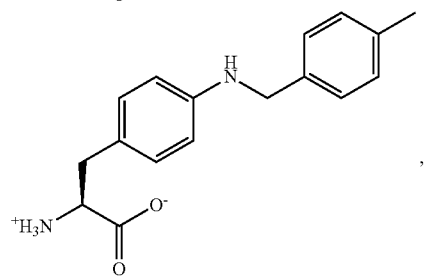

,

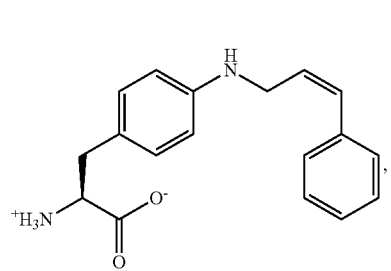

,

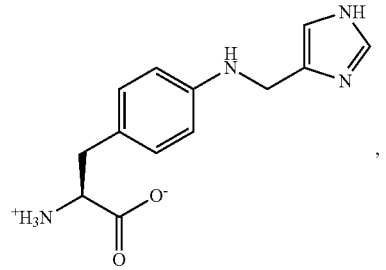

,

-continued

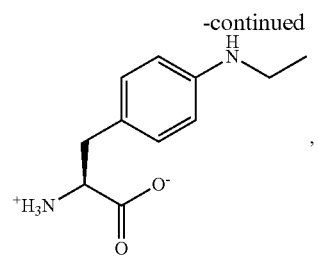

,

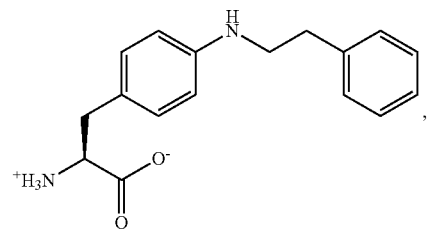

,

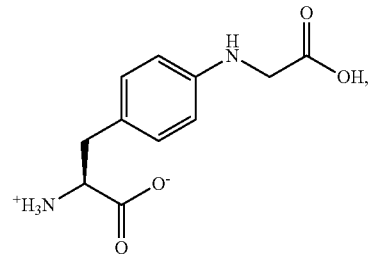

,

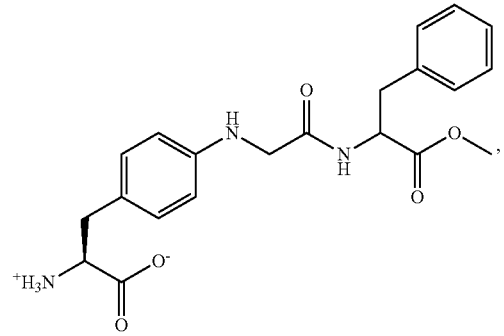

,

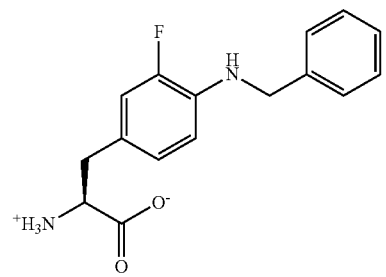

,

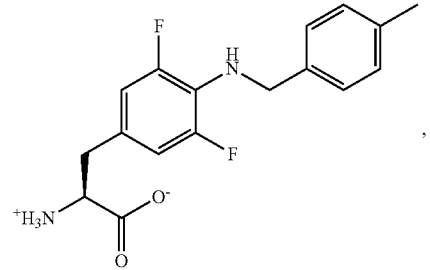

,

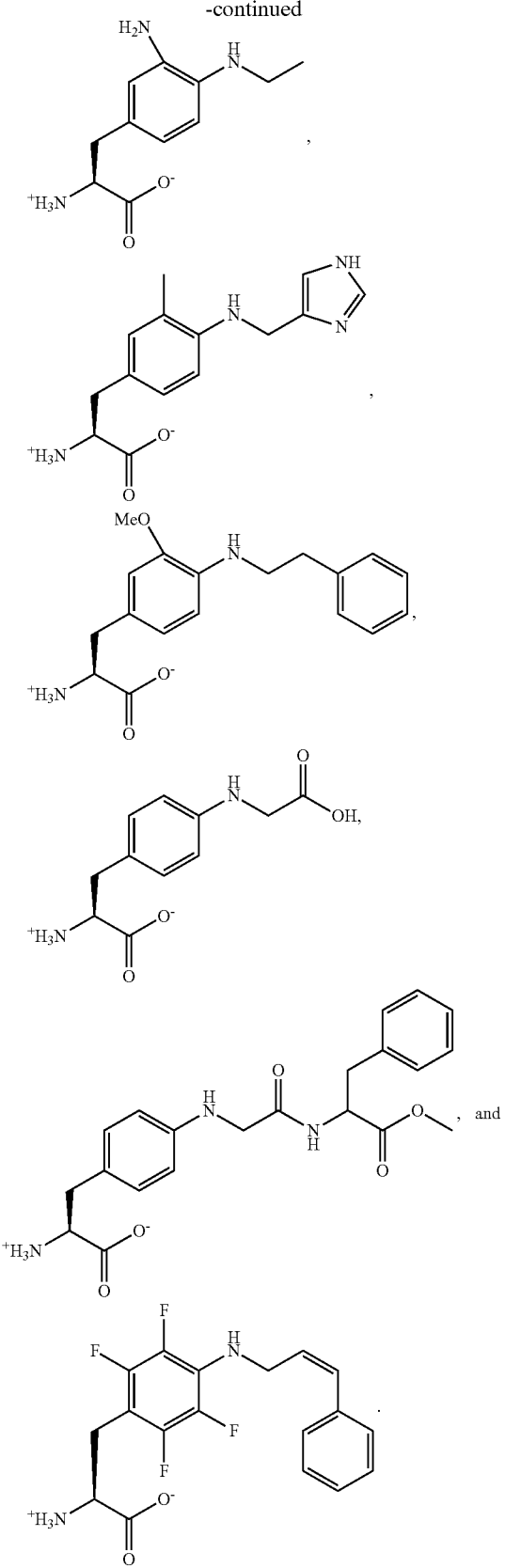

Such non-natural amino acids may also be in the form of a salt, or may be incorporated into a non-natural amino acid polypeptide, polymer, polysaccharide, or a polynucleotide and optionally reductively alkylated.

Non-limiting exemplary syntheses of non-natural amino acid polypeptides containing amino acids of Formula (C) is presented in FIG. 15, wherein the masked amine moieties of non-natural amino acids Formula (B) contained in polypeptides are initially reduced to give non-natural amino acids of Formula (A) containing aromatic amine moieties incorporated into non-natural amino acid polypeptides. Such aromatic amine moieties are then reductive alkylated with carbonyl-containing reagents described above to give polypeptides containing non-natural amino acids of Formula (C). Such reactions may also be applied to non-natural amino acids incorporated into synthetic polymers, polysaccharides, or polynucleotides. Additionally, such reactions may be applied to non-incorporated non-natural amino acids. By way of example the reducing agent used to reduce masked amine moieties includes, but is not limited to, TCEP, $Na_2S$, $Na_2S_2O_4$, $LiAlH_4$, $B_2H_6$, and $NaBH_4$. By way of example only, reductive alkylation may occur in aqueous buffers with a pH of about 4 to about 7 and using a mild reducing agent, such as, by way of example only, sodium cyanoborohydride ($NaBCNH_3$). In addition, other reducing agents may be used for reductive alkylation including, but not limited to, TCEP, $Na_2S$, $Na_2S_2O_4$, $LiAlH_4$, $B_2H_6$, and $NaBH_4$.

Figure 16:
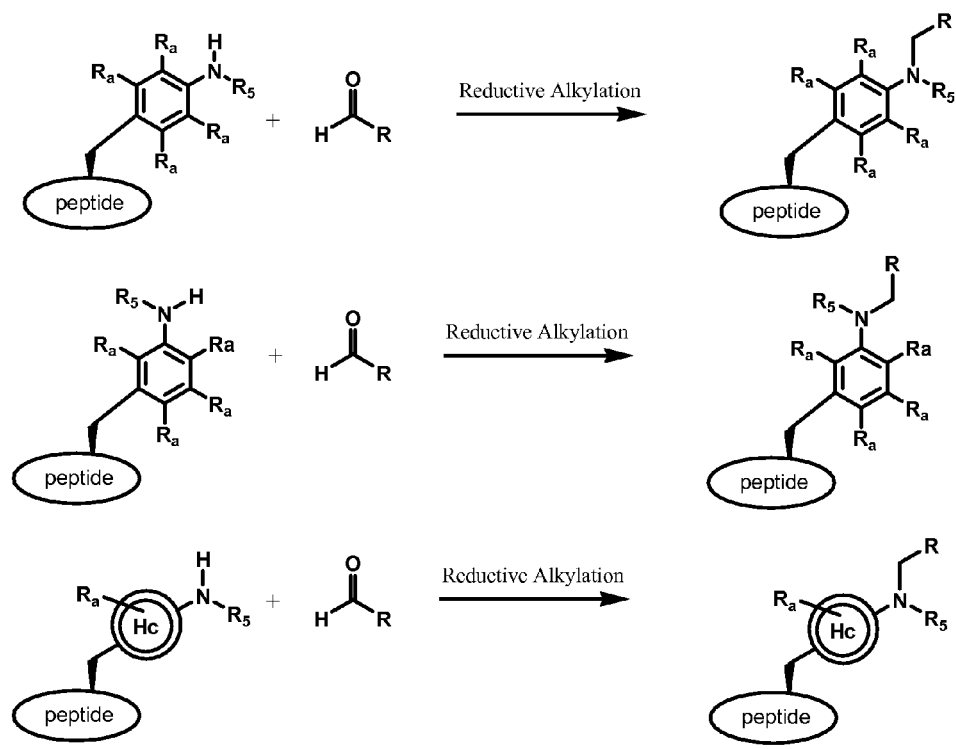
FIG. 16 presents illustrative, non-limiting examples of the formation of polypeptides with aromatic amine-containing non-natural amino acids by reductive alkylations with aldehyde-containing reagents.

Presented in FIG. 16 are non-limiting exemplary syntheses of non-natural amino acid polypeptides containing amino acids of Formula (C) by reductive alkylation of secondary aromatic amine moieties, contained in non-natural amino acids of Formula (A), with carbonyl-containing reagents described above. Such reductive alkylations give polypeptides containing non-natural amino acids with tertiary aromatic amine moieties. Such reactions may also be applied to non-natural amino acids incorporated into synthetic polymers, polysaccharides, or polynucleotides. Additionally, such reactions may be applied to non-incorporated non-natural amino acids. By way of example only, reductive alkylation may occur in aqueous buffers with a pH of about 4 to about 7 and using a mild reducing agent, such as, by way of example only, sodium cyanoborohydride ($NaBCNH_3$). In addition, other reducing agents may be used for reductive alkylation including, but not limited to, TCEP, $Na_2S$, $Na_2S_2O_4$, $LiAlH_4$, $B_2H_6$, and $NaBH_4$.

Compounds of Formula (C) may also be formed by the reductive alkylation of compounds of Formula (A) with reagents containing at least two carbonyl moieties, including, but not limited to, diketones, ketoaldehydes and dialdehydes. By way of example, such reagents may have the structure corresponding to

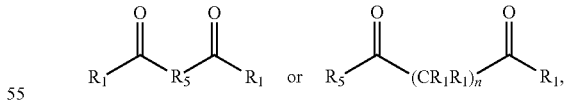

wherein;
each $R_1$ is independently selected from H, optionally substituted alkyl, optionally substituted alkene, optionally substituted alkyne, optionally substituted cycloalkyl, optionally substituted heterocycle, optionally substituted aryl, or optionally substituted heteroaryl;
$R_5$ is alkylene, substituted alkylene, alkenylene, substituted alkenylene, alkynylene, substituted alkynylene, polyalkylene oxide, substituted polyalkylene oxide, cycloalkylene, substituted cycloalkylene, arylene, substituted arylene, heteroarylene, substituted heteroarylene, heterocycloalkylene, substituted heterocycloalkylene, —C(O)R"—C(O)OR"—, —C(O)N(R")—, -(alkylene or substituted alkylene)-N(R")-(alkenylene or substituted alkenylene)-N(R")—, -(alkylene or substituted alkylene)-ON(R")—, -(alkylene or substituted alkylene)-C(O)SR"—, wherein each R" is independently hydrogen, alkyl, substituted alkyl, alkenyl, substituted alkenyl, alkoxy, substituted alkoxy, substituted alkylene, alkenylene, substituted alkenylene, alkynylene, substituted alkynylene, aryl, substituted aryl, heteroaryl, substituted heteroaryl, heterocycle, substituted heterocycle, alkaryl, substituted alkaryl, aralkyl, or substituted aralkyl;

or R$_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')

C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—; each R' is independently H, alkyl, or substituted alkyl; n is 1, 2, or 3.

C. Structure and Synthesis of Non-Natural Amino Acids: Aminated Amino Acids

Non-natural amino acids with electrophilic reactive groups, such as, by way of example only, an aldehyde group, a masked aldehyde group (which is a functional group which can be readily converted into an aldehyde group), or a protected aldehyde group (which has reactivity similar to an aldehyde group upon deprotection) allow for a variety of reactions to link molecules via various reactions, including but not limited to, reductive amination reactions with aromatic amine containing reagents. Such aminated non-natural amino acids include amino acids having the structure of Formula (D):

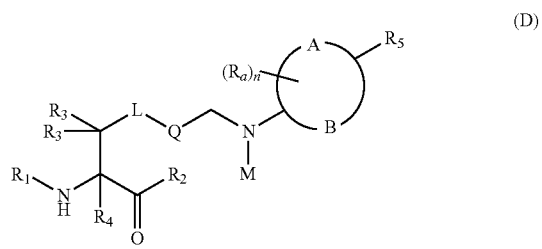

(D)

wherein:

L is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

Q is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R")-(alkylene or substituted alkylene)-, —CSN(R")—, —CSN(R')-(alkylene or substituted alkylene)-, —N(R')CO—, —N(R')CO-(alkylene or substituted alkylene)-, —N(R')C(O)O—, —S(O)$_k$N(R')—, —N(R')C(O)N(R')—, —N(R')C(S)N(R')—, —N(R")S(O)$_k$N(R')—, —N(R')—N═, —C(R")═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R$_1$ is H, an amino protecting group, resin, amino acid, polypeptide, or polynucleotide; and R$_2$ is OH, an ester protecting group, resin, amino acid, polypeptide, or polynucleotide;

each of R$_3$ and R$_4$ is independently H, halogen, lower alkyl, or substituted lower alkyl, or R$_3$ and R$_4$ or two R$_3$ groups optionally form a cycloalkyl or a heterocycloalkyl;

each $R_a$ is independently selected from the group consisting of H, halogen, alkyl, —NO$_2$, —CN, substituted alkyl, —N(R')$_2$, —C(O)$_k$R', —C(O)N(R')$_2$, —OR', and —S(O)$_k$R', where k is 1, 2, or 3;

M is H or —CH$_2$R$_5$;

R$_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R'', —C(O)OR'', —C(O)N(R'')$_2$, —C(O)NHCH(R'')$_2$, -(alkylene or substituted alkylene)-N(R'')$_2$, -(alkenylene or substituted alkenylene)-N(R'')$_2$, -(alkylene or substituted alkylene)-(aryl or substituted aryl), -(alkenylene or substituted alkenylene)-(aryl or substituted aryl), -(alkylene or substituted alkylene)-ON(R'')$_2$, -(alkylene or substituted alkylene)-C(O)SR'', -(alkylene or substituted alkylene)-S—S-(aryl or substituted aryl), wherein each R'' is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or R$_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—;

or R$_5$ and any R$_a$ optionally form a cycloalkyl or a heterocycloalkyl;

each R' is independently H, alkyl, or substituted alkyl;

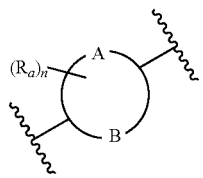

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently CR$_a$, or N; and

B is independently CR$_a$, N, O, or S.

The structure

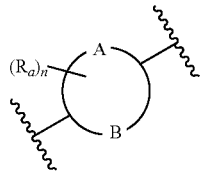

(as presented in all examples herein) does not present the relative orientations of "A," "B," "R$_a$," and the other substituent represented by the line and squiggle; rather these four features of this structure may be oriented in any chemically-sound manner (along with other features of this structure), as illustrated by example herein.

One embodiment of the non-natural amino acid containing a protected aldehyde moiety has the structure of Formula (E),

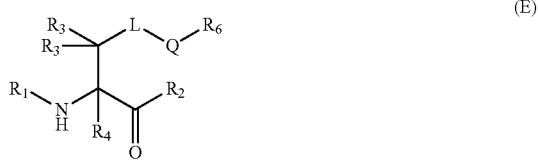

(E)

wherein:

L is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

Q is optional, and when present is a linker selected from the group consisting of lower alkylene, substituted lower alkylene, lower alkenylene, substituted lower alkenylene, lower heteroalkylene, substituted lower heteroalkylene, —O-(alkylene or substituted alkylene)-, —S-(alkylene or substituted alkylene)-, where k is 1, 2, or 3, —S(O)$_k$-(alkylene or substituted alkylene)-, —C(O)-(alkylene or substituted alkylene)-, —C(S)-(alkylene or substituted alkylene)-, —NR'-(alkylene or substituted alkylene)-, —CON(R")-(alkylene or substituted alkylene)-, —CSN(R")—, —CSN(R')-(alkylene or substituted alkylene)-, —N(R')CO-(alkylene or substituted alkylene)-, and where each R' is independently H, alkyl, or substituted alkyl;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

each $R_a$ is independently selected from the group consisting of H, halogen, alkyl, —NO$_2$, —CN, substituted alkyl, —N(R')$_2$, —C(O)$_k$R', —C(O)N(R')$_2$, —OR', and —S(O)$_k$R', where k is 1, 2, or 3;

$R_6$ is an aldehyde, a protected aldehyde or a masked aldehyde, wherein the protecting group includes, but is not limited to,

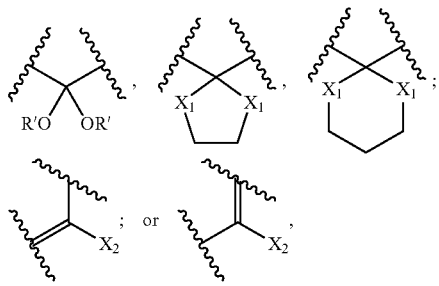

where each $X_1$ is independently selected from the group consisting of —O—, —S—, —N(H)—, —N(R)—, —N(Ac)—, and —N(OMe)-; $X_2$ is —OR, —OAc, —SR, —N(R)$_2$, —N(R)(Ac), —N(R)(OMe), or N$_3$, and where each R' and R is independently H, alkyl, or substituted alkyl. Such non-natural amino acids may also be in the form of a salt, or may be incorporated into a non-natural amino acid polypeptide, polymer, or a polynucleotide. Such non-natural amino acids may also be incorporated into a non-natural amino acid polypeptide and then post-translationally modified by deprotecting to form an aldehyde group "in-situ" followed by reductive amination of the aldehyde with an aromatic amine containing reagent, thereby forming non-natural amino acids having the structure of Formula (D) as part of the non-natural amino acid polypeptide. In addition, non-natural amino acids having the structure of Formula (E) may also be incorporated into a polymer or a polynucleotide and are deprotecting to form an aldehyde group "in-situ" followed by reductive amination of the aldehyde with an aromatic amine containing reagent thereby forming non-natural amino acids having the structure of Formula (D) as part of the polymer, or polynucleotide.

Figure 17:
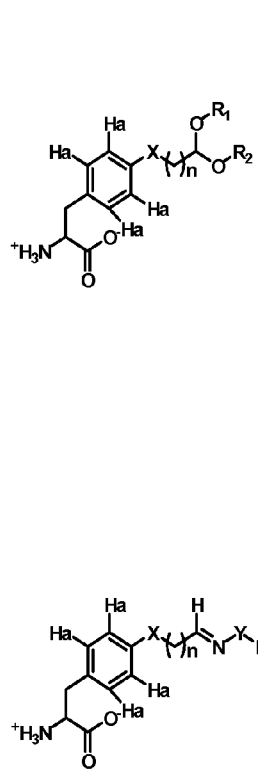
FIG. 17 presents illustrative, non-limiting examples of aromatic protected aldehyde containing non natural amino acids described herein. Such non-natural amino acids may be used in or incorporated into any of the methods, compositions, techniques and strategies for making, purifying, characterizing, and using non-natural amino acids, non-natural amino acid polypeptides and modified non-natural amino acid polypeptides described herein.
Figure 17:
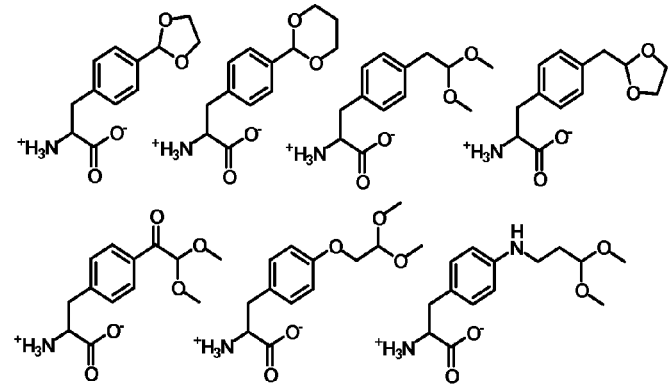
Figure 17:
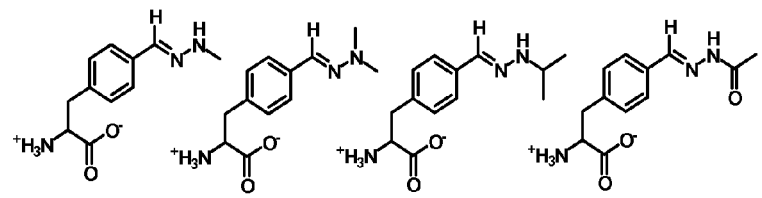
Figure 17:
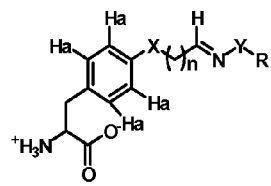
Figure 17:
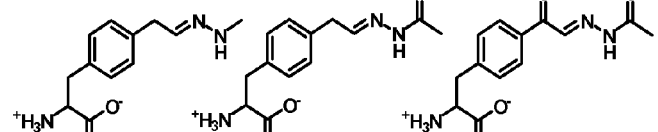
Figure 17:
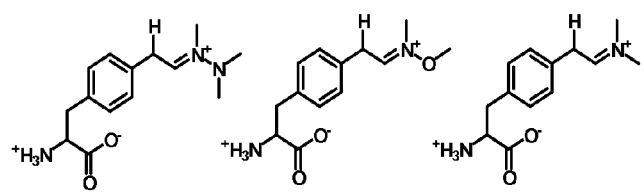

Non-limiting examples of such non-natural amino acids containing protected aldehyde moieties are shown in FIG. 17.

Compounds of Formula (D) may be formed, after deprotection of the aldehyde group of compounds of Formula (E), followed by the reductive amination of compounds of Formula (D) with aromatic amine containing reagents. Such aromatic amine containing reagents have the structure corresponding to

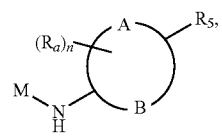

wherein,

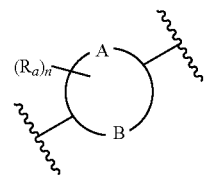

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently CR$_a$, or N; and

B is independently CR$_a$, N, O, or S.

each $R_a$ is independently selected from the group consisting of H, halogen, alkyl, —NO$_2$, —CN, substituted alkyl, —N(R')$_2$, —C(O)$_k$R', —C(O)N(R')$_2$, —OR', and —S(O)$_k$R', where k is 1, 2, or 3; n is 0, 1, 2, 3, 4, 5, or 6;

M is H or —CH$_2$R$_5$;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or $R_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—; wherein each R' is independently hydrogen, alkyl, substituted alkyl, alkenyl, substituted alkenyl, alkoxy, substituted alkoxy, substituted alkylene, alkenylene, substituted alkenylene, alkynylene, substituted alkynylene, aryl, substituted aryl, heteroaryl, substituted heteroaryl, heterocycle, substituted heterocycle, alkaryl, substituted alkaryl, aralkyl, or substituted aralkyl.

Figure 18:
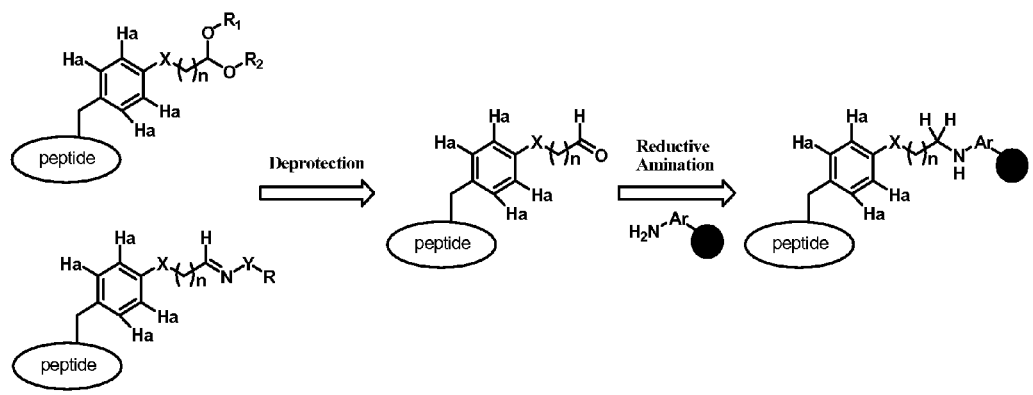
FIG. 18 presents illustrative, non-limiting examples of the formation of polypeptides with aldehyde-containing non-natural amino acids by post-translational deprotecting/unmasking of a protected/masked precursor followed by reductive aminations with aromatic amine-containing reagents.

A non-limiting exemplary synthesis of non-natural amino acid polypeptides containing amino acids of Formula (D) as presented in FIG. 18, wherein protected aldehyde moieties of non-natural amino acids of Formula (E) contained in polypeptides are initially deprotected to give non-natural amino acids containing aldehyde moieties incorporated into non-natural amino acid polypeptides. Such aldehyde moieties are then reductively aminated with aromatic amine-containing reagents described above to give polypeptides containing non-natural amino acids of Formula (D). Such reactions may also be applied to non-natural amino acids incorporated into synthetic polymers, polysaccharides, or polynucleotides. Additionally, such reactions may be applied to non-incorporated non-natural amino acids. By way of example the protected aldehyde is deprotected by acid catalyzed deprotection. By way of example only, reductive amination may occur in aqueous buffers with a pH of about 4 to about 7 and using a mild reducing agent, such as, by way of example only, sodium cyanoborohydride (NaBCNH$_3$). In addition, other reducing agents may be used for reductive alkylation including, but not limited to, TCEP, Na$_2$S, Na$_2$S$_2$O$_4$, LiAlH$_4$, B$_2$H$_6$, and NaBH$_4$.

Figure 19:
FIG. 19 presents illustrative, non-limiting examples of the site selective reductive alkylation and reductive amination of non-natural amino acid polypeptides.
Figure 19:

Shown in FIG. 19 are a non-limiting representation of the formation of non-natural amino acids of Formula (C) by reductive alkylation of the aromatic amine moiety of non-natural amino acids of Formula (A), and a non-limiting representation of the formation of non-natural amino acids of Formula (D) by reductive amination of a deprotected aldehyde moiety on non-natural amino acids of Formula (E). Depicted in FIG. 19 is the specificity and selectivity of the reductive alkylation reaction, wherein only the aromatic amine moiety of non-natural amino acids of Formula (A) is reductively alkylated while other amine moieties, thiols and disulfide bonds are not reduced or do not react under the reaction conditions used. Also depicted in FIG. 19 is the specificity and selectivity of the reductive amination reaction, wherein only the deprotected aldehyde moiety of non-natural amino acids of Formula (E) is reductively aminated while other carboxylate moieties, thiols and disulfide bonds are not reduced or do not react under the reaction conditions used. Such selective, site-specific derivatizations, reductive alkylation or reductive amination reactions may allow for modification of polypeptides/proteins to design agonists and/or antagonists, site-specific pegylation of polypeptides/proteins, site-specific conjugation of polypeptides/proteins, prodrug design, polypeptide/protein glycosylation, polypeptide/protein dimerization, small molecule drug conjugates of polypeptides/proteins, and small molecule drug conjugates of antibodies.

Modification of non-natural amino acids described herein using reductive alkylation or reductive amination reactions have any or all of the following advantages. First, aromatic amines can be reductively alkylated with carbonyl-containing compounds, including aldehydes, and ketones, in a pH range of about 4 to about 10 (and in certain embodiments in a pH range of about 4 to about 7) to generate substituted amine, including secondary and tertiary amine, linkages. Second, under these reaction conditions the chemistry is selective for non-natural amino acids as the sidechains of naturally occurring amino acids are unreactive. This allows for site-specific derivatization of polypeptides which have incorporated non-natural amino acids containing aromatic amine moieties or protected aldehyde moieties, including, by way of example, recombinant proteins. Such derivatized polypeptides and proteins can thereby be prepared as defined homogeneous products. Third, the mild conditions needed to effect the reaction of an aromatic amine moiety on an amino acid, which has been incorporated into a polypeptide, with an aldehyde-containing reagent generally do not irreversibly destroy the tertiary structure of the polypeptide (excepting, of course, where the purpose of the reaction is to destroy such tertiary structure). Similarly, the mild conditions needed to effect the reaction of an aldehyde moiety on an amino acid, which has been incorporated into a polypeptide and deprotected, with an aromatic amine-containing reagent generally do not irreversibly destroy the tertiary structure of the polypeptide (excepting, of course, where the purpose of the reaction is to destroy such tertiary structure). Fourth, the reaction occurs rapidly at room temperature, which allows the use of many types of polypeptides or reagents that would otherwise be unstable at higher temperatures. Fifth, the reaction occurs readily is aqueous conditions, again allowing use of polypeptides and reagents incompatible (to any extent) with non-aqueous solutions. Six, the reaction occurs readily even when the ratio of polypeptide or amino acid to reagent is stoichiometric, stoichiometric-like, or near-stoichiometric, so that it is unnecessary to add excess reagent or polypeptide to obtain a useful amount of reaction product. Seventh, the resulting amine can be produced regioselectively and/or regiospecifically, depending upon the design of the amine and carbonyl portions of the reactants. Finally, the reductive alkylation of aromatic amines with aldehyde-containing reagents, and the reductive amination of aldehydes with aromatic amine containing reagents, generates amine, including secondary and tertiary amine, linkages which are stable under biological conditions.

Figure 20:
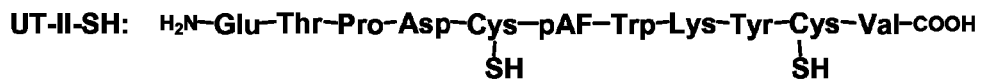
FIG. 20 presents illustrative, non-limiting examples of the reductive alkylations of reduced urotension-II (UT-II-SH) with propionaldehyde (I) and benzaldehyde (II) and the corresponding HPLC chromatograms.
Figure 20:
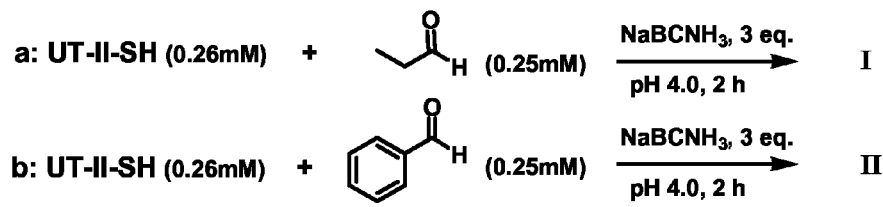
Figure 20:
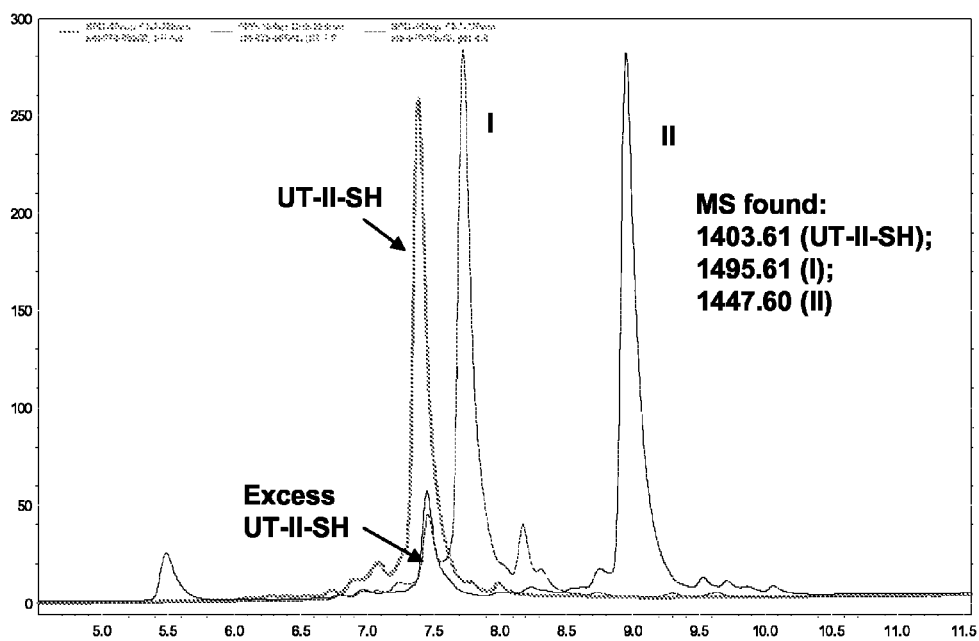

Shown in FIG. 20 are non-limiting examples of the specificity and selectivity of the reductive alkylation of aromatic amine moieties on amino acid residues next to a cysteine residue. The reductive alkylation of reduced urotensin-II (UT-II-SH) with propionaldehyde (I) or benzaldehyde (II) demonstrates that one product is predominantly formed from the respective reactions, and that the free thiol group did not react. Also shown in FIG. 20 are the speed of the reactions, which was about 2 hours, and the stoichiometric or near-stoichiometric relationship between the reduced urotensin-II (UT-II-SH) and the respective aldehyde containing reagents. Additionally, the MS data for UT-II-SH, I, and II are presented.

Figure 21:
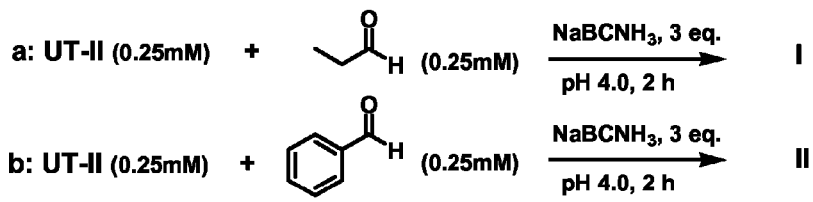
FIG. 21 presents illustrative, non-limiting examples of reductive alkylations of urotension-II (UT-II) with propionaldehyde (I) and benzaldehyde (II) and the corresponding HPLC chromatograms.
Figure 21:
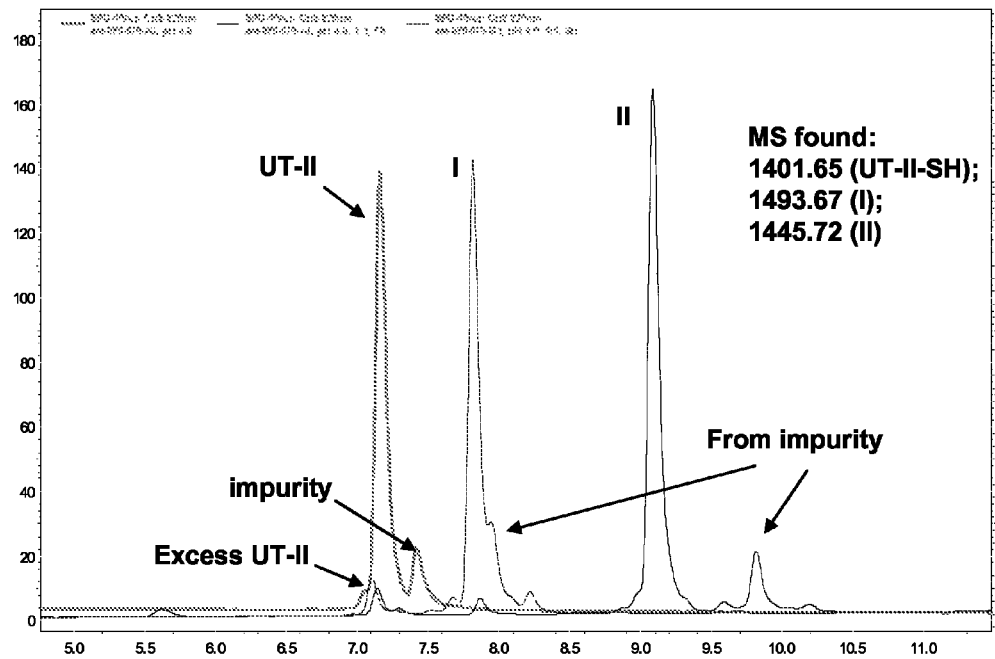

Shown in FIG. 21 are non-limiting examples of the specificity and selectivity of the reductive alkylation of aromatic amine moieties on amino acid residues next to a cysteine residue. The reductive alkylation of urotensin-II (UT-II) with propionaldehyde (I) or benzaldehyde (II) demonstrates that one product was predominantly formed from the respective reactions, and that the disulfide bond did not react. Also shown in FIG. 21 are the speed of the reactions, which was about 2 hours, and the stoichiometric or near-stoichiometric relationship between the urotensin-II (UT-II) and the respective aldehyde containing reagents. Additionally, the MS data for UT-II-SH, I, and II are presented.

Figure 22:
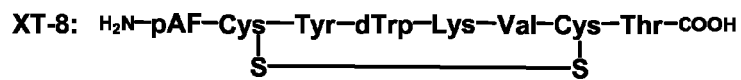
FIG. 22 presents illustrative, non-limiting examples of reductive alkylations of peptide XT-8 with propionaldehyde (I) and benzaldehyde (II), isobutaldehyde (III) and pivalaldehyde (IV) and the corresponding HPLC chromatograms.
Figure 22:
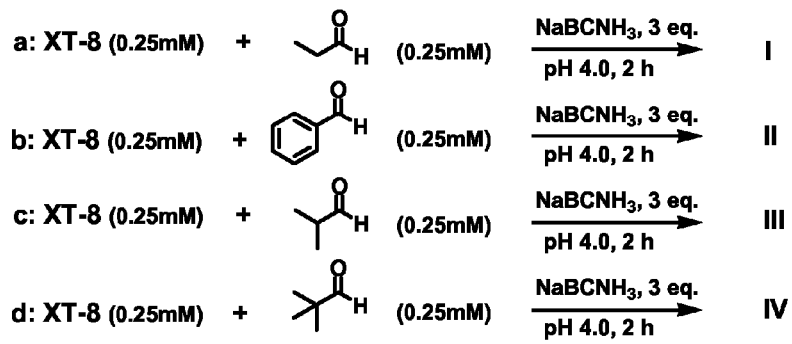
Figure 22:
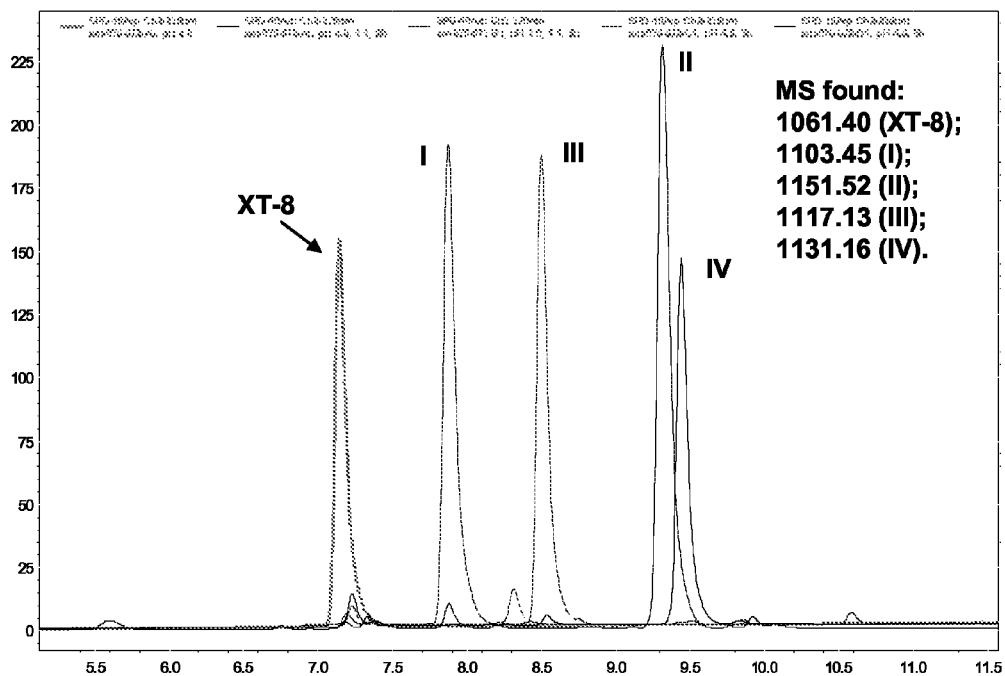

Further non-limiting examples of the specificity and selectivity of the reductive alkylation reactions of aromatic amine moieties on terminal amino acid residues are shown in FIG. 22, wherein the reductive alkylation of peptide XT-8 with propionaldehyde (I), benzaldehyde (II), isobutaldehyde (III) and pivalaldehyde (IV), demonstrates that one product was predominantly formed from the respective reactions, and that the disulfide bond did not react. Also shown in FIG. 22 are the speed of the reactions, which was about 2 hours, and the stoichiometric or near-stoichiometric relationship between the XT-8 and the respective aldehyde containing reagents. Additionally, the MS data for XT-8, I, II, III, and IV are presented.

Figure 23:
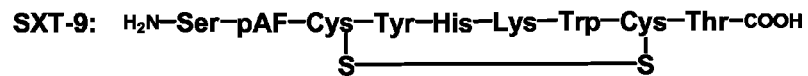
FIG. 23 presents illustrative, non-limiting examples of reductive alkylations of peptide SXT-9 with propionaldehyde (I), benzaldehyde (II), isobutaldehyde (III) and pivalaldehyde (IV) and the corresponding HPLC chromatograms.
Figure 23:
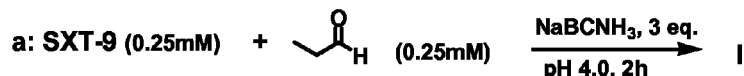
Figure 23:
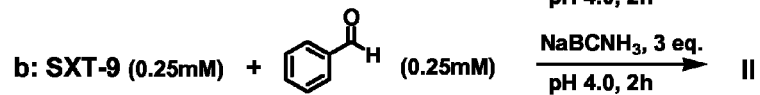
Figure 23:
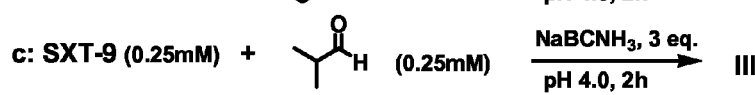
Figure 23:
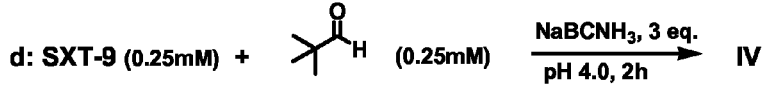
Figure 23:
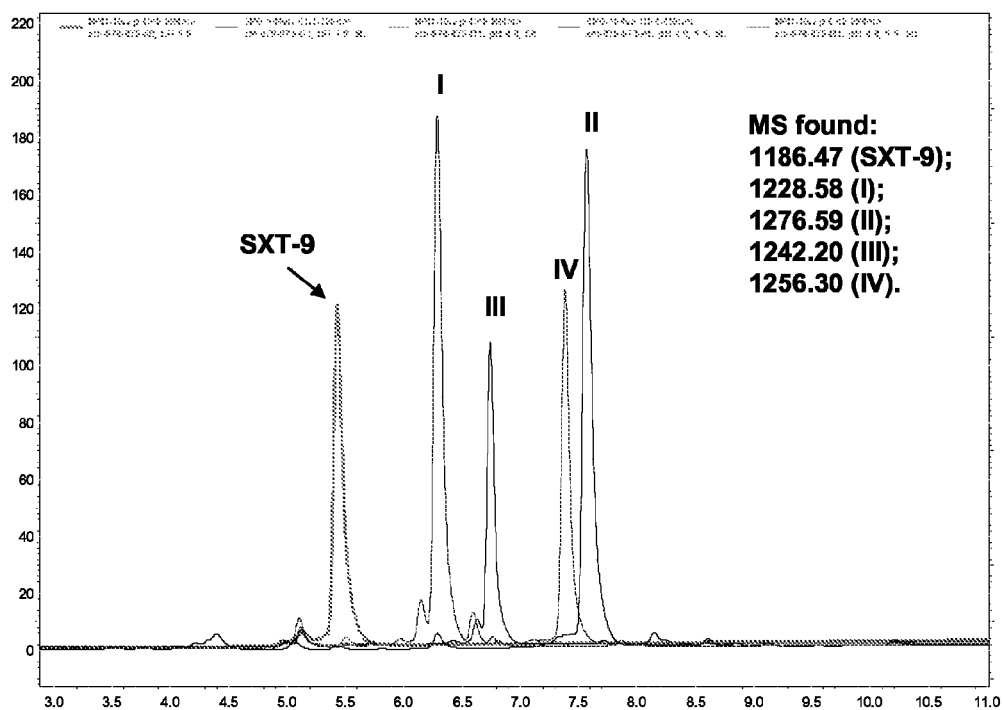

Further non-limiting examples of the specificity and selectivity of the reductive alkylation reactions of aromatic amine moieties on amino acid residues which are next to various N-terminal amino acids are shown in FIGS. 23-27. In FIG. 23 the reductive alkylation of peptide SXT-9 (N-terminal serine) with propionaldehyde (I), benzaldehyde (II), isobutaldehyde (III) and pivalaldehyde (IV), shows the speed of the reactions, which was about 2 hours, and the stoichiometric or near-stoichiometric relationship between the SXT-9 and the respective aldehyde containing reagents. In addition, FIG. 23 demonstrates that one product was predominantly formed from the respective reactions, that the disulfide bond did not react, and that the N-Ser residue has minimal effect on the selectivity. Additionally, the MS data for SXT-9, I, II, III, and IV are presented.

Figure 24:
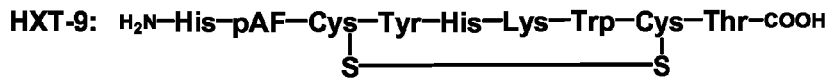
FIG. 24 presents illustrative, non-limiting examples of reductive alkylations of peptide HXT-9 with propionaldehyde (I), benzaldehyde (II), isobutaldehyde (III) and pivalaldehyde (IV) and the corresponding HPLC chromatograms.
Figure 24:
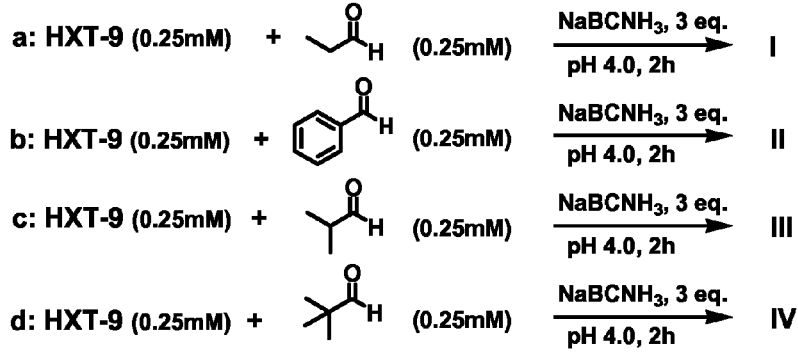
Figure 24:
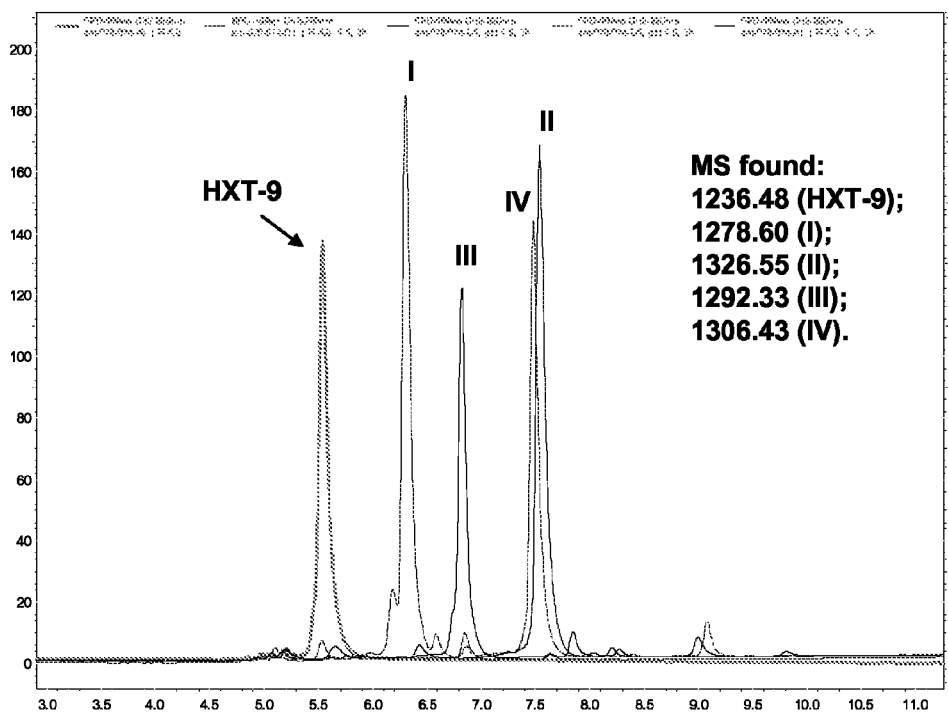

In FIG. 24 the reductive alkylation of peptide HXT-9 (N-terminal histidine) with propionaldehyde (I), benzaldehyde (II), isobutaldehyde (III) and pivalaldehyde (IV), shows the speed of the reactions, which was about 2 hours, and the stoichiometric or near-stoichiometric relationship between the HXT-9 and the respective aldehyde containing reagents. In addition, FIG. 24 demonstrates that one product was predominantly formed from the respective reactions, that the disulfide bond did not react, and that the N-His residue has minimal effect on the selectivity. Also, the MS data for HXT-9, I, II, III, and IV are shown.

Figure 25:
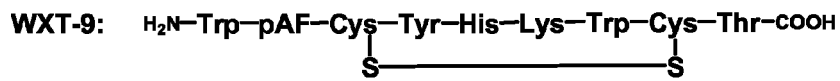
FIG. 25 presents illustrative, non-limiting examples of reductive alkylations of peptide WXT-9 with propionaldehyde (I), benzaldehyde (II) and isobutaldehyde (III) and the corresponding HPLC chromatograms.
Figure 25:
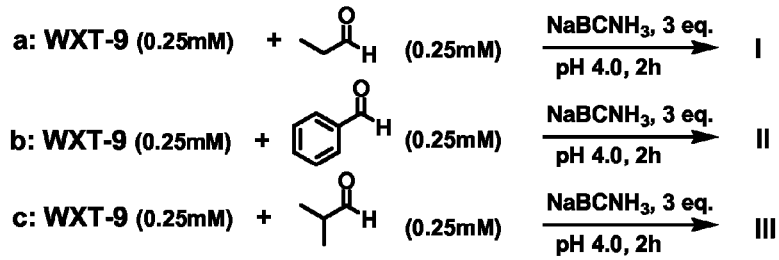
Figure 25:
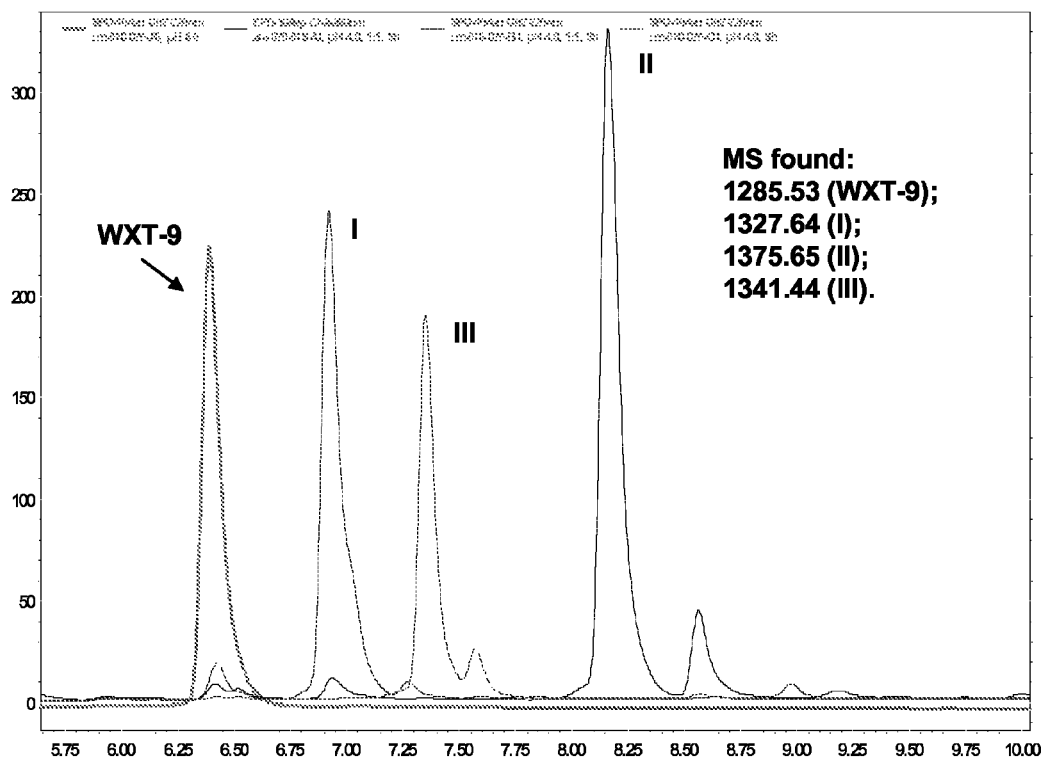

In FIG. 25 the reductive alkylation of peptide WXT-9 (N-terminal tryptophan) with propionaldehyde (I), benzaldehyde (II), isobutaldehyde (III) and pivalaldehyde (IV), shows the speed of the reactions, which was about 2 hours, and the stoichiometric or near-stoichiometric relationship between the WXT-9 and the respective aldehyde containing reagents. In addition, FIG. 25 demonstrates that one product was predominantly formed from the respective reactions, that the disulfide bond did not react, and that the N-Trp residue has minimal effect on the selectivity. Also, the MS data for WXT-9, I, II, and III are shown.

Figure 26:
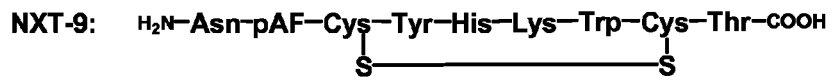
FIG. 26 presents illustrative, non-limiting examples of reductive alkylations of peptide NXT-9 with propionaldehyde (I) and benzaldehyde (II) and the corresponding HPLC chromatograms.
Figure 26:
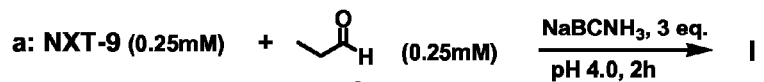
Figure 26:
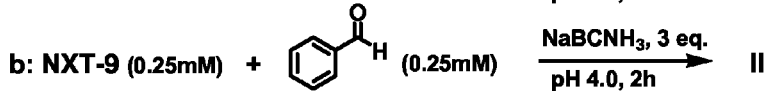
Figure 26:
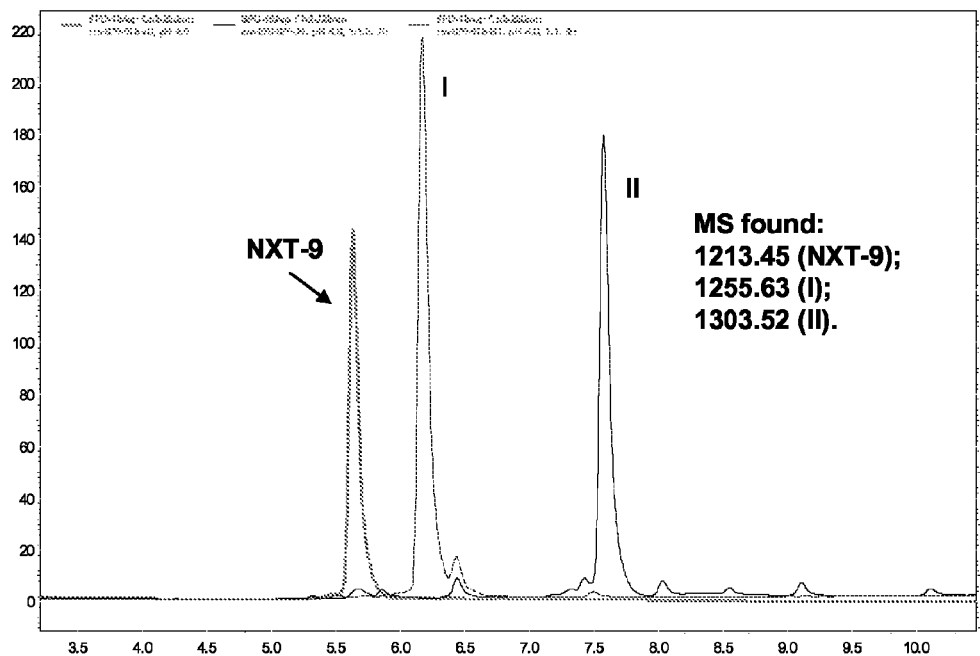

In FIG. 26 the reductive alkylation of peptide NXT-9 (N-terminal asparagine) with propionaldehyde (I), benzaldehyde (II), isobutaldehyde (III) and pivalaldehyde (IV), shows the speed of the reactions, which was about 2 hours, and the stoichiometric or near-stoichiometric relationship between the NXT-9 and the respective aldehyde containing reagents. In addition, FIG. 26 demonstrates that one product was predominantly formed from the respective reactions, that the disulfide bond did not react, and that the N-Asn residue has minimal effect on the selectivity. Also, the MS data for NXT-9, I, and II are shown.

Figure 27:
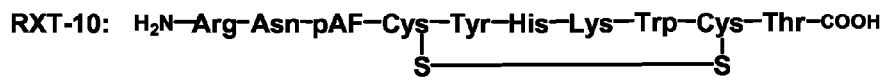
FIG. 27 presents illustrative, non-limiting examples of reductive alkylations of peptide RXT-10 with propionaldehyde (I) and benzaldehyde (II) and the corresponding HPLC chromatograms.
Figure 27:
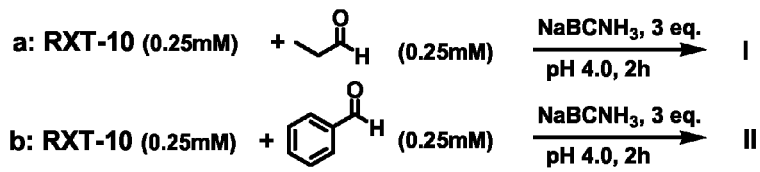
Figure 27:
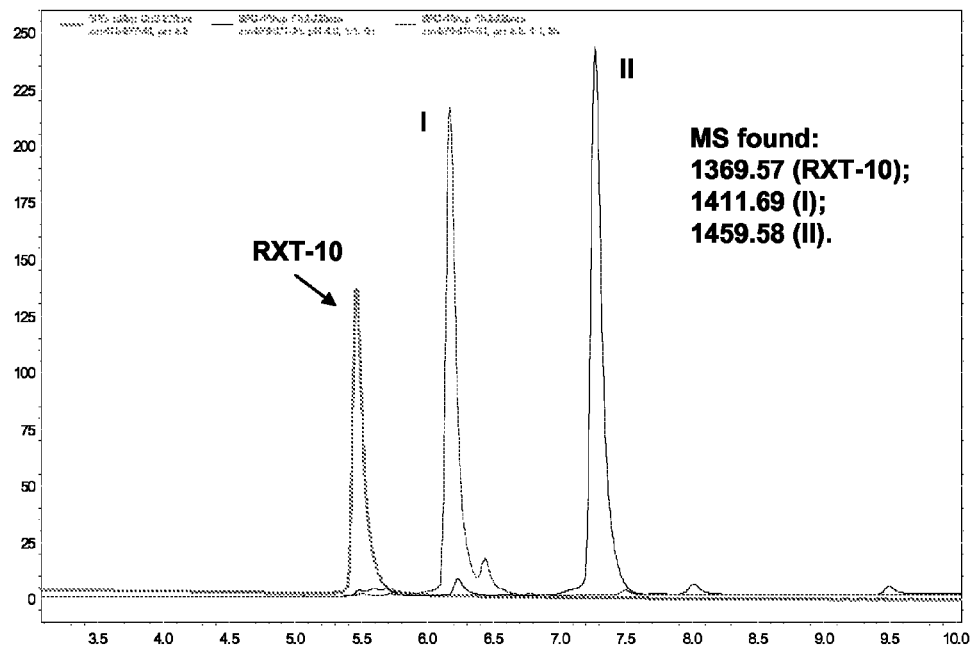

In FIG. 27 the reductive alkylation of peptide RXT-10 (N-terminal arginine) with propionaldehyde (I) and benzaldehyde (II) shows the speed of the reactions, which was about 2 hours, and the stoichiometric or near-stoichiometric relationship between the RXT-10 and the respective aldehyde containing reagents. In addition, FIG. 27 demonstrates that one product was predominantly formed from the respective reactions, that the disulfide bond did not react, and that the N-Arg residue has minimal effect on the selectivity. Also, the MS data for RXT-10, I, and II are shown.

Figure 28:
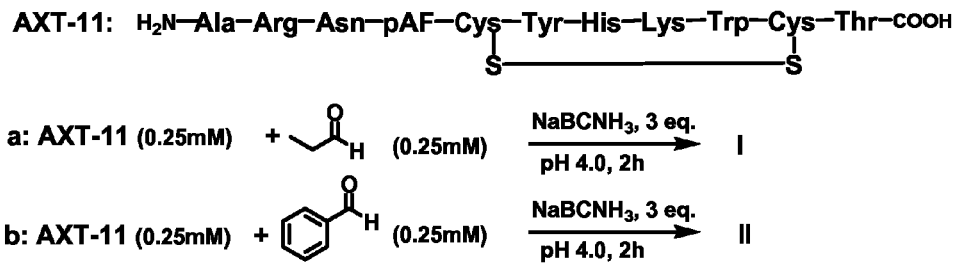
FIG. 28 presents illustrative, non-limiting examples of reductive alkylations of peptide AXT-11 with propionaldehyde (I) and benzaldehyde (II) and the corresponding HPLC chromatograms.
Figure 28:
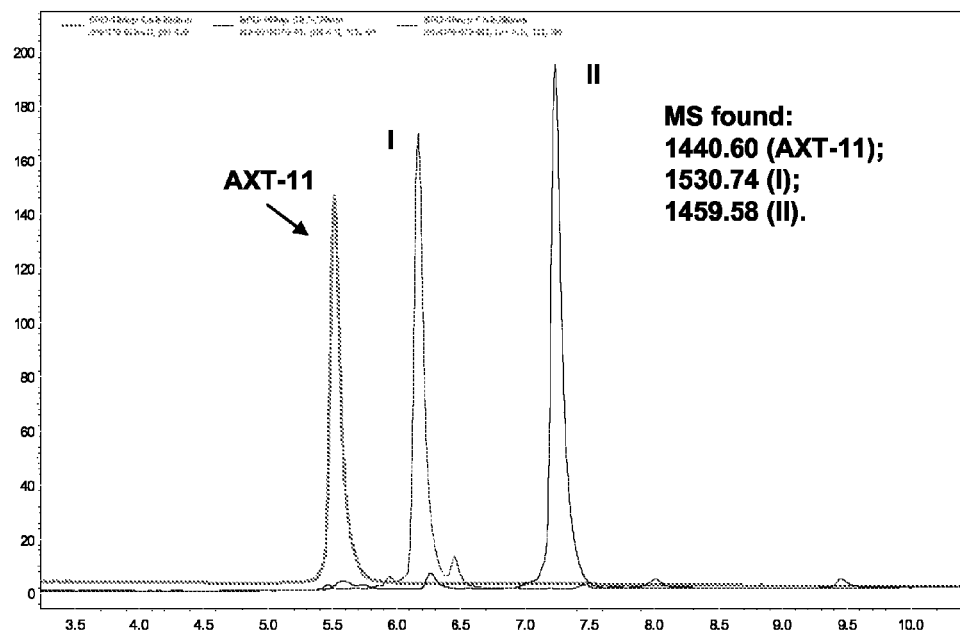

A further non-limiting example of the specificity and selectivity of the reductive alkylation reactions of aromatic amine moieties on amino acid residues in a peptide is shown in FIG. 28, wherein the reductive alkylation of peptide AXT-11 with propionaldehyde (I) and benzaldehyde (II) shows the speed of the reactions, which was about 2 hours, and the stoichiometric or near-stoichiometric relationship between the AXT-11 and the respective aldehyde containing reagents. In addition, FIG. 28 demonstrates that one product was predominantly formed from the respective reactions, that the disulfide bond did not react, and that the N-Ala residue has minimal effect on the selectivity. Also MS data for AXT-11, I, and II are presented.

Figure 29:
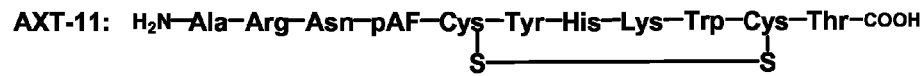
FIG. 29 presents illustrative, non-limiting examples of reductive alkylations of peptide AXT-11 with different aldehydes (I-III) and the corresponding HPLC chromatograms.
Figure 29:
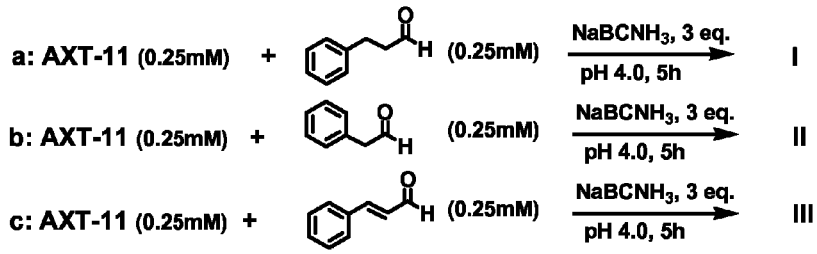
Figure 29:
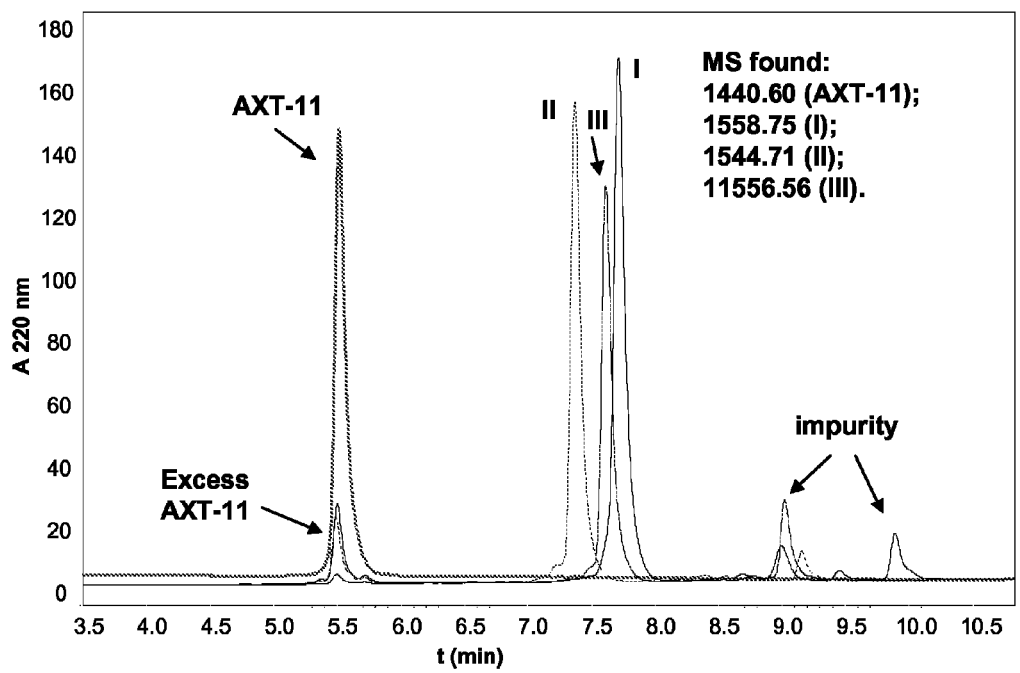
Figure 30:
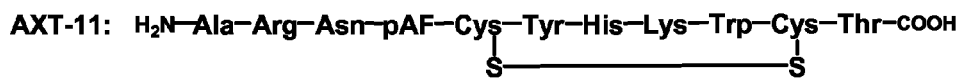
FIG. 30 presents illustrative, non-limiting examples of reductive alkylations of peptide AXT-11 with different aldehydes (IV-VII) and the corresponding HPLC chromatograms.
Figure 30:
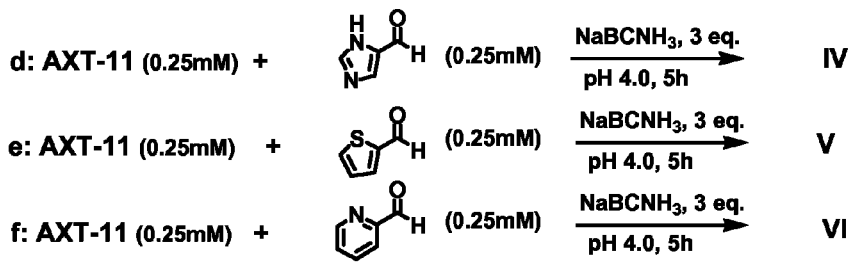
Figure 30:
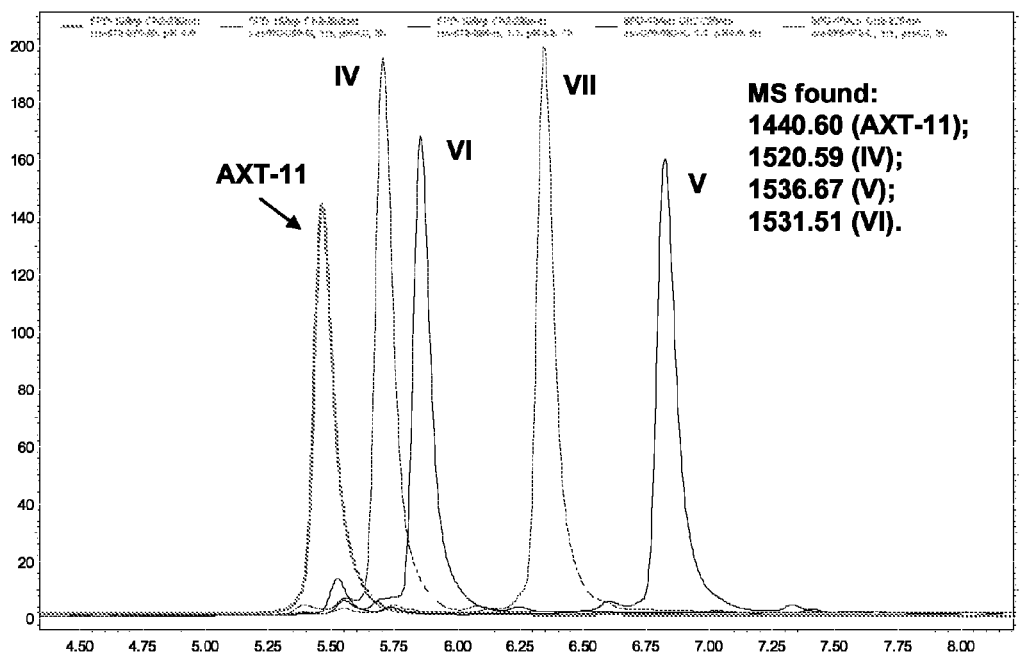

Further non-limiting examples of the specificity and selectivity of the reductive alkylation reactions of aromatic amine moieties on amino acid residues in a peptide with various aldehyde containing reagents are shown in FIGS. 29-30. In FIG. 29 the reductive alkylation of peptide AXT-11 with various aldehyde containing reagents shows the speed of the reactions, which was about 5 hours, and the stoichiometric or near-stoichiometric relationship between the AXT-11 and the respective aldehyde containing reagents. In addition, FIG. 29 demonstrates that one product was predominantly formed from the respective reactions, and that the disulfide bond did not react. Also, MS data for AXT-11, I, II, and III are presented. In FIG. 30 the reductive alkylation of peptide AXT-11 with various heteroaromatic aldehyde containing reagents shows the speed of the reactions, which was about 5 hours, and the stoichiometric or near-stoichiometric relationship between the AXT-11 and the respective aldehyde containing reagents. In addition, FIG. 30 demonstrates that one product was predominantly formed from the respective reactions, and that the disulfide bond did not react. Also, MS data for AXT-11, IV, V, VI are presented.

Figure 31:
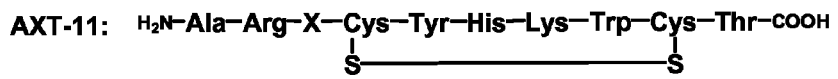
FIG. 31 presents illustrative, non-limiting examples of competitive reactions of peptide AXT-11 with an aldehyde and a 1,3-diketone (I-III) and the corresponding HPLC chromatograms.
Figure 31:
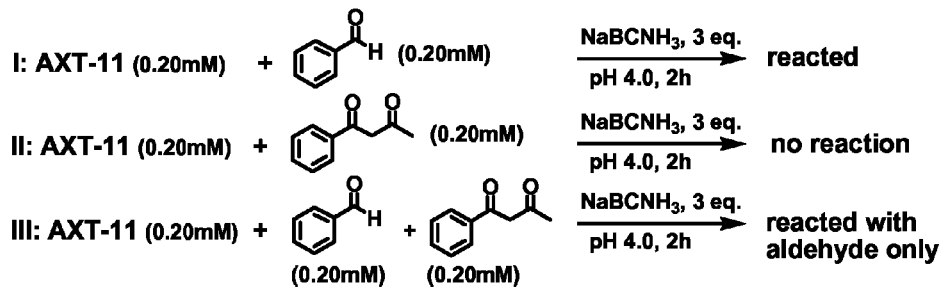
Figure 31:
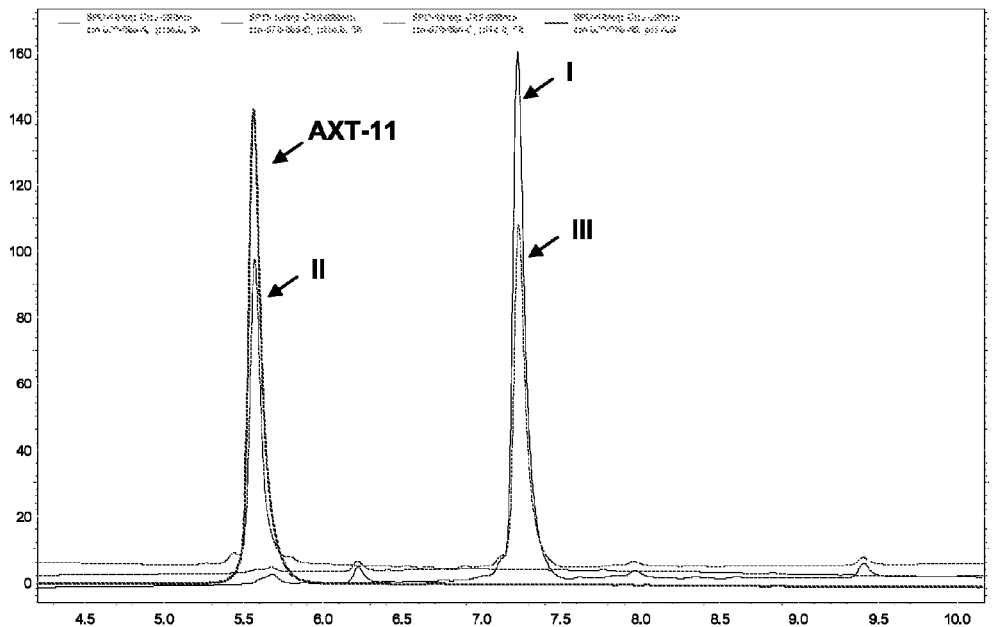
Figure 32:
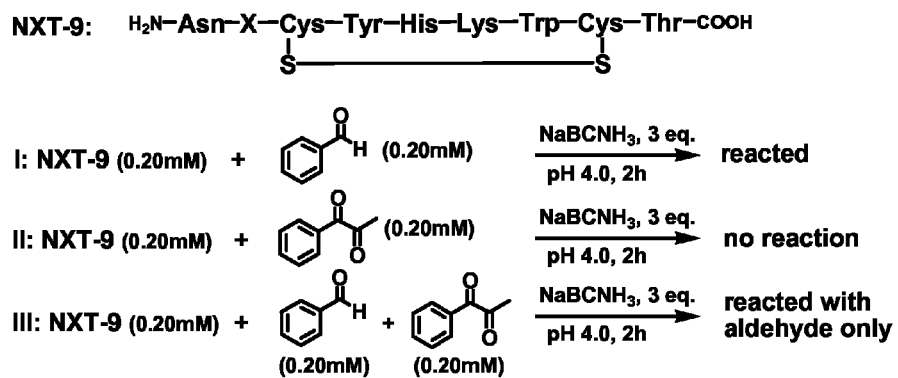
FIG. 32 presents illustrative, non-limiting examples of competitive reactions of peptide NXT-9 with an aldehyde and a 1,2-diketone (I-III) and the corresponding HPLC chromatograms.
Figure 32:
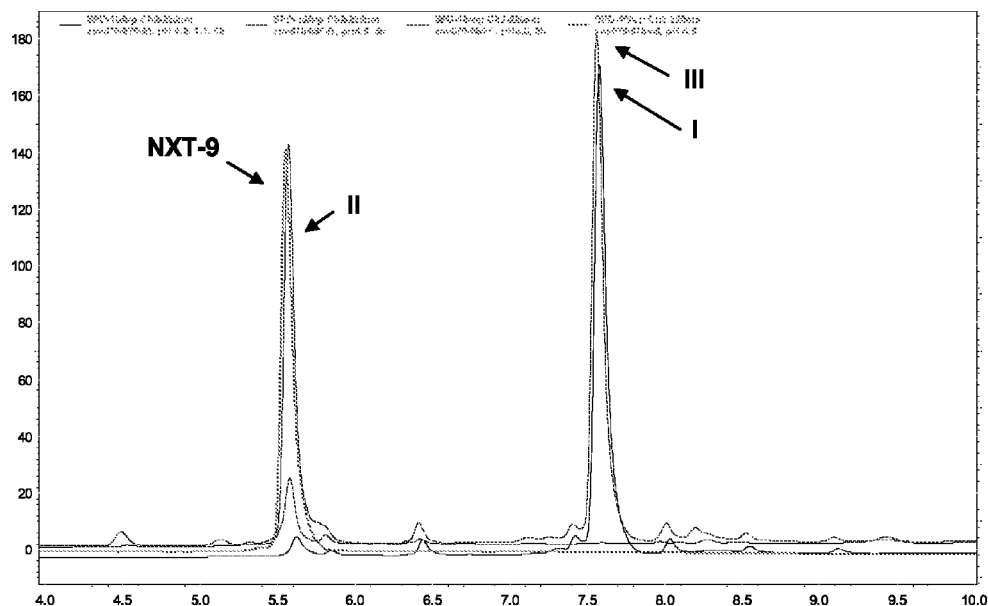
Figure 33:
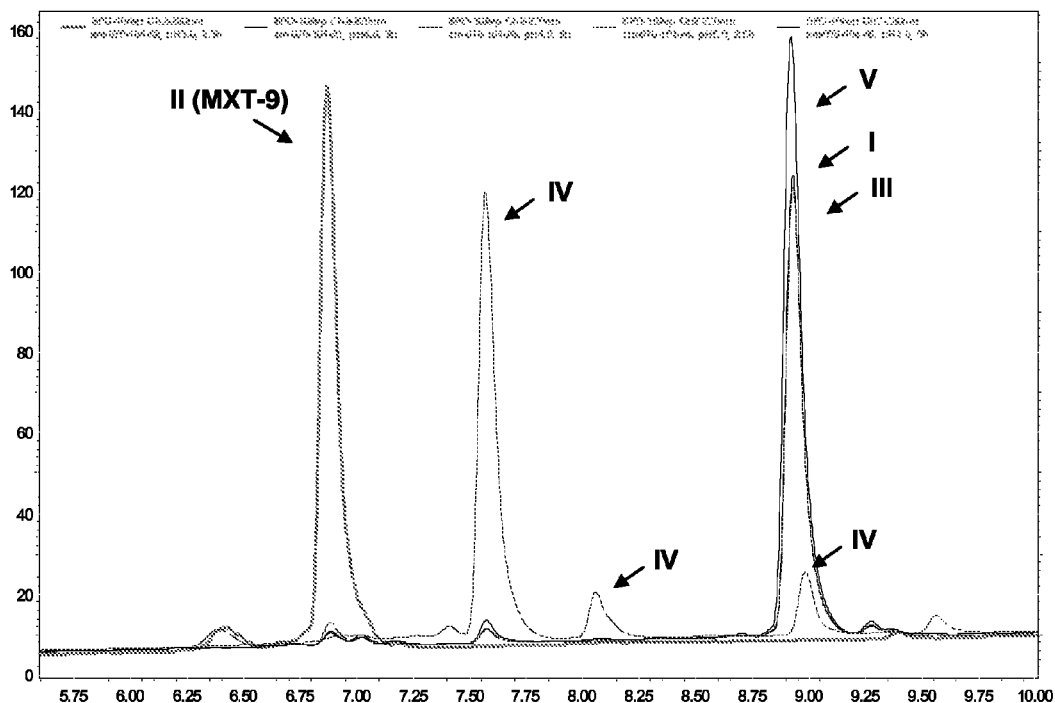
FIG. 33 presents illustrative, non-limiting examples of competitive reactions of peptide MXT-9 with different aldehydes and ketones (I-V) and the corresponding HPLC chromatograms.

FIGS. 31-33 show non-limiting examples of the specificity and selectivity of the reductive alkylation reactions of aromatic amine moieties on amino acid residues in a peptide, wherein the aromatic amine moieties are reacted with either an aldehyde containing reagent, a ketone containing reagent or a mixture thereof. In FIG. 31 the reductive alkylation of peptide AXT-11 with an aldehyde containing reagent, a ketone containing reagent or a mixture thereof shows the speed of the reactions, which was about 2 hours, and the stoichiometric or near-stoichiometric relationship between the AXT-11 and the respective aldehyde containing reagents. In addition, FIG. 31 demonstrates that under the reaction conditions used, only the aldehyde containing reagent reacted with the aromatic amine moiety and only one product was predominantly formed. Again, the disulfide bond did not react. In FIG. 32 the reductive alkylation of peptide NXT-9 with an aldehyde containing reagent, a ketone containing reagent or a mixture thereof shows the speed of the reactions, which was about 2 hours, and the stoichiometric or near-stoichiometric relationship between the NXT-10 and the respective aldehyde containing reagents. In addition, FIG. 32 demonstrates that under the reaction conditions used, only the aldehyde containing reagent reacted with the aromatic amine moiety and only one product was predominantly formed. Again, the disulfide bond did not react. In FIG. 33 the reductive alkylation of peptide MXT-9 with an aldehyde containing reagent, a ketone containing reagent or a mixture thereof demonstrates that under the reaction conditions used, only the aldehyde containing reagent reacted with the aromatic amine moiety and only one product was predominantly formed. Again, the disulfide bond did not react.

Figure 34:
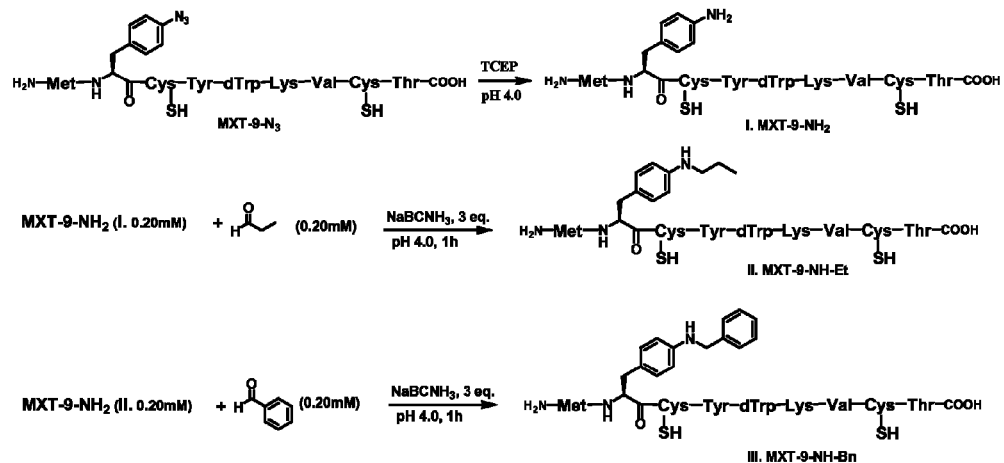
FIG. 34 presents illustrative, non-limiting examples of reduction of peptide MXT-9-N3 to MXT-9NH2 (I), followed by reductive alkylations with propionaldehyde (II) and benzaldehyde (III) and the corresponding HPLC chromatograms.
Figure 34:
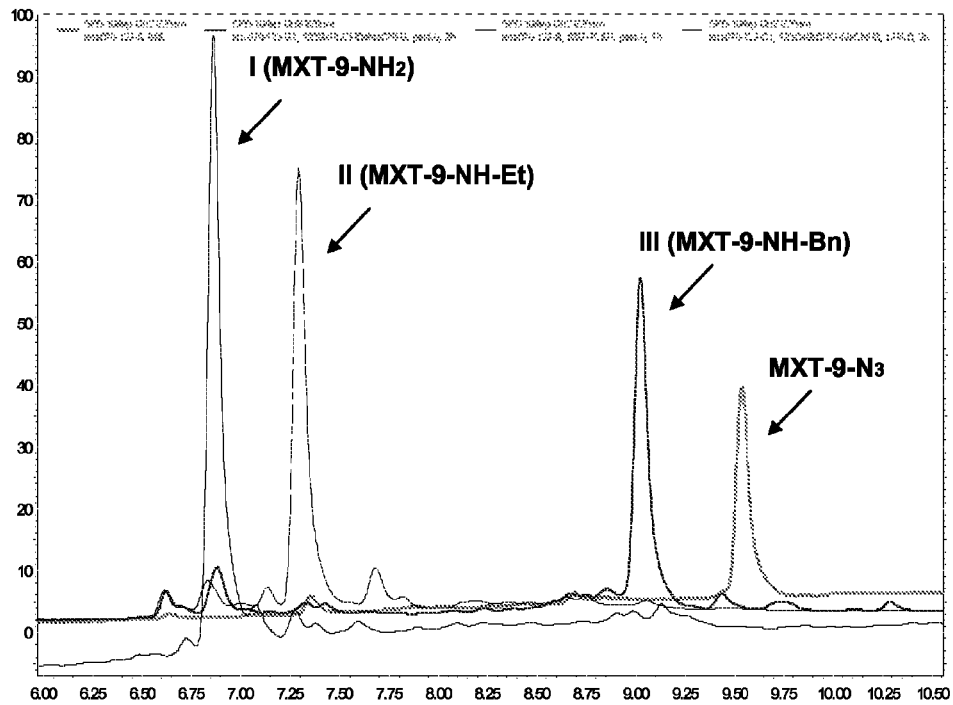

A non-limiting example of the deprotecting (or unmasking) of a protected (or masked) aromatic amine moiety on an amino acid in a peptide, followed by reductive alkylation of the resulting aromatic amine moiety with various aldehyde containing reagents is shown in FIG. 34. Reduction of the azide on peptide MXT-9-N3 with TCEP gave the primary aromatic amine moiety on peptide MXT-9NH2 (I). Subsequent reductive alkylations of MXT-9NH2 (I) with propionaldehyde (II) or benzaldehyde (III) then yields the corresponding alkylated peptides. FIG. 34 demonstrates the ability to form aromatic amine moieties after incorporation of a non-natural amino acid containing a protected or masked amine group. Also shown are the speed of the reactions, which was about 1 hour, the stoichiometric or near-stoichiometric relationship between the MXT-9NH2 (I) and the respective aldehyde containing reagents, only one product was predominantly formed, and the thiol groups did not react.

D. Cellular Uptake of Non-Natural Amino Acids

Non-natural amino acid uptake by a cell is one issue that is considered when designing and selecting non-natural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which non-natural amino acids, if any, are taken up by cells. See, e.g., the toxicity assays in, e.g., the U.S. Patent Publication No. 2004/198637 entitled "Protein Arrays," which is herein incorporated by reference in its entirety; and Liu, D. R. & Schultz, P. G. (1999) *Progress toward the evolution of an organism with an expanded genetic code. PNAS United States* 96:4780-4785. Although uptake is easily analyzed with various assays, an alternative to designing non-natural amino acids that are amenable to cellular uptake pathways is to provide biosynthetic pathways to create amino acids in vivo.

E. Biosynthesis of Non-Natural Amino Acids

Many biosynthetic pathways already exist in cells for the production of amino acids and other compounds. While a biosynthetic method for a particular non-natural amino acid may not exist in nature, including but not limited to, in a cell, the methods and compositions described herein provide such methods. For example, biosynthetic pathways for non-natural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce non-natural amino acids.

A variety of methods are available for producing novel enzymes for use in biosynthetic pathways or for evolution of existing pathways. For example, recursive recombination, including but not limited to, as developed by Maxygen, Inc. (available on the world wide web at www.maxygen.com), is optionally used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.*, 91:10747-10751. Similarly DesignPath™, developed by Genencor (available on the world wide web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, those identified through functional genomics, and molecular evolution and design. Diversa Corporation (available on the world wide web at diversa.com) also provides technology for rapidly screening libraries of genes and gene pathways, including but not limited to, to create new pathways.

Typically, the non-natural amino acid produced with an engineered biosynthetic pathway as described herein is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and a non-natural amino acid is generated, in vivo selections are optionally used to further optimize the production of the non-natural amino acid for both ribosomal protein synthesis and cell growth.

F. Additional Synthetic Methodology

The non-natural amino acids described herein may be synthesized using methodologies described in the art or using the techniques described herein or by a combination thereof. As an aid, the following table provides various starting electrophiles and nucleophiles that may be combined to create a desired functional group. The information provided is meant to be illustrative and not limiting to the synthetic techniques described herein.

TABLE

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |

TABLE-continued

Examples of Covalent Linkages and Precursors Thereof

| Covalent Linkage Product | Electrophile | Nucleophile |
| --- | --- | --- |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In general, carbon electrophiles are susceptible to attack by complementary nucleophiles, including carbon nucleophiles, wherein an attacking nucleophile brings an electron pair to the carbon electrophile in order to form a new bond between the nucleophile and the carbon electrophile.

Suitable carbon nucleophiles include, but are not limited to alkyl, alkenyl, aryl and alkynyl Grignard, organolithium, organozinc, alkyl-, alkenyl, aryl- and alkynyl-tin reagents (organostannanes), alkyl-, alkenyl-, aryl- and alkynyl-borane reagents (organoboranes and organoboronates); these carbon nucleophiles have the advantage of being kinetically stable in water or polar organic solvents. Other carbon nucleophiles include phosphorus ylids, enol and enolate reagents; these carbon nucleophiles have the advantage of being relatively easy to generate from precursors well known to those skilled in the art of synthetic organic chemistry. Carbon nucleophiles, when used in conjunction with carbon electrophiles, engender new carbon-carbon bonds between the carbon nucleophile and carbon electrophile.

Non-carbon nucleophiles suitable for coupling to carbon electrophiles include but are not limited to primary and secondary amines, thiols, thiolates, and thioethers, alcohols, alkoxides, azides, semicarbazides, and the like. These non-carbon nucleophiles, when used in conjunction with carbon electrophiles, typically generate heteroatom linkages (C-X-C), wherein X is a heteroatom, e.g. oxygen or nitrogen.

VI. Polypeptides with Non-Natural Amino Acids

The compositions and methods described herein provide for the incorporation of at least one non-natural amino acid into a polypeptide. The non-natural amino acid may be present at any location on the polypeptide, including any terminal position or any internal position of the polypeptide. Preferably, the non-natural amino acid does not destroy the activity and/or the tertiary structure of the polypeptide relative to the homologous naturally-occurring amino acid polypeptide, unless such destruction of the activity and/or tertiary structure was one of the purposes of incorporating the non-natural amino acid into the polypeptide. Further, the incorporation of the non-natural amino acid into the polypeptide may modify to some extent the activity (e.g., manipulating the therapeutic effectiveness of the polypeptide, improving the safety profile of the polypeptide, adjusting the pharmacokinetics, pharmacologics and/or pharmacodynamics of the polypeptide (e.g., increasing water solubility, bioavailability, increasing serum half-life, increasing therapeutic half-life, modulating immunogenicity, modulating biological activity, or extending the circulation time), providing additional functionality to the polypeptide, incorporating a tag, label or detectable signal into the polypeptide, easing the isolation properties of the polypeptide, and any combination of the aforementioned modifications) and/or tertiary structure of the polypeptide relative to the homologous naturally-occurring amino acid polypeptide without fully causing destruction of the activity and/or tertiary structure. Such modifications of the activity and/or tertiary structure are often one of the goals of effecting such incorporations, although of course, the incorporation of the non-natural amino acid into the polypeptide may also have little effect on the activity and/or tertiary structure of the polypeptide relative to the homologous naturally-occurring amino acid polypeptide. Correspondingly, non-natural amino acid polypeptides, compositions comprising non-natural amino acid polypeptides, methods for making such polypeptides and polypeptide compositions, methods for purifying, isolating, and characterizing such polypeptides and polypeptide compositions, and methods for using such polypeptides and polypeptide compositions are considered within the scope of the present disclosure. Further, the non-natural amino acid polypeptides described herein may also be ligated to another polypeptide (including, by way of example, a non-natural amino acid polypeptide or a naturally-occurring amino acid polypeptide).

The non-natural amino acid polypeptides described herein may be produced biosynthetically or non-biosynthetically. By biosynthetically is meant any method utilizing a translation system (cellular or non-cellular), including use of at least one of the following components: a polynucleotide, a codon, a tRNA, and a ribosome. By non-biosynthetically is meant any method not utilizing a translation system: this approach can be further divided into methods utilizing solid state peptide synthetic methods, solid phase peptide synthetic methods, methods that utilize at least one enzyme, and methods that do not utilize at least one enzyme; in addition any of this sub-divisions may overlap and many methods may utilize a combination of these sub-divisions.

The methods, compositions, strategies and techniques described herein are not limited to a particular type, class or family of polypeptides or proteins. Indeed, virtually any polypeptides may include at least one non-natural amino acids described herein. By way of example only, the polypeptide can be homologous to a therapeutic protein selected from the group consisting of: alpha-1 antitrypsin, angiostatin, antihemolytic factor, antibody, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, any interferon-like molecule or member of the IFN family, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone. The non-natural amino acid polypeptide may also be homologous to any polypeptide member of the growth hormone supergene family. Non-limiting examples of peptides/proteins which may incorporate non-natural amino acids containing an aromatic amine moiety are shown in FIGS. 20-34.

The non-natural amino acid polypeptides may be further modified as described elsewhere in this disclosure or the non-natural amino acid polypeptide may be used without further modification. Incorporation of a non-natural amino acid into a polypeptide can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), etc. Proteins that include a non-natural amino acid can have enhanced or even entirely new catalytic or biophysical properties. By way of example only, the following properties are optionally modified by inclusion of a non-natural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one non-natural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology,* 4:645-652.

Further, the sidechain of the non-natural amino acid component(s) of a polypeptide can provide a wide range of additional functionality to the polypeptide; by way of example only, and not as a limitation, the sidechain of the non-natural amino acid portion of a polypeptide may include any of the following: a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof.

In one aspect, a composition includes at least one protein with at least one, including but not limited to, at least two, at least three, at least four, at least five, at least six, at least seven, at least eight, at least nine, or at least ten or more non-natural amino acids. The non-natural amino acids can be the same or different, including but not limited to, there can be 1, 2, 3, 4, 5, 6, 7, 8, 9, 10 11, 12, 13, 14, 15, 16, 17, 18, 19, 20, or more different sites in the protein that comprise 1, 2, 3, 4, 5, 6, 7, 8, 9, 10, 11, 12, 13, 14, 15, 16, 17, 18, 19, 20, or more different non-natural amino acids. In another aspect, a composition includes a protein with at least one, but fewer than all, of a particular amino acid present in the protein is substituted with the non-natural amino acid. For a given protein with more than one non-natural amino acids, the non-natural amino acids can be identical or different (including but not limited to, the protein can include two or more different types of non-natural amino acids, or can include two of the same non-natural amino acid). For a given protein with more than two non-natural amino acids, the non-natural amino acids can be the same or different.

Although embodiments of the non-natural amino acid polypeptides described herein may be chemically synthesized via solid phase peptide synthesis methods (e.g., on a solid resin), by solution phase peptide synthesis methods, and/or without the aid of enzymes, other embodiments of the non-natural amino acid polypeptides described herein allow synthesis via a cell membrane, cellular extract, or lysate system or via an in vivo system, i.e., using the cellular machinery of a prokaryotic or eukaryotic cell. In further or additional embodiments, one of the key features of the non-natural amino acid polypeptides described herein is that they may be synthesized utilizing ribosomes. In further or additional embodiments of the non-natural amino acid polypeptides described herein, the non-natural amino acid polypeptides may be synthesized by a combination of solid resins, without the aid of enzymes, via the aid of ribosomes, via an in vitro system, via an in vivo system or any combination thereof.

Synthesis of non-natural amino acid polypeptides via ribosomes and/or an in vivo system has distinct advantages and characteristic from a non-natural amino acid polypeptide synthesized on a solid resin or without the aid of enzymes. These advantages or characteristics include different impurity profiles, a system utilizing ribosomes and/or an in vivo system will have impurities stemming from the biological system utilized, including host cell proteins, membrane portions, and lipids, whereas the impurity profile from a system utilizing a solid resin and/or without the aid of enzymes will include organic solvents, protecting groups, resin materials, coupling reagents and other chemicals used in the synthetic procedures. In addition, the isotopic pattern of the non-natural amino acid polypeptide synthesized via the use of ribosomes and/or an in vivo system will mirror the isotopic pattern of the feedstock utilized for the cells; on the other hand, the isotopic pattern of the non-natural amino acid polypeptide synthesized on a solid resin and/or without the aid of enzymes will mirror the isotopic pattern of the amino acids utilized in the synthesis. Further, the non-natural amino acid synthesized via the use of ribosomes and/or an in vivo system will be substantially free of the D-isomers of the amino acids and/or will be able to readily incorporate internal cysteine amino acids into the structure of the polypeptide, and/or will rarely provide internal amino acid deletion polypeptides. On the other hand, a non-natural amino acid polypeptide synthesized via a solid resin and/or without the use of enzymes will have a higher content of D-isomers of the amino acids and/or a lower content of internal cysteine amino acids and/or a higher percentage of internal amino acid deletion polypeptides. Furthermore, one of skill in the art will be able to differentiate a non-natural amino acid polypeptide synthesized by use of a ribosome and/or an in vivo system from a non-natural amino acid polypeptide synthesized via a solid resin and/or without the use of enzymes.

In a certain embodiment is a method of making a compound or salt thereof containing at least one non-natural amino acid selected from the group consisting of:

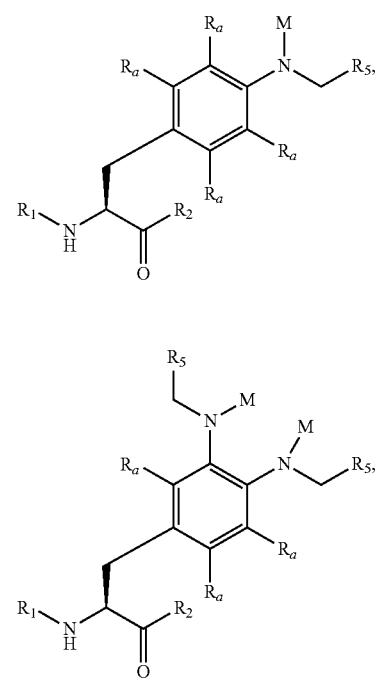

-continued

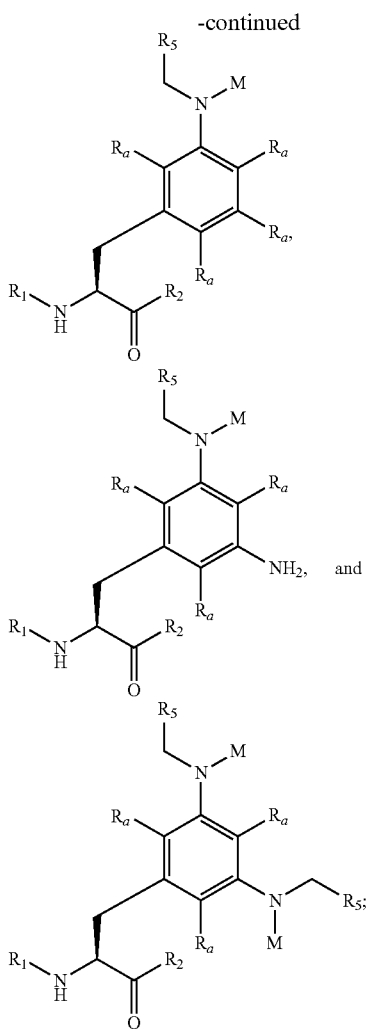

wherein the compound is formed by a reductive alkylation of an aromatic amino moiety on at least one non-natural amino acid comprising the aromatic amino moiety with at least one reactant comprising at least one aldehyde moiety;

each $R_a$ is independently selected from the group consisting of H, halogen, alkyl, —$NO_2$, —CN, substituted alkyl, —N(R')$_2$, —C(O)$_k$R', —C(O)N(R')$_2$, —OR', and —S(O)$_k$R', where k is 1, 2, or 3;

M is H or —$CH_2R_5$; or the M-N—C($R_5$) moiety may form a 4 to 7 membered ring structure;

$R_1$ is H, an amino protecting group, resin, amino acid, polypeptide, or polynucleotide;

$R_2$ is OH, an ester protecting group, resin, amino acid, polypeptide, or polynucleotide;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or $R_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—; or R$_5$ and any R$_a$ optionally form a cycloalkyl or a heterocycloalkyl; and each R' is independently H, alkyl, or substituted alkyl.

In other embodiments is a method of making a compound or salt thereof, wherein R$_1$ and R$_2$ of at least one non-natural amino acid is H and OH respectively. In some embodiments is a method of making a compound, wherein R$_a$ of at least one non-natural amino acid is a halogen. In other embodiments is a method of making a compound or salt thereof, wherein both R$_1$ and R$_2$ of at least one non-natural amino acid are polypeptides. In some embodiments is a method of making a compound or salt thereof, wherein X of at least one non-natural amino acid is a biologically active agent selected from the group consisting of a peptide, protein, enzyme, antibody, drug, dye, lipid, nucleosides, oligonucleotide, cell, virus, liposome, microparticle, and micelle. In some embodiments is a method of making a compound or salt thereof, wherein X of at least one non-natural amino acid is a drug selected from the group consisting of an antibiotic, fungicide, anti-viral agent, anti-inflammatory agent, anti-tumor agent, cardiovascular agent, anti-anxiety agent, hormone, growth factor, and steroidal agent. In other embodiments is a method of making a compound or salt thereof, wherein X of at least one non-natural amino acid is an enzyme selected from the group consisting of horseradish peroxidase, alkaline phosphatase, β-galactosidase, and glucose oxidase. In some embodiments is a method of making a compound or salt thereof, wherein X of at least one non-natural amino acid is a detectable label selected from the group consisting of a fluorescent, phosphorescent, chemiluminescent, chelating, electron dense, magnetic, intercalating, radioactive, chromophoric, and energy transfer moiety. In further embodiments is a method of making a compound or salt thereof, wherein X of the non-natural amino acid is a polymer comprising alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, or substituted aralkyl.

In other embodiments is a method of making a compound or salt thereof, wherein the polymer comprises polyalkylene oxide or substituted polyalkylene oxide. In some embodiments is a method of making a compound or salt thereof, wherein the polymer comprises -[(alkylene or substituted alkylene)-O-(hydrogen, alkyl, or substituted alkyl)]$_x$, wherein x is from 20-10,000. In other embodiments is a method of making a compound or salt thereof, wherein the polymer is m-PEG having a molecular weight ranging from about 2 to about 40 KDa.

In further embodiments is a method of making a compound or salt thereof wherein at least one non-natural amino acid is selected from a group:

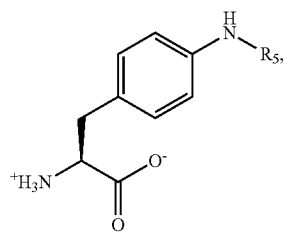

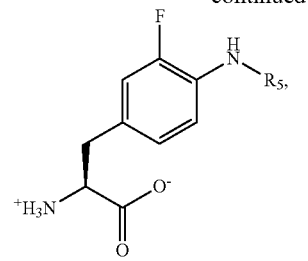

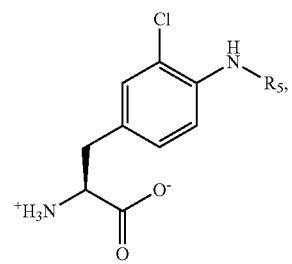

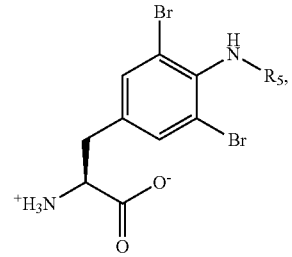

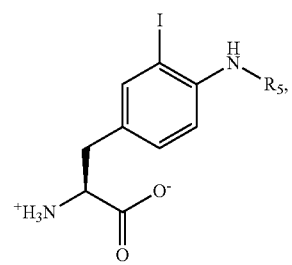

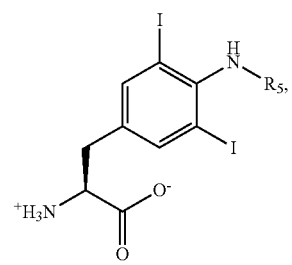

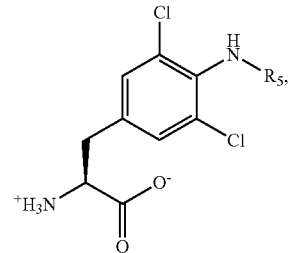

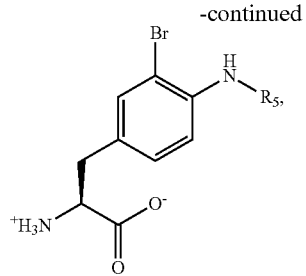
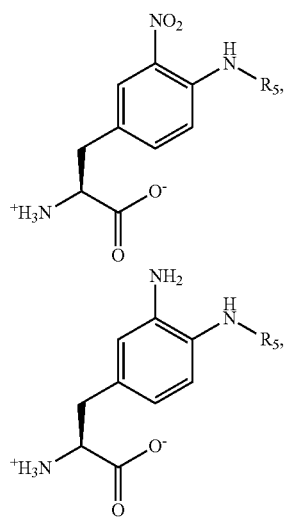
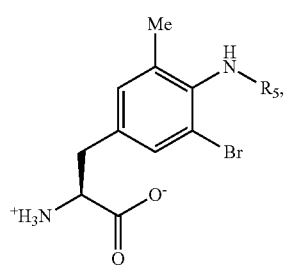
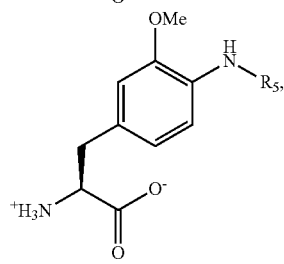
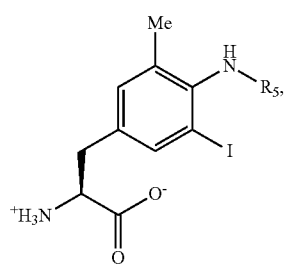
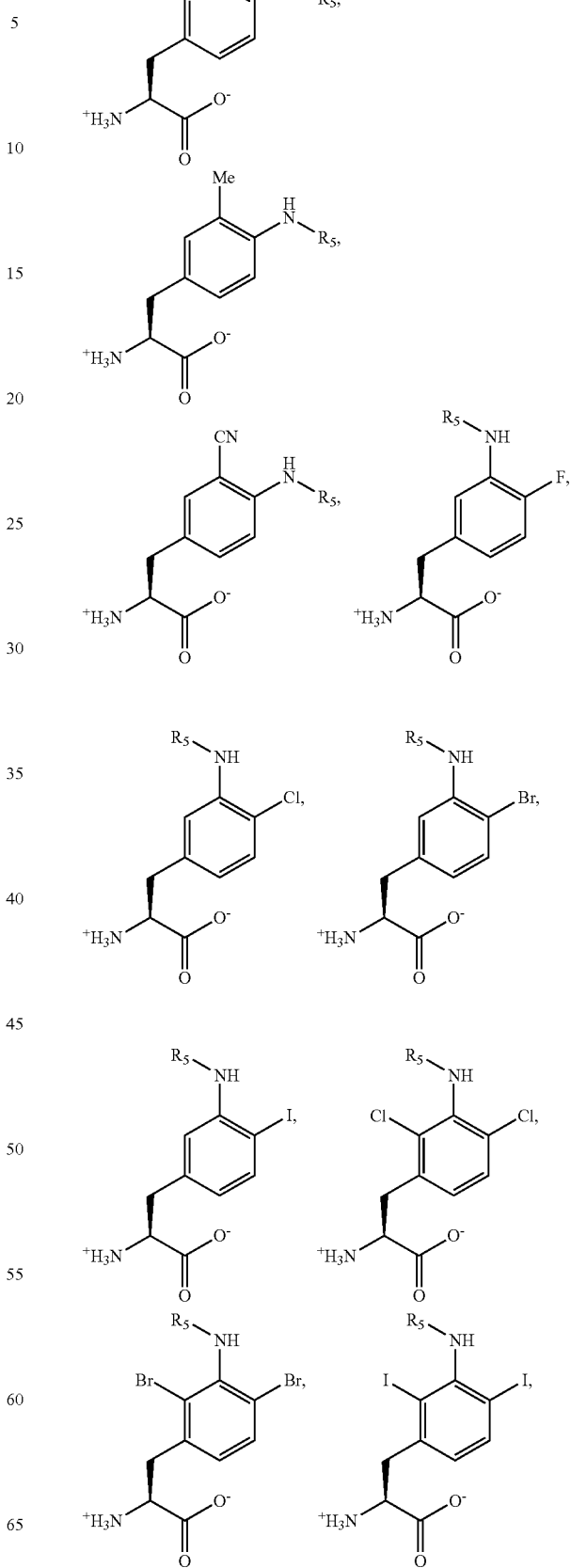

-continued
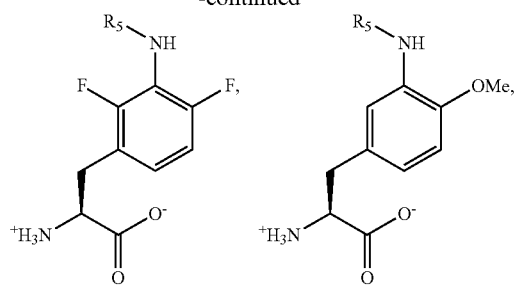
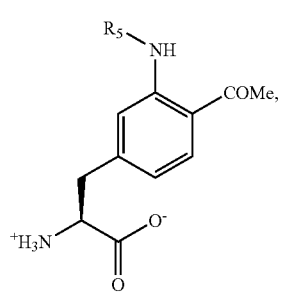
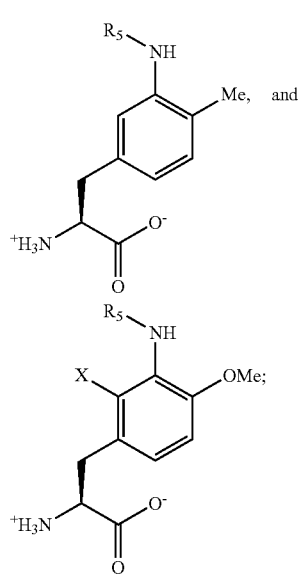
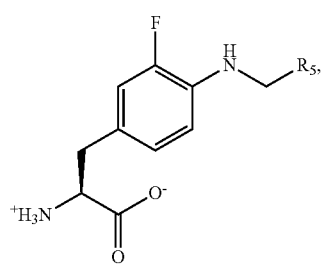
wherein X is a halogen.
In some embodiments is a method of making a compound or salt thereof wherein at least one non-natural amino acid is selected from a group:
-continued
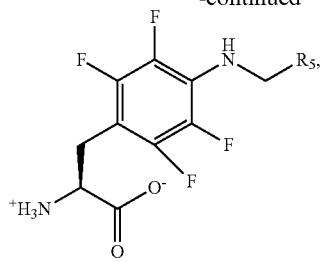
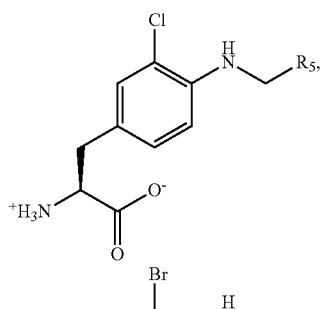
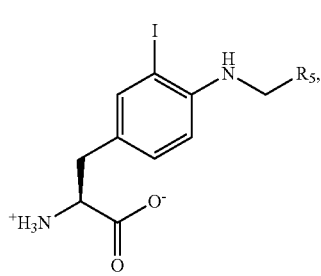
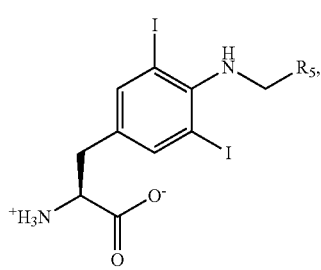
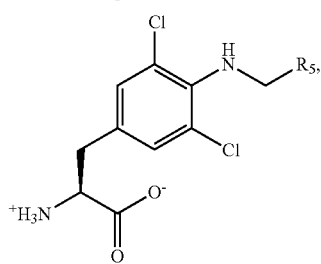

99
-continued
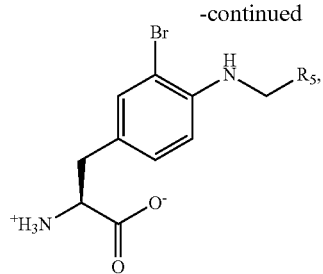
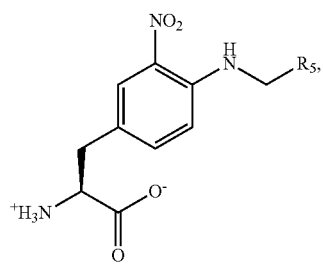
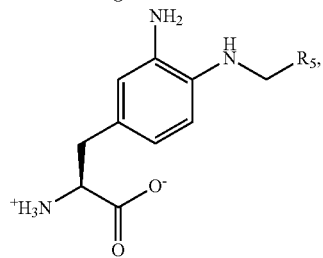
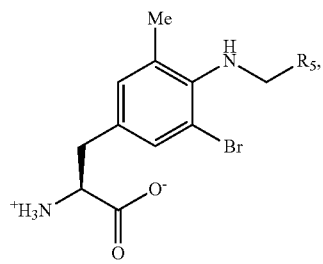
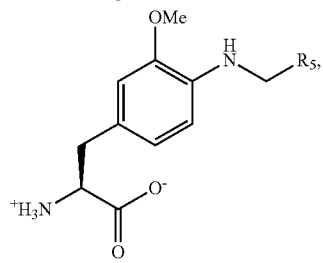
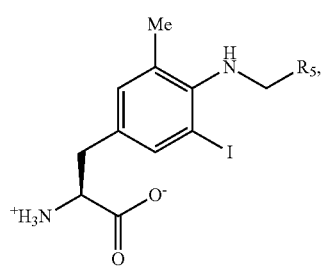
100
-continued
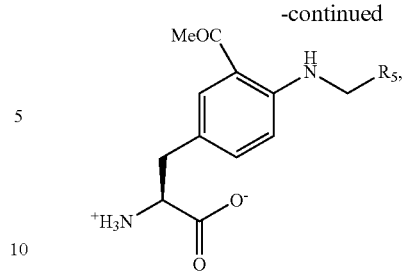
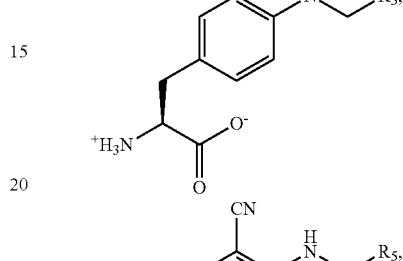
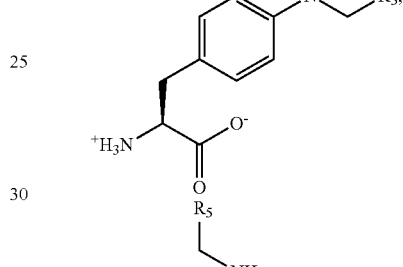
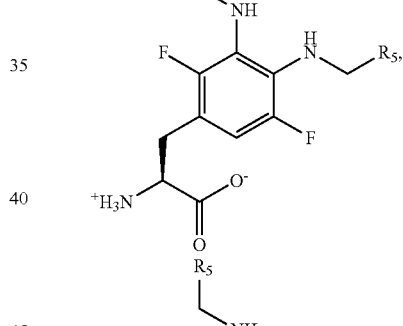
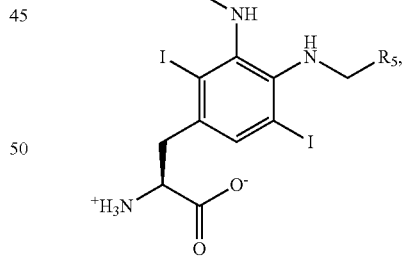
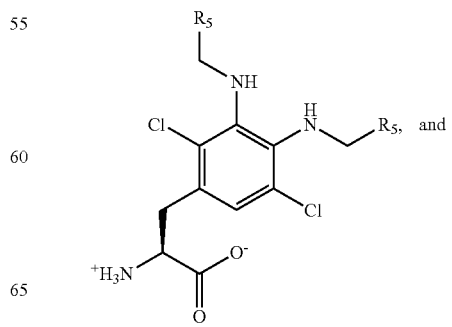
and

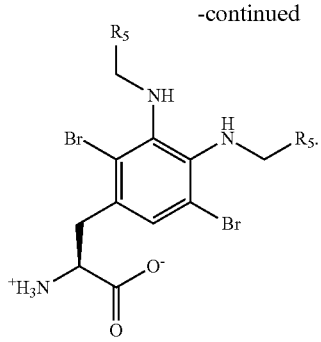
In further embodiments is a method of making a compound or salt thereof wherein at least one non-natural amino acid is selected from a group:
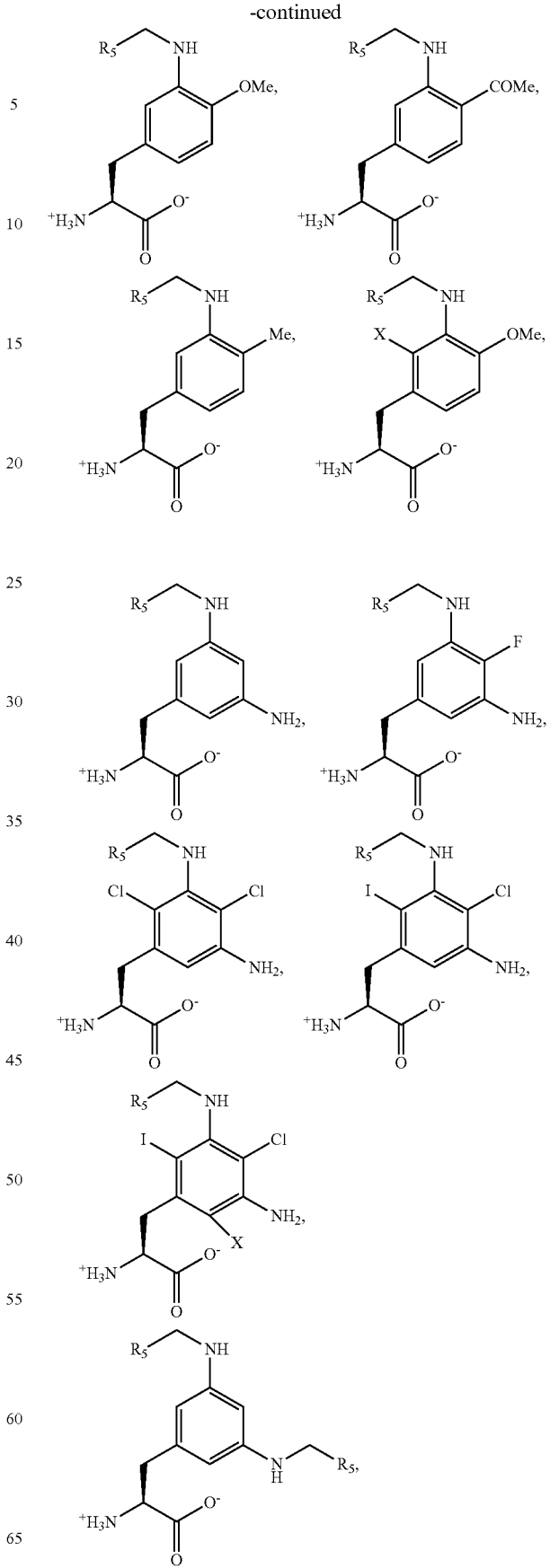

103
-continued

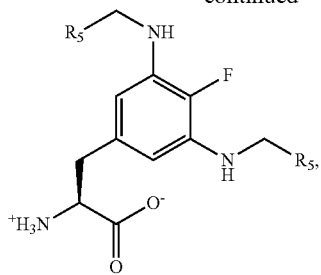

wherein X is a halogen.

In other embodiments is a method of making a compound or salt thereof containing at least one non-natural amino acid selected from the group consisting of:

104
-continued

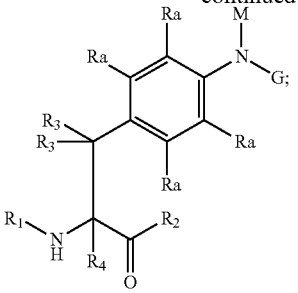

wherein the compound is formed by a reductive alkylation of an aromatic amino moiety on the at least one non-natural amino acid comprising the aromatic amino moiety with at least one reactant comprising at least one aldehyde moiety;

each $R_a$ is independently selected from the group consisting of H, halogen, alkyl, —$NO_2$, —CN, substituted alkyl, —N(R')$_2$, —C(O)$_k$R', —C(O)N(R')$_2$, —OR', and —S(O)$_k$R', where k is 1, 2, or 3;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

M is H or —$CH_2R_5$;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or $R_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer; a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—; or two R$_5$ groups optionally form a cycloalkyl or a heterocycloalkyl; or R$_5$ and any R$_a$ optionally form a cycloalkyl or a heterocycloalkyl; with a proviso that when R$_1$ is H then R$_2$ is not OH, or when R$_2$ is OH then R$_1$ is not H; and G is an amine protecting group.

In some embodiments is a method of making a compound or salt thereof wherein the amine protecting group is selected from the group consisting of:

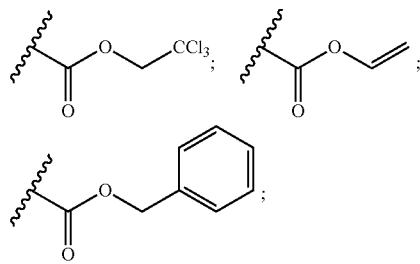

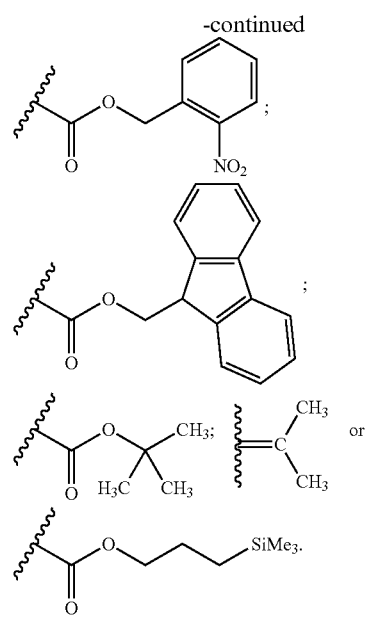

In other embodiments is a method of making a compound or salt thereof wherein both R$_1$ and R$_2$ are polypeptides.

In some embodiments is a method of making a compound or salt thereof wherein at least one aldehyde moiety has the structure corresponding to:

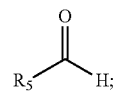

wherein; R$_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR'; or R$_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—.

In other embodiments is a method of making a compound or salt thereof having the structure of:

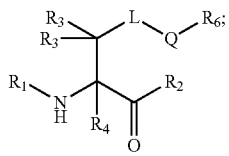

wherein L is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; Q is optional, and when present is a linker selected from the group consisting of lower alkylene, substituted lower alkylene, lower alkenylene, substituted lower alkenylene, lower heteroalkylene, substituted lower heteroalkylene, —O—(alkylene or substituted alkylene)-, —S-(alkylene or substituted alkylene)-, —S(O)$_k$(alkylene or substituted alkylene)-, where k is 1, 2, or 3, —C(O)-(alkylene or substituted alkylene)-, —C(S)-(alkylene or substituted alkylene)-, —NR'-(alkylene or substituted alkylene)-, —CON(R")-(alkylene or substituted alkylene)-, —CSN(R')-(alkylene or substituted alkylene)-, —N(R')CO-(alkylene or substituted alkylene)-, where each R' is independently H, alkyl, or substituted alkyl; R$_1$ is H, an amino protecting group, resin, amino acid, polypeptide, or polynucleotide; and R$_2$ is OH, an ester protecting group, resin, amino acid, polypeptide, or polynucleotide; each of R$_3$ and R$_4$ is independently H, halogen, lower alkyl, or substituted lower alkyl, or R$_3$ and R$_4$ or two R$_3$ groups optionally form a cycloalkyl or a heterocycloalkyl; each R$_a$ is independently selected from the group consisting of H, halogen, alkyl, —NO$_2$, —CN, substituted alkyl, —N(R')$_2$, —C(O)$_k$R', —C(O)N(R')$_2$, —OR', and —S(O)$_k$R', where k is 1, 2, or 3; R$_6$ is a protected aldehyde or a masked aldehyde, wherein the protecting group includes, but is not limited to,

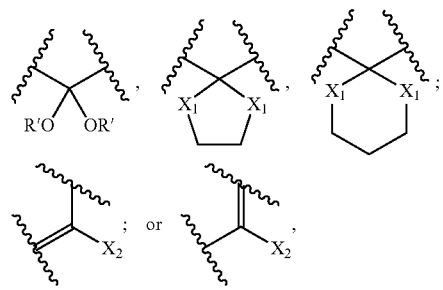

where each X$_1$ is independently selected from the group consisting of —O—, —S—, —N(H)—, —N(R)—, —N(Ac)—, and —N(OMe)-; X$_2$ is —OR, —OAc, —SR, —N(R)$_2$, —N(R)(Ac), —N(R)(OMe), or N$_3$, and where each R' and R is independently H, alkyl, or substituted alkyl.

In other embodiments is a method of making a compound or salt thereof wherein X$_1$ is 0. In some embodiments is a method of making a compound or salt thereof wherein both R$_1$ and R$_2$ are polypeptides.

VII. Compositions and Methods Comprising Nucleic Acids and Oligonucleotides

A. General Recombinant Nucleic Acid Methods for Use Herein

In numerous embodiments of the methods and compositions described herein, nucleic acids encoding a polypeptide of interest (including by way of example a GH polypeptide) will be isolated, cloned and often altered using recombinant methods. Such embodiments are used, including but not limited to, for protein expression or during the generation of variants, derivatives, expression cassettes, or other sequences derived from a polypeptide. In some embodiments, the sequences encoding the polypeptides are operably linked to a heterologous promoter.

Also described herein are cells that can produce nonnatural amino acid polypeptides wherein at least one nonnatural amino acid on the polypeptide comprises a sidechain having an aromatic amine moiety or a masked or protected aldehyde moiety. Cells that biosynthesize at least one non-natural amino acid polypeptide may be produced using the techniques, methods, compositions and strategies described herein or variants thereof.

A nucleotide sequence encoding a polypeptide comprising a non-natural amino acid may be synthesized on the basis of the amino acid sequence of the parent polypeptide, and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

The non-natural amino acid methods and compositions described herein utilize routine techniques in the field of recombinant genetics. Basic texts disclosing the general methods of use for the non-natural amino acid methods and compositions described herein include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes or polynucleotides which include selector codons for production of proteins that include non-natural amino acids, orthogonal tRNAs, orthogonal synthetases, and pairs thereof.

Various types of mutagenesis are used in the non-natural amino acid methods and compositions described herein for a variety of purposes, including but not limited to, to produce novel synthetases or tRNAs, to mutate tRNA molecules, to mutate polynucleotides encoding synthetases, to produce libraries of tRNAs, to produce libraries of synthetases, to produce selector codons, to insert selector codons that encode non-natural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the non-natural amino acid methods and compositions described herein. In one embodiment, mutagenesis can be guided by known information of the naturally occurring molecule or altered or mutated naturally occurring molecule, including but not limited to, sequence, sequence comparisons, physical properties, crystal structure or the like.

The texts and examples found herein describe these procedures. Additional information is found in the following publications and references cited within: Ling et al., *Approaches to DNA mutagenesis: an overview, Anal Biochem.* 254(2): 157-178 (1997); Dale et al., *Oligonucleotide-directed random mutagenesis using the phosphorothioate method, Methods Mol. Biol.* 57:369-374 (1996); Smith, *In vitro mutagenesis, Ann. Rev. Genet.* 19:423-462 (1985); Botstein & Shortie, *Strategies and applications of in vitro mutagenesis, Science* 229:1193-1201 (1985); Carter, *Site-directed mutagenesis, Biochem. J.* 237:1-7 (1986); Kunkel, *The efficiency of oligonucleotide directed mutagenesis*, in *Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Bass et al., *Mutant Trp repressors with new DNA-binding specificities, Science* 242:240-245 (1988); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100: 468-500 (1983); Zoller & Smith, *Oligonucleotide-directed mutagenesis: a simple method using two oligonucleotide primers and a single-stranded DNA template, Methods in Enzymol.* 154:329-350 (1987); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8785 (1985); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Sayers et al., *5'-3' Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Improved enzymatic in vitro reactions in the gapped duplex DNA approach to oligonucleotide-directed construction of mutations, Nucl. Acids Res.* 16: 7207 (1988); Fritz et al., *Oligonucleotide-directed construction of mutations: a gapped duplex DNA procedure without enzymatic reactions in vitro, Nucl. Acids Res.* 16: 6987-6999 (1988); Kramer et al., *Point Mismatch Repair, Cell* 38:879-

887 (1984); Carter et al., *Improved oligonucleotide site-directed mutagenesis using M13 vectors*, Nucl. Acids Res. 13: 4431-4443 (1985); Carter, *Improved oligonucleotide-directed mutagenesis using M13 vectors*, Methods in Enzymol. 154: 382-403 (1987); Eghtedarzadeh & Henikoff, *Use of oligonucleotides to generate large deletions*, Nucl. Acids Res. 14: 5115 (1986); Wells et al., *Importance of hydrogen-bond formation in stabilizing the transition state of subtilisin*, Phil. Trans. R. Soc. Lond. A 317: 415-423 (1986); Nambiar et al., *Total synthesis and cloning of a gene coding for the ribonuclease S protein*, Science 223: 1299-1301 (1984); Sakmar and Khorana, *Total synthesis and expression of a gene for the alpha subunit of bovine rod outer segment guanine nucleotide-binding protein (transducin)*, Nucl. Acids Res. 14: 6361-6372 (1988); Wells et al., *Cassette mutagenesis: an efficient method for generation of multiple mutations at defined sites*, Gene 34:315-323 (1985); Grundström et al., *Oligonucleotide-directed mutagenesis by microscale 'shot-gun' gene synthesis*, Nucl. Acids Res. 13: 3305-3316 (1985); Mandecki, *Oligonucleotide-directed double-strand break repair in plasmids of Escherichia coli: a method for site-specific mutagenesis*, Proc. Natl. Acad. Sci. USA, 83:7177-7181 (1986); Arnold, *Protein engineering for unusual environments*, Current Opinion in Biotechnology 4:450-455 (1993); Sieber, et al., Nature Biotechnology, 19:456-460 (2001). W. P. C. Stemmer, Nature 370, 389-91 (1994); and, I. A. Lorimer, I. Pastan, Nucleic Acids Res. 23, 3067-8 (1995). Additional details on many of the above methods can be found in *Methods in Enzymology* Volume 154, which also describes useful controls for trouble-shooting problems with various mutagenesis methods.

The methods and compositions described herein also include use of eukaryotic host cells, non-eukaryotic host cells, and organisms for the in vivo incorporation of a non-natural amino acid via orthogonal tRNA/RS pairs. Host cells are genetically engineered (including but not limited to, transformed, transduced or transfected) with the polynucleotides corresponding to the polypeptides described herein or constructs which include a polynucleotide corresponding to the polypeptides described herein, including but not limited to, a vector corresponding to the polypeptides described herein, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. The vector can be, for example, in the form of a plasmid, a cosmid, a phage, a bacterium, a virus, a naked polynucleotide, or a conjugated polynucleotide. The vectors are introduced into cells and/or microorganisms by standard methods including electroporation (Fromm et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., Nature 327, 70-73 (1987)), and/or the like.

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Several well-known methods of introducing target nucleic acids into cells are available, any of which can be used in methods and compositions described herein. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs corresponding to the polypeptides described herein. The bacteria are grown to log phase and the plasmids within the bacteria can be isolated by a variety of methods known in the art (see, for instance, Sambrook). In addition, kits are commercially available for the purification of plasmids from bacteria, (see, e.g., Easy-Prep™, FlexiPrep™, both from Pharmacia Biotech; Strata-Clean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, *Gene* 8:81 (1979); Roberts, et al., *Nature*, 328:731 (1987); Schneider, E., et al., *Protein Expr. Purif.* 6(1):10-14 (1995); Ausubel, Sambrook, Berger (all supra). A catalogue of bacteria and bacteriophages useful for cloning is provided, e.g., by the ATCC, e.g., *The ATCC Catalogue of bacteria and bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

B. Selector Codons

Selector codons encompassed within the methods and compositions described herein expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), a unnatural codon, a four or more base codon, a rare codon, or the like. There is a wide range in the number of selector codons that can be introduced into a desired gene or polynucleotide including but not limited to, one or more, two or more, three or more, 4, 5, 6, 7, 8, 9, 10 or more in a single polynucleotide encoding at least a portion of a polypeptide of interest.

In one embodiment, the methods involve the use of a selector codon that is a stop codon for the incorporation of one or more non-natural amino acids in vivo. For example, an O-tRNA is produced that recognizes the stop codon, including but not limited to, UAG, and is aminoacylated by an O—RS with a desired non-natural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5'-3' *Exonuclease in phosphorothioate-based oligonucleotide-directed mutagenesis. Nucleic Acids Res*, 16:791-802. When the O—RS, O-tRNA and the nucleic acid that encodes the polypeptide of interest are combined in vivo, the non-natural amino acid is incorporated in response to the UAG codon to give a polypeptide containing the non-natural amino acid at the specified position.

Non-natural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry*, 32:7939 (1993). In this case, the synthetic tRNA competes with the naturally occurring tRNAArg, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.*, 25:4685 (1997). Components of the present invention can be generated to use these rare codons in vivo.

The incorporation of non-natural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Selector codons also comprise extended codons, including but not limited to, four or more base codons, such as, four, five, six or more base codons. Examples of four base codons include, but are not limited to, AGGA, CUAG, UAGA, CCCU and the like. Examples of five base codons include, but are not limited to, AGGAC, CCCCU, CCCUC, CUAGA, CUACU, UAGGC and the like. A feature of the methods and compositions described herein includes using extended codons based on frameshift suppression. Four or more base codons can insert, including but not limited to, one or multiple non-natural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple non-natural amino acids can be encoded in the same cell using a four or more base codon. See, Anderson et al., (2002) *Exploring the Limits of Codon and Anticodon Size, Chemistry and Biology*, 9:237-244; Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate non-natural amino acids into proteins using in vitro biosynthetic methods. See, e.g., Ma et al., (1993) *Biochemistry*, 32:7939; and Hohsaka et al., (1999) *J. Am. Chem. Soc.*, 121:34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.*, 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.*, 298:195. In one embodiment, extended codons based on rare codons or nonsense codons can be used in the methods and compositions described herein, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology*, 20:177-182, and see also, Wu, Y., et. al. (2002) J. Am. Chem. Soc. 124: 14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol* 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.*, 121:11585-6; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See, Meggers et al., (2000) *J. Am. Chem. Soc.*, 122:10714. Because extended codons and unnatural codons are intrinsically orthogonal to natural codons, the non-natural amino acid methods described herein can take advantage of this property to generate orthogonal tRNAs for them.

A translational bypassing system can also be used to incorporate a non-natural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions described herein is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, for example, one or more selector codon for the incorporation of a non-natural amino acid. For example, a nucleic acid for a protein of interest is mutagenized to include one or more selector codon, providing for the incorporation of the one or more non-natural amino acids. The methods and compositions described herein include any such variant, including but not limited to, mutant, versions of any protein, for example, including at least one non-natural amino acid. Similarly, the methods and compositions described herein include corresponding nucleic acids, i.e., any nucleic acid with one or more selector codon that encodes one or more non-natural amino acid.

Nucleic acid molecules encoding a protein of interest, including by way of example only, GH polypeptide may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of a polypeptide are well known in the art, such as those described in U.S. Pat. No. 6,608,183, which is incorporated by reference herein, and standard mutagenesis techniques.

VIII. In Vivo Generation of Polypeptides Comprising Non-Natural Amino Acids

The polypeptides described herein can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Pat. No. 7,045,337, entitled "In vivo incorporation of unnatural amino acids" and U.S. Pat. No. 7,083,970, entitled "Methods and compositions for the production of orthogonal tRNA-aminoacyl tRNA synthetase pairs" which are incorporated by reference herein. These methods involve generating a translational machinery that functions independently of the synthetases and tRNAs endogenous to the translation system (and are therefore sometimes referred to as "orthogonal"). In one embodiment the translation system comprises a polynucleotide encoding the polypeptide; the polynucleotide can be mRNA that was transcribed from the corresponding DNA, or the mRNA may arise from an RNA viral vector; further the polynucleotide comprises a selector codon corresponding to the predesignated site of incorporation for the non-natural amino acid. The translation further comprises a tRNA comprising the non-natural amino acid, where the tRNA is specific to the aforementioned selector codon; in further embodiments, the non-natural amino acid is aminoacylated. In further or additional embodiments, the translation system comprises an aminoacyl synthetase specific for the tRNA, and in other or further embodiments, the translation system comprises an orthogonal tRNA and an orthogonal aminoacyl tRNA synthetase. In further or additional embodiments, the translation system comprises at least one of the following: a plasmid comprising the aforementioned polynucleotide (typically in the form of DNA), genomic DNA comprising the aforementioned polynucleotide (typically in the form of DNA), or genomic DNA into which the aforementioned polynucleotide has been integrated (in further embodiments, the integration is stable integration). In further or additional embodiments of the translation system, the selector codon is selected from the group consisting of an amber codon, ochre codon, opal codon, a unique codon, a rare codon, an unnatural codon, a five-base codon, and a four-base codon. In further or additional embodiments of the translation system, the tRNA is a suppressor tRNA. In further or additional embodiments, the non-natural amino acid polypeptide is synthesized by a ribosome.

In further or additional embodiments, the translation system comprises an orthogonal tRNA (O-tRNA) and an orthogonal aminoacyl tRNA synthetase (O—RS). Typically, the O—RS preferentially aminoacylates the O-tRNA with at least one non-natural amino acid in the translation system and the O-tRNA recognizes at least one selector codon that is not recognized by other tRNAs in the system. The translation system thus inserts the non-natural amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for in the methods described herein to produce the non-natural amino acid polypeptides described herein. For example, keto-specific O-tRNA/aminoacyl-tRNA synthetases are described in Wang, L., et al., *Proc. Natl. Acad. Sci. USA* 100:56-61 (2003) and Zhang, Z. et al., *Biochem.* 42(22):6735-6746 (2003). Exemplary O—RS, or portions thereof, are encoded by polynucleotide sequences and include amino acid sequences disclosed in U.S. Patent Application Publications 2003/0082575 and 2003/0108885, each incorporated herein by reference. Corresponding O-tRNA molecules for use with the O—RSs are also described in U.S. Pat. No. 7,045,337, entitled "In vivo incorporation of unnatural amino acids" and U.S. Pat. No. 7,083,970, entitled "Methods and compositions for the production of orthogonal tRNA-aminoacyl tRNA synthetase pairs" which are incorporated by reference herein. In addition, Mehl et al. in J. Am. Chem. Soc. 2003; 125:935-939 and Santoro et al. Nature Biotechnology 2002 October; 20:1044-1048, which are incorporated by reference in their entirety herein, discuss screening methods and aminoacyl tRNA synthetase and tRNA molecules for the incorporation of p-aminophenylalanine into polypeptides.

Exemplary O-tRNA sequences suitable for use in the methods described herein include, but are not limited to, nucleotide sequences SEQ ID NOs: 1-3 as disclosed in U.S. Patent Application Publication 2003/0108885 (Ser. No. 10/126,931) which is incorporated by reference herein. Other examples of O-tRNA/aminoacyl-tRNA synthetase pairs specific to particular non-natural amino acids are described in U.S. Patent Application Publication 2003/0082575 (Ser. No. 10/126,927) which is incorporated by reference herein. O—RS and O-tRNA that incorporate both keto- and azide-containing amino acids in *S. cerevisiae* are described in Chin, J. W., et al., *Science* 301:964-967 (2003).

Use of O-tRNA/aminoacyl-tRNA synthetases involves selection of a specific codon which encodes the non-natural amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O—RSs, O-tRNAs, and orthogonal O-tRNA/O—RS pairs that can be used to incorporate a non-natural amino acid are described in Wang, L., et al., *Science* 292: 498-500 (2001); Chin, J. W., et al., *J. Am. Chem. Soc.* 124:9026-9027 (2002); Zhang, Z. et al., *Biochemistry* 42: 6735-6746 (2003). Methods and compositions for the in vivo incorporation of non-natural amino acids are described in U.S. Patent Application Publication 2003/0082575 (Ser. No. 10/126,927) which is incorporated by reference herein. Methods for selecting an orthogonal tRNA-tRNA synthetase pair for use in in vivo translation system of an organism are also described in U.S. Pat. No. 7,045,337, entitled "In vivo incorporation of unnatural amino acids" and U.S. Pat. No. 7,083,970, entitled "Methods and compositions for the production of orthogonal tRNA-aminoacyl tRNA synthetase pairs" which are incorporated by reference herein. In addition PCT Publication No. WO 04/035743 entitled "Site Specific Incorporation of Keto Amino Acids into proteins, which is incorporated by reference in its entirety, describes orthogonal RS and tRNA pairs for the incorporation of keto amino acids. PCT Publication No. WO 04/094593 entitled "Expanding the Eukaryotic Genetic Code," which is incorporated by reference herein in its entirety, describes orthogonal RS and tRNA pairs for the incorporation of non-naturally encoded amino acids in eukaryotic host cells.

Methods for producing at least one recombinant orthogonal aminoacyl-tRNA synthetase (O—RS) comprise: (a) generating a library of (optionally mutant) RSs derived from at least one aminoacyl-tRNA synthetase (RS) from a first organism, including but not limited to, a prokaryotic organism, such as *Methanococcus jannaschii, Methanobacterium thermoautotrophicum, Halobacterium, Escherichia coli, A. fulgidus, P. furiosus, P. horikoshii, A. pernix, T. thermophilus*, or the like, or a eukaryotic organism; (b) selecting (and/or screening) the library of RSs (optionally mutant RSs) for members that aminoacylate an orthogonal tRNA (O-tRNA) in the presence of a non-natural amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-natural amino acid, thereby providing the at least one recombinant O—RS; wherein the at least one recombinant O—RS preferentially aminoacylates the O-tRNA with the non-natural amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-natural amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber codon, ochre codon, opal codon, a unique codon, a rare codon, an unnatural codon, a five-base codon, and a four-base codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is a β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tRNA in the absence of the non-natural amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene, including but not limited to, a chloramphenicol acetyltransferase (CAT) gene); and, identifying cells that survive or show a specific screening response in a first medium supplemented with the non-natural amino acid and a screening or selection agent, but fail to survive or to show the specific response in a second medium not supplemented with the non-natural amino acid and the selection or screening agent, thereby providing surviving cells or screened cells with the at least one recombinant O—RS. For example, a CAT identification protocol optionally acts as a positive selection and/or a negative screening in determination of appropriate O—RS recombinants. For instance, a pool of clones is optionally replicated on growth plates containing CAT (which comprises at least one selector codon) either with or without one or more non-natural amino acid. Colonies growing exclusively on the plates containing non-natural amino acids are thus regarded as containing recombinant O—RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a *eubacterium*, a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-natural amino acid, but fail to survive or show a specific screening response in a second medium supplemented with the non-natural amino acid, thereby providing surviving or screened cells with the at least one recombinant O—RS, wherein the at least one recombinant O—RS is specific for the non-natural amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia coli*, a fungi, a yeast, an archaebacteria, a eubacteria, a plant, an insect, a protist, etc.). Also, some aspects include wherein the negative selection marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O—RS) can further comprise: (d) isolating the at least one recombinant O—RS; (e) generating a second set of O—RS (optionally mutated) derived from the at least one recombinant O—RS; and, (f) repeating steps (b) and (c) until a mutated O—RS is obtained that comprises an ability to preferentially aminoacylate the O-tRNA. Optionally, steps (d)-(f) are repeated, including but not limited to, at least about two times. In one aspect, the second set of mutated O—RS derived from at least one recombinant O—RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the non-natural amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS (O—RS), thereby providing at least one recombinant O-tRNA; wherein the at least one recombinant O-tRNA recognizes a selector codon and is not efficiency recognized by the RS from the second organism and is preferentially aminoacylated by the O—RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii, Methanobacterium thermoautotrophicum, Escherichia coli, Halobacterium*, etc.), eukaryotes, mammals, fungi, yeasts, archaebacteria, eubacteria, plants, insects, protists, etc. Additionally, the recombinant tRNA is optionally aminoacylated by a non-natural amino acid, wherein the non-natural amino acid is biosynthesized in vivo either naturally or through genetic manipulation. The non-natural amino acid is optionally added to a growth medium for at least the first or second organism.

In one aspect, selecting (including but not limited to, negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS (O—RS) can include: introducing a positive selection or screening marker gene, wherein the positive marker gene comprises a drug resistance gene (including but not limited to, β-lactamase gene, comprising at least one of the selector codons, such as at least one amber stop codon) or a gene essential to the organism, or a gene that leads to detoxification of a toxic agent, along with the O—RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least recombinant tRNA is aminoacylated by the O—RS and inserts an amino acid into a translation product encoded by the positive marker gene, in response to the at least one selector codons. In another embodiment, the concentration of the selection and/or screening agent is varied.

Methods for generating specific O-tRNA/O—RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS (O—RS), thereby providing at least one recombinant O-tRNA. The at least one recombinant O-tRNA recognizes a selector codon and is not efficiency recognized by the RS from the second organism and is preferentially aminoacylated by the O—RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-natural amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the non-natural amino acid, thereby providing the at least one specific O-tRNA/O—RS pair, wherein the at least one specific O-tRNA/O—RS pair comprises at least one recombinant O—RS that is specific for the non-natural amino acid and the at least one recombinant O-tRNA. Specific O-tRNA/O—RS pairs produced by the methods are included. For example, the specific O-tRNA/O—RS pair can include, including but not limited to, a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, *Methanococcus jannaschii*).

Methods for selecting an orthogonal tRNA-tRNA synthetase pair for use in an in vivo translation system of a second organism are also included in the methods described herein. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms described herein comprise a variety of organism and a variety of combinations. In one embodiment, the organisms are optionally a prokaryotic organism, including but not limited to, *Methanococcus jannaschii, Methanobacterium thermoautotrophicum, Halobacterium, Escherichia coli, A. fulgidus, P. furiosus, P. horikoshii, A. pernix, T. thermophilus*, or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like.

A. Expression in Non-Eukaryotes and Eukaryotes

The techniques disclosed in this section can be applied to the expression in non-eukaryotes and eukaryotes of the non-natural amino acid polypeptides described herein.

To obtain high level expression of a cloned polynucleotide, one typically subclones polynucleotides encoding a desired polypeptide into an expression vector that contains a strong promoter to direct transcription, a transcription/translation terminator, and if for a nucleic acid encoding a protein, a ribosome binding site for translational initiation. Suitable bacterial promoters are described in, e.g., in Sambrook et al. and Ausubel et al. Bacterial expression systems for expressing polypeptides are available in, including but not limited to, *E. coli, Bacillus* sp., *Pseudomonas fluorescens, Pseudomonas aeruginosa, Pseudomonas putida*, and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are also commercially available. In cases where orthogonal tRNAs and aminoacyl tRNA synthetases (described elsewhere herein) are used to express the polypeptides, host cells for expression are selected based on their ability to use the orthogonal components. Exemplary host cells include Gram-positive bacteria (including but not limited to *B. brevis* or *B. subtilis*, or *Streptomyces*) and Gram-negative bacteria (*E. coli* or *Pseudomonas fluorescens, Pseudomonas aeruginosa, Pseudomonas putida*), as well as yeast and other eukaryotic cells. Cells comprising O-tRNA/O—RS pairs can be used as described herein.

A eukaryotic host cell or non-eukaryotic host cell as described herein provides the ability to synthesize polypeptides which comprise non-natural amino acids in large useful quantities. In one aspect, the composition optionally includes, but is not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the polypeptides that comprises a non-natural amino acid, or an amount that can be achieved with in vivo polypeptide production methods (details on recombinant protein production and purification are provided herein). In another aspect, the protein is optionally present in the composition at a concentration of, including but not limited to, at least 10 micrograms of polypeptide per liter, at least 50 micrograms of polypeptide per liter, at least 75 micrograms of polypeptide per liter, at least 100 micrograms of polypeptide per liter, at least 200 micrograms of polypeptide per liter, at least 250 micrograms of polypeptide per liter, at least 500 micrograms of polypeptide per liter, at least 1 milligram of polypeptide per liter, or at least 10 milligrams of polypeptide per liter or more, in, including but not limited to, a cell lysate, a buffer, a pharmaceutical buffer, or other liquid suspension (including but not limited to, in a volume of, anywhere from about 1 nl to about 100 L or more). The production of large quantities (including but not limited to, greater that that typically possible with other methods, including but not limited to, in vitro translation) of a protein in a eukaryotic cell including at least one non-natural amino acid is a feature of the methods, techniques and compositions described herein.

A eukaryotic host cell or non-eukaryotic host cell as described herein provides the ability to biosynthesize proteins that comprise non-natural amino acids in large useful quantities. For example, proteins comprising a non-natural amino acid can be produced at a concentration of, including but not limited to, at least 10 µg/liter, at least 50 µg/liter, at least 75 µg/liter, at least 100 µg/liter, at least 200 µg/liter, at least 250 µg/liter, or at least 500 µg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

1. Expression Systems, Culture, and Isolation

The techniques disclosed in this section can be applied to the expression systems, culture and isolation of the non-natural amino acid polypeptides described herein. Non-natural amino acid polypeptides may be expressed in any number of suitable expression systems including, but not limited to, yeast, insect cells, mammalian cells, and bacteria. A description of exemplary expression systems is provided herein.

Yeast

As used herein, the term "yeast" includes any of the various yeasts capable of expressing a gene encoding the non-natural amino acid polypeptide. Such yeasts include, but are not limited to, ascosporogenous yeasts (Endomycetales), basidiosporogenous yeasts and yeasts belonging to the Fungi imperfecti (*Blastomycetes*) group. The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodosporidium, Sporidiobolus, Filobasidium*, and *Filobasidiella*. Yeasts belonging to the Fungi Imperfecti (*Blastomycetes*) group are divided into two families, Sporobolomycetaceae (e.g., genera *Sporobolomyces* and *Bullera*) and Cryptococcaceae (e.g., genus *Candida*).

In certain embodiments, the species within the genera *Pichia, Kluyveromyces, Saccharomyces, Schizosaccharomyces, Hansenula, Torulopsis*, and *Candida*, including, but not limited to, *P. pastoris, P. guillerimondii, S. cerevisiae, S. carlsbergensis, S. diastaticus, S. douglasii, S. kluyveri, S. norbensis, S. oviformis, K. lactis, K. fragilis, C. albicans, C. maltosa*, and *H. polymorpha* are used in the methods, techniques and compositions described herein.

The selection of suitable yeast for expression of the non-natural amino acid polypeptide is within the skill of one of ordinary skill in the art. In selecting yeast hosts for expression, suitable hosts may include, but are not limited to, those shown to have, by way of example, good secretion capacity, low proteolytic activity, and overall robustness. Yeast are generally available from a variety of sources including, but not limited to, the Yeast Genetic Stock Center, Department of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a non-natural amino acid polypeptide, are included in the progeny intended by this definition.

Expression and transformation vectors, including extrachromosomal replicons or integrating vectors, have been developed for transformation into many yeast hosts. For example, expression vectors have been developed for *S. cerevisiae* (Sikorski et al., Genetics (1998) 122:19; Ito et al., J. Bacteriol. (1983) 153:163; Hinnen et al., Proc. Natl. Acad. Sci. USA (1978) 75:1929); *C. albicans* (Kurtz et al., Mol. Cell. Biol. (1986) 6:142); *C. maltosa* (Kunze et al., J. Basic Microbiol. (1985) 25:141); *H. polymorpha* (Gleeson et al., J. Gen. Microbiol. (1986) 132:3459; Roggenkamp et al., Mol. Gen. Genet. (1986) 202:302); *K. fragilis* (Das et al., J. Bacteriol. (1984) 158:1165); *K. lactis* (De Louvencourt et al., J. Bacteriol. (1983) 154:737; Van den Berg et al., Bio/Technology (1990) 8:135); *P. guillerimondii* (Kunze et al., J. Basic Microbiol. (1985) 25:141); *P. pastoris* (U.S. Pat. Nos. 5,324,639; 4,929,555; and U.S. Pat. No. 4,837,148;

Cregg et al., Mol. Cell. Biol. (1985) 5:3376); *Schizosaccharomyces pombe* (Beach et al., Nature (1982) 300:706); *A. nidulans* (Ballance et al., Biochem. Biophys. Res. Commun. (1983) 112:284-89; Tilburn et al., Gene (1983) 26:205-221; and Yelton et al., Proc. Natl. Acad. Sci. USA (1984) 81:1470-74); *A. niger* (Kelly and Hynes, EMBO J. (1985) 4:475-479); *T. reesia* (EP 0 244 234); and filamentous fungi such as, e.g., *Neurospora, Penicillium, Tolypocladium* (WO 91/00357), each herein incorporated by reference in their entirety.

Control sequences for yeast vectors include, but are not limited to, promoter regions from genes such as alcohol dehydrogenase (ADH) (EP 0 284 044); enolase; glucokinase; glucose-6-phosphate isomerase; glyceraldehyde-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Miyanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255:12073); and other glycolytic enzymes, such as pyruvate decarboxylase, triosephosphate isomerase, and phosphoglucose isomerase (Holland et al., BIOCHEMISTRY (1978) 17:4900; Hess et al., J. ADV. ENZYME REG. (1969) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. By way of example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein in their entirety. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2μ plasmid origin is suitable for yeast. A suitable selection gene for use in yeast is the trp1 gene present in the yeast plasmid. See Tschumper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts include, but are not limited to, either the transformation of spheroplasts or of intact yeast host cells treated with alkali cations. By way of example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING: A LAB. MANUAL (2001). Yeast host cells may then be cultured using standard techniques known to those of ordinary skill in the art.

Other methods for expressing heterologous proteins in yeast host cells are well known to those of ordinary skill in the art. See generally U.S. Patent Publication No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Pat. Nos. RE37,343 and RE35,749; PCT Published Patent Applications WO 99/07862; WO 98/37208; and WO 98/26080; European Patent Applications EP 0 946 736; EP 0 732 403; EP 0 480 480; WO 90/10277; EP 0 340 986; EP 0 329 203; EP 0 324 274; and EP 0 164 556. See also Gellissen et al., ANTONIE VAN LEEUWENHOEK (1992) 62(1-2):79-93; Romanos et al., YEAST (1992) 8(6):423-488; Goeddel, METHODS IN ENZYMOLOGY (1990) 185:3-7, each incorporated by reference herein in its entirety.

The yeast host strains may be grown in fermentors during the amplification stage using standard feed batch fermentation methods. The fermentation methods may be adapted to account for differences in a particular yeast host's carbon utilization pathway or mode of expression control. By way of example, fermentation of a *Saccharomyces* yeast host may require a single glucose feed, complex nitrogen source (e.g., casein hydrolysates), and multiple vitamin supplementation, whereas, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. PROTEIN CHEM. (1990) 9:95; and Fieschko et al., BIOTECH. BIOENG. (1987) 29:1113, each incorporated by reference herein in its entirety.

Such fermentation methods, however, may have certain common features independent of the yeast host strain employed. By way of example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, each incorporated by reference herein in its entirety.

Baculovirus-Infected Insect Cells

The term "insect host" or "insect host cell" refers to an insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a non-natural amino acid polypeptide, are included in the progeny intended by this definition.

The selection of suitable insect cells for expression of a polypeptide is well known to those of ordinary skill in the art. Several insect species are well described in the art and are commercially available including, but not limited to, *Aedes aegypti, Bombyx mori, Drosophila melanogaster, Spodoptera frugiperda,* and *Trichoplusia ni*. In selecting insect hosts for expression, suitable hosts may include, but are not limited to, those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with a sequence homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are described in SUMMERS AND SMITH, TEXAS AGRICULTURAL EXPERIMENT STATION BULLETIN NO. 1555 (1987), herein incorporated by reference. See also, RICHARDSON, 39 METHODS IN MOLECULAR BIOLOGY: BACULOVIRUS EXPRESSION PROTOCOLS (1995); AUSUBEL ET AL., CURRENT PROTOCOLS IN MOLECULAR BIOLOGY 16.9-16.11 (1994); KING AND POSSEE, THE BACULOVIRUS SYSTEM: A LABORATORY GUIDE (1992); and O'REILLY ET AL., BACULOVIRUS EXPRESSION VECTORS: A LABORATORY MANUAL (1992).

The production of various heterologous proteins using baculovirus/insect cell expression systems is described in the following references and such techniques can be adapted to produce the non-natural amino acid polypeptides described herein. See, e.g., U.S. Pat. Nos. 6,368,825; 6,342,216; 6,338,846; 6,261,805; 6,245,528, 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032 WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/02628; WO 92/01801; WO 90/14428; WO 90/10078; WO 90/02566; WO 90/02186; WO 90/01556; WO 89/01038; WO 89/01037; WO 88/07082., each incorporated by reference herein in its entirety.

Vectors that are useful in baculovirus/insect cell expression systems are known include, but are not limited to, insect expression and transfer vectors derived from the baculovirus *Autographacaliformica* nuclear polyhedrosis virus (AcNPV), which is a helper-independent, viral expression vector. Viral expression vectors derived from this system usually use the strong viral polyhedrin gene promoter to drive expression of heterologous genes. See generally, O'Reilly ET AL., BACULOVIRUS EXPRESSION VECTORS: A LABORATORY MANUAL (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller, ANN. REV. MICROBIOL. (1988) 42:177) and a prokaryotic ampicillin-resistance (amp) gene and origin of replication for selection and propagation in *E. coli*.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, VIROLOGY 170:31 (1989). Other commercially available vectors include, for example, PBlueBac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Illustrative methods for introducing heterologous DNA into the desired site in the baculovirus virus are described in SUMMERS AND SMITH, TEXAS AGRICULTURAL EXPERIMENT STATION BULLETIN NO. 1555 (1987); Smith et al., MOL. CELL. BIOL. (1983) 3:2156; Luckow and Summers, VIROLOGY (1989) 170:31. By way of example, the insertion can be into a gene such as the polyhedrin gene, by homologous double crossover recombination; insertion can also be into a restriction enzyme site engineered into the desired baculovirus gene. See Miller et al., BIOESSAYS (1989) 11(4):91.

Transfection may be accomplished by electroporation using methods described in TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHNIQUES (1999) 26(1):36; Graves et al., BIOCHEMISTRY (1998) 37:6050; Nomura et al., J. BIOL. CHEM. (1998) 273 (22):13570; Schmidt et al., PROTEIN EXPRESSION AND PURIFICATION (1998) 12:323; Siffert et al., NATURE GENETICS (1998) 18:45; TILKINS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190:139; Jakobsson et al., J. BIOL. CHEM. (1996) 271:22203; Rowles et al., J. BIOL. CHEM. (1996) 271(37):22376; Reverey et al., J. BIOL. CHEM. (1996) 271(39):23607-10; Stanley et al., J. BIOL. CHEM. (1995) 270:4121; Sisk et al., J. VIROL. (1994) 68(2):766; and Peng et al., BIOTECHNIQUES (1993) 14(2):274. Commercially available liposomes include, for example, Cellfectin® and Lipofectin® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18(19):5667; and Mann and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., *The Regulation of Baculovirus Gene Expression* in THE MOLECULAR BIOLOGY OF BACULOVIRUSES (1986); EP 0 127 839 and 0 155 476) and the gene encoding the p10 protein (Vlak et al., J. GEN. VIROL. (1988) 69:765.

The newly formed baculovirus expression vector is packaged into an infectious recombinant baculovirus and subsequently grown plaques may be purified by techniques such as those described in Miller et al., BIOESSAYS (1989) 11 (4): 91; SUMMERS AND SMITH, TEXAS AGRICULTURAL EXPERIMENT STATION BULLETIN No. 1555 (1987).

Recombinant baculovirus expression vectors have been developed for infection into several insect cells. For example, recombinant baculoviruses have been developed for, inter alia, *Aedes aegypti* (ATCC No. CCL-125), *Bombyx mori* (ATCC No. CRL-8910), *Drosophila melanogaster* (ATCC No. 1963), *Spodoptera frugiperda*, and *Trichoplusia ni*. See Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, 519 (*Spodoptera frugiperda*) (ATCC No. CRL-1711), Sf21 (*Spodoptera frugiperda*) (Invitrogen Corp., Cat. No. 11497-013 (Carlsbad, Calif.)), Tri-368 (*Trichopulsia ni*), and High-Five™ BTI-TN-5B1-4 (*Trichopulsia ni*).

Cells and culture media are commercially available for both direct and fusion expression of heterologous polypeptides in a baculovirus/expression.

E. Coli, Pseudomonas, and Other Prokaryotes:

Bacterial expression techniques are well known in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity Frequently, a plurality of markers are present, which provide for different characteristics.

A bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al., ANNU. REV. GENET. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057; Yelverton et al., NUCL. ACIDS RES. (1981) 9:731; U.S. Pat. No. 4,738,921; IFNPub. Nos. 036 776 and 121 775], each is herein incorporated by reference in its entirety. The β-galactosidase (bla) promoter system [Weissmann (1981) "The cloning of interferon and other mistakes." In Interferon 3 (Ed. I. Gresser)], bacteriophage lambda PL [Shimatake et al., NATURE (1981) 292:128] and T5 [U.S. Pat. No. 4,689,406], each is herein incorporated by reference in its entirety promoter systems also provide useful promoter sequences. Preferred methods encompassed herein utilize strong promoters, such as the T7 promoter to induce polypeptide production at high levels. Examples of such vectors include, but are not limited to, the pET29 series from Novagen, and the pPOP vectors described in WO99/05297, which is herein incorporated by reference in its entirety. Such expression systems produce high levels of polypeptide in the host without compromising host cell viability or growth parameters.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433, which is herein incorporated by reference in its entirety]. For example, the tac promoter is a hybrid trp-lac promoter comprised of both trp promoter and lac operon sequences that is regulated by the lac repressor [Amann et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. MOL. BIOL. (1986) 189: 113; Tabor et al., Proc Natl. Acad. Sci. (1985) 82:1074]. In addition, a hybrid promoter can also be comprised of a bacteriophage promoter and an *E. coli* operator region (IFNPub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of mRNA to the ribosome by the pairing of bases between the SD sequence and the 3' and of *E. coli* 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in *Escherichia coli*", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a polypeptide, are included in the progeny intended by this definition.

The selection of suitable host bacteria for expression of a polypeptide is well known to those of ordinary skill in the art. In selecting bacterial hosts for expression, suitable hosts may include those shown to have, inter alia, good inclusion body formation capacity, low proteolytic activity, good secretion capacity, good soluble protein production capability, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. In one embodiment of the methods described and encompassed herein, the *E. coli* host includes, but is not limited to, strains of BL21, DH10B, or derivatives thereof. In another embodiment of the methods described and encompassed herein, the *E. coli* host is a protease minus strain including, but not limited to, OMP- and LON-. In another embodiment, the bacterial host is a species of *Pseudomonas*, such a *P. fluorescens, P. aeruginosa,* and *P. putida*. An example of a *Pseudomonas* strain is *P. fluorescens* biovar I, strain MB101 (Dow Chemical).

Once a recombinant host cell strain has been established (i.e., the expression construct has been introduced into the host cell and host cells with the proper expression construct are isolated), the recombinant host cell strain is cultured under conditions appropriate for production of polypeptides. The method of culture of the recombinant host cell strain will be dependent on the nature of the expression construct utilized and the identity of the host cell. Recombinant host strains are normally cultured using methods that are well known to the art. Recombinant host cells are typically cultured in liquid medium containing assimilatable sources of carbon, nitrogen, and inorganic salts and, optionally, containing vitamins, amino acids, growth factors, and other proteinaceous culture supplements well known to the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the polypeptide accumulates intracellularly) or harvesting of culture supernatant in either batch or continuous formats. For production in prokaryotic host cells, batch culture and cell harvest are preferred.

In one embodiment, the non-natural amino acid polypeptides described herein are purified after expression in recombinant systems. The polypeptides may be purified from host cells or culture medium by a variety of methods known to the art. Normally, many polypeptides produced in bacterial host cells may be poorly soluble or insoluble (in the form of inclusion bodies). In one embodiment, amino acid substitutions may readily be made in the polypeptides that are selected for the purpose of increasing the solubility of the recombinantly produced polypeptide utilizing the methods disclosed herein as well as those known in the art. In the case of insoluble polypeptide, the polypeptide may be collected from host cell lysates by centrifugation or filtering and may further be followed by homogenization of the cells. In the case of poorly soluble polypeptide, compounds including, but not limited to, polyethylene imine (PEI) may be added to induce the precipitation of partially soluble polypeptide. The precipitated protein may then be conveniently collected by centrifugation or filtering. Recombinant host cells may be disrupted or homogenized to release the inclusion bodies from within the cells using a variety of methods well known to those of ordinary skill in the art. Host cell disruption or homogenization may be performed using well known techniques including, but not limited to, enzymatic cell disruption, sonication, dounce homogenization, or high pressure release disruption. In one embodiment of the methods described and encompassed herein, the high pressure release technique is used to disrupt the *E. coli* host cells to release the inclusion bodies of the polypeptides. When handling inclusion bodies of polypeptides, it is advantageous to minimize the homogenization time on repetitions in order to maximize the yield of inclusion bodies without loss due to factors such as solubilization, mechanical shearing or proteolysis.

Insoluble or precipitated polypeptides may then be solubilized using any of a number of suitable solubilization agents known to the art. By way of example, the polypeptides are solubilized with urea or guanidine hydrochloride. The volume of the solubilized polypeptides should be minimized so that large batches may be produced using conveniently manageable batch sizes. This factor may be significant in a large-scale commercial setting where the recombinant host may be grown in batches that are thousands of liters in volume. In addition, when manufacturing polypeptides in a large-scale commercial setting, in particular for human pharmaceutical uses, the avoidance of harsh chemicals that can damage the machinery and container, or the protein product itself, should be avoided, if possible. It has been shown in the methods described and encompassed herein that the milder denaturing agent urea can be used to solubilize the polypeptide inclusion bodies in place of the harsher denaturing agent guanidine hydrochloride. The use of urea significantly reduces the risk of damage to stainless steel equipment utilized in the manufacturing and purification process of a polypeptide while efficiently solubilizing the polypeptide inclusion bodies.

In the case of soluble polypeptides, the peptides may be secreted into the periplasmic space or into the culture medium. In addition, soluble peptides may be present in the cytoplasm of the host cells. The soluble peptide may be concentrated prior to performing purification steps. Standard techniques, including but not limited to those described herein, may be used to concentrate soluble peptide from, by way of example, cell lysates or culture medium. In addition, standard techniques, including but not limited to those described herein, may be used to disrupt host cells and release soluble peptide from the cytoplasm or periplasmic space of the host cells.

When the polypeptide is produced as a fusion protein, the fusion sequence is preferably removed. Removal of a fusion sequence may be accomplished by methods including, but not limited to, enzymatic or chemical cleavage. Enzymatic removal of fusion sequences may be accomplished using methods well known to those in the art. The choice of enzyme for removal of the fusion sequence will be determined by the identity of the fusion, and the reaction conditions will be specified by the choice of enzyme. Chemical cleavage may be accomplished using reagents, including but not limited to, cyanogen bromide, TEV protease, and other reagents. The cleaved polypeptide is optionally purified from the cleaved fusion sequence by well known methods. Such methods will be determined by the identity and properties of the fusion sequence and the polypeptide. Methods for purification may include, but are not limited to, size-exclusion chromatography, hydrophobic interaction chromatography, ion-exchange chromatography or dialysis or any combination thereof.

The polypeptide is also optionally purified to remove DNA from the protein solution. DNA may be removed by any suitable method known to the art, including, but not limited to, precipitation or ion exchange chromatography. In one embodiment, DNA is removed by precipitation with a nucleic acid precipitating agent, such as, but not limited to, protamine sulfate. The polypeptide may be separated from the precipitated DNA using standard well known methods including, but not limited to, centrifugation or filtration. Removal of host nucleic acid molecules is an important factor in a setting where the polypeptide is to be used to treat humans and the methods described herein reduce host cell DNA to pharmaceutically acceptable levels.

Methods for small-scale or large-scale fermentation may also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

Human forms of the non-natural amino acid polypeptides described herein can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the non-natural amino acid polypeptides described herein include, but are not limited to, separating deamidated and clipped forms of a polypeptide variant from the corresponding intact form.

Any of the following exemplary procedures can be employed for purification of a non-natural amino acid polypeptide described herein: affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

Polypeptides encompassed within the methods and compositions described herein, including but not limited to, polypeptides comprising non-natural amino acids, antibodies to polypeptides comprising non-natural amino acids, binding partners for polypeptides comprising non-natural amino acids, etc., may be purified, either partially or substantially to homogeneity, according to standard procedures known to and used by those of skill in the art. Accordingly, polypeptides described herein may be recovered and purified by any of a number of methods well known in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and any combination thereof. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against non-natural amino acids (or polypeptides comprising non-natural amino acids) are used as purification reagents, including but not limited to, for affinity-based purification of polypeptides comprising one or more non-natural amino acid(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production.

In addition to other references noted herein, a variety of purification/protein folding methods are well known in the art, including, but not limited to, those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods,* 2nd Edition Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein.

One advantage of producing polypeptides comprising at least one non-natural amino acid in a eukaryotic host cell or non-eukaryotic host cell is that typically the polypeptides will be folded in their native conformations. However, in certain embodiments of the methods and compositions described herein, after synthesis, expression and/or purification, polypeptides can possess a conformation different from the desired conformations of the relevant polypeptides. In one aspect of the methods and compositions described herein, the expressed protein is optionally denatured and then renatured. This optional denaturation and renaturation is accomplished utilizing methods known in the art, including but not limited to, by adding a chaperonin to the polypeptide of interest, and by solubilizing the proteins in a chaotropic agent including, but not limited to, guanidine HCl, and utilizing protein disulfide isomerase.

In general, it is occasionally desirable to denature and reduce expressed polypeptides and then to cause the polypeptides to re-fold into the preferred conformation. By way of example, such re-folding may be accomplished with the addition guanidine, urea, DTT, DTE, and/or a chaperonin to a translation product of interest. Methods of reducing, denaturing and renaturing proteins are well known to those of skill in the art (see, the references above, and Debinski, et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of a non-natural amino acid polypeptide, the polypeptide thus produced may be misfolded and thus lacks or has reduced biological activity. The bioactivity of the protein may be restored by "refolding". In one embodiment, a misfolded polypeptide is refolded by solubilizing (where the polypeptide is also insoluble), unfolding and reducing the polypeptide chain using, by way of example, one or more chaotropic agents (including, but not limited to, urea and/or guanidine) and a reducing agent capable of reducing disulfide bonds (including, but not limited to, dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. An unfolded or misfolded polypeptide may be refolded using standard methods known in the art, such as those described in U.S. Pat. Nos. 4,511,502, 4,511,503, and 4,512, 922, each of which is herein incorporated by reference in its entirety. The polypeptide may also be cofolded with other proteins to form heterodimers or heteromultimers. After refolding or cofolding, the polypeptide may be further purified.

Purification of non-natural amino acid polypeptides may be accomplished using a variety of techniques, including but not limited those described herein, by way of example hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, the non-natural amino acid polypeptides may be exchanged into different buffers and/or concentrated by any of a variety of methods known to the art, including, but not limited to, diafiltration and dialysis. hGH that is provided as a single purified protein may be subject to aggregation and precipitation. In certain embodiments the purified non-natural amino acid polypeptides may be at least 90% pure (as measured by reverse phase high performance liquid chromatography, RP-HPLC, or sodium dodecyl sulfate-polyacrylamide gel electrophoresis, SDS-PAGE). In certain other embodiments the purified non-natural amino acid polypeptides may be at least 95% pure, or at least 98% pure, or at least 99% or greater purity. Regardless of the exact numerical value of the purity of the non-natural amino acid polypeptides, the non-natural amino acid polypeptides is sufficiently pure for use as a pharmaceutical product or for further processing, including but not limited to, conjugation with a water soluble polymer such as PEG.

In certain embodiments the non-natural amino acid polypeptides molecules may be used as therapeutic agents in the absence of other active ingredients or proteins (other than excipients, carriers, and stabilizers, serum albumin and the like), and in certain embodiments the non-natural amino acid polypeptides molecules they may be complexed with another polypeptide or a polymer.

2. Purification of Non-Natural Amino Acid Polypeptides
  General Purification Methods The techniques disclosed in this section can be applied to the general purification of the non-natural amino acid polypeptides described herein. Any one of a variety of isolation steps may be performed on the cell lysate extract, culture medium, inclusion bodies, periplasmic space of the host cells, cytoplasm of the host cells, or other material comprising the desired polypeptide or on any polypeptide mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), Bio-Rad Laboratories, Inc. (Hercules, Calif.), and Amersham Biosciences, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (Amersham Biosciences, Piscataway, N.J.).

Examples of fraction collectors include RediFrac Fraction Collector, FRAC-100 and FRAC-200 Fraction Collectors, and SUPERFRAC® Fraction Collector (Amersham Biosciences, Piscataway, N.J.). Mixers are also available to form pH and linear concentration gradients. Commercially available mixers include Gradient Mixer GM-1 and In-Line Mixers (Amersham Biosciences, Piscataway, N.J.).

The chromatographic process may be monitored using any commercially available monitor. Such monitors may be used to gather information like UV, fluorescence, pH, and conductivity. Examples of detectors include Monitor UV-1, UVICORD® S II, Monitor UV-M II, Monitor UV-900, Monitor UPC-900, Monitor pH/C-900, and Conductivity Monitor (Amersham Biosciences, Piscataway, N.J.). Indeed, entire systems are commercially available including the various AKTA® systems from Amersham Biosciences (Piscataway, N.J.).

In one embodiment of the methods and compositions described herein, for example, the polypeptide may be reduced and denatured by first denaturing the resultant purified polypeptide in urea, followed by dilution into TRIS buffer containing a reducing agent (such as DTT) at a suitable pH. In another embodiment, the polypeptide is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured polypeptide mixture may then be further isolated or purified.

As stated herein, the pH of the first polypeptide mixture may be adjusted prior to performing any subsequent isolation steps. In addition, the first polypeptide mixture or any subsequent mixture thereof may be concentrated using techniques known in the art. Moreover, the elution buffer comprising the first polypeptide mixture or any subsequent mixture thereof may be exchanged for a buffer suitable for the next isolation step using techniques well known to those of ordinary skill in the art.

Ion Exchange Chromatography

The techniques disclosed in this section can be applied to the ion-chromatography of the non-natural amino acid polypeptides described herein. In one embodiment, and as an optional, additional step, ion exchange chromatography may be performed on the first polypeptide mixture. See generally ION EXCHANGE CHROMATOGRAPHY: PRINCIPLES AND METHODS (Cat. No. 18-1114-21, Amersham Biosciences (Piscataway, N.J.)). Commercially available ion exchange columns include HITRAP®, HIPREP®, and HILOAD® Columns (Amersham Biosciences, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, N.J.). Anion or cation exchange column chromatography may be performed on the polypeptide at any stage of the purification process to isolate substantially purified polypeptide. The cation exchange chromatography step may be performed using any suitable cation exchange matrix. Cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing. Following adsorption of the polypeptide to the cation exchanger matrix, substantially purified polypeptide may be eluted by contacting the matrix with a buffer having a sufficiently high pH or ionic strength to displace the polypeptide from the matrix. Suitable buffers for use in high pH elution of substantially purified polypeptide include, but are not limited to, citrate, phosphate, formate, acetate, HEPES, and MES buffers ranging in concentration from at least about 5 mM to at least about 100 mM.

Reverse-Phase Chromatography

The techniques disclosed in this section can be applied to the reverse-phase chromatography of the non-natural amino acid polypeptides described herein. RP-HPLC may be performed to purify proteins following suitable protocols that are known to those of ordinary skill in the art. See, e.g., Pearson et al., ANAL BIOCHEM. (1982) 124:217-230 (1982); Rivier et al., J. CHROM. (1983) 268:112-119; Kunitani et al., J. CHROM. (1986) 359:391-402. RP-HPLC may be performed on the polypeptide to isolate substantially purified polypeptide. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about $C_{18}$, resins may be used. Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. A suitable elution buffer containing an ion pairing agent and an organic modifier such as methanol, isopropanol, tetrahydrofuran, acetonitrile or ethanol, may be used to elute the polypeptide from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, ammonium acetate and acetonitrile solutions.

Hydrophobic Interaction Chromatography Purification Techniques

The techniques disclosed in this section can be applied to the hydrophobic interaction chromatography purification of the non-natural amino acid polypeptides described herein. Hydrophobic interaction chromatography (HIC) may be performed on the polypeptide. See generally HYDROPHOBIC INTERACTION CHROMATOGRAPHY HANDBOOK: PRINCIPLES AND METHODS (Cat. No. 18-1020-90, Amersham Biosciences (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (Amersham Biosciences, Piscataway, N.J.). Briefly, prior to loading, the HIC column may be equilibrated using standard buffers known to those of ordinary skill in the art, such as an acetic acid/sodium chloride solution or HEPES containing ammonium sulfate Ammonium sulfate may be used as the buffer for loading the HIC column. After loading the polypeptide, the column may then washed using standard buffers and conditions to remove unwanted materials but retaining the polypeptide on the HIC column. The polypeptide may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the polypeptide molecules. The eluant may then be concentrated, for example, by filtration such as diafiltration or ultrafiltration. Diafiltration may be utilized to remove the salt used to elute polypeptide.

Other Purification Techniques

The techniques disclosed in this section can be applied to other purification techniques of the non-natural amino acid polypeptides described herein. Yet another isolation step using, for example, gel filtration (GEL FILTRATION: PRINCIPLES AND METHODS (Cat. No. 18-1022-18, Amersham Biosciences, Piscataway, N.J., which is herein incorporated by reference in its entirety), hydroxyapatite chromatography (suitable matrices include, but are not limited to, HA-Ultrogel, High Resolution (Calbiochem), CHT Ceramic Hydroxyapatite (BioRad), Bio-Gel HTP Hydroxyapatite (BioRad)), HPLC, expanded bed adsorption, ultrafiltration, diafiltration, lyophilization, and the like, may be performed on the first polypeptide mixture or any subsequent mixture thereof, to remove any excess salts and to replace the buffer with a suitable buffer for the next isolation step or even formulation of the final drug product. The yield of polypeptide, including substantially purified polypeptide, may be monitored at each step described herein using various techniques, including but not limited to those described herein. Such techniques may also used to assess the yield of substantially purified polypeptide following the last isolation step. By way of example, the yield of polypeptide may be monitored using any of several reverse phase high pressure liquid chromatography columns, having a variety of alkyl chain lengths such as cyano RP-HPLC, $C_{18}$RP-HPLC; as well as cation exchange HPLC and gel filtration HPLC.

In certain embodiments, the yield of polypeptide after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the polypeptide in the starting material for each purification step.

Purity may be determined using standard techniques, such as SDS-PAGE, or by measuring polypeptide using Western blot and ELISA assays. For example, polyclonal antibodies may be generated against proteins isolated from negative control yeast fermentation and the cation exchange recovery. The antibodies may also be used to probe for the presence of contaminating host cell proteins.

RP-HPLC material Vydac C4 (Vydac) consists of silica gel particles, the surfaces of which carry C4-alkyl chains. The separation of polypeptide from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The polypeptide fractions which are within the IPC limits are pooled.

DEAE Sepharose (Pharmacia) material consists of diethylaminoethyl (DEAE)-groups which are covalently bound to the surface of Sepharose beads. The binding of polypeptide to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and polypeptide is eluted with a buffer with increased ionic strength. The column is packed with DEAE Sepharose fast flow. The column volume is adjusted to assure a polypeptide load in the range of 3-10 mg polypeptide/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, polypeptide is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at −70° C.

Additional methods include, but are not limited to, steps to remove endotoxins. Endotoxins are lipopoly-saccharides (LPSs) which are located on the outer membrane of Gram-negative host cells, such as, for example, *Escherichia coli*. Methods for reducing endotoxin levels include, but are not limited to, purification techniques using silica supports, glass powder or hydroxyapatite, reverse-phase, affinity, size-exclusion, anion-exchange chromatography, hydrophobic interaction chromatography, a combination of these methods, and the like. Modifications or additional methods may be required to remove contaminants such as co-migrating proteins from the polypeptide of interest. Methods for measuring endotoxin levels are known to one of ordinary skill in the art and include, but are not limited to, *Limulus Amebocyte* Lysate (LAL) assays.

Additional methods and procedures include, but are not limited to, SDS-PAGE coupled with protein staining methods, immunoblotting, matrix assisted laser desorption/ionization-mass spectrometry (MALDI-MS), liquid chromatography/mass spectrometry, isoelectric focusing, analytical anion exchange, chromatofocusing, and circular dichroism In certain embodiments the non-natural amino acids described herein may be biosynthetically incorporated into polypeptides, thereby making non-natural amino acid polypeptides. In other embodiments, such amino acids are incorporated at a specific site within the polypeptide. In other embodiments, such amino acids incorporated into the polypeptide using a translation system. In other embodiments, such translation systems comprise: (i) a polynucleotide encoding the polypeptide, wherein the polynucleotide comprises a selector codon corresponding to the pre-designated site of incorporation of the above amino acids, and (ii) a tRNA comprising the amino acid, wherein the tRNA is specific to the selector codon. In other embodiments of such translation systems, the polynucleotide is mRNA produced in the translation system. In other embodiments of such translation systems, the translation system comprises a plasmid or a phage comprising the polynucleotide. In other embodiments of such translation systems, the translation system comprises genomic DNA comprising the polynucleotide. In other embodiments of such translation systems, the polynucleotide is stably integrated into the genomic DNA.

In other embodiments of such translation systems, the translation system comprises tRNA specific for a selector codon selected from the group consisting of an amber codon, ochre codon, opal codon, a unique codon, a rare codon, an unnatural codon, a five-base codon, and a four-base codon. In other embodiments of such translation systems, the tRNA is a suppressor tRNA. In other embodiments of such translation systems, the translation system comprises a tRNA that is aminoacylated to the amino acids above. In other embodiments of such translation systems, the translation system comprises an aminoacyl synthetase specific for the tRNA. In other embodiments of such translation systems, the translation system comprises an orthogonal tRNA and an orthogonal aminoacyl tRNA synthetase. In other embodiments of such translation systems, the polypeptide is synthesized by a ribosome, and in further embodiments the translation system is an in vivo translation system comprising a cell selected from the group consisting of a bacterial cell, archeaebacterial cell, and eukaryotic cell. In other embodiments the cell is an *Escherichia coli* cell, yeast cell, a cell from a species of *Pseudomonas*, mammalian cell, plant cell, or an insect cell. In other embodiments of such translation systems, the translation system is an in vitro translation system comprising cellular extract from a bacterial cell, archeaebacterial cell, or eukaryotic cell. In other embodiments, the cellular extract is from an *Escherichia coli* cell, a cell from a species of *Pseudomonas*, yeast cell, mammalian cell, plant cell, or an insect cell. In other embodiments at least a portion of the polypeptide is synthesized by solid phase or solution phase peptide synthesis, or a combination thereof, while in other embodiments further comprise ligating the polypeptide to another polypeptide. In other embodiments the non-natural amino acids described herein may be biosynthetically incorporated into polypeptides, wherein the polypeptide is a protein homologous to a therapeutic protein selected from the group consisting of: alpha-1 antitrypsin, angiostatin, antihemolytic factor, antibody, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, any interferon-like molecule or member of the IFN family, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

B. In Vivo Post-Translational Modifications

By producing proteins or polypeptides of interest with at least one non-natural amino acid in eukaryotic cells, such polypeptides may include eukaryotic post-translational modifications. In certain embodiments, a protein includes at least one non-natural amino acid and at least one post-translational modification that is made in vivo by a eukaryotic cell, where the post-translational modification is not made by a prokaryotic cell. By way of example, the post-translation modification includes, but is not limited to, acetylation, acylation, lipid modification, palmitoylation, palmitate addition, phosphorylation, glycolipid-linkage modification, glycosylation, and the like. In one aspect, the post-translational modification includes attachment of an oligosaccharide (including but not limited to, (GlcNAc-Man)$_2$-Man-GlcNAc-GlcNAc)) to an asparagine by a GlcNAc-asparagine linkage. See Table 1 which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

TABLE 1

Examples of oligosaccharides through GLCNAC-linkage

| Type | Base Structure |
|---|---|
| HIGH-MANNOSE | 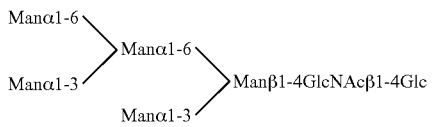 |
| HYBRID | 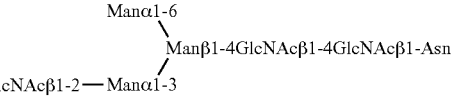 |
| COMPLEX | 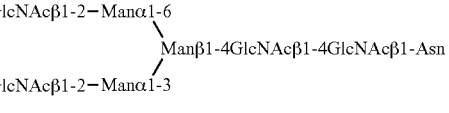 |
| XYLOSE | 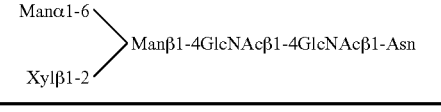 |

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin and the like), assembly into a multisubunit protein or macromolecular assembly, translation to another site in the cell (including but not limited to, to organelles, such as the endoplasmic reticulum, the golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like.

One advantage of a non-natural amino acid is that it presents additional chemical moieties that can be used to add additional molecules. These modifications can be made in vivo in a eukaryotic or non-eukaryotic cell, or in vitro. Thus, in certain embodiments, the post-translational modification is through the non-natural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In polypeptides described herein or produced using the methods described herein, other more selective reactions can be used, including, but not limited to, the reaction of a non-natural keto-amino acid with hydrazides or aminooxy compounds, in vitro and in vivo. See, e.g., Cornish, et al., (1996) *J. Am. Chem. Soc.,* 118:8150-8151; Mahal, et al., (1997) *Science,* 276:1125-1128; Wang, et al., (2001) *Science* 292: 498-500; Chin, et al., (2002) *J. Am. Chem. Soc.* 124:9026-9027; Chin, et al., (2002) *Proc. Natl. Acad. Sci.,* 99:11020-11024; Wang, et al., (2003) *Proc. Natl. Acad. Sci.,* 100:56-61; Zhang, et al., (2003) *Biochemistry,* 42:6735-6746; and, Chin, et al., (2003) *Science,* 301:964-7. This allows the selective labeling of virtually any protein with a host of reagents including fluorophores, crosslinking agents, saccharide derivatives and cytotoxic molecules. See also, U.S. Pat. No. 6,927,042 entitled "Glycoprotein synthesis" filed Jan. 16, 2003, which is incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligation, PNAS* 99:19-24.

IX. Alternate Systems for Producing Non-Natural Amino Acid Polypeptides

Several strategies have been employed to introduce non-natural amino acids into proteins in non-recombinant host cells, mutagenized host cells, or in cell-free systems. The alternate systems disclosed in this section can be applied to production of the non-natural amino acid. By way of example, derivatization of amino acids with reactive sidechains such as Lys, Cys and Tyr resulted in the conversion of lysine to $N^2$-acetyl-lysine. Chemical synthesis also provides a straightforward method to incorporate non-natural amino acids. With the recent development of enzymatic ligation and native chemical ligation of peptide fragments, it is possible to make larger proteins. See, e.g., P. E. Dawson and S. B. H. Kent, *Annu. Rev. Biochem.,* 69:923 (2000). Chemical peptide ligation and native chemical ligation are described in U.S. Pat. No. 6,184,344, U.S. Patent Publication No. 2004/0138412, U.S. Patent Publication No. 2003/0208046, WO 02/098902, and WO 03/042235, which are herein incorporated by reference in their entirety. A general in vitro biosynthetic method in which a suppressor tRNA chemically acylated with the desired non-natural amino acid is added to an in vitro extract capable of supporting protein biosynthesis, has been used to site-specifically incorporate over 100 non-natural amino acids into a variety of proteins of virtually any size. See, e.g., V. W. Cornish, D. Mendel and P. G. Schultz, *Angew. Chem. Int. Ed. Engl.,* 1995, 34:621 (1995); C. J. Noren, S. J. Anthony-Cahill, M. C. Griffith, P. G. Schultz, *A general method for site-specific incorporation of unnatural amino acids into proteins, Science* 244 182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111 8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.,* 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the non-natural amino acid analog. Induction of expression of the recombinant protein results in the accumulation of a protein containing the non-natural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.,* 284:29 (2000); trifluoromethionine has been used to replace methionine in bacteriophage T4 lysozyme to study its interaction with chitooligosaccharide ligands by $^{19}F$ NMR, see, e.g., H. Duewel, E. Daub, V. Robinson and J. F. Honek, *Biochemistry,* 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.,* 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.,* 9:1665 (1990); J. O. Boles, K. Lewinski, M. Kunkle, J. D. Odom, B. Dunlap, L. Lebioda and M. Hatada, *Nat. Struct. Biol.,* 1:283 (1994); N. Budisa, B. Steipe, P. Demange, C. Eckerskorn, J. Kellermann and R. Huber, *Eur. J. Biochem.,* 230:788 (1995); and, N. Budisa, W. Karnbrock, S. Steinbacher, A. Humm, L. Prade, T. Neuefeind, L. Moroder and R. Huber, *J. Mol. Biol.,* 270:616 (1997). Methionine analogs with alkene or alkyne functionalities have also been incorporated efficiently, allowing for additional modification of proteins by chemical means. See, e.g., J. C. M. van Hest and D. A. Tirrell, *FEBS Lett.,* 428:68 (1998); J. C. M. van Hest, K. L. Kiick and D.

A. Tirrell, *J. Am. Chem. Soc.*, 122:1282 (2000); and, K. L. Kiick and D. A. Tirrell, Tetrahedron, 56:9487 (2000); U.S. Pat. No. 6,586,207; U.S. Patent Publication 2002/0042097, which are herein incorporated by reference in their entirety.

The success of this method depends on the recognition of the non-natural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. By way of example only, replacement of $Ala^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry*, 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.*, 364:272 (1995); and, N. Sharma, R. Furter, P. Kast and D. A. Tirrell, *FEBS Lett.*, 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S, Nishimura, *J. Biol. Chem.*, 275:40324 (2000).

Another strategy to incorporate non-natural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science*, 292:501 (2001). ValRS can misaminoacylate tRNAVal with Cys, Thr, or aminobutyrate (Abu); these noncognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —$CH_3$ in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. *General nature of the genetic code for proteins. Nature*, 192:1227-1232 (1961); Kaiser, E. T. *Synthetic approaches to biologically active peptides and proteins including enzymes, Acc Chem Res*, 22:47-54 (1989); Nakatsuka, T., Sasaki, T., Kaiser, E. T. *Peptide segment coupling catalyzed by the semisynthetic enzyme thiosubtilisin, J Am Chem Soc*, 109: 3808-3810 (1987); Schnolzer, M., Kent, S B H. *Constructing proteins by dovetailing unprotected synthetic peptides: backbone-engineered HIV protease, Science*, 256(5054): 221-225 (1992); Chaiken, I. M. *Semisynthetic peptides and proteins, CRC Crit Rev Biochem*, 11(3):255-301 (1981); Offord, R. E. *Protein engineering by chemical means? Protein Eng.*, 1(3): 151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science*, 266(5183): 243 (1994).

Chemical modification has been used to introduce a variety of non-natural side chains, including cofactors, spin labels and oligonucleotides into proteins in vitro. See, e.g., Corey, D. R., Schultz, P. G. *Generation of a hybrid sequence-specific single-stranded deoxyribonuclease, Science*, 238(4832):1401-1403 (1987); Kaiser, E. T., Lawrence D. S., Rokita, S. E. *The chemical modification of enzymatic specificity, Annu. Rev Biochem*, 54:565-595 (1985); Kaiser, E. T., Lawrence, D. S. *Chemical mutation of enzyme active sites, Science*, 226(4674):505-511 (1984); Neet, K. E., Nanci A, Koshland, D. E. *Properties of thiol-subtilisin, J. Biol. Chem.*, 243(24):6392-6401 (1968); Polgar, L. (ed.)., M. L. Bender, *A new enzyme containing a synthetically formed active site. Thiol-subtilisin. J. Am Chem Soc*, 88:3153-3154 (1966); and, Pollack, S. J., Nakayama, G. Schultz, P. G. *Introduction of nucleophiles and spectroscopic probes into antibody combining sites, Science*, 224 (4881):1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem*, 483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci*, 8604-8608 (1986).

Previously, it has been shown that non-natural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotrophic for a particular amino acid. See, e.g., Noren, C. J., Anthony-Cahill, Griffith, M. C., Schultz, P. G. *A general method for site-specific incorporation of unnatural amino acids into proteins, Science*, 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am Chem Soc*, 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.*, vol. 202, 301-06 (199); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with a non-natural amino acid. Conventional site-directed mutagenesis was used to introduce the stop codon TAG, at the site of interest in the protein gene. See, e.g., Sayers, J. R., Schmidt, W. Eckstein, F. *5',3' Exonuclease in*

*phosphorothioate-based olignoucleotide-directed mutagensis, Nucleic Acids Res,* 791-802 (1988). When the acylated suppressor tRNA and the mutant gene were combined in an in vitro transcription/translation system, the non-natural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins, Science,* 197-200 (1992).

Microinjection techniques have also been used to incorporate non-natural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science,* 268:439 (1995); and, D. A. Dougherty, *Curr. Opin. Chem. Biol.,* 4:645 (2000). A *Xenopus* oocyte was coinjected with two RNA species made in vitro: an mRNA encoding the target protein with a UAG stop codon at the amino acid position of interest and an amber suppressor tRNA aminoacylated with the desired non-natural amino acid. The translational machinery of the oocyte then inserts the non-natural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.,* 271: 19991 (1996); the incorporation of biotinylated amino acids to identify surface-exposed residues in ion channels, see, e.g., J. P. Gallivan, H. A. Lester and D. A. Dougherty, *Chem. Biol.,* 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, Cell, 96:89 (1999); and, T. Lu, A. Y. Ting, J. Mainland, L. Y. Jan, P. G. Schultz and J. Yang, *Nat. Neurosci.,* 4:239 (2001).

The ability to incorporate non-natural amino acids directly into proteins in vivo offers a wide variety of advantages including but not limited to high yields of mutant proteins, technical ease, the potential to study the mutant proteins in cells or possibly in living organisms and the use of these mutant proteins in therapeutic treatments. The ability to include non-natural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.,* 7:419 (1998).

It may also be possible to obtain expression of a desired polynucleotide using a cell-free (in-vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D.-M. and J. R. Swartz, *Biotechnology and Bioengineering,* 74:309-316 (2001); Kim, D.-M. and J. R. Swartz, *Biotechnology Letters,* 22, 1537-1542, (2000); Kim, D.-M., and J. R. Swartz, *Biotechnology Progress,* 16, 385-390, (2000); Kim, D.-M., and J. R. Swartz, *Biotechnology and Bioengineering,* 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of polypeptides comprising a non-natural amino acid include the mRNA-peptide fusion technique. See, e.g., R. Roberts and J. Szostak, *Proc. Natl. Acad. Sci.* (*USA*) 94 12297-12302 (1997); A. Frankel, et al., *Chemistry & Biology* 10, 1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of polypeptides comprising one or more non-natural amino acids to identify polypeptides having desired properties. More recently, in vitro ribosome translations with purified components have been reported that permit the synthesis of peptides substituted with non-natural amino acids. See, e.g., A. Forster et al., *Proc. Natl. Acad. Sci.* (USA) 100 6353 (2003).

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3, elongation factor T (EF-Tu), or termination factors. Cell-free systems may also be coupled transcription/translation systems wherein DNA is introduced to the system, transcribed into mRNA and the mRNA translated as described in Current Protocols in Molecular Biology (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, *Science,* 236:1532-1539; McCorkle et al., 1987, *Concepts Biochem.* 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')$_3$'-termini (Illangakekare et al., 1995 *Science* 267:643-647), and an RNA molecule which can transfer an amino acid from one RNA molecule to another (Lohse et al., 1996, *Nature* 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in *Chemistry and Biology* 2003, 10:1077-1084 and U.S. Patent Application Publication 2003/0228593, which are incorporated by reference herein.

Chemical aminoacylation methods include, but are not limited to, those introduced by Hecht and coworkers (Hecht, S. M. *Acc. Chem. Res.* 1992, 25, 545; Heckler, T. G.; Roesser, J. R.; Xu, C.; Chang, P.; Hecht, S. M. *Biochemistry* 1988, 27, 7254; Hecht, S. M.; Alford, B. L.; Kuroda, Y.; Kitano, S. *J. Biol. Chem.* 1978, 253, 4517) and by Schultz, Chamberlin, Dougherty and others (Cornish, V. W.; Mendel, D.; Schultz, P. G. *Angew. Chem. Int. Ed. Engl.* 1995, 34, 621; Robertson, S. A.; Ellman, J. A.; Schultz, P. G. *J. Am. Chem. Soc.* 1991, 113, 2722; Noren, C. J.; Anthony-Cahill, S. J.; Griffith, M. C.; Schultz, P. G. *Science* 1989, 244, 182; Bain, J. D.; Glabe, C. G.; Dix, T. A.; Chamberlin, A. R. *J. Am. Chem. Soc.* 1989, 111, 8013; Bain, J. D. et al. *Nature* 1992, 356, 537; Gallivan, J. P.; Lester, H. A.; Dougherty, D. A. *Chem. Biol.* 1997, 4, 740; Turcatti, et al. *J. Biol. Chem.* 1996, 271, 19991; Nowak, M. W. et al. *Science,* 1995, 268, 439; Saks, M. E. et al. *J. Biol. Chem.* 1996, 271, 23169; Hohsaka, T. et al. *J. Am. Chem. Soc.* 1999, 121, 34), which are incorporated by reference herein, to avoid the use of synthetases in aminoacylation. Such methods or other chemical aminoacylation methods may be used to aminoacylate tRNA molecules.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate aminoacylation of the 3' terminus of the tRNA.

Ribozymes can be generated by in vitro selection using a partially randomized r24mini conjugated with tRNAAsnCCCG, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Immobilization on a substrate may be used to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin. Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. *Methods* 2005; 36:239-4 describe a column-based aminoacylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0).

The aminoacylated tRNAs can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing E. coli lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Stephan in *Scientist* 2005 Oct. 10; pages 30-33 describes additional methods to incorporate non-naturally encoded amino acids into proteins. Lu et al. in *Mol Cell.* 2001 October; 8(4):759-69 describe a method in which a protein is chemically ligated to a synthetic peptide containing unnatural amino acids (expressed protein ligation).

X. Post-Translational Modifications of Non-Natural Amino Acid Components of a Polypeptide Methods, compositions, techniques and strategies have been developed to site-specifically incorporate non-natural amino acids during the in vivo translation of proteins. By incorporating a non-natural amino acid with a sidechain chemistry that is orthogonal to those of the naturally-occurring amino acids, this technology makes possible the site-specific derivatization of recombinant proteins. As a result, a major advantage of the methods, compositions, techniques and strategies described herein is that derivatized proteins can now be prepared as defined homogeneous products. However, the methods, compositions, reaction mixtures, techniques and strategies described herein are not limited to non-natural amino acid polypeptides formed by in vivo protein translation techniques, but includes non-natural amino acid polypeptides formed by any technique, including by way of example only in vitro techniques, expressed protein ligation, chemical synthesis, ribozyme-based techniques (see, e.g., section herein entitled "Expression in Alternate Systems").

The ability to incorporate non-natural amino acids into recombinant proteins broadly expands the chemistries which may be implemented for post-translational derivatization, wherein such derivatization occurs either in vivo or in vitro. More specifically, protein derivatization utilizing the reductive alkylation or reductive amination reactions between a carbonyl containing compound, such as, by way of example, aldehydes, and an aromatic amine to form an alkylated amine, including a secondary amine or a tertiary amine, linkage on a non-natural amino acid portion of a polypeptide offers several advantages. First, the naturally occurring amino acids (a) do not contain aromatic amine groups that can react with carbonyl groups to form alkylated aromatic amines, thereby creating secondary amine or tertiary amine linkages, and (b) aromatic amine groups can react with carbonyl containing groups to form alkylated amines, including secondary amines or tertiary amines, and thus reagents designed to form such alkylated amines will react site-specifically with the non-natural amino acid component of the polypeptide (assuming of course that the non-natural amino acid and the corresponding reagent have been designed to form alkylated amines and the corresponding amine linkage). Such site specific derivatization is illustrated in FIGS. 19-34, wherein the sidechain containing an aromatic amine is preferentially reductively alkylated over sidechains containing protonated amines or imidizole moieties. Second, such alkylated aromatic amines have amine linkages which are stable under biological conditions, suggesting that proteins derivatized by such linkages are valid candidates for therapeutic applications. Third, the stability of such amine linkage can be manipulated based on the identity (i.e., the functional groups and/or structure) of the non-natural amino acid to which the linkage has been formed. In some embodiments, the alkylated amine, including a secondary amine or a tertiary amine, linkage to the non-natural amino acid polypeptide has a decomposition half life less than one hour, in other embodiments less than 1 day, in other embodiments less than 2 days, in other embodiments less than 1 week and in other embodiments more than 1 week. In yet other embodiments, the resulting alkylated amine, including a secondary amine or a tertiary amine, is stable for at least four weeks under biological conditions. In yet other embodiments, the resulting alkylated amine, including a secondary amine or a tertiary amine, is stable for at least three weeks under biological conditions. In yet other embodiments, the resulting alkylated amine, including a secondary amine or a tertiary amine, is stable for at least two weeks under biological conditions. In yet other embodiments, the resulting alkylated amine, including a secondary amine or a tertiary amine, is stable for at least one week under biological conditions. In other embodiments the resulting alkylated amine, including a secondary amine or a tertiary amine, linkage is stable for at least 6 days under biological conditions. In other embodiments the resulting alkylated amine, including a secondary amine or a tertiary amine, linkage is stable for at least 5 days under biological conditions. In other embodiments the resulting alkylated amine, including a secondary amine or a tertiary amine, linkage is stable for at least 4 days under biological conditions. In other embodiments the resulting alkylated amine, including a secondary amine or a tertiary amine, linkage is stable for at least 3 days under biological conditions. In other embodiments the resulting alkylated amine, including a secondary amine or a tertiary amine, linkage is stable for at least 2 days under biological conditions. In other embodiments the resulting alkylated amine, including a secondary amine or a tertiary amine, linkage is stable for at least 1 day under biological conditions. In other embodiments the resulting alkylated amine, including a secondary amine or a tertiary amine, linkage is stable for up to 24 hours under biological conditions. In other embodiments the resulting alkylated amine, including a secondary amine or a tertiary amine, linkage is stable for up to 12 hours under biological conditions. In other embodiments the resulting alkylated amine, including a secondary amine or a tertiary amine, linkage is stable for up to 6 hours under biological conditions. In other embodiments the resulting alkylated amine, including a secondary amine or a tertiary amine, linkage is stable for up to 3 hours under biological conditions. In other embodiments the resulting alkylated amine, including a secondary amine or a tertiary amine, linkage is stable for up to 2 hours under biological conditions. In other embodiments the resulting alkylated amine, including a secondary amine or a tertiary amine, linkage is stable for up to 1 hour under biological conditions. In yet other embodiments, the resulting alkylated amine, including a secondary amine or a tertiary amine, is stable for at least two weeks under mildly acidic conditions, in other embodiments the resulting alkylated amine, including a secondary amine or a tertiary amine, linkage is stable for at least 5 days under mildly acidic conditions. In other embodiments, the non-natural amino acid polypeptide is stable for at least 1 day in a pH between about 2 and about 8; in other embodiments, from a pH of about 2 to about 6; in other embodiment, in a pH of about 2 to about 4. In other embodiments, the non-natural amino acid polypeptide is stable for at least 1 day in a pH between about 6 and about 10; in other embodiments, from a pH of about 4 to about 8; in other embodiment, in a pH of about 4 to about 10. In other embodiments, the non-natural amino acid polypeptide is stable for at least 1 day in a pH between about 2 and about 5; in other embodiments, from a pH of about 3 to about 7; in other embodiment, in a pH of about 3 to about 10. In other embodiments, using the strategies, methods, compositions and techniques described herein, the synthesis of alkylated amine, including secondary amine or tertiary amine linkages to a non-natural amino acid polypeptide, may vary to alter the decomposition half-life to the needs required (e.g., for a therapeutic use such as sustained release, or a diagnostic use, commercial products, or an industrial use or a military use).

The non-natural amino acid polypeptides described above are useful for, including but not limited to, novel therapeutics, diagnostics, catalytic enzymes, industrial enzymes, binding proteins (including but not limited to, antibodies and antibody fragments), and including but not limited to, the study of protein structure and function. See, e.g., Dougherty, (2000) *Unnatural Amino Acids as Probes of Protein Structure and Function, Current Opinion in Chemical Biology,* 4:645-652. Other uses for the non-natural amino acid polypeptides described above include, by way of example only, assay-based, cosmetic, plant biology, environmental, energy-production, and/or military uses. However, the non-natural amino acid polypeptides described above can undergo further modifications so as to incorporate new or modified functionalities, including manipulating the therapeutic effectiveness of the polypeptide, improving the safety profile of the polypeptide, adjusting the pharmacokinetics, pharmacologics and/or pharmacodynamics of the polypeptide (e.g., increasing water solubility, bioavailability, increasing serum half-life, increasing therapeutic half-life, modulating immunogenicity, modulating biological activity, or extending the circulation time), providing additional functionality to the polypeptide, incorporating a tag, label or detectable signal into the polypeptide, easing the isolation properties of the polypeptide, and any combination of the aforementioned modifications.

The methods, compositions, strategies and techniques described herein are not limited to a particular type, class or family of polypeptides or proteins. Indeed, virtually any polypeptides may include at least one non-natural amino acids described herein. By way of example only, the polypeptide can be homologous to a therapeutic protein selected from the group consisting of: alpha-1 antitrypsin, angiostatin, antihemolytic factor, antibody, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, I309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, any interferon-like molecule or member of the IFN family, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone. The non-natural amino acid polypeptide may also be homologous to any polypeptide member of the growth hormone supergene family.

Such modifications include the incorporation of further functionality onto the non-natural amino acid component of the polypeptide, including but not limited to, a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof.

Thus, by way of example only, a non-natural amino acid polypeptide containing any one of the following amino acids may be further modified using the methods and compositions described herein:

(a)

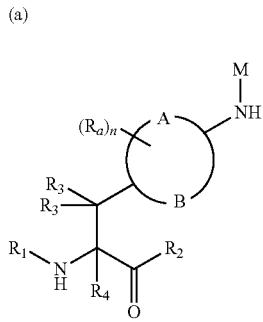

(A)

wherein:

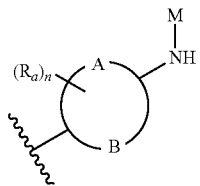

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently $CR_a$, or N;
B is independently $CR_a$, N, O, or S;
each $R_a$ is independently selected from the group consisting of H, halogen, alkyl, —$NO_2$, —CN, substituted alkyl, —$N(R')_2$, —$C(O)_kR'$, —$C(O)N(R')_2$, —OR', and —$S(O)_k$ R', where k is 1, 2, or 3; and n is 0, 1, 2, 3, 4, 5, or 6;
$R_1$ is H, an amino protecting group, resin, amino acid, polypeptide, or polynucleotide; and
$R_2$ is OH, an ester protecting group, resin, amino acid, polypeptide, or polynucleotide;
each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;
M is H or —$CH_2R_5$; or the M-N—$C(R_5)$ moiety may form a 4 to 7 membered ring structure;
$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O) R", —C(O)OR", —$C(O)N(R")_2$, —$C(O)NHCH(R")_2$, -(alkylene or substituted alkylene)-$N(R")_2$, -(alkenylene or substituted alkenylene)-$N(R")_2$, -(alkylene or substituted alkylene)-(aryl or substituted aryl), -(alkenylene or substituted alkenylene)-(aryl or substituted aryl), -(alkylene or substituted alkylene)-$ON(R")_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or $R_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —$S(O)_k$— where k is 1, 2, or 3, —$S(O)_k$ (alkylene or substituted alkylene)-, —C(S)—, —C(S)-(alkylene or substituted alkylene)-, —CSN(R')—, —CSN (R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S $(O)_k$-(alkylene or substituted alkylene)-S—, -(alkylene or substituted alkylene)-S—S—, —$S(O)_kN(R')$—, —N(R') C(O)N(R')—, —N(R')C(S)N(R')—, —$N(R')S(O)_kN$ (R')—, —N(R')—N═, —C(R')═N—, —C(R')═N—N (R')—, —C(R')═N—N═, —$C(R')_2$—N═N—, and —$C(R')_2$—N(R')—N(R')—;

or $R_5$ and any $R_a$ optionally form a cycloalkyl or a heterocycloalkyl; and each R' is independently H, alkyl, or substituted alkyl.

Such non-natural amino acids include, but are not limited to, the amino acids with the following structures:

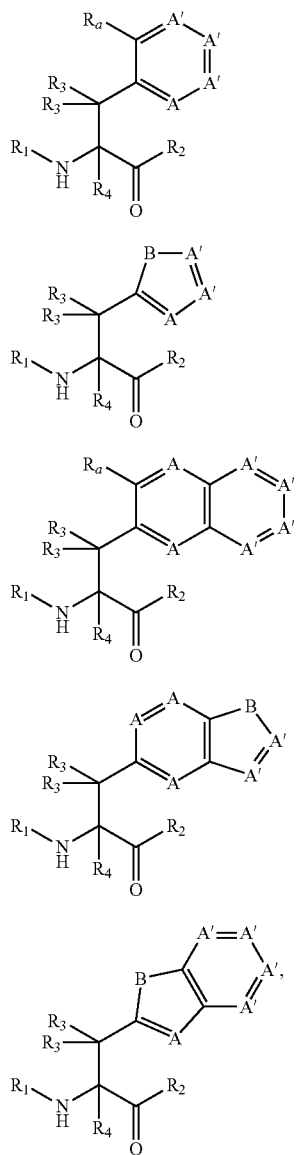

wherein, each A' is independently selected from $CR_a$, N, or

and up to two A' may be

with the remaining A' selected from $CR_a$, or N.

In addition, such non-natural amino acids include, but are not limited to, the amino acids with the following structures:

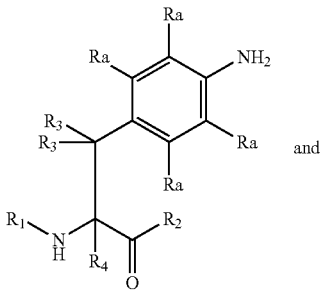

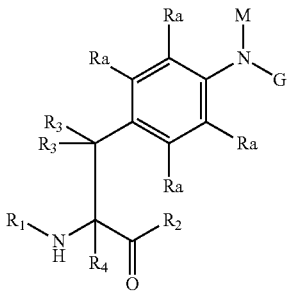

wherein; G is an amine protecting group, including, but not limited to,

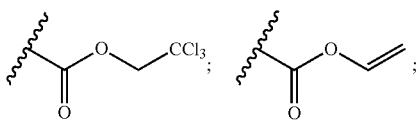

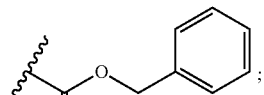

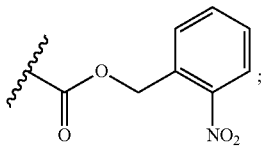

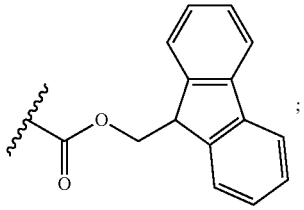

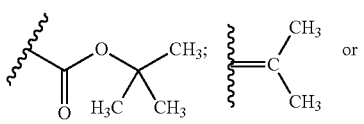

-continued

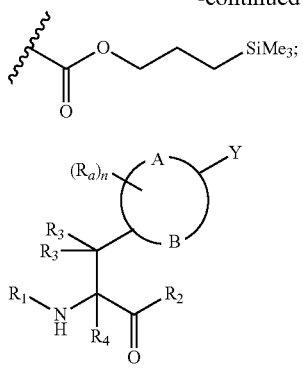

(B)

wherein:

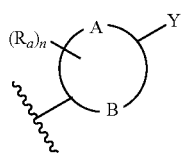

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently $CR_a$, or N;

B is independently $CR_a$, N, O, or S;

each $R_a$ is independently selected from the group consisting of H, halogen, alkyl, —$NO_2$, —CN, substituted alkyl, —$N(R')_2$, —$C(O)_kR'$, —$C(O)N(R')_2$, —OR', and —$S(O)_k$R', where k is 1, 2, or 3; and n is 0, 1, 2, 3, 4, 5, or 6;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

Y is —NH—$NH_2$, —NH—NHR', —CR'=NR', —$NO_2$, or —$N_3$, and each R' is independently H, alkyl, or substituted alkyl.

In addition, such non-natural amino acids include, but are not limited to, the amino acids with the following structures:

(VIII)

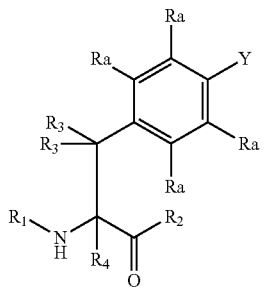

(IX)

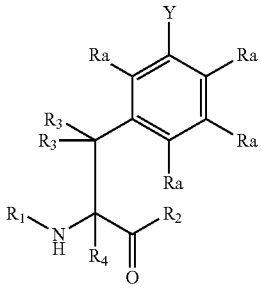

(X)

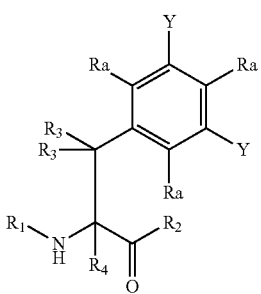

(XI)

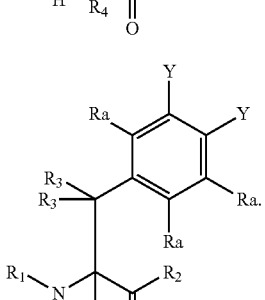

(c)

(C)

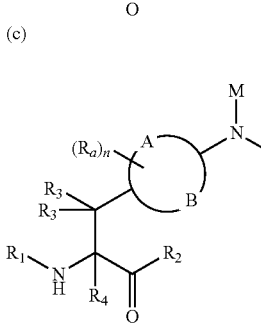

wherein:

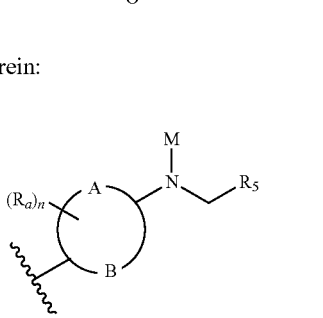

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently $CR_a$, or N;

B is independently $CR_a$, N, O, or S;

each $R_a$ is independently selected from the group consisting of H, halogen, alkyl, —NO$_2$, —CN, substituted alkyl, —N(R')$_2$, —C(O)$_k$R', —C(O)N(R')$_2$, —OR', and —S(O)$_k$R', where k is 1, 2, or 3; and n is 0, 1, 2, 3, 4, 5, or 6;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

M is H or —CH$_2$R$_5$; or the M-N—C(R$_5$) moiety may form a 4 to 7 membered ring structure;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or $R_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photo- cleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—; or $R_5$ and any $R_a$ optionally form a cycloalkyl or a heterocycloalkyl; and each R' is independently H, alkyl, or substituted alkyl.

Such non-natural amino acids include, but are not limited to, the amino acids with the following structures:

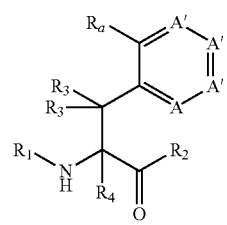

(XII)

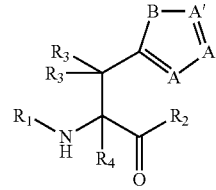

(XIII)

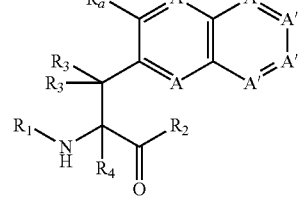

(XIV)

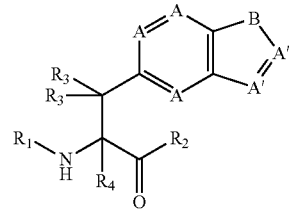

(XV)

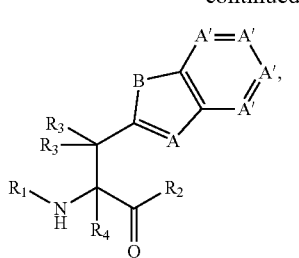
(XVI)

wherein, each A' is independently selected from $CR_a$, N, or

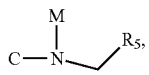

and up to two A' may be

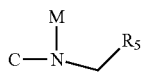

with the remaining A' selected from $CR_a$, or N.

(d)

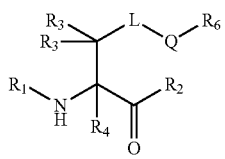
(E)

wherein:
L is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
Q is optional, and when present is a linker selected from the group consisting of lower alkylene, substituted lower alkylene, lower alkenylene, substituted lower alkenylene, lower heteroalkylene, substituted lower heteroalkylene, —O-(alkylene or substituted alkylene)-, —S-(alkylene or substituted alkylene)-, where k is 1, 2, or 3, —S(O)$_k$(alkylene or substituted alkylene)-, —C(O)-(alkylene or substituted alkylene)-, —C(S)-(alkylene or substituted alkylene)-, —NR'-(alkylene or substituted alkylene)-, —CON(R")-(alkylene or substituted alkylene)-, —CSN(R')-(alkylene or substituted alkylene)-, —N(R')CO-(alkylene or substituted alkylene)-, and where each R' is independently H, alkyl, or substituted alkyl;
$R_1$ is H, an amino protecting group, resin, amino acid, polypeptide, or polynucleotide; and
$R_2$ is OH, an ester protecting group, resin, amino acid, polypeptide, or polynucleotide;
each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

each $R_a$ is independently selected from the group consisting of H, halogen, alkyl, —NO$_2$, —CN, substituted alkyl, —N(R')$_2$, —C(O)$_k$R', —C(O)N(R')$_2$, —OR', and —S(O)$_k$R', where k is 1, 2, or 3;
$R_6$ is a protected aldehyde or a masked aldehyde, wherein the protecting group includes, but is not limited to,

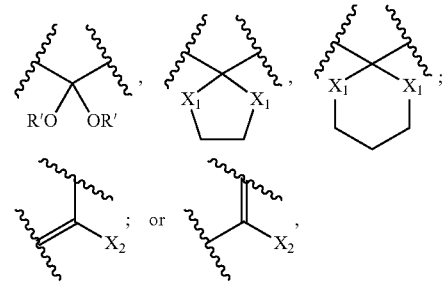

where each $X_1$ is independently selected from the group consisting of —O—, —S—, —N(H)—, —N(R)—, —N(Ac)—, and —N(OMe)-; $X_2$ is —OR, —OAc, —SR, —N(R)$_2$, —N(R)(Ac), —N(R)(OMe), or $N_3$, and where each R' and R is independently H, alkyl, or substituted alkyl;

(e)

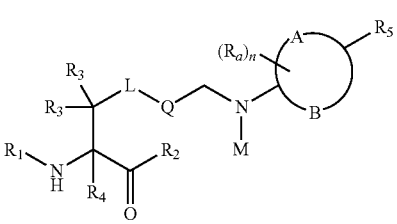
(D)

wherein:
L is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
Q is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R")-(alkylene or substituted alkylene)-, —CSN(R")—, —CSN(R')-(alkylene or substituted alkylene)-, —N(R')CO—, —N(R')CO-(alkylene or substituted alkylene)-, —N(R')C(O)O—, —S(O)$_k$N(R')—, —N(R')C(O)N(R')—, —N(R')C(S)N(R')—, —N(R")S(O)$_k$N(R')—, —N(R')—N═, —C(R")═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R₁ is H, an amino protecting group, resin, amino acid, polypeptide, or polynucleotide; and R₂ is OH, an ester protecting group, resin, amino acid, polypeptide, or polynucleotide;

each of R₃ and R₄ is independently H, halogen, lower alkyl, or substituted lower alkyl, or R₃ and R₄ or two R₃ groups optionally form a cycloalkyl or a heterocycloalkyl;

each R$_a$ is independently selected from the group consisting of H, halogen, alkyl, —NO₂, —CN, substituted alkyl, —N(R')₂, —C(O)$_k$R', —C(O)N(R')₂, —OR', and —S(O)$_k$R', where k is 1, 2, or 3; n is 0, 1, 2, 3, 4, 5, or 6;

M is H or —CH₂R₅;

R₅ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")₂, —C(O)NHCH(R")₂, -(alkylene or substituted alkylene)-N(R")₂, -(alkenylene or substituted alkenylene)-N(R")₂, -(alkylene or substituted alkylene)-(aryl or substituted aryl), -(alkenylene or substituted alkenylene)-(aryl or substituted aryl), -(alkylene or substituted alkylene)-ON(R")₂, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or R₅ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')₂—N═N—, and —C(R')₂—N(R')—N(R')—;

or R₅ and any R$_a$ optionally form a cycloalkyl or a heterocycloalkyl;

each R' is independently H, alkyl, or substituted alkyl;

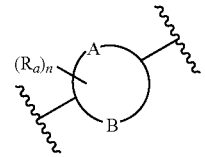

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently CR$_a$, or N; and

B is independently CR$_a$, N, O, or S.

In one aspect of the methods and compositions described herein are compositions that include at least one polypeptide with at least one, including but not limited to, at least two, at least three, at least four, at least five, at least six, at least seven, at least eight, at least nine, or at least ten or more non-natural amino acids that have been post-translationally modified. The post-translationally-modified non-natural amino acids can be the same or different, including but not limited to, there can be 1, 2, 3, 4, 5, 6, 7, 8, 9, 10 11, 12, 13, 14, 15, 16, 17, 18, 19, 20, or more different sites in the protein that comprise 1, 2, 3, 4, 5, 6, 7, 8, 9, 10, 11, 12, 13, 14, 15, 16, 17, 18, 19, 20, or more different post-translationally-modified non-natural amino acids. In another aspect, a composition includes a polypeptide with at least one, but fewer than all, of a particular amino acid present in the polypeptide is substituted with the post-translationally-modified non-natural amino acid. For a given polypeptide with more than one post-translationally-modified non-natural amino acids, the post-translationally-modified non-natural amino acids can be identical or different (including but not limited to, the polypeptide can include two or more different types of post-translationally-modified non-natural amino acids, or can include two of the same post-translationally-modified non-natural amino acid). For a given polypeptide with more than two post-translationally-modified non-natural amino acids, the post-translationally-modified non-natural amino acids can be the same, different or a combination of a multiple post-translationally-modified non-natural amino acid of the same kind with at least one different post-translationally-modified non-natural amino acid.

A. Methods for Post-Translationally Modifying Non-Natural Amino Acid Polypeptides Using a Single Post-Translational Modification Step: Reductive Alkylation Reactions of Aromatic Amine-Containing Non-Natural Amino Acids with Carbonyl-Containing Reagents The sidechains of the naturally occurring amino acids lack highly nucleophilic sites. Therefore, the incorporation of a non-natural amino acid with a nucleophilic-containing sidechain, including, by way of example only, an amino acid containing an aromatic amine group or a substituted aromatic amine group, makes possible the site-specific alkylation of this sidechain via nucleophilic addition to a carbonyl containing reagent, including an aldehyde-containing reagent, followed by a reduction reaction. This reductive alkylation reaction generates an amine linkage, including secondary and tertiary amines.

The methods for derivatizing and/or further modifying may be conducted with naturally generated polypeptides or chemically synthesized polypeptides that has been purified prior to the reductive alkylation step or after the reductive alkylation step. In addition, the methods for derivatizing and/or further modifying may be conducted with on synthetic polymers, polysaccharides, or polynucleotides which have been purified before or after such modifications.

Post-translational modification of polypeptides based upon reductive alkylation of an aromatic amine-containing polypeptide with an aldehyde-containing reagent has distinct advantages. First, aromatic amines can be reductively alkylated with carbonyl-containing compounds, including aldehydes, and ketones, in a pH range of about 4 to about 10 (and in further embodiments in a pH range of about 4 to about 7) with a reducing agent, such as $NaBCNH_3$, to generate secondary or tertiary amine linkages. Other reducing agents which may be used include, but are not limited to, TCEP, $Na_2S$, $Na_2S_2O_4$, $LiAlH_4$, $B_2H_6$, and $NaBH_4$. Second, under these reaction conditions the chemistry is selective for non-natural amino acids as the sidechains of naturally occurring amino acids are unreactive. This allows for site-specific derivatization of polypeptides which have incorporated non-natural amino acids containing aromatic amine moieties or protected aldehyde moieties, including, by way of example, recombinant proteins. Such derivatized polypeptides and proteins can thereby be prepared as defined homogeneous products. Third, the mild conditions needed to effect the reaction of an aromatic amine moiety on an amino acid, which has been incorporated into a polypeptide, with an aldehyde-containing reagent generally do not irreversibly destroy the tertiary structure of the polypeptide (excepting, of course, where the purpose of the reaction is to destroy such tertiary structure). Similarly, the mild conditions needed to effect the reaction of an aldehyde moiety on an amino acid, which has been incorporated into a polypeptide and deprotected, with an aromatic amine-containing reagent generally do not irreversibly destroy the tertiary structure of the polypeptide (excepting, of course, where the purpose of the reaction is to destroy such tertiary structure). Fourth, the reaction occurs rapidly at room temperature, which allows the use of many types of polypeptides or reagents that would otherwise be unstable at higher temperatures. Fifth, the reaction occurs readily is aqueous conditions, again allowing use of polypeptides and reagents incompatible (to any extent) with non-aqueous solutions. Six, the reaction occurs readily even when the ratio of polypeptide or amino acid to reagent is stoichiometric, stoichiometric-like, or near-stoichiometric, so that it is unnecessary to add excess reagent or polypeptide to obtain a useful amount of reaction product. Seventh, the resulting amine can be produced regioselectively and/or regiospecifically, depending upon the design of the amine and carbonyl-portions of the reactants. Finally, the reductive alkylation of aromatic amines with aldehyde-containing reagents, and the reductive amination of aldehydes with aromatic amine containing reagents, generates amine, including secondary and tertiary amine, linkages which are stable under biological conditions.

By way of example only, the following non-natural amino acids may be reductively alkylated with aldehyde-containing reagents described herein, (a)

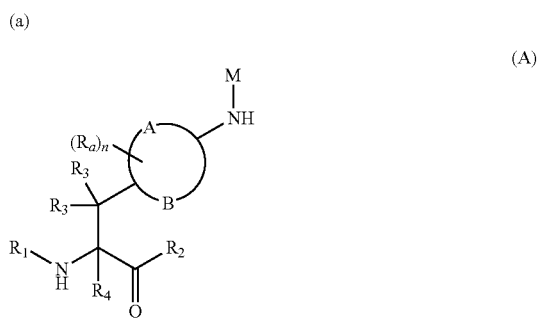

(A)

wherein:

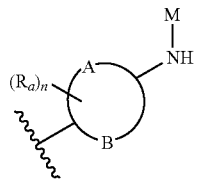

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently $CR_a$, or N;

B is independently $CR_a$, N, O, or S;

each $R_a$ is independently selected from the group consisting of H, halogen, alkyl, $—NO_2$, $—CN$, substituted alkyl, $—N(R')_2$, $—C(O)_kR'$, $—C(O)N(R')_2$, $—OR'$, and $—S(O)_k R'$, where k is 1, 2, or 3; and n is 0, 1, 2, 3, 4, 5, or 6;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

M is H or $—CH_2R_5$, or the $M-N—C(R_5)$ moiety may form a 4 to 7 membered ring structure;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or R$_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$ (alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-, -(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—;

or R$_5$ and any R$_a$ optionally form a cycloalkyl or a heterocycloalkyl; and each R' is independently H, alkyl, or substituted alkyl.

Such non-natural amino acids include, but are not limited to, the amino acids with the following structures:

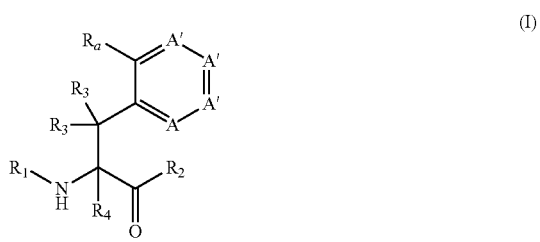

(I)

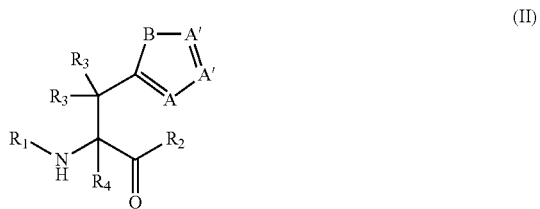

(II)

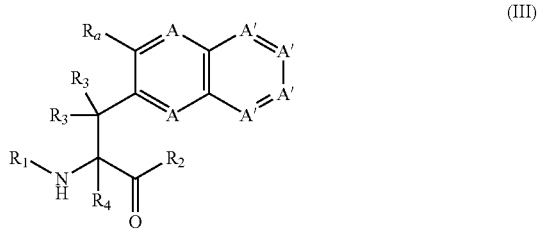

(III)

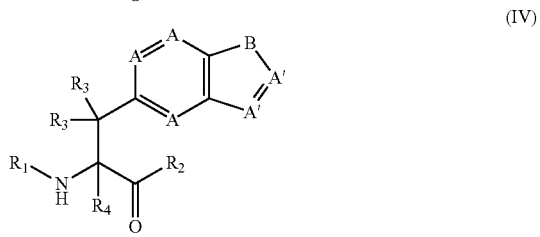

(IV)

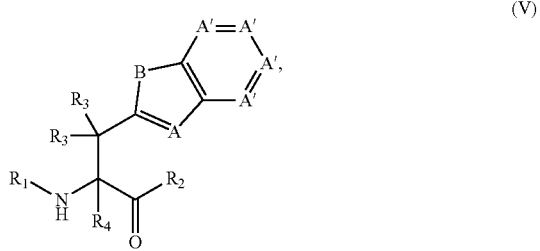

(V)

wherein, each A' is independently selected from CR$_a$, N, or

and up to two A' may be

with the remaining A' selected from $CR_a$, or N.

In addition, such non-natural amino acids include, but are not limited to, the amino acids with the following structures:

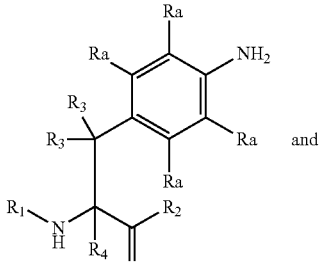
(VI)

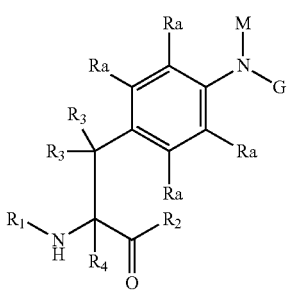
(VII)

wherein; G is an amine protecting group, including, but not limited to,

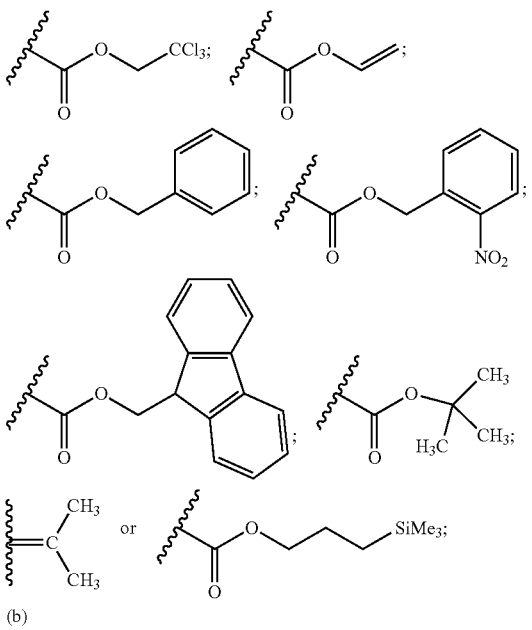
(b)

-continued

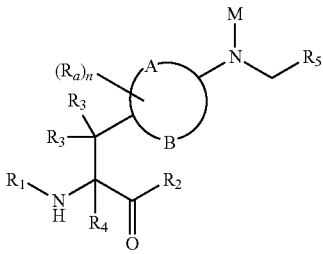
(C)

wherein:

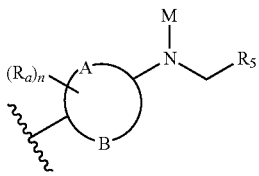

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently $CR_a$, or N;

B is independently $CR_a$, N, O, or S;

each $R_a$ is independently selected from the group consisting of H, halogen, alkyl, —$NO_2$, —CN, substituted alkyl, —$N(R')_2$, —$C(O)_kR'$, —$C(O)N(R')_2$, —OR', and —$S(O)_k$ R', where k is 1, 2, or 3; and n is 0, 1, 2, 3, 4, 5, or 6;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

M is H or —$CH_2R_5$; or the M-N—$C(R_5)$ moiety may form a 4 to 7 membered ring structure;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O) R", —C(O)OR", —C(O)N(R")_2, —C(O)NHCH(R")_2, -(alkylene or substituted alkylene)-N(R")_2, -(alkenylene or substituted alkenylene)-N(R")_2, -(alkylene or substituted alkylene)-(aryl or substituted aryl), -(alkenylene or substituted alkenylene)-(aryl or substituted aryl), -(alkylene or substituted alkylene)-ON(R")_2, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or $R_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$ (alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S (O)$_k$-(alkylene or substituted alkylene)-S—, -(alkylene or substituted alkylene)-S—S—, —S(O)$_k$N(R')—, —N(R') C(O)N(R')—, —N(R')C(S)N(R')—, —N(R')S(O)$_k$N (R')—, —N(R')—N=, —C(R')=N—, —C(R')=N—N (R')—, —C(R')=N—N=, —C(R')$_2$—N=N—, and —C(R')$_2$—N(R')—N(R')—;

or $R_5$ and any $R_a$ optionally form a cycloalkyl or a heterocycloalkyl; and each R' is independently H, alkyl, or substituted alkyl.

Such non-natural amino acids include, but are not limited to, the amino acids with the following structures:

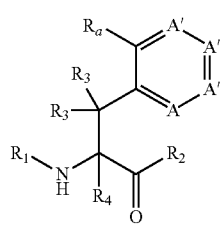
(XII)

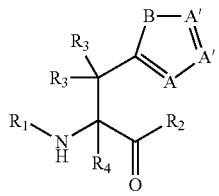
(XIII)

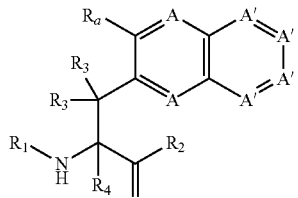
(XIV)

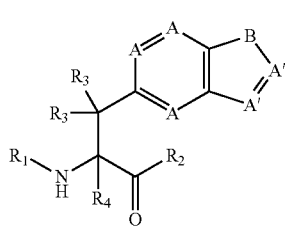
(XV)

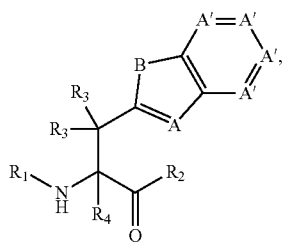
(XVI)

wherein, each A' is independently selected from CR$_a$, N, or

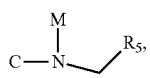

and up to two A' may be

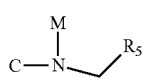

with the remaining A' selected from CR$_a$, or N.

Such reductive alkylation reactions post-translationally modify aromatic amine-containing non-natural amino acid polypeptides into non-natural amino acid polypeptides which contain mono-alkylated or di-alkylated aromatic amine-containing non-natural amino acids.

The types of polypeptides that comprise such aromatic amine-containing non-natural amino acids is practically unlimited as long as the aromatic amine-containing non-natural amino acid is located on the polypeptide so that the aldehyde-containing reagent can react with the aromatic amine group and not create a resulting modified non-natural amino acid that destroys the tertiary structure of the polypeptide (excepting, of course, if such destruction is the purpose of the reaction).

By way of example only, the carbonyl-containing reagents that are reactive with the aromatic amine-containing non-natural amino acids described herein, and which can also be used to further modify aromatic amine-containing non-natural amino acid polypeptides, include aldehyde-containing compounds with the following structure,

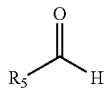

wherein;

R₅ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")₂, —C(O)NHCH(R")₂, -(alkylene or substituted alkylene)-N(R")₂, -(alkenylene or substituted alkenylene)-N(R")₂, -(alkylene or substituted alkylene)-(aryl or substituted aryl), -(alkenylene or substituted alkenylene)-(aryl or substituted aryl), -(alkylene or substituted alkylene)-ON(R")₂, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or R₅ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)ₖ— where k is 1, 2, or 3, —S(O)ₖ(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)ₖ-(alkylene or substituted alkylene)-S—, -(alkylene or substituted alkylene)-S—S—, —S(O)ₖN(R')—, —N(R')C(O)N(R')—, —N(R')C(S)N(R')—, —N(R')S(O)ₖN(R')—, —N(R')—N═, —C(R')═N—, —C(R')═N—N(R')—, —C(R')═N—N═, —C(R')₂—N═N—, and —C(R')₂—N(R')—N(R')—; each R' is independently H, alkyl, or substituted alkyl.

In addition, by way of example only, the carbonyl-containing reagents that are reactive with the aromatic amine-containing non-natural amino acids described herein and which can be used to further modify aromatic amine-containing non-natural amino acid polypeptides, are dicarbonyl-containing compounds, including diketones, ketoaldehydes and dialdehydes, with the following structures,

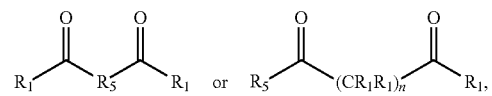

wherein;

each R₁ is independently selected from H, optionally substituted alkyl, optionally substituted alkene, optionally substituted alkyne, optionally substituted cycloalkyl, optionally substituted heterocycle, optionally substituted aryl, or optionally substituted heteroaryl;

R₅ is alkylene, substituted alkylene, alkenylene, substituted alkenylene, alkynylene, substituted alkynylene, polyalkylene oxide, substituted polyalkylene oxide, cycloalkylene, substituted cycloalkylene, arylene, substituted arylene, heteroarylene, substituted heteroarylene, heterocycloalkylene, substituted heterocycloalkylene, —C(O)R"—C(O)OR"—, —C(O)N(R")—, -(alkylene or substituted alkylene)-N(R")-(alkenylene or substituted alkenylene)-N(R")—, -(alkylene or substituted alkylene)-ON(R")—, -(alkylene or substituted alkylene)-C(O)SR"—, wherein each R" is independently hydrogen, alkyl, substituted alkyl, alkenyl, substituted alkenyl, alkoxy, substituted alkoxy, substituted alkylene, alkenylene, substituted alkenylene, alkynylene, substituted alkynylene, aryl, substituted aryl, heteroaryl, substituted heteroaryl, heterocycle, substituted heterocycle, alkaryl, substituted alkaryl, aralkyl, or substituted aralkyl;

or R₅ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O, -(alkylene or substituted alkylene)-O—N=CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—; each R' is independently H, alkyl, or substituted alkyl; n is 1, 2, or 3.

The types of carbonyl-containing reagents which can react with aromatic amine-containing non-natural amino acids is practically unlimited as long as the aromatic amine-containing non-natural amino acid is located on the polypeptide so that the carbonyl-containing reagent can react with the aromatic amine group and not create a resulting modified non-natural amino acid that destroys the tertiary structure of the polypeptide (excepting, of course, if such destruction is the purpose of the reaction). Such carbonyl-containing reagents include, but are not limited to, reagents containing at least one aldehyde moiety and reagents containing at least two aldehyde moieties.

Additionally, the reaction between an aldehyde moiety and an aromatic amine moiety is facile and such reductive alkylation reactions have at least one of the following characteristics: (i) occurs in a pH range of about 4 to about 7, (ii) generates an amine linkage which is stable under biological conditions; (iii) is site-specific; (iv) does not irreversibly destroy the tertiary structure of a polypeptide; (v) occurs rapidly at room temperature; (vi) occurs readily is aqueous conditions; (vii) occurs readily when the ratio of the non-natural amino acid comprising the aromatic amine moiety to the aldehyde-containing reactant is stoichiometric, stoichiometric-like or near stoichiometric; and (viii) is regioselective and/or regiospecific. The orthogonal nature of the reductive alkylation reactions results in the regioselectivity and/or regiospecificity, thereby allowing for site specific post-translational modification of non-natural amino acid polypeptides without affecting other amino acids in polypeptide containing the non-natural amino acid(s).

Illustrative embodiments of methods for reductively alkylating an aromatic amine-containing non-natural amino acid in a polypeptide are presented in FIGS. 20-34. Certain embodiments, include a single reductive alkylation of an aromatic amine-containing non-natural amino acid on a polypeptide with a carbonyl-containing reagent, including an aldehyde-containing reagent, producing a secondary amine moiety, whereas other embodiments include two reductive alkylations of an aromatic amine-containing non-natural amino acid on a polypeptide with a carbonyl-containing reagent, including an aldehyde-containing reagent, producing a tertiary amine moiety. Additionally, certain embodiments include a single reductive alkylation of an aromatic amine-containing non-natural amino acid on a polypeptide with a reagent containing at least two carbonyl groups, thereby producing a secondary amine moiety. Still other embodiments include double reductive alkylations of an aromatic amine-containing non-natural amino acid on a polypeptide with a reagent containing at least two carbonyl groups, thereby producing a tertiary amine moiety. In these illustrative embodiments, an aldehyde-containing reagent is added to a buffered solution (pH of about 4 to about 7) of an aromatic amine-containing non-natural amino acid polypeptide and a reducing agent such as, by way of example only, sodium cyanoborohydride. The reaction proceeds at ambient temperature, and the resulting alkylated aromatic amine-containing non-natural amino acid polypeptide may be purified by HPLC, FPLC or size-exclusion chromatography.

In other embodiments, multiple linker chemistries can react site-specifically with an aromatic amine-containing non-natural amino acid polypeptide. In one embodiment, the linker methods described herein utilize linkers containing the carbonyl functionality, including an aldehyde functionality, on at least one linker termini (mono, bi- or multi-functional). The reductive alkylation of an aromatic amine-containing polypeptide with an aldehyde-derivatized linker generates a stable amine linkage. Bi- and/or multi-functional linkers, also known as heterofunctional linkers (e.g., carbonyl, including an aldehyde, with one, or more, other linking chemistries) allow the site-specific connection of different molecules (e.g., other polypeptides, polynucleic acids, polymers or small molecules) to the non-natural amino acid polypeptide, while mono-functional linkers, also known as homofunctional linkers (carbonyl-substituted, including aldehyde substituted, on all termini) facilitate the site-specific dimer- or oligomerization of the aromatic amine non-natural amino acid polypeptide. By combining this linker strategy with the in vivo translation technology described herein, it becomes possible to specify the three-dimensional structures of chemically-elaborated proteins.

B. Methods for Post-Translationally Modifying Non-Natural Amino Acid Polypeptides Using Two Post-Translational Modification Steps: Formation of Aromatic Amine-Containing Non-Natural Amino Acids Followed by Reductive Alkylation Reactions of Aromatic Amine-Containing Non-Natural Amino Acids with Carbonyl-Containing Reagents Aromatic amine-containing amino acids can be translationally incorporated into polypeptides prior to reductive alkylation with carbonyl-containing reagents, including aldehyde-containing reagents. Alternatively, precursors of aromatic amine-containing amino acids, such as amino acids containing substituted aromatic moieties, can be translationally incorporated into polypeptides and subsequently transformed into aromatic amine-containing amino acids prior to reductive alkylation with carbonyl-containing reagents. The latter method involves two post-translational modifications, whereas the former involves only a single post-translational modification. The methods for derivatizing and/or further modifying may be conducted with naturally generated polypeptides or chemically synthesized polypeptides which may be purified prior to, or after, these modification methods. In addition, the methods for derivatizing and/or further modifying may be conducted with on synthetic polymers, polysaccharides, or polynucleotides which may be purified prior to, or after, these modification methods.

By way of example only, the following non-natural amino acids can be reduced to generate aromatic amine-containing amino acids,

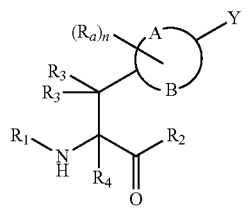

(B)

wherein:

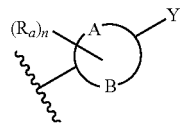

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently $CR_a$, or N;

B is independently $CR_a$, N, O, or S;

each $R_a$ is independently selected from the group consisting of H, halogen, alkyl, $-NO_2$, $-CN$, substituted alkyl, $-N(R')_2$, $-C(O)_kR'$, $-C(O)N(R')_2$, $-OR'$, and $-S(O)_k R'$, where k is 1, 2, or 3; and n is 0, 1, 2, 3, 4, 5, or 6;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

Y is $-NH-NH_2$, $-NH-NHR'$, $-CR'=NR'$, $-NO_2$, or $-N_3$, and each R' is independently H, alkyl, or substituted alkyl.

Such non-natural amino acids include, but are not limited to, the amino acids with the following structure:

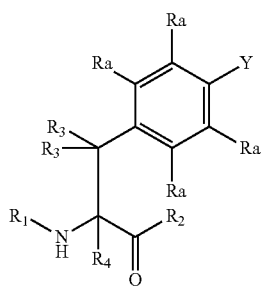

(VIII)

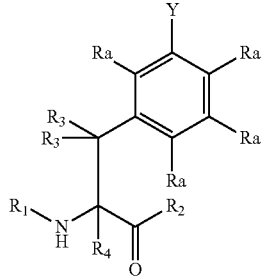

(IX)

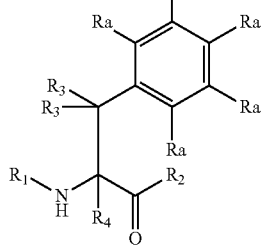

(X)

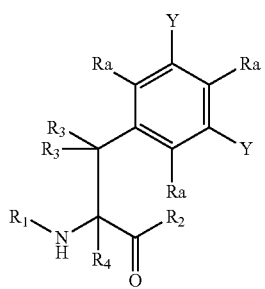

(XI)

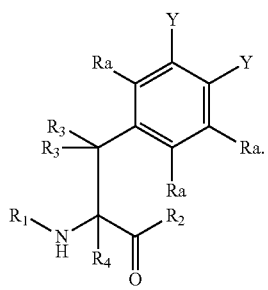

Illustrative embodiments for reductively generating an aromatic amine-containing non-natural amino acid on a natural polypeptide, synthetic polymer, polysaccharide, polynucleotide or chemically synthesized polypeptide are presented in FIGS. 14 and 15. Certain embodiments include reduction of imine substituents into aromatic primary amine-containing non-natural amino acids, imine substituents into aromatic secondary amine-containing non-natural amino acids, reduction of hydrazine amine substituents into aromatic primary amine-containing non-natural amino acids, reduction of hydrazine amine substituents into aromatic secondary amine-containing non-natural amino acids, reduction of nitro-substituents into aromatic primary amine-containing non-natural amino acids, and reduction of azido-substituents into aromatic primary amine-containing non-natural amino acids. In these illustrative embodiments, substituted aromatic moieties are reduced in a buffered solution (pH of about 4 to about 7), and the reducing agents used includes, but is not limited to, TCEP, $Na_2S$, $Na_2S_2O_4$, $LiAlH_4$, $B_2H_6$, $NaBH_4$ or $NaBCNH_3$. The reaction proceeds at ambient temperature and the resulting aromatic amine-containing non-natural amino acid natural polypeptide, synthetic polymer, polysaccharide, polynucleotide or chemically synthesized polypeptide may be purified by HPLC, FPLC or size-exclusion chromatography.

Reductive alkylation of such aromatic amine-containing amino acid generated from the reduction of substituted aromatic moiety-containing amino acids is as described in section A: *Methods for Post-Translationally Modifying Non-Natural Amino Acid Polypeptides using a Single Post-Translational Modification Step: Reductive Alkylation Reactions of Aromatic Amine-Containing Non-Natural Amino Acids with Aldehyde-Containing Reagents*. Illustrative embodiments of reductive alkylation of aromatic amine-containing amino acid generated by reductions of a protected (or masked) amine is presented in FIGS. 15 and 34. The reductive alkylation step follows the first post-translational step which reductively generates aromatic amine-containing non-natural amino acids on polypeptides The reductive alkylations are the second post-translationally reactions which thereby modify aromatic amine-containing non-natural amino acid polypeptides into non-natural amino acid polypeptides with alkylated aromatic amine-containing non-natural amino acids. Such post-translational modifications or post incorporation modifications may also be applied to aromatic amine containing amino acids incorporated into on synthetic polymers, polysaccharides, polynucleotides or chemically synthesized polypeptides.

The types of polypeptides that comprise such aromatic amine-containing non-natural amino acids is practically unlimited as long as the aromatic amine-containing non-natural amino acid is located on the polypeptide so that the carbonyl-containing reagent, including aldehyde-containing reagents, can react with the aromatic amine group and not create a resulting modified non-natural amino acid that destroys the tertiary structure of the polypeptide (excepting, of course, if such destruction is the purpose of the reaction).

By way of example only, the aldehyde-containing reagents that are reactive with the aromatic amine-containing non-natural amino acids described herein, and can also be used to further modify aromatic amine-containing non-natural amino acid polypeptides are compounds with the following structure,

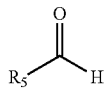

wherein;
$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O) R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or $R_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S (O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—; each R' is independently H, alkyl, or substituted alkyl.

In addition, by way of example only, the carbonyl-containing reagents that are reactive with the aromatic amine-containing non-natural amino acids described herein and which can be used to further modify aromatic amine-containing non-natural amino acid polypeptides, are dicarbonyl-containing compounds, including diketones, ketoaldehydes and dialdehydes, with the following structures,

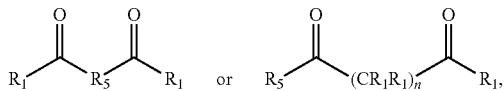

wherein;

each R$_1$ is independently selected from H, optionally substituted alkyl, optionally substituted alkene, optionally substituted alkyne, optionally substituted cycloalkyl, optionally substituted heterocycle, optionally substituted aryl, or optionally substituted heteroaryl;

R$_5$ is alkylene, substituted alkylene, alkenylene, substituted alkenylene, alkynylene, substituted alkynylene, polyalkylene oxide, substituted polyalkylene oxide, cycloalkylene, substituted cycloalkylene, arylene, substituted arylene, heteroarylene, substituted heteroarylene, heterocycloalkylene, substituted heterocycloalkylene, —C(O)R"—C(O)OR"—, —C(O)N(R")—, -(alkylene or substituted alkylene)-N(R")-(alkenylene or substituted alkenylene)-N(R")—, -(alkylene or substituted alkylene)-ON(R")—, -(alkylene or substituted alkylene)-C(O)SR"—, wherein each R" is independently hydrogen, alkyl, substituted alkyl, alkenyl, substituted alkenyl, alkoxy, substituted alkoxy, substituted alkylene, alkenylene, substituted alkenylene, alkynylene, substituted alkynylene, aryl, substituted aryl, heteroaryl, substituted heteroaryl, heterocycle, substituted heterocycle, alkaryl, substituted alkaryl, aralkyl, or substituted aralkyl;

or R$_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—; each R' is independently H, alkyl, or substituted alkyl; n is 1, 2, or 3.

The types of carbonyl-containing reagents which can react with aromatic amine-containing non-natural amino acids is practically unlimited as long as the aromatic amine-containing non-natural amino acid is located on the polypeptide so that the carbonyl-containing reagent, including aldehyde-containing reagents, can react with the aromatic amine group and not create a resulting modified non-natural amino acid that destroys the tertiary structure of the polypeptide (excepting, of course, if such destruction is the purpose of the reaction). Such carbonyl-containing reagents include, but are not limited to, reagents containing at least one carbonyl moiety and/or reagents containing at least two carbonyl moieties.

Additionally, the reaction between an carbonyl moiety, by way of example only an aldehyde moiety, and an aromatic amine moiety is facile and such reductive alkylation reactions have at least one of the following characteristics: (i) occurs in a pH range of about 4 to about 7, (ii) generates an amine linkage which is stable under biological conditions; (iii) is site-specific; (iv) does not irreversibly destroy the tertiary structure of a polypeptide; (v) occurs rapidly at room temperature; (vi) occurs readily is aqueous conditions; (vii) occurs readily when the ratio of the non-natural amino acid comprising the aromatic amine moiety to the aldehyde-containing reactant is stoichiometric, stoichiometric-like or near stoichiometric; and (viii) is regioselective and/or regio-specific. The orthogonal nature of the reductive alkylation reactions results in the regioselectivity and/or regiospecificity, thereby allowing for site specific post-translational modification of non-natural amino acid polypeptides without affecting other amino acids in the non-natural amino acid polypeptide.

Certain embodiments, include a single reductive alkylation of the aromatic amine moiety with a carbonyl-containing reagent producing a secondary amine moiety, whereas other embodiments include two reductive alkylations of the aromatic amine moiety with two carbonyl-containing reagents producing a tertiary amine moiety. The carbonyl-containing reagents in this embodiment may be identical or different. Additionally, certain embodiments include a single reductive alkylation of the aromatic amine moiety with a reagent containing at least two carbonyl groups, thereby producing a secondary amine moiety. Still other embodiments include two reductive alkylations, also referred to as double reductive alkylation, of the aromatic amine moiety with a reagent containing at least two carbonyl groups, thereby producing a cyclic, tertiary amine moiety. In these illustrative embodiments, the carbonyl-containing reagent is added to a buffered solution (pH of about 4 to about 7) of the aromatic amine-containing non-natural amino acid on a natural polypeptide, synthetic polymer, polysaccharide, polynucleotide or chemically synthesized polypeptide and a reducing agent such as, by way of example only, $NaBCNH_3$, TCEP, $Na_2S$, $Na_2S_2O_4$, $LiAlH_4$, $B_2H_6$, and $NaBH_4$. The reaction proceeds at ambient temperature and the resulting alkylated aromatic amine-containing non-natural amino acid polypeptide may be purified by HPLC, FPLC or size-exclusion chromatography.

In other embodiments, multiple linker chemistries can react site-specifically with an aromatic amine-containing non-natural amino acid polypeptide. In one embodiment, the linker methods described herein utilize linkers containing the carbonyl functionality, including aldehyde functionality, on at least one linker termini (mono, bi- or multi-functional). The reductive alkylation of a carbonyl-derivatized linker with an aromatic amine-containing polypeptide generates a stable amine linkage. Bi- and/or multi-functional linkers, also known as heterofunctional linkers (e.g., aldehyde with one, or more, other linking chemistries) allow the site-specific connection of different molecules (e.g., other polypeptides, polynucleic acids, polymers or small molecules) to the non-natural amino acid polypeptide, while mono-functional linkers, also known as homofunctional linkers (e.g. aldehyde-substituted on all termini) facilitate the site-specific dimer- or oligomerization of the aromatic amine non-natural amino acid polypeptide. By combining this linker strategy with the in vivo translation technology described herein, it becomes possible to specify the three-dimensional structures of chemically-elaborated polypeptides.

C. Methods for Post-Translationally Modifying Non-Natural Amino Acid Polypeptides Using a Two Post-Translational Modification Steps: Deprotection of Protected Aldehyde-Containing Non-Natural Amino Acids Followed by Reductive Amination of the Aldehyde-Containing Non-Natural Amino Acids with Aromatic Amine-Containing Reagents The incorporation of non-natural amino acids with masked or protected electrophilic-containing sidechain, into polypeptides allows for site-specific reductive amination of the sidechains. Such non-natural amino acids include masked or protected carbonyl groups, such as, by way of example only, amino acids containing masked aldehyde groups or protected aldehyde groups, and wherein the site-specific reductive amination is accomplished, upon unmasking or deprotection of the aldehyde, via nucleophilic addition of an aromatic amine to the available aldehyde-containing sidechain. This reductive amination reaction generates an amine linkage, including secondary and tertiary amines. The methods for derivatizing and/or further modifying may be conducted with naturally generated polypeptides or chemically synthesized polypeptides which have been purified prior to the reductive amination step or after the reductive amination step. In addition, the methods for derivatizing and/or further modifying may be conducted with on synthetic polymers, polysaccharides, or polynucleotides which may be purified prior to, or after, these modification methods.

By way of example only, the following non-natural amino acids are the type of masked/protected aldehyde moiety-containing amino acids which may be incorporated into polypeptides, then unmasked/deprotected prior to reductively aminated the available aldehyde containing sidechain to generate an amine linkage.

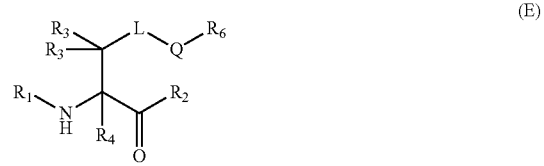

(E)

wherein:

L is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

Q is optional, and when present is a linker selected from the group consisting of lower alkylene, substituted lower alkylene, lower alkenylene, substituted lower alkenylene, lower heteroalkylene, substituted lower heteroalkylene, —O-(alkylene or substituted alkylene)-, —S-(alkylene or substituted alkylene)-, where k is 1, 2, or 3, —S(O)$_k$ (alkylene or substituted alkylene)-, —C(O)-(alkylene or substituted alkylene)-, —C(S)-(alkylene or substituted alkylene)-, —NR'-(alkylene or substituted alkylene)-, —CON(R")-(alkylene or substituted alkylene)-, —CSN(R')-(alkylene or substituted alkylene)-, —N(R')CO-(alkylene or substituted alkylene)-, and where each R' is independently H, alkyl, or substituted alkyl;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

each $R_a$ is independently selected from the group consisting of H, halogen, alkyl, —$NO_2$, —CN, substituted alkyl, —N(R')$_2$, —C(O)$_k$R', —C(O)N(R')$_2$, —OR', and —S(O)$_k$R', where k is 1, 2, or 3;

$R_6$ is a protected aldehyde or a masked aldehyde, wherein the protecting group includes, but is not limited to,

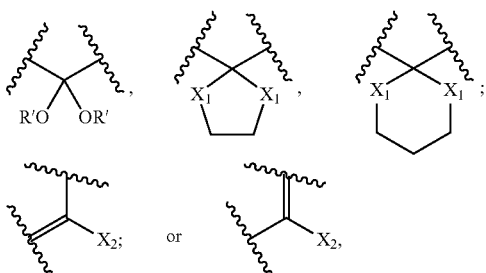

where each X₁ is independently selected from the group consisting of —O—, —S—, —N(H)—, —N(R)—, —N(Ac)—, and —N(OMe)-; X₂ is —OR, —OAc, —SR, —N(R)₂, —N(R)(Ac), —N(R)(OMe), or N₃, and where each R' and R is independently H, alkyl, or substituted alkyl.

Such non-natural amino acids may also be in the form of a salt, or may be incorporated into a non-natural amino acid polypeptide, polymer, or a polynucleotide. Such non-natural amino acids may also be incorporated into a non-natural amino acid polypeptide and then post-translationally modified by deprotecting to form an aldehyde group "in-situ" followed by reductive amination of the aldehyde with an aromatic amine containing reagent. In addition, non-natural amino acids having the structure of Formula (E) may also be incorporated into a polymer or a polynucleotide and are deprotecting to form an aldehyde group "in-situ" followed by reductive amination of the aldehyde with an aromatic amine containing reagent.

By way of example only, the aromatic amine-containing reagents which are reactive with the unmasked/deprotected aldehyde-containing non-natural amino acids described herein are compounds with the following structure:

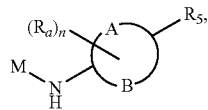

wherein,

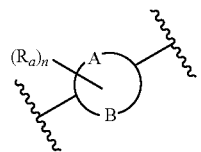

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;
A is independently $CR_a$, or N;
B is independently $CR_a$, N, O, or S;
each $R_a$ is independently selected from the group consisting of H, halogen, alkyl, —NO₂, —CN, substituted alkyl, —N(R')₂, —C(O)ₖR', —C(O)N(R')₂, —OR', and —S(O)ₖR', where k is 1, 2, or 3; n is 0, 1, 2, 3, 4, 5, or 6;
M is H or —CH₂R₅;
R₅ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")₂, —C(O)NHCH(R")₂, -(alkylene or substituted alkylene)-N(R")₂, -(alkenylene or substituted alkenylene)-N(R")₂, -(alkylene or substituted alkylene)-(aryl or substituted aryl), -(alkenylene or substituted alkenylene)-(aryl or substituted aryl), -(alkylene or substituted alkylene)-ON(R")₂, -(alkenylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';
or R₅ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)ₖ— where k is 1, 2, or 3, —S(O)ₖ (alkylene or substituted alkylene)-, —C(S)—, —C(S)-(alkylene or substituted alkylene)-, —CSN(R')—, —CSN(R')-(alkylene or substituted alkylene)-, —N(R')CO- (alkylene or substituted alkylene)-, —N(R')C(O)O—, -(alkylene or substituted alkylene)-O—N═CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—; each R' is independently H, alkyl, or substituted alkyl.

Such reagents include compounds having the following structures,

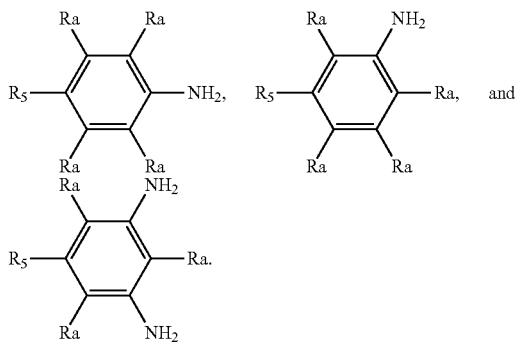

These compounds may also be used to further modify aldehyde-containing non-natural amino acid polypeptides (naturally or chemically synthesized), synthetic polymers, polysaccharides, or polynucleotides.

These reductive amination reactions post-translationally modify unmasked/deprotected aldehyde-containing non-natural amino acid polypeptides into non-natural amino acid polypeptides which contain aromatic amine-containing non-natural amino acid. The types of polypeptides that comprise such aromatic amine-containing non-natural amino acids is practically unlimited as long as the unmasked/deprotected aldehyde-containing non-natural amino acid is located on the polypeptide such that the aromatic amine-containing reagent can react with the available aldehyde group and not create a resulting modified non-natural amino acid that destroys the tertiary structure of the polypeptide (excepting, of course, if such destruction is the purpose of the reaction).

Additionally, the reaction between an aldehyde moiety and an aromatic amine moiety is facile and such reductive amination reactions have at least one of the following characteristics: (i) occurs in a pH range of about 4 to about 7, (ii) generates an amine linkage which is stable under biological conditions; (iii) is site-specific; (iv) does not irreversibly destroy the tertiary structure of a polypeptide; (v) occurs rapidly at room temperature; (vi) occurs readily is aqueous conditions; (vii) occurs readily when the ratio of the non-natural amino acid comprising the aldehyde moiety to the aromatic amine-containing reactant is stoichiometric, stoichiometric-like or near stoichiometric; and (viii) is regioselective and/or regiospecific. The orthogonal nature of the reductive amination reactions results in the regioselectivity and/or regiospecificity, thereby allowing for site specific post-translational modification of non-natural amino acid polypeptides without affecting other amino acids in the non-natural amino acid polypeptide.

An illustrative embodiment of reductively aminating an unmasked or deprotected aldehyde-containing non-natural amino acid on a polypeptide is presented in FIG. 18. In addition, certain embodiments include a single reductive amination of an unmasked or deprotected aldehyde-containing non-natural amino acid on a polypeptide with an aromatic amine-containing reagent, thereby producing a secondary amine moiety. Additionally, certain embodiments include a reductive amination of a carbonyl-containing non-natural amino acid on a polypeptide, in which the carbonyl moiety contains at least two unmasked or deprotected aldehyde groups, with an aromatic amine-containing reagent, thereby producing a cyclic tertiary amine moiety. Still other embodiments include two reductive aminations of an unmasked or deprotected aldehyde-containing non-natural amino acid on a polypeptide containing at least two aldehyde groups, with two identical or two different aromatic amine-containing reagents thereby producing two secondary amine moieties. In these illustrative embodiments, an aromatic amine-containing reagent is added to a buffered solution (pH of about 4 to about 7) of an unmasked or deprotected aldehyde-containing non-natural amino acid polypeptide and a reducing agent such as, by way of example only, TCEP, Na$_2$S, Na$_2$S$_2$O$_4$, LiAlH$_4$, B$_2$H$_6$, NaBH$_4$ or NaBCNH$_3$. The reaction proceeds at ambient temperature and the resulting aminated aldehyde-containing non-natural amino acid polypeptide may be purified by HPLC, FPLC or size-exclusion chromatography.

In other embodiments, multiple linker chemistries can react site-specifically with an unmasked or deprotected aldehyde-containing non-natural amino acid polypeptide. In one embodiment, the linker methods described herein utilize linkers containing the aromatic amine functionality on at least one linker termini (mono, bi- or multi-functional). The reductive amination of an aromatic amine-derivatized linker with an unmasked or deprotected aldehyde-containing polypeptide generates a stable amine linkage. Bi- and/or multifunctional linkers, also known as heterofunctional linkers (e.g., aromatic amine with one, or more, other linking chemistries) allow the site-specific connection of different molecules (e.g., other polypeptides, polynucleic acids, polymers or small molecules) to the non-natural amino acid polypeptide, while mono-functional linkers, also known as homofunctional linkers (aromatic amine-substituted on all termini) facilitate the site-specific dimer- or oligomerization of the unmasked or deprotected aldehyde-containing non-natural amino acid polypeptide. By combining this linker strategy with the in vivo translation technology described herein, it becomes possible to specify the three-dimensional structures of chemically-elaborated proteins.

D. Example of Adding Functionality: Macromolecular Polymers Coupled to Non-Natural Amino Acid Polypeptides Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to the non-natural amino acid polypeptides described herein to modulate biological properties of the non-natural amino acid polypeptide (or the corresponding natural amino acid polypeptide), and/or provide new biological properties to the non-natural amino acid polypeptide (or the corresponding natural amino acid polypeptide). These macromolecular polymers can be linked to the non-natural amino acid polypeptide via the non-natural amino acid, or any functional substituent of the non-natural amino acid, or any substituent or functional group added to the non-natural amino acid.

Water soluble polymers can be coupled to the non-natural amino acids incorporated into polypeptides (natural or synthetic), polynucleotides, poly saccharides or synthetic polymers. The water soluble polymers may be coupled via a non-natural amino acid incorporated in the polypeptide or any functional group or substituent of a non-natural amino acid, or any functional group or substituent added to a non-natural amino acid. In some cases, the non-natural amino acid polypeptides described herein comprise one or more non-natural amino acid(s) linked to water soluble polymers and one or more naturally-occurring amino acids coupled to water soluble polymers. Covalent attachment of hydrophilic polymers to a biologically active molecule represents one approach to increasing water solubility (such as in a physiological environment), bioavailability, increasing serum half-life, increasing therapeutic half-life, modulating immunogenicity, modulating biological activity, or extending the circulation time of the biologically active molecule, including proteins, peptides, and particularly hydrophobic molecules. Additional important features of such hydrophilic polymers may include biocompatibility, lack of toxicity, and lack of immunogenicity. For therapeutic use of the end-product preparation, a pharmaceutically acceptable polymer may be used.

Examples of hydrophilic polymers include, but are not limited to, polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing. The water soluble polymer may be any structural form including but not limited to linear, forked or branched. In some embodiments, polymer backbones that are water-soluble, with from about 2 to about 300 termini, are particularly useful. Multifunctional polymer derivatives include, but are not limited to, linear polymers having two termini, each terminus being bonded to a functional group which may be the same or different. In some embodiments, the water polymer comprises a poly(ethylene glycol) moiety. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the poly(ethylene glycol) molecule is a branched polymer. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da. Those of ordinary skill in the art will recognize that the foregoing list for substantially water soluble backbones is by no means exhaustive and is merely illustrative, and that all polymeric materials having the qualities described above are contemplated as being suitable for use in methods and compositions described herein.

As described above, one example of a hydrophilic polymer is poly(ethylene glycol), abbreviated PEG, which has been used extensively in pharmaceuticals, on artificial implants, and in other applications where biocompatibility, lack of toxicity, and lack of immunogenicity are of importance. The polymer:polyepetide embodiments described herein will use PEG as an example hydrophilic polymer with the understanding that other hydrophilic polymers may be similarly utilized in such embodiments.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects.

The term "PEG" is used broadly to encompass any polyethylene glycol molecule, without regard to size or to modification at an end of the PEG, and can be represented as linked to a non-natural amino acid polypeptide by the formula:

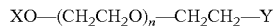

where n is 2 to 10,000 and X is H or a terminal modification, including but not limited to, a $C_{1-4}$ alkyl, a protecting group, or a terminal functional group. The term PEG includes, but is not limited to, poly(ethylene glycol) in any of its forms, including bifunctional PEG, multiarmed PEG, derivatized PEG, forked PEG, branched PEG (with each chain having a molecular weight of from about 1 kDa to about 100 kDa, from about 1 kDa to about 50 kDa, or from about 1 kDa to about 20 kDa), pendent PEG (i.e. PEG or related polymers having one or more functional groups pendent to the polymer backbone), or PEG with degradable linkages therein. In one embodiment, PEG in which n is from about 20 to about 2000 is suitable for use in the methods and compositions described herein. In some embodiments, the water polymer comprises a poly(ethylene glycol) moiety. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the poly(ethylene glycol) molecule is a branched polymer. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da. A wide range of PEG molecules are described in, including but not limited to, the Shearwater Polymers, Inc. catalog, Nektar Therapeutics catalog, incorporated herein by reference.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182: 1379 (1981), Zalipsky et al. Eur. Polym. J. 19:1177 (1983)), hydrazide (See, e.g., Andresz et al. Makromol. Chem. 179: 301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In some cases, a PEG terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-natural amino acids (including but not limited to, aromatic amine groups).

Figure 35:
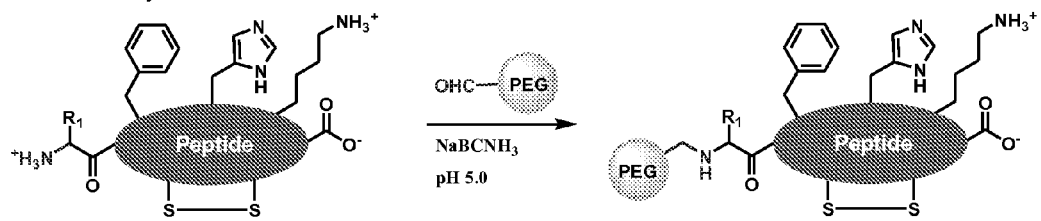
FIG. 35 presents illustrative, non-limiting examples and comparison PEGylation of peptides by N-terminal PEGylation and PEGylation of aromatic amine-containing non-natural amino acids described herein.
Figure 35:
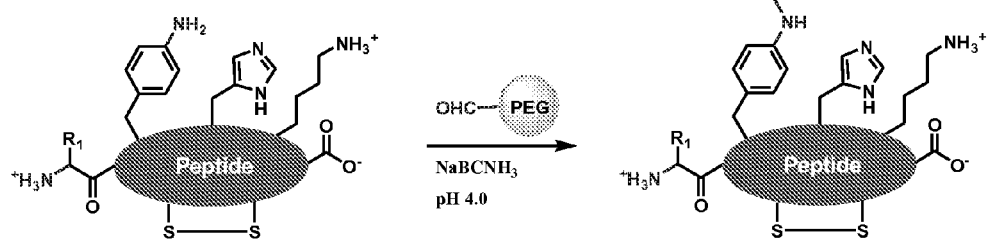
Figure 35:
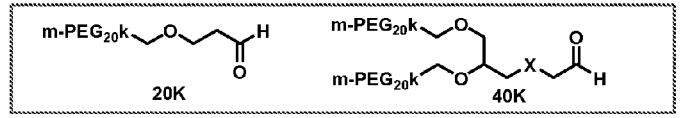

It is noted that the other end of the PEG, which is shown in the above formula by Y, will attach either directly or indirectly to a polypeptide (synthetic or natural), polynucleotide, polysaccharide or synthetic polymer via a non-natural amino acid. When Y is an aldehyde group, then the aldehyde-containing PEG reagent can react with an aromatic amine-containing non-natural amino acid in a polypeptide to form a PEG group linked to the polypeptide via an amine linkage. Examples of appropriate reaction conditions, purification methods and reagents are described throughout this specification and the accompanying Figures. FIG. 35 presents a schematic illustrating the comparison between N-terminal PEGylation and PEGylation based on reductive alkylation of aromatic amine moieties on amino acids which have been incorporated into peptides. The figure illustrates that under the reaction conditions used the PEGylation of a natural peptide is only easily achieved at the terminal amine, whereas under the reaction conditions used for PEGylation of non-natural peptides with incorporated non-natural amino acids containing aromatic moieties may be achieved at the site of incorporation of the non-natural amino acid into the sequence, without any reaction at the protonated terminal amine. The site of PEGylation depends on the site of incorporation of the non-natural amino acid containing the aromatic amine moiety. Such a site may be a terminal site, or it may be at any site within the peptide sequence.

Figure 36:
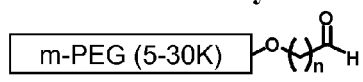
FIG. 36 presents illustrative, non-limiting examples of PEG aldehyde reagents used to PEGylate aromatic amine-containing non-natural amino acids incorporated into peptides.
Figure 36:
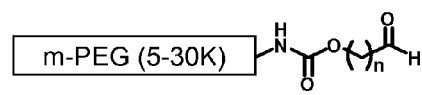
Figure 36:
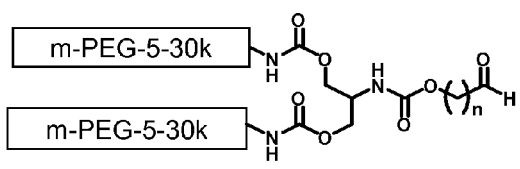
Figure 36:
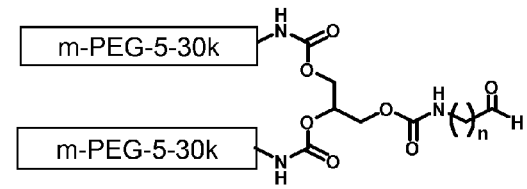

By way of example only and not as a limitation on the types or classes of PEG reagents that may be used with the compositions, methods, techniques and strategies described herein, FIG. 36 presents illustrative examples of aldehyde-containing PEG reagents that can react with aromatic amine-containing non-natural amino acid polypeptides to form non-natural amino acid polypeptides linked to the PEG group via an amine linkage. Also presented in FIG. 36 are examples of branched aldehyde-containing PEG reagents that can react with aromatic amine-containing non-natural amino acid polypeptides to form non-natural amino acid polypeptides linked to PEG groups.

Heterobifunctional derivatives are also particularly useful when it is desired to attach different molecules to each terminus of the PEG polymer. In some embodiments, one end of the PEG contains an aldehyde moiety which can react with an aromatic amine group present in a non-natural amino acid to form an amine linkage between the PEG and the peptide, while the other end of the PEG contains other functionality which may undergo further reaction by treatment with an appropriate agent. By way of example such functionality may be an amine group available to act as a nucleophile on a variety of electrophiles, including carbonyl containing reagents.

Thus, in some embodiments, the polypeptide comprising the non-natural amino acid is linked to a water soluble polymer, such as polyethylene glycol (PEG), via the side chain of the non-natural amino acid. The non-natural amino acid methods and compositions described herein provide a highly efficient method for the selective modification of proteins with PEG derivatives, which involves the selective incorporation of non-natural amino acids, including but not limited to, those amino acids containing functional groups or substituents not found in the 20 naturally incorporated amino acids, into proteins in response to a selector codon and the subsequent modification of those amino acids with a suitably reactive PEG derivative. Known chemistry methodologies of a wide variety are suitable for use with the non-natural amino acid methods and compositions described herein to incorporate a water soluble polymer into the protein.

The polymer backbone can be linear or branched. Branched polymer backbones are generally known in the art. Typically, a branched polymer has a central branch core moiety and a plurality of linear polymer chains linked to the central branch core. PEG is used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(—PEG-OH)_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/ 0143596; WO 96/21469; and WO 93/21259, each of which is incorporated by reference herein in its entirety, can also be used as the polymer backbone.

Branched PEG can also be in the form of a forked PEG represented by $PEG(—YCHZ_2)_n$, where Y is a linking group and Z is an activated terminal group linked to CH by a chain of atoms of defined length. Yet another branched form, the pendant PEG, has reactive groups, such as carboxyl, along the PEG backbone rather than at the end of PEG chains. FIG. 36 shows non-limiting examples of branched aldehyde-containing PEG reagents used in the methods described herein.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

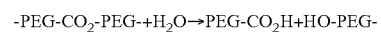

-PEG-$CO_2$-PEG-+$H_2O$→PEG-$CO_2$H+HO-PEG-

It is understood by those skilled in the art that the term poly(ethylene glycol) or PEG represents or includes all the forms known in the art including but not limited to those disclosed herein. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

The methods and compositions described herein may be used to produce substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated polypeptide preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods described herein, and have a mixture with a predetermined proportion of mono-polymer:protein conjugates.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating hydrophilic polymer:polypeptide/protein conjugates, the term "therapeutically effective amount" further refers to an amount which gives the desired benefit to a patient. The amount will vary from one individual to another and will depend upon a number of factors, including the overall physical condition of the patient and the underlying condition to be treated. A therapeutically effective amount of the present compositions may be readily ascertained by one skilled in the art using publicly available materials and procedures.

The number of water soluble polymers linked to a modified or unmodified non-natural amino acid polypeptide (i.e., the extent of PEGylation or glycosylation) described herein can be adjusted to provide an altered (including but not limited to, increased or decreased) pharmacologic, pharmacokinetic or pharmacodynamic characteristic such as in vivo half-life. In some embodiments, the half-life of the polypeptide is increased at least about 10, 20, 30, 40, 50, 60, 70, 80, 90 percent, two fold, five-fold, 10-fold, 50-fold, or at least about 100-fold over an unmodified polypeptide.

In one embodiment, a polypeptide comprising an aromatic amine-containing non-natural amino acid is modified with a PEG derivative that contains a terminal aldehyde moiety that is linked directly to the PEG backbone. In another embodiment, a polypeptide comprising an aromatic amine-containing non-natural amino acid is modified with a branched PEG derivative that contains a terminal aldehyde moiety, with each chain of the branched PEG having a MW ranging from about 10-40 kDa and, in other embodiments, from about 5-20 kDa.

In some embodiments, the aldehyde-terminal PEG derivative will have the structure:

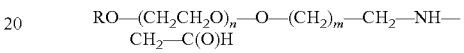

where R is a simple alkyl (methyl, ethyl, propyl, etc.), m is 2-10 and n is 100-1,000 (i.e., average molecular weight is between 5-40 kDa). The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In another embodiment, a polypeptide comprising a aromatic amine amino acid is modified with a branched PEG derivative that contains a terminal aldehyde moiety thus forming an amine bond with each chain of the branched PEG having a MW ranging from about 10-40 kDa and, in other embodiments, from about 5-20 kDa. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

Several reviews and monographs on the functionalization and conjugation of PEG are available. See, for example, Harris, *Macromol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and WO 93/15189, and for conjugation between activated polymers and enzymes including but not limited to Coagulation Factor VIII (WO 94/15625), haemoglobin (WO 94/09027), oxygen carrying molecule (U.S. Pat. No. 4,412,989), ribonuclease and superoxide dismutase (Veronese at al., *App. Biochem. Biotech.* 11: 141-52 (1985)), all of which are herein incorporated by reference in their entirety.

If necessary, the PEGylated non-natural amino acid polypeptides described herein obtained from the hydrophobic chromatography can be purified further by one or more procedures known to those skilled in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta A Z, PROTEIN PURIFICATION METHODS, A PRACTICAL APPROACH (Harris & Angal, Eds.) IRL Press 1989, 293-306). The purity of the non-natural amino acid polypeptide:PEG conjugate can be assessed by proteolytic degradation (including but not limited to, trypsin cleavage) followed by mass spectrometry analysis. Pepinsky R B., et. al., *J. Pharmcol. & Exp. Ther.* 297(3):1059-66 (2001).

Figure 37:
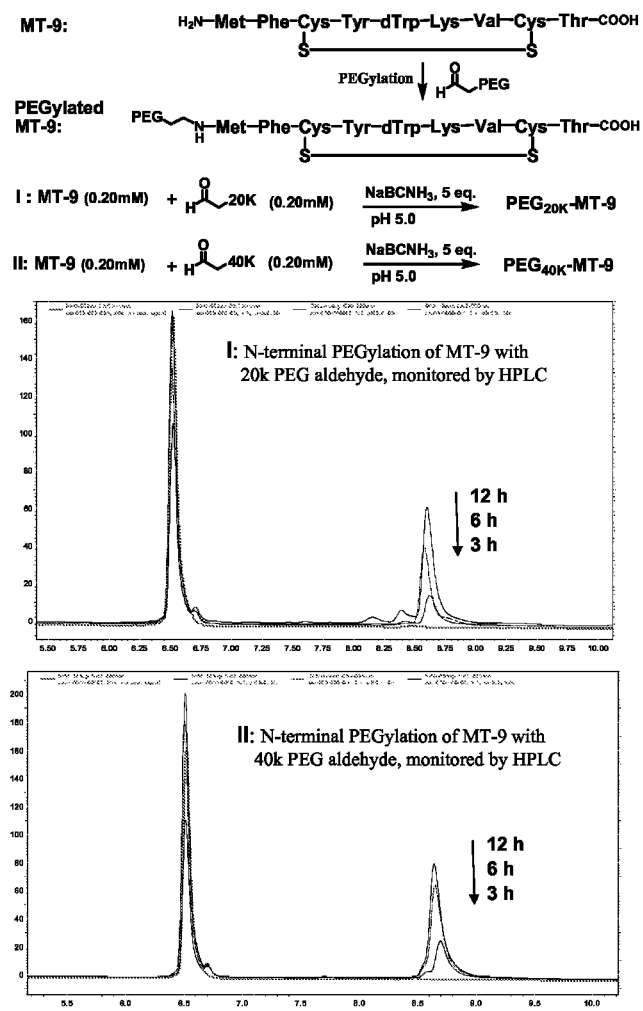
FIG. 37 presents illustrative, non-limiting examples of PEGylation of MT-9 by N-terminal reductive alkylation.
Figure 38:
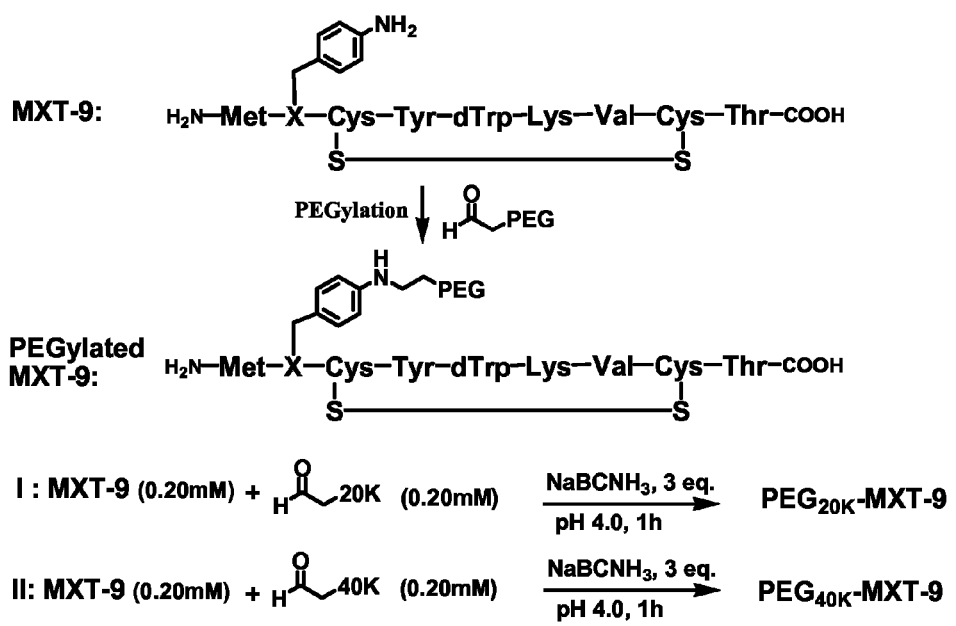
FIG. 38 presents illustrative, non-limiting examples of PEGylation of MXT-9 by reductive alkylation of aromatic amine-containing non-natural amino acid incorporated into MXT-9.
Figure 38:
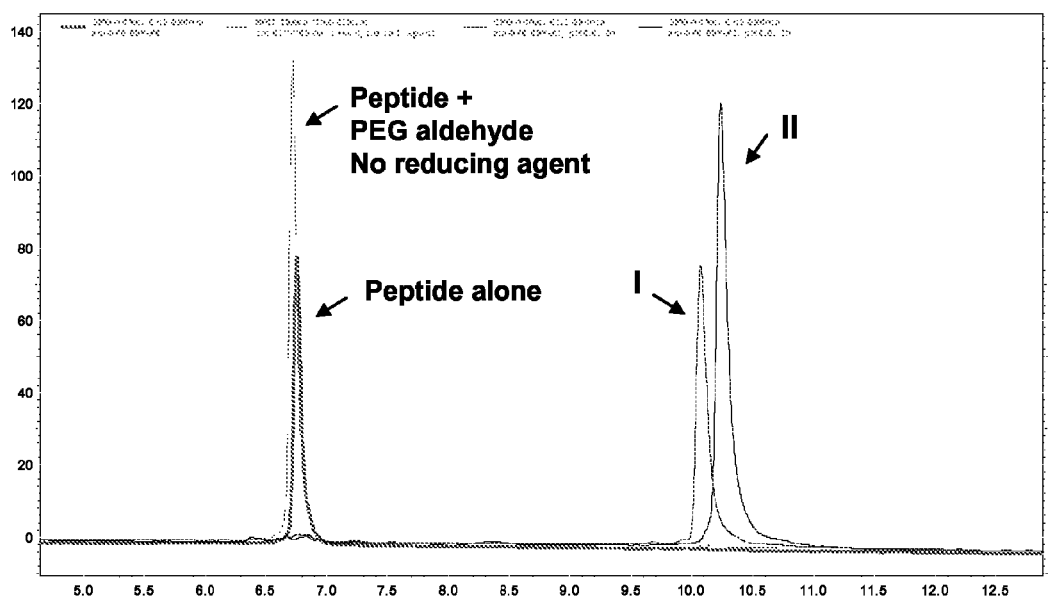

PEGylation of natural polypeptides by reductive alkylation of the terminal amine moiety requires more time than that required for PEGylation of an aromatic amine moiety on a non-natural amino acid. Additionally, the latter PEGylation method is site specific and may occur at any site in the polypeptide where the non-natural amino acid has been incorporated. FIG. 37 shows the PEGylation of a terminal amine of a peptide MT-9 using stoichiometric or near stoichiometric ratios, at pH 5, requires at least twelve hours for about 50% PEGylation to occur. In contrast, FIG. 38 shows is a non-limiting example of the PEGylation of a peptide which contains an amino acid containing an aromatic amine moiety, including but not limited to pAF2 (p-amino-phenylalanine). In FIG. 38 the peptide MT-9 is near complete PEGylation with 20 k PEG aldehyde or 40 k PEG aldehyde in stoichiometric or near stoichiometric ratios, at pH 4, after reacting for about one hour.

This demonstrates the beneficial characteristics of PEGylation using reductive alkylation of an amino acid containing an aromatic amine moiety, such as selectivity (only PEGylation at the aromatic amine containing amino acid); fast reaction time (about one hour versus twelve hours); stoichiometric or near stoichiometric ratios rather than an excess of PEG aldehyde reagent (thereby using less reagent); and specificity (in contrast to only N-terminal PEGylation, PEGylation via reductive alkylation of an amino acid containing an aromatic amine moiety may occur at any anywhere in the peptide sequence).

Figure 39:
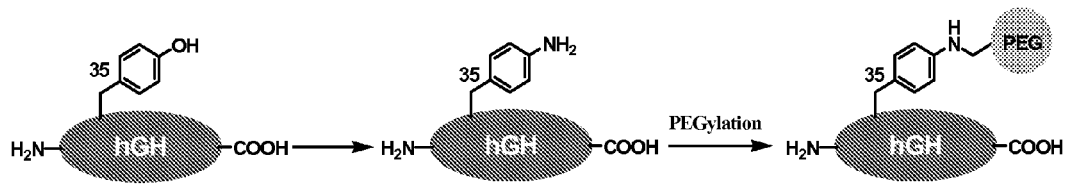
FIG. 39 presents illustrative, non-limiting examples of PEGylation of hGH and IFNα by reductive alkylation of aromatic amine-containing non-natural amino acid incorporated into hGH and IFNα.
Figure 39:
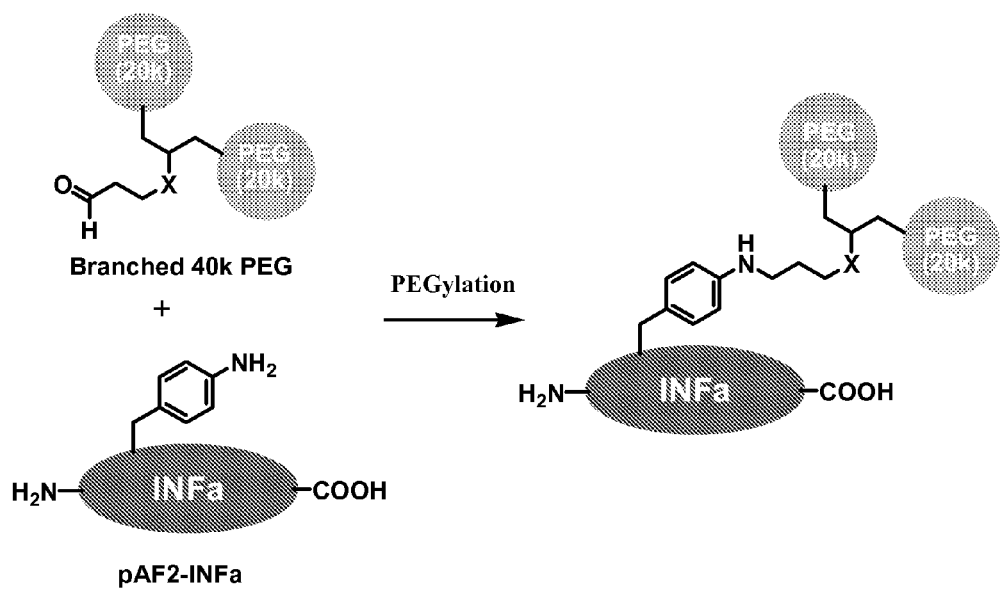

A non-limiting example of the PEGylation of hGH ("human growth hormone") is shown in FIG. 39, wherein the tyrosine residue at position 35 of the hGH protein has been translationally replaced with an amino acid containing an aromatic amine moiety, including but not limited to pAF2 (p-amino-phenylalanine), which is then reductively alkylated with a PEG containing an aldehyde moiety. Also shown in FIG. 39 is a non-limiting example of the PEGylation of IFNα, wherein an amino acid containing an aromatic amine moiety, including but not limited to pAF2, is incorporated into the IFNα sequence and is subsequently reductively alkylated with a branched PEG containing an aldehyde moiety.

A water soluble polymer linked to a non-natural amino acid of a polypeptide described herein can be further derivatized or substituted without limitation.

E. Further Examples of Modifications Using Site-Specific Derivatization

A non-limiting example of the selective, site-specific derivatization of polypeptides/proteins is shown in FIGS. 20-34, wherein reductive alkylation of the aromatic amine moiety, including but not limited to pAF2 (p-amino-phenylalanine), occurs preferentially over other sidechain groups such as, by way of example lysine, or any end group derivatization. Such selective, site-specific derivatization may allow for modification of polypeptides/proteins to design agonists and/or antagonists, site specific pegylation of polypeptides/proteins, prodrug design, polypeptide/protein glycosylation, polypeptide/protein dimerization, small molecule drug conjugates of polypeptides/proteins, and small molecule drug conjugates of antibodies.

F. Enhancing Affinity for Serum Albumin

Various molecules can also be fused to the non-natural amino acid polypeptides described herein to modulate the half-life in serum. In some embodiments, molecules are linked or fused to the modified or unmodified non-natural amino acid polypeptides described herein to enhance affinity for endogenous serum albumin in an animal.

For example, in some cases, a recombinant fusion of a polypeptide and an albumin binding sequence is made. Exemplary albumin binding sequences include, but are not limited to, the albumin binding domain from streptococcal protein G (see, e.g., Makrides et al., *J. Pharmacol. Exp. Ther.* 277:534-542 (1996) and Sjolander et al., *J, Immunol. Methods* 201:115-123 (1997)), or albumin-binding peptides such as those described in, e.g., Dennis, et al., *J. Biol. Chem.* 277:35035-35043 (2002).

In other embodiments, the modified or unmodified non-natural amino acid polypeptides described herein are acylated with fatty acids. In some cases, the fatty acids promote binding to serum albumin. See, e.g., Kurtzhals, et al., *Biochem. J.* 312:725-731 (1995).

In other embodiments, the modified or unmodified non-natural amino acid polypeptides described herein are fused directly with serum albumin (including but not limited to, human serum albumin) Those of skill in the art will recognize that a wide variety of other molecules can also be linked to non-natural amino acid polypeptides, modified or unmodified, as described herein, to modulate binding to serum albumin or other serum components.

G. Glycosylation of Non-Natural Amino Acid Polypeptides Described Herein

The methods and compositions described herein include polypeptides incorporating one or more non-natural amino acids bearing saccharide residues. The saccharide residues may be either natural (including but not limited to, N-acetylglucosamine) or non-natural (including but not limited to, 3-fluorogalactose). The saccharides may be linked to the non-natural amino acids either by an N- or O-linked glycosidic linkage (including but not limited to, N-acetylgalactose-L-serine) or a non-natural linkage (including but not limited to, a heterocycle, including a nitrogen-containing heterocycle, linkage or the corresponding C- or S-linked glycoside).

The saccharide (including but not limited to, glycosyl) moieties can be added to the non-natural amino acid polypeptides either in vivo or in vitro. In some embodiments, a polypeptide comprising an aromatic amine-containing non-natural amino acid is modified with a saccharide derivatized with an aldehyde group to generate the corresponding glycosylated polypeptide linked via an amine linkage. In other embodiments, a polypeptide comprising a protected aldehyde-containing non-natural amino acid which, upon deprotection, is modified with a saccharide derivatized with an aromatic amine group to generate the corresponding glycosylated polypeptide linked via an amine linkage. Once attached to the non-natural amino acid, the saccharide may be further elaborated by treatment with glycosyltransferases and other enzymes to generate an oligosaccharide bound to the non-natural amino acid polypeptide. See, e.g., H. Liu, et al. *J. Am. Chem. Soc.* 125: 1702-1703 (2003).

H. Use of Linking Groups and Applications, Including Polypeptide Dimers and Multimers In addition to adding functionality directly to the non-natural amino acid polypeptide, the non-natural amino acid portion of the polypeptide may first be modified with a multifunctional (e.g., bi-, tri, tetra-) linker molecule that then subsequently is further modified. That is, at least one end of the multifunctional linker molecule reacts with at least one non-natural amino acid in a polypeptide and at least one other end of the multifunctional linker is available for further functionalization. If all ends of the multifunctional linker are identical, then (depending upon the stoichiometric conditions) homomultimers of the non-natural amino acid polypeptide may be formed. If the ends of the multifunctional linker have distinct chemical reactivities, then at least one end of the multifunctional linker group will be bound to the non-natural amino acid polypeptide and the other end can subsequently react with a different functionality, including by way of example only: a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof.

The multifunctional linker group has the general structure:

(XIV)

wherein:

each X is an aldehyde or an aromatic amine;

each L is independently selected from the group consisting of alkylene, substituted alkylene, alkenylene, substituted alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, -(alkylene or substituted alkylene)NR'C(O)O-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—;

wherein R' is independently H, alkyl, or substituted alkyl;

L$_1$ is optional, and when present, is —C(R')$_p$—NR'—C(O)O-(alkylene or substituted alkylene)- where p is 0, 1, or 2;

W is an aldehyde or an aromatic amine; and n is 1 to 3.

The methods and compositions described herein also provide for polypeptide combinations, such as homodimers, heterodimers, homomultimers, or heteromultimers (i.e., trimers, tetramers, etc.). By way of example only, the following description focuses on the GH supergene family members, however, the methods, techniques and compositions described in this section can be applied to virtually any other polypeptide which can provide benefit in the form of dimers and multimers, including by way of example only: alpha-1 antitrypsin, angiostatin, antihemolytic factor, antibody, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, any interferon-like molecule or member of the IFN family, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

Thus, encompassed within the methods, techniques and compositions described herein are a GH supergene family member polypeptide containing one or more non-natural amino acids bound to another GH supergene family member or variant thereof or any other polypeptide that is a non-GH supergene family member or variant thereof, either directly to the polypeptide backbone or via a linker. Due to its increased molecular weight compared to monomers, the GH supergene family member dimer or multimer conjugates may exhibit new or desirable properties, including but not limited to different pharmacological, pharmacokinetic, pharmacodynamic, modulated therapeutic half-life, or modulated plasma half-life relative to the monomeric GH supergene family member. In some embodiments, the GH supergene family member dimers described herein will modulate the dimerization of the GH supergene family member receptor. In other embodiments, the GH supergene family member dimers or multimers described herein will act as a GH supergene family member receptor antagonist, agonist, or modulator.

In some embodiments, the GH supergene family member polypeptides are linked directly, including but not limited to, via an Asn-Lys amide linkage or Cys-Cys disulfide linkage. In some embodiments, the linked GH supergene family member polypeptides, and/or the linked non-GH supergene family member, will comprise different non-natural amino acids to facilitate dimerization, including but not limited to, a first GH supergene family member, and/or the linked non-GH supergene family member, polypeptide comprising an aromatic amine-containing non-natural amino acid conjugated to a second GH supergene family member polypeptide comprising a aldehyde-containing non-natural amino acid and the polypeptides are reacted via reductive alkylation, forming an amine linkage between the two.

Alternatively, the two GH supergene family member polypeptides, and/or the linked non-GH supergene family members, are linked via a linker. Any hetero- or homo-bifunctional linker can be used to link the two GH supergene family members, and/or the linked non-GH supergene family member, polypeptides, which can have the same or different primary sequence. In some cases, the linker used to tether the GH supergene family member, and/or the linked non-GH supergene family member, polypeptides together can be a bifunctional PEG reagent.

In some embodiments, the methods and compositions described herein provide for water-soluble bifunctional linkers that have a dumbbell structure that includes: a) aldehyde-containing moiety on at least a first end of a polymer backbone; and b) at least a second functional group on a second end of the polymer backbone. The second functional group can be the same or different as the first functional group. The second functional group, in some embodiments, is not reactive with the first functional group. The methods and compositions described herein provide, in some embodiments, water-soluble compounds that comprise at least one arm of a branched molecular structure. For example, the branched molecular structure can be dendritic.

In some embodiments, the methods and compositions described herein provide multimers comprising one or more GH supergene family member formed by reactions with water soluble activated polymers that have the structure:

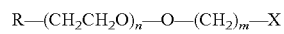

R—(CH$_2$CH$_2$O)$_n$—O—(CH$_2$)$_m$—X wherein n is from about 5 to about 3,000, m is 2-10, X can be a carbonyl (including an aldehyde)-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

I. Example of Adding Functionality: Easing the Isolation Properties of a Polypeptide A naturally-occurring or non-natural amino acid polypeptide may be difficult to isolate from a sample for a number of reasons, including but not limited to the solubility or binding characteristics of the polypeptide. For example, in the preparation of a polypeptide for therapeutic use, such a polypeptide may be isolated from a recombinant system that has been engineered to overproduce the polypeptide. However, because of the solubility or binding characteristics of the polypeptide, achieving a desired level of purity often proves difficult. The methods, compositions, techniques and strategies described herein provide a solution to this situation.

Using the methods, compositions, techniques and strategies described herein, one of skill in the art can produce an alkylated amine-containing non-natural amino acid polypeptide that is homologous to the desired polypeptide, wherein the alkylated amine-containing non-natural amino acid polypeptide has improved isolation characteristics. In one embodiment, a homologous non-natural amino acid polypeptide is produced biosynthetically. In a further or additional embodiment, the non-natural amino acid has incorporated into its structure one of the non-natural amino acids described herein. In a further or additional embodiment, the non-natural amino acid is incorporated at a terminal or internal position and is further incorporated site specifically.

In one embodiment, the resulting non-natural amino acid, as produced biosynthetically, already has the desired improved isolation characteristics. In further or additional embodiments, the non-natural amino acid comprises an amine linkage to a group that provides the improved isolation characteristics. In further or additional embodiments, the non-natural amino acid is further modified to form an alkylated amine-containing non-natural amino acid polypeptide, wherein the modification provides an amine linkage to a group that provides the improved isolation characteristics. In some embodiments, such a group is directly linked to the non-natural amino acid, and in other embodiments, such a group is linked via a linker group to the non-natural amino acid. In certain embodiments, such a group is connected to the non-natural amino acid by a single chemical reaction, in other embodiments a series of chemical reactions is required to connect such a group to the non-natural amino acid. Preferably, the group imparting improved isolation characteristics is linked site specifically to the non-natural amino acid in the non-natural amino acid polypeptide and is not linked to a naturally occurring amino acid under the reaction conditions utilized.

In further or additional embodiments the resulting non-natural amino acid polypeptide is homologous to the GH supergene family members, however, the methods, techniques and compositions described in this section can be applied to virtually any other polypeptide which can benefit from improved isolation characteristics, including by way of example only: alpha-1 antitrypsin, angiostatin, antihemolytic factor, antibody, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, I309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, any interferon-like molecule or member of the IFN family, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

In further or additional embodiments, the group imparting improved isolation characteristics improves the water solubility of the polypeptide; in other embodiments, the group improves the binding properties of the polypeptide; in other embodiments, the group provides new binding properties to the polypeptide (including, by way of example only, a biotin group or a biotin-binding group). In embodiments wherein the group improves the water solubility of the polypeptide, the group is selected from the water soluble polymers described herein, including by way of example only, any of the PEG polymer groups described herein.

J. Example of Adding Functionality: Detecting the Presence of a Polypeptide

A naturally-occurring or non-natural amino acid polypeptide may be difficult to detect in a sample (including an in vivo sample and an in vitro sample) for a number of reasons, including but not limited to the lack of a reagent or label that can readily bind to the polypeptide. The methods, compositions, techniques and strategies described herein provide a solution to this situation.

Using the methods, compositions, techniques and strategies described herein, one of skill in the art can produce an alkylated amine-containing non-natural amino acid polypeptide that is homologous to the desired polypeptide, wherein the alkylated amine-containing non-natural amino acid polypeptide allows the detection of the polypeptide in an in vivo sample and an in vitro sample. In one embodiment, a homologous non-natural amino acid polypeptide is produced biosynthetically. In a further or additional embodiment, the non-natural amino acid has incorporated into its structure one of the non-natural amino acids described herein. In a further or additional embodiment, the non-natural amino acid is incorporated at a terminal or internal position and is further incorporated site specifically.

In one embodiment, the resulting non-natural amino acid, as produced biosynthetically, already has the desired detection characteristics. In further or additional embodiments, the non-natural amino acid comprises an amine linkage to a group that provides the improved detection characteristics. In further or additional embodiments, the non-natural amino acid is further modified to form an alkylated amine-containing non-natural amino acid polypeptide, wherein the modification provides an amine linkage to a group that provides the improved detection characteristics. In some embodiments, such a group is directly linked to the non-natural amino acid, and in other embodiments, such a group is linked via a linker group to the non-natural amino acid. In certain embodiments, such a group is connected to the non-natural amino acid by a single chemical reaction, in other embodiments a series of chemical reactions is required to connect such a group to the non-natural amino acid. Preferably, the group imparting improved detection characteristics is linked site specifically to the non-natural amino acid in the non-natural amino acid polypeptide and is not linked to a naturally occurring amino acid under the reaction conditions utilized.

In further or additional embodiments the resulting non-natural amino acid polypeptide is homologous to the GH supergene family members, however, the methods, techniques and compositions described in this section can be applied to virtually any other polypeptide which needs to be detected in an in vivo sample and an in vitro sample, including by way of example only: alpha-1 antitrypsin, angiostatin, antihemolytic factor, antibody, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, any interferon-like molecule or member of the IFN family, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

In further or additional embodiments, the group imparting improved detection characteristics is selected from the group consisting of a label; a dye; an affinity label; a photoaffinity label; a spin label; a fluorophore; a radioactive moiety; a moiety incorporating a heavy atom; an isotopically labeled moiety; a biophysical probe; a phosphorescent group; a chemiluminescent group; an electron dense group; a magnetic group; a chromophore; an energy transfer agent; a detectable label; and any combination of the above.

K. Example of Adding Functionality: Improving the Therapeutic Properties of a Polypeptide A naturally-occurring or non-natural amino acid polypeptide will be able to provide a certain therapeutic benefit to a patient with a particular disorder, disease or condition. Such a therapeutic benefit will depend upon a number of factors, including by way of example only: the safety profile of the polypeptide, and the pharmacokinetics, pharmacologics and/or pharmacodynamics of the polypeptide (e.g., water solubility, bioavailability, serum half-life, therapeutic half-life, immunogenicity, biological activity, or circulation time). In addition, it may be advantageous to provide additional functionality to the polypeptide, such as an attached cytotoxic compound or drug, or it may be desirable to attach additional polypeptides to form the homo- and heteromultimers described herein. Such modifications preferably do not destroy the activity and/or tertiary structure of the original polypeptide. The methods, compositions, techniques and strategies described herein provide solutions to these issues.

Using the methods, compositions, techniques and strategies described herein, one of skill in the art can produce an alkylated amine-containing non-natural amino acid polypeptide that is homologous to the desired polypeptide, wherein the alkylated amine-containing non-natural amino acid polypeptide has improved therapeutic characteristics. In one embodiment, a homologous non-natural amino acid polypeptide is produced biosynthetically. In a further or additional embodiment, the non-natural amino acid has incorporated into its structure one of the non-natural amino acids described herein. In a further or additional embodiment, the non-natural amino acid is incorporated at a terminal or internal position and is further incorporated site specifically.

In one embodiment, the resulting non-natural amino acid, as produced biosynthetically, already has the desired improved therapeutic characteristics. In further or additional embodiments, the non-natural amino acid comprises an amine linkage to a group that provides the improved therapeutic characteristics. In further or additional embodiments, the non-natural amino acid is further modified to form an alkylated amine-containing non-natural amino acid polypeptide, wherein the modification provides an amine linkage to a group that provides the improved therapeutic characteristics. In some embodiments, such a group is directly linked to the non-natural amino acid, and in other embodiments, such a group is linked via a linker group to the non-natural amino acid. In certain embodiments, such a group is connected to the non-natural amino acid by a single chemical reaction, in other embodiments a series of chemical reactions is required to connect such a group to the non-natural amino acid. Preferably, the group imparting improved therapeutic characteristics is linked site specifically to the non-natural amino acid in the non-natural amino acid polypeptide and is not linked to a naturally occurring amino acid under the reaction conditions utilized.

In further or additional embodiments the resulting non-natural amino acid polypeptide is homologous to the GH supergene family members, however, the methods, techniques and compositions described in this section can be applied to virtually any other polypeptide which can benefit from improved therapeutic characteristics, including by way of example only: alpha-1 antitrypsin, angiostatin, antihemolytic factor, antibody, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, any interferon-like molecule or member of the IFN family, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropia, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

In further or additional embodiments, the group imparting improved therapeutic characteristics improves the water solubility of the polypeptide; in other embodiments, the group improves the binding properties of the polypeptide; in other embodiments, the group provides new binding properties to the polypeptide (including, by way of example only, a biotin group or a biotin-binding group). In embodiments wherein the group improves the water solubility of the polypeptide, the group is selected from the water soluble polymers described herein, including by way of example only the PEG polymer groups. In further or additional embodiments the group is a cytotoxic compound, whereas in other embodiments the group is a drug. In further embodiments the linked drug or cytotoxic compound can be cleaved from the non-natural amino acid polypeptide so as to deliver the drug or cytotoxic compound to a desired therapeutic location. In other embodiments, the group is a second polypeptide, including by way of example, an alkylated amine-containing non-natural amino acid polypeptide, further including by way of example, a polypeptide that has the same amino acid structure as the first non-natural amino acid polypeptide.

In further or additional embodiments, the alkylated amine-containing non-natural amino acid polypeptide is a modified alkylated amine-containing non-natural amino acid polypeptide. In further or additional embodiments, the alkylated amine-containing non-natural amino acid polypeptide increases the bioavailability of the polypeptide relative to the homologous naturally-occurring amino acid polypeptide. In further or additional embodiments, the alkylated amine-containing non-natural amino acid polypeptide increases the safety profile of the polypeptide relative to the homologous naturally-occurring amino acid polypeptide. In further or additional embodiments, the alkylated amine-containing non-natural amino acid polypeptide increases the water solubility of the polypeptide relative to the homologous naturally-occurring amino acid polypeptide. In further or additional embodiments, the alkylated amine-containing non-natural amino acid polypeptide increases the therapeutic half-life of the polypeptide relative to the homologous naturally-occurring amino acid polypeptide. In further or additional embodiments, the alkylated amine-containing non-natural amino acid polypeptide increases the serum half-life of the polypeptide relative to the homologous naturally-occurring amino acid polypeptide. In further or additional embodiments, the alkylated amine-containing non-natural amino acid polypeptide extends the circulation time of the polypeptide relative to the homologous naturally-occurring amino acid polypeptide. In further or additional embodiments, the alkylated amine-containing non-natural amino acid polypeptide modulates the biological activity of the polypeptide relative to the homologous naturally-occurring amino acid polypeptide. In further or additional embodiments, the alkylated amine-containing non-natural amino acid polypeptide modulates the immunogenicity of the polypeptide relative to the homologous naturally-occurring amino acid polypeptide.

XI. Therapeutic Uses of Modified Polypeptides

For convenience, the "modified or unmodified" non-natural polypeptides described in this section have been described generically and/or with specific examples. However, the "modified or unmodified" non-natural polypeptides described in this section should not be limited to just the generic descriptions or specific example provided in this section, but rather the "modified or unmodified" non-natural polypeptides described in this section apply equally well to all "modified or unmodified" non-natural polypeptides comprising at least one amino acid which falls within the scope of Formulas (A)-(E) and (I)-(XVI), including any sub-formulas or specific compounds that fall within the scope of Formulas (A)-(E) and (I)-(XVI) that are described in the specification, claims and figures herein.

The modified or unmodified non-natural amino acid polypeptides described herein, including homo- and heteromultimers thereof find multiple uses, including but not limited to: therapeutic, diagnostic, assay-based, industrial, cosmetic, plant biology, environmental, energy-production, and/or military uses. As a non-limiting illustration, the following therapeutic uses of modified or unmodified non-natural amino acid polypeptides are provided.

The modified or unmodified non-natural amino acid polypeptides described herein are useful for treating a wide range of disorders, conditions, or diseases. Administration of the modified or unmodified non-natural amino acid polypeptide products described herein results in any of the activities demonstrated by commercially available polypeptide preparations in humans. Average quantities of the modified or unmodified non-natural amino acid polypeptide product may vary and in particular should be based upon the recommendations and prescription of a qualified physician. The exact amount of the modified or unmodified non-natural amino acid polypeptide is a matter of preference subject to such factors as the exact type of condition being treated, the condition of the patient being treated, as well as the other ingredients in the composition. The amount to be given may be readily determined by one skilled in the art based upon therapy with the modified or unmodified non-natural amino acid polypeptide.

A. Administration and Pharmaceutical Compositions

The "modified or unmodified" non-natural amino acid polypeptides described herein, including homo- and hetero-multimers thereof find multiple uses, including but not limited to: therapeutic, diagnostic, assay-based, industrial, cosmetic, plant biology, environmental, energy-production, and/or military uses. As a non-limiting illustration, the following therapeutic uses of "modified or unmodified" non-natural amino acid polypeptides are provided.

The "modified or unmodified" non-natural amino acid polypeptides described herein are useful for treating a wide range of disorders. Administration of the "modified or unmodified" non-natural amino acid polypeptide products described herein results in any of the activities demonstrated by commercially available polypeptide preparations in humans. Average quantities of the "modified or unmodified" non-natural amino acid polypeptide product may vary and in particular should be based upon the recommendations and prescription of a qualified physician. The exact amount of the "modified or unmodified" non-natural amino acid polypeptide is a matter of preference subject to such factors as the exact type of condition being treated, the condition of the patient being treated, as well as the other ingredients in the composition. The amount to be given may be readily determined by one skilled in the art based upon therapy with the "modified or unmodified" non-natural amino acid polypeptide.

The non-natural amino acid polypeptides, modified or unmodified, as described herein (including but not limited to, synthetases, proteins comprising one or more non-natural amino acid, etc.) are optionally employed for therapeutic uses, including but not limited to, in combination with a suitable pharmaceutical carrier. Such compositions, for example, comprise a therapeutically effective amount of the non-natural amino acid polypeptides, modified or unmodified, as described herein, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the non-natural amino acid polypeptides, modified or unmodified, as described herein.

Therapeutic compositions comprising one or more of the non-natural amino acid polypeptides, modified or unmodified, as described herein are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of non-natural to natural amino acid homologues (including but not limited to, comparison of a polypeptide modified to include one or more non-natural amino acids to a natural amino acid polypeptide), i.e., in a relevant assay.

Administration is by any of the routes normally used for introducing a molecule into ultimate contact with blood or tissue cells. The non-natural amino acid polypeptides, modified or unmodified, as described herein, are administered in any suitable manner, optionally with one or more pharmaceutically acceptable carriers. Suitable methods of administering the non-natural amino acid polypeptides, modified or unmodified, as described herein, to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions described herein.

The non-natural amino acid polypeptides described herein and compositions comprising such polypeptides may be administered by any conventional route suitable for proteins or peptides, including, but not limited to parenterally, e.g. injections including, but not limited to, subcutaneously or intravenously or any other form of injections or infusions. Polypeptide pharmaceutical compositions comprising non-natural amino acid polypeptides described herein, may be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, as described herein, can also be administered via liposomes. Such administration routes and appropriate formulations are generally known to those of skill in the art. The non-natural amino acid polypeptides described herein, may be used alone or in combination with other suitable components, including but not limited to, a pharmaceutical carrier.

The non-natural amino acid polypeptides, modified or unmodified, as described herein, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, IFN, GH, G-CSF, GM-CSF, IFNs, interleukins, antibodies, and/or any other pharmaceutically delivered protein), along with formulations in current use, provide preferred routes of administration and formulation for the non-natural amino acid polypeptides, modified or unmodified, as described herein.

The dose administered to a patient, in the context compositions and methods described herein, is sufficient to have a beneficial therapeutic response in the patient over time. The dose is determined by the efficacy of the particular formulation, and the activity, stability or serum half-life of the non-natural amino acid polypeptides, modified or unmodified, employed and the condition of the patient, as well as the body weight or surface area of the patient to be treated. The size of the dose is also determined by the existence, nature, and extent of any adverse side-effects that accompany the administration of a particular formulation, or the like in a particular patient.

In determining the effective amount of the formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-non-natural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The pharmaceutical formulations described herein can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, the pharmaceutical formulations described herein are administered at a rate determined by the LD-50 or ED-50 of the relevant formulation, and/or observation of any side-effects of the non-natural amino acid polypeptides, modified or unmodified, at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Non-natural amino acid polypeptides, modified or unmodified, as described herein, can be administered directly to a mammalian subject. Administration is by any of the routes normally used for introducing a polypeptide to a subject. The non-natural amino acid polypeptides, modified or unmodified, as described herein, include those suitable for oral, rectal, topical, inhalation (including but not limited to, via an aerosol), buccal (including but not limited to, sublingual), vaginal, parenteral (including but not limited to, subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations can be presented in unit-dose or multi-dose sealed containers, such as ampoules and vials. The non-natural amino acid polypeptides, modified or unmodified, as described herein, can be prepared in a mixture in a unit dosage injectable form (including but not limited to, solution, suspension, or emulsion) with a pharmaceutically acceptable carrier. The non-natural amino acid polypeptides, modified or unmodified, as described herein, can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Freeze-drying is a commonly employed technique for presenting proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al. Pharm. Res. 8(3):285-291 (1991).

The spray drying of pharmaceuticals is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried and these include: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. U.S. Pat. Nos. 6,235,710 and 6,001,800, which are herein incorporated by reference in their entirety, describe the preparation of recombinant erythropoietin by spray drying.

The pharmaceutical compositions described herein may comprise a pharmaceutically acceptable carrier, excipient or stabilizer. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) for the non-natural amino acid polypeptides, modified or unmodified, described herein, (see, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins, 1999)). Suitable carriers include buffers containing succinate, phosphate, borate, HEPES, citrate, imidazole, acetate, bicarbonate, and other organic acids; antioxidants including but not limited to, ascorbic acid; low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, asparagine, arginine, histidine or histidine derivatives, methionine, glutamate, or lysine; monosaccharides, disaccharides, and other carbohydrates, including but not limited to, trehalose, sucrose, glucose, mannose, or dextrins; chelating agents including but not limited to, EDTA and edentate disodium; divalent metal ions including but not limited to, zinc, cobalt, or copper; sugar alcohols including but not limited to, mannitol or sorbitol; salt-forming counter ions including but not limited to, sodium; and/or nonionic surfactants, including but not limited to Tween™ (including but not limited to, Tween 80 (polysorbate 80) and Tween 20 (polysorbate 20), Pluronics™ and other pluronic acids, including but not limited to, and other pluronic acids, including but not limited to, pluronic acid F68 (poloxamer 188), or PEG. Suitable surfactants include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize PEGylated non-natural amino acid polypeptides against one or more stresses including but not limited to stress that results from agitation. Some of the above may be referred to as "bulking agents." Some may also be referred to as "tonicity modifiers." Antimicrobial preservatives may also be applied for product stability and antimicrobial effectiveness; suitable preservatives include but are not limited to, benzyl alcohol, benzalkonium chloride, metacresol, methyl/propyl parabene, cresol, and phenol, or a combination thereof.

The non-natural amino acid polypeptides, modified or unmodified, as described herein, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 267-277 (1981); Langer, *Chem. Tech.*, 12: 98-105 (1982), ethylene vinyl acetate (Langer et al., supra) or poly-D-(-)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (U. Sidman et al., *Biopolymers*, 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Eppstein et al., *Proc. Natl. Acad. Sci. USA.*, 82: 3688-3692 (1985); Hwang et al., *Proc. Natl. Acad. Sci. U.S.A.*, 77: 4030-4034 (1980); EP 52,322; EP 36,676; EP 143,949; Japanese Pat. Appln. 83-118008; U.S. Pat. Nos. 4,485,045, 4,619,794, 5,021,234, and 4,544,545; and EP 102,324.

Liposomally entrapped polypeptides can be prepared by methods described in, e.g., DE 3,218,121; Eppstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; EP 143,949; Japanese Pat. Appln. 83-118008; U.S. Pat. Nos. 4,485,045, 4,619,794, 5,021,234, and U.S. Pat. No. 4,544,545; and EP 102,324. Composition and size of liposomes are well known or able to be readily determined empirically by one skilled in the art. Some examples of liposomes as described in, e.g., Park J W, et al., *Proc. Natl. Acad. Sci. USA* 92:1327-1331 (1995); Lasic D and Papahadjpoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochim. Biophys. Acta* 1591(1-3):109-118 (2002); Mamot C, et al., *Cancer Res.* 63: 3154-3161 (2003).

The dose administered to a patient in the context of the compositions, formulations and methods described herein, should be sufficient to cause a beneficial response in the subject over time. Generally, the total pharmaceutically effective amount of the non-natural amino acid polypeptides, modified or unmodified, as described herein, administered parenterally per dose is in the range of about 0.01 µg/kg/day to about 100 µg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available products approved for use in humans. Generally, a polymer:polypeptide conjugate, including by way of example only, a PEGylated polypeptide, as described herein, can be administered by any of the routes of administration described above.

In some embodiments is a method for treating a disorder, condition or disease comprising administering a therapeutically effective amount of a polypeptide comprising at least one non-natural amino acid selected from the group consisting of:

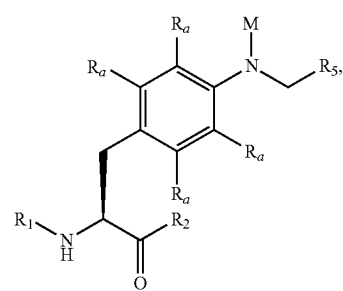

-continued

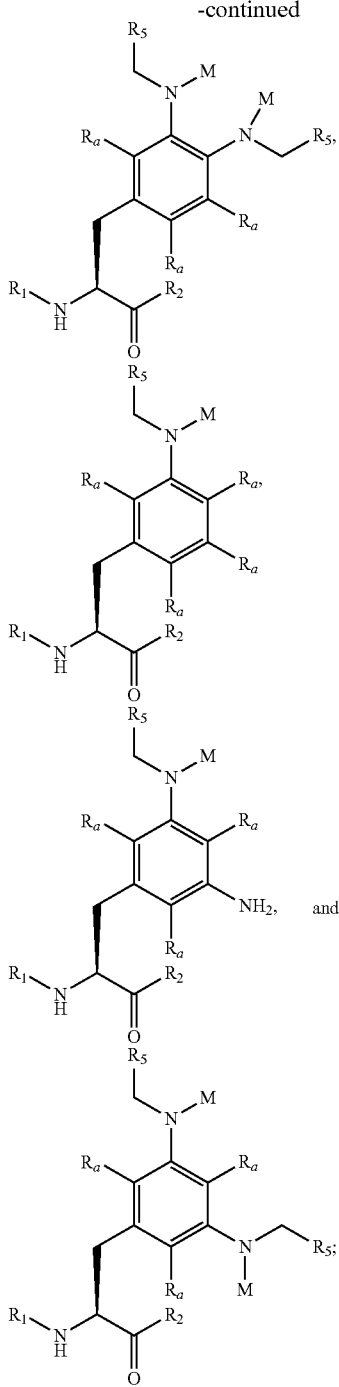

wherein each $R_a$ is independently selected from the group consisting of H, halogen, alkyl, —NO$_2$, —CN, substituted alkyl, —N(R')$_2$, —C(O)$_k$R', —C(O)N(R')$_2$, —OR', and —S(O)$_k$R', where k is 1, 2, or 3;

M is H or —CH$_2$R$_5$; or the M-N—C(R$_5$) moiety may form a 4 to 7 membered ring structure;

R$_1$ is H, an amino protecting group, resin, amino acid, polypeptide, or polynucleotide;

R$_2$ is OH, an ester protecting group, resin, amino acid, polypeptide, or polynucleotide;

R$_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or R$_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —S(O)$_k$— where k is 1, 2, or 3, —S(O)$_k$ (alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—;

or $R_5$ and any $R_a$ optionally form a cycloalkyl or a heterocycloalkyl; and each R' is independently H, alkyl, or substituted alkyl with a proviso that when $R_1$ is H then $R_2$ is not OH, or when $R_2$ is OH then $R_1$ is not H.

In other embodiments is a method for treating a disorder, condition or disease, further comprising administering a pharmaceutically acceptable carrier with the therapeutically effective amount of the polypeptide. In further embodiments is a method for treating a disorder, condition or disease, wherein $R_1$ and $R_2$ are both polypeptides. In some embodiments is a method for treating a disorder, condition or disease, wherein X is a water-soluble polymer. In other embodiments is a method for treating a disorder, condition or disease, wherein X is a derivative of polyethylene glycol. In a further embodiment is a method for treating a disorder, condition or disease, wherein X is a cytotoxic compound. In some embodiments is a method for treating a disorder, condition or disease, wherein X is a drug.

In some embodiments is a method for treating a disorder, condition or disease, wherein X is a second polypeptide. In other embodiments is a method for treating a disorder, condition or disease, wherein the second polypeptide is a peptide containing a non-natural amino acid polypeptide.

In some embodiments is a method for treating a disorder, condition or disease, wherein the polypeptide is a protein homologous to a therapeutic protein selected from the group consisting of: alpha-1 antitrypsin, angiostatin, antihemolytic factor, antibody, antibody fragment, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropia, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

In other embodiments is a method for treating a disorder, condition or disease, wherein the at least one non-natural amino acid is incorporated at a specific site within the polypeptide. In some embodiments is a method for treating a disorder, condition or disease, wherein the polypeptide is synthesized by a ribosome. In some embodiments is a method for treating a disorder, condition or disease, wherein the polypeptide comprising at least one non-natural amino acid is stable in aqueous solution for at least 1 month. In other embodiments is a method for treating a disorder, condition or disease, wherein the polypeptide comprising at least one non-natural amino acid is stable for at least 2 weeks. In some embodiments is a method for treating a disorder, condition or disease, wherein the polypeptide comprising at least one non-natural amino acid is stable for at least 5 days.

In a further embodiment is a method for detecting the presence of a polypeptide in a patient, the method comprising administering an effective amount of a homologous non-natural amino acid polypeptide comprising at least one non-natural amino acid selected from the group consisting of:

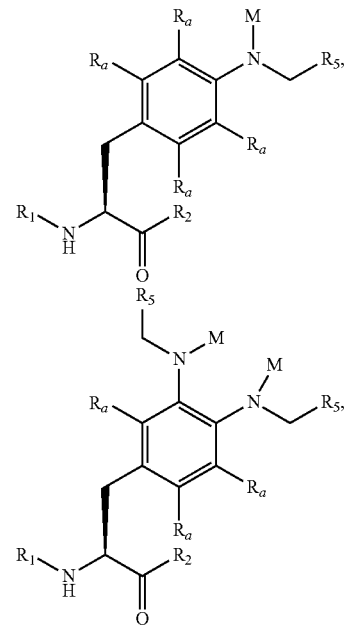

-continued

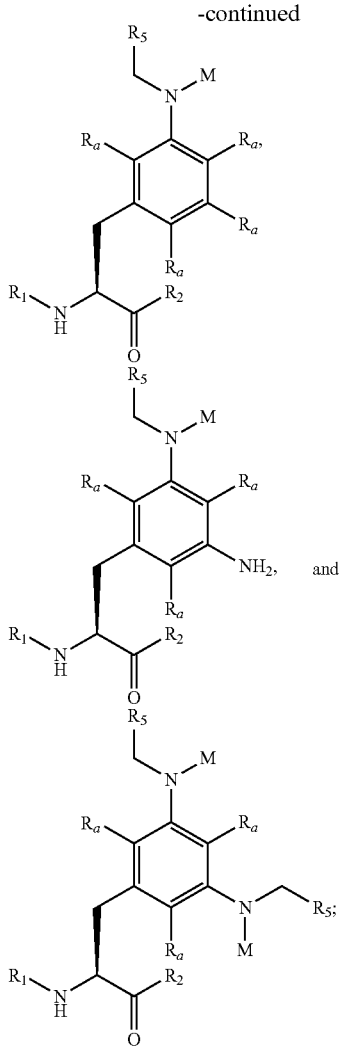

wherein each $R_a$ is independently selected from the group consisting of H, halogen, alkyl, —$NO_2$, —CN, substituted alkyl, —$N(R')_2$, —$C(O)_kR'$, —$C(O)N(R')_2$, —OR', and —$S(O)_kR'$, where k is 1, 2, or 3;

M is H or —$CH_2R_5$; or the M-N—$C(R_5)$ moiety may form a 4 to 7 membered ring structure;

$R_1$ is H, an amino protecting group, resin, amino acid, polypeptide, or polynucleotide;

$R_2$ is OH, an ester protecting group, resin, amino acid, polypeptide, or polynucleotide;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —$C(O)N(R")_2$, —$C(O)NHCH(R")_2$, -(alkylene or substituted alkylene)-$N(R")_2$, -(alkenylene or substituted alkenylene)-$N(R")_2$, -(alkylene or substituted alkylene)-(aryl or substituted aryl), -(alkenylene or substituted alkenylene)-(aryl or substituted aryl), -(alkylene or substituted alkylene)-$ON(R")_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or $R_5$ is L-X, where, X is a selected from the group consisting of a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof; and L is optional, and when present is a linker selected from the group consisting of alkylene, substituted alkylene, alkenylene, substituted alkenylene, —O—, —O-(alkylene or substituted alkylene)-, -(alkylene or substituted alkylene)-O—, —C(O)—, —C(O)-(alkylene or substituted alkylene)-, -(alkylene or substituted alkylene)-C(O)—, —C(O)N(R')—, —C(O)N(R')-(alkylene or substituted alkylene)-, -(alkylene or substituted alkylene)-C(O)N(R'), —OC(O)N(R')—, —OC(O)N(R')-(alkylene or substituted alkylene)-, -(alkylene or substituted alkylene)-OC(O)N(R')—, —N(R')C(O)—, —NR'C(O)-(alkylene or substituted alkylene)-, -(alkylene or substituted alkylene)-NR'C(O)—, —S—, —S-(alkylene or substituted alkylene)-, —$S(O)_k$— where k is 1, 2, or 3, —$S(O)_k$(alkylene or substituted alkylene)-, —C(S)—, —C(S)-(alkylene or substituted alkylene)-, —CSN(R')—, —CSN(R')-(alkylene or substituted alkylene)-, —N(R')CO-(alkylene or substituted alkylene)-, —N(R')C(O)O—, -(alkylene or substituted alkylene)-O—N=CR'—, -(alkylene or substituted alkylene)-C(O)NR'-(alkylene or substituted alkylene)-, -(alkylene or substituted alkylene)-S(O)$_k$-(alkylene or substituted alkylene)-S—, -(alkylene or substituted alkylene)-S—S—, —$S(O)_kN(R')$—, —N(R')C(O)N(R')—, —N(R')C(S)N(R')—, —$N(R')S(O)_kN$(R')—, —N(R')—N=, —C(R')=N—, —C(R')=N—N(R')—, —C(R')=N—N=, —$C(R')_2$—N=N—, and —$C(R')_2$—N(R')—N(R')—;

or $R_5$ and any $R_a$ optionally form a cycloalkyl or a heterocycloalkyl;

each R' is independently H, alkyl, or substituted alkyl; and with a proviso that when $R_1$ is H then $R_2$ is not OH, or when $R_2$ is OH then $R_1$ is not H.

In other embodiments is a method for detecting the presence of a polypeptide in a patient wherein the at least one non-natural acid is incorporated at a specific site within the polypeptide. In some embodiments is a method for detecting the presence of a polypeptide in a patient, wherein the non-natural amino acid is incorporated using a translation system. In some embodiments is a method for detecting the presence of a polypeptide in a patient, wherein the non-natural amino acid is incorporated into the polypeptide using a translation system and a post translation modification system. In other embodiments is a method for detecting the presence of a polypeptide in a patient, wherein the at least one non-natural amino acid is stable in aqueous solution for at least 1 month. In some embodiments is a method for detecting the presence of a polypeptide in a patient, wherein the at least one non-natural amino acid is stable for at least 2 weeks. In other embodiments is a method for detecting the presence of a polypeptide in a patient, wherein the at least one non-natural amino acid is stable for at least 5 days.

In some embodiments is a method for detecting the presence of a polypeptide in a patient, wherein the polypeptide is a protein homologous to a therapeutic protein selected from the group consisting of: alpha-1 antitrypsin, angiostatin, antihemolytic factor, antibody, apolipoprotein, apoprotein, atrial natriuretic factor, atrial natriuretic polypeptide, atrial peptide, C-X-C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropia, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

EXAMPLES

The following examples describe methods for synthesis of aromatic amine containing amino acids.

Example 1a

Synthesis of 3-chloro-4-amino-phenylalanine 3-chloro-4-amino-phenylalanine was synthesized according to the method in FIG. 11.

Example 1b

Synthesis of 3-iodo-4-amino-phenylalanine 3-iodo-4-amino-phenylalanine was synthesized according to the method in FIG. 11.

Example 1c

Synthesis of 3-methoxy-4-amino-phenylalanine 3-methoxy-4-amino-phenylalanine was synthesized according to the method in FIG. 12.

Example 1d

Synthesis of 3-fluoro-4-amino-phenylalanine 3-fluoro-4-amino-phenylalanine was synthesized according to the method in FIG. 12.

Example 1e

Synthesis of N-methyl-p-amino-phenylalanine

N-methyl-p-amino-phenylalanine was synthesized according to the method in FIG. 13.

Example 1f

Synthesis of N-ethyl-p-amino-phenylalanine

N-ethyl-p-amino-phenylalanine was synthesized according to the method in FIG. 13.

The following examples describe methods for cloning and expression of a modified polypeptide followed by post-translational modification Example 2

PEGylation of hGH

This example details cloning and expression of a modified polypeptide in *E. coli*. An introduced translation system that comprises an orthogonal tRNA (O-tRNA) and an orthogonal aminoacyl tRNA synthetase (O—RS) is used to express the polypeptide containing a non-natural amino acid. The O—RS preferentially aminoacylates the O-tRNA with a non-natural amino acid. In turn the translation system inserts the non-natural amino acid into the polypeptide, in response to an encoded selector codon. The transformation of *E. coli* with plasmids containing the modified gene and the orthogonal aminoacyl tRNA synthetase/tRNA pair (specific for the desired non-natural amino acid) allows the site-specific incorporation of non-natural amino acid into the polypeptide. The transformed *E. coli*, grown at 37° C. in media containing between 0.01-100 mM of the particular non-natural amino acid, expresses modified polypeptide with high fidelity and efficiency. The His-tagged polypeptide containing a non-natural amino acid is produced by the *E. coli* host cells as inclusion bodies or aggregates. The aggregates are solubilized and affinity purified under denaturing conditions in 6M guanidine HCl. Refolding is performed by dialysis at 4° C. overnight in 50 mM TRIS-HCl, pH8.0, 40 μM $CuSO_4$, and 2% (w/v) Sarkosyl. The material is then dialyzed against 20 mM TRIS-HCl, pH 8.0, 100 mM NaCl, 2 mM $CaCl_2$, followed by removal of the His-tag. See Boissel et al., (1993) 268:15983-93. Methods for purification of polypeptides are well known in the art and are confirmed by SDS-PAGE, Western Blot analyses, or electrospray-ionization ion trap mass spectrometry and the like.

By way of example, hGH polypeptide with p-aminophenylalanine substituted for the tyrosine at position 35 (H6-hGH Y35pAF2) was generated in *E. coli* cells using constructs that encode for hGH, and an orthogonal tRNA synthetase-orthogonal tRNA pair for the non-natural amino acid. The expressed protein was purified using IMAC and IEX chromatography. The protein was dialyzed into 10 mM Sodium Phosphate, 20 g/L glycine, 5 g/L mannitol, pH 7.0 and was then concentrated to 350 uM. The pH of the sample was adjusted to pH 4.0 using 10% acetic acid.

Figure 40:
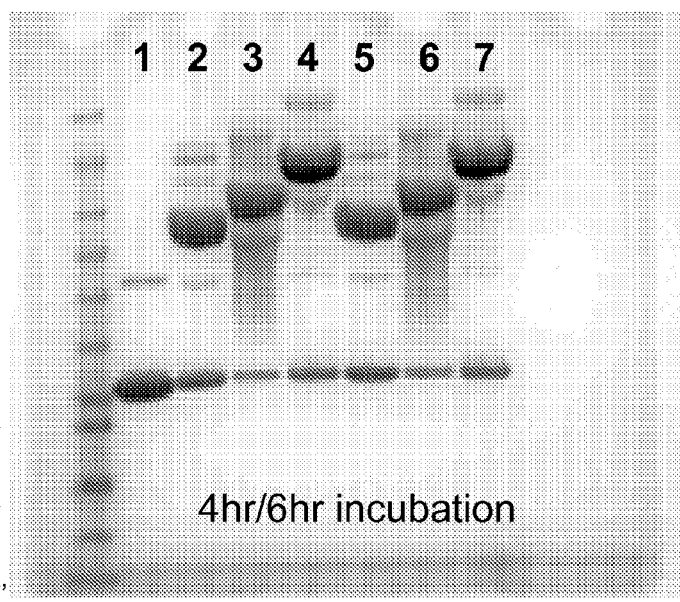
FIG. 40 presents illustrative, non-limiting image of an electrophoresis gel of various hGH PEGylations.
Figure 40:
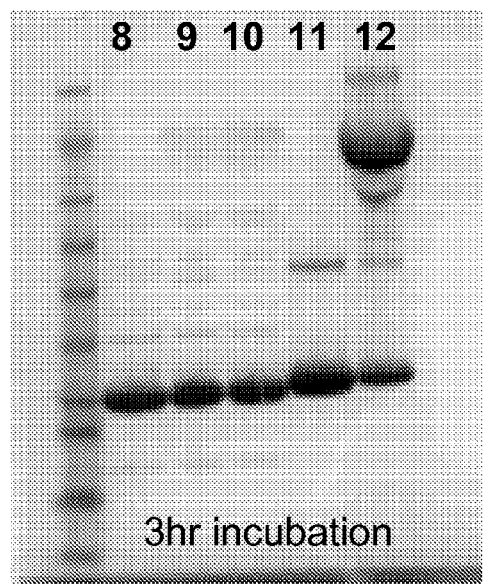

Post translational modification of H6-hGH Y35pAF2 was demonstrated by the pegylation of H6-hGH Y35pAF2 by reductive alkylation of the p-aminophenylalanine with various PEG-aldehydes. A non-limiting procedure for such pegylation is outlined in FIG. 39 and is described herein as follows: 100 ul PEGylation reactions were set-up using 20K, 30K, and 40K PEG aldehyde. The PEG aldehyde was in 20 mM acetate buffer at pH 4.0. Each reaction had a 1:1 molar ratio of PEG to protein, and a 5:1 molar ratio of $NaCNBH_3$ solubilized in DMF:protein. The reactions were incubated at either 4 degrees or at room temperature and were analyzed by SDS-PAGE after 3, 4, 6 and 16 hrs. Gel electrophoresis of the resulting peptides are shown in the FIG. 40

The following examples describe methods for modification of polypeptides by post-translational modification as shown in FIGS. 20-34, wherein X is p-aminophenylalanine.

Example 3a

Reductive Alkylations of Reduced Urotensin-II (UT-II-SH) with Propionaldehyde and Benzaldehyde A mixture of 3 equivalents of $NaBCNH_3$ at pH 4 was added to a mixture of 0.25 mM propionaldehyde (or 0.25 mM benzaldehyde) and 0.25 mM reduced urotensin and allowed to react for 2 hours. Analysis of the product mixture was by HPLC with the following conditions: 0-50% B (A, 0.05% TFA in water; B, 60% acetonitrile and 0.05% TFA in water), flow rate: 1.5 mL/min; column: Zorbax Extend C18, 3.5 m, 4.6×50 mm.

Example 3b

Reductive Alkylations of Urotensin-II (UT-II) with Propionaldehyde and Benzaldehyde A mixture of 3 equivalents of $NaBCNH_3$ at pH 4 was added to a mixture of 0.25 mM propionaldehyde (or 0.25 mM benzaldehyde) and 0.25 mM urotensin and allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3c

Reductive Alkylations of Peptide XT-8 with Propionaldehyde, Benzaldehyde, Isobutaldehyde and Pivalaldehyde A mixture of 3 equivalents of $NaBCNH_3$ at pH 4 was added to a mixture of 0.25 mM propionaldehyde (or 0.25 mM benzaldehyde, or 0.25 mM isobutaldehyde or 0.25 mM pivalaldehyde) and 0.25 mM XT-8 were allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3d

Reductive Alkylations of Peptide SXT-9 with Propionaldehyde, Benzaldehyde, Isobutaldehyde and Pivalaldehyde A mixture of 3 equivalents of $NaBCNH_3$ at pH 4 was added to a mixture of 0.25 mM propionaldehyde (or 0.25 mM benzaldehyde, or 0.25 mM isobutaldehyde or 0.25 mM pivalaldehyde) and 0.25 mM SXT-9 were allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3e

Reductive Alkylations of Peptide HXT-9 with Propionaldehyde, Benzaldehyde, Isobutaldehyde and Pivalaldehyde A mixture of 3 equivalents of $NaBCNH_3$ at pH 4 was added to a mixture of 0.25 mM propionaldehyde (or 0.25 mM benzaldehyde, or 0.25 mM isobutaldehyde or 0.25 mM pivalaldehyde) and 0.25 mM HXT-9 were allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3f

Reductive Alkylations of Peptide WXT-9 with Propionaldehyde, Benzaldehyde, and Isobutaldehyde A mixture of 3 equivalents of $NaBCNH_3$ at pH 4 was added to a mixture of 0.25 mM propionaldehyde (or 0.25 mM benzaldehyde, or 0.25 mM isobutaldehyde) and 0.25 mM WXT-9 were allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3g

Reductive Alkylations of Peptide NXT-9 with Propionaldehyde, and Benzaldehyde

A mixture of 3 equivalents of $NaBCNH_3$ at pH 4 was added to a mixture of 0.25 mM propionaldehyde (or 0.25 mM benzaldehyde) and 0.25 mM NXT-9 were allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3h

Reductive Alkylations of Peptide RXT-10 with Propionaldehyde or Benzaldehyde

A mixture of 3 equivalents of $NaBCNH_3$ at pH 4 was added to a mixture of 0.25 mM propionaldehyde (or 0.25 mM benzaldehyde) and 0.25 mM RXT-10 were allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3i

Reductive Alkylations of Peptide AXT-11 with Propionaldehyde or Benzaldehyde

A mixture of 3 equivalents of $NaBCNH_3$ at pH 4 was added to a mixture of 0.25 mM propionaldehyde (or 0.25 mM benzaldehyde) and 0.25 mM AXT-11 were allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3j

Reductive Alkylations of Peptide AXT-11 with 3-Phenylpropanal, 2-Phenylacetaldehyde, or Cinnamaldehyde A mixture of 3 equivalents of $NaBCNH_3$ at pH 4 was added to a mixture of 0.25 mM 3-phenylpropanal (or 0.25 mM 2-phenylacetaldehyde or 0.25 mM cinnamaldehyde) and 0.25 mM AXT-11 were allowed to react for 5 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3k

Reductive Alkylations of Peptide AXT-11 with 1H-Imidazole-5-Carbaldehyde, Thiophene-2-Carbaldehyde, Picolinaldehyde, or Quinoline-4-Carbaldehyde A mixture of 3 equivalents of $NaBCNH_3$ at pH 4 was added to a mixture of 0.25 mM of 1H-imidazole-5-carbaldehyde (or 0.25 mM thiophene-2-carbaldehyde, or 0.25 mM picolinaldehyde, or 0.25 mM quinoline-4-carbaldehyde) and 0.25 mM AXT-11 were allowed to react for 5 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3l

Reductive Alkylations of Peptide AXT-11 with Benzaldehyde, 1-Phenylbutane-1,3-Dione, or a Mixture of Benzaldehyde and 1-Phenylbutane-1,3-Dione A mixture of 3 equivalents of $NaBCNH_3$ at pH 4 was added to a mixture of 0.20 mM of benzaldehyde, (or 0.20 mM 1-phenylbutane-1,3-dione, or a mixture of 0.20 mM benzaldehyde and 0.20 mM 1-phenylbutane-1,3-dione) and 0.20 mM AXT-11 were allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3m

Reductive Alkylations of Peptide NXT-9 with Benzaldehyde, 1-Phenylpropane-1,2-Dione, or a Mixture of Benzaldehyde and 1-Phenylpropane-1,2-Dione A mixture of 3 equivalents of $NaBCNH_3$ at pH 4 was added to a mixture of 0.20 mM of benzaldehyde, (or 0.20 mM 1-phenylpropane-1,2-dione, or a mixture of 0.20 mM benzaldehyde and 0.20 mM 1-phenylpropane-1,2-dione) and 0.20 mM NXT-9 were allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3n

Reductive Alkylations of Peptide MXT-9 with Benzaldehyde, Acetophenone, a Mixture of Benzaldehyde and Acetophenone, a Mixture of Benzaldehyde and Propionaldehyde, or a Mixture of Benzaldehyde and Butan-2-One A mixture of 3 equivalents of $NaBCNH_3$ at pH 4 was added to a mixture of 0.20 mM of benzaldehyde, (or 0.20 mM acetophenone, or a mixture of 0.20 mM benzaldehyde and 0.20 mM acetophenone, or a mixture of 0.20 mM benzaldehyde and 0.20 mM propionaldehyde, or a mixture of 0.20 mM benzaldehyde and 0.20 mM butan-2-one) and 0.20 mM MXT-9 were allowed to react for 2 hours. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

Example 3o

Reduction of Peptide MXT-9-N$_3$ Followed by Reductive Alkylations of Peptide MXT-9-NH$_2$ with Propionaldehyde or Benzaldehyde A mixture of MXT-9-N$_3$ was reduced with TCEP giving the peptide MXT-9-NH$_2$. A mixture of 3 equivalents of NaBCNH$_3$ at pH 4 was added to a mixture of 0.20 mM of propionaldehyde, (or 0.20 mM benzaldehyde) and 0.20 mM MXT-9-NH$_2$ were allowed to react for 1 hour. Analysis of the product mixture was by HPLC with the following conditions: 5-60% B (A, 0.05% TFA in water; B, 60% acetonitrile and 0.05% TFA in water), flow rate: 1.5 mL/min; column: Zorbax Extend C18, 3.5 m, 4.6×50 mm.

The following examples describe methods to measure and compare the in vitro and in vivo activity of a modified therapeutically active non-natural amino acid polypeptide to the in vitro and in vivo activity of a therapeutically active natural amino acid polypeptide.

Example 4

Measurement of Non-Natural Amino Acid Polypeptide Activity and Affinity

This example details the measurement of non-natural amino acid polypeptide activity and affinity of non-natural amino acid polypeptides for their receptor, binding partner, or ligand.

Protein for the non-natural amino acid polypeptide receptor, binding partner, or ligand is expressed and isolated according to methods known to those of ordinary skill in the art. The Biocore™ system is used to analyze the binding of non-natural amino acid polypeptide to its receptor. Similarly, a binding partner or ligand may be used in this assay.

Approximately 600-800 RUs of soluble receptor is immobilized on a Biacore™ CM5 chip, using a standard amine-coupling procedure, as recommended by the manufacturer. Various concentrations of wild type or (modified) non-natural amino acid polypeptide in HBS-EP buffer (Biacore™, Pharmacia) are injected over the surface at a flow rate of 40 µl/min for 4-5 minutes, and dissociation was monitored for 15 minutes post-injection. The surface is regenerated by a 15 second pulse of 4.5M MgCl$_2$. Only a minimal loss of binding affinity (1-5%) is observed after at least 100 regeneration cycles. A reference cell with no receptor immobilized is used to subtract any buffer bulk effects and non-specific binding.

Kinetic binding data obtained from (modified) non-natural amino acid polypeptide titration experiments is processed with BiaEvaluation 4.1 software (BIACORE™). Equilibrium dissociation constants (Kd) are calculated as ratios of individual rate constants ($k_{off}/k_{on}$).

Stable Cell Lines are established expressing receptor, binding partner, or ligand for the non-natural amino acid polypeptide. Cells are electroporated with a construct that containing the receptor, binding partner, or ligand cDNA. Transfected cells are allowed to recover for 48 hours before cloning. Receptor, binding partner, or ligand expressing transfectants are identified by surface staining with antibody against the receptor and are analyzed on a FACS Array (BD Biosciences, San Diego, Calif.). Stably transfected cell clones are established upon further rounds of repeated subcloning of desired transfectants. Such cells are used in cell binding assays.

Cells ($3\times10^6$) are incubated in duplicate in PBS/1% BSA (100 µl) in the absence or presence of various concentrations (volume: 10 µl) of unlabeled natural amino acid polypeptide or a negative control polypeptide and in the presence of $^{125}$I-(modified) non-natural amino acid polypeptide (approx. 100,000 cpm or 1 ng) at 0° C. for 90 minutes (total volume: 120 µl). Cells are then resuspended and layered over 200 µl ice cold FCS in a 350 µl plastic centrifuge tube and centrifuged (1000 g; 1 minute). The pellet is collected by cutting off the end of the tube and pellet and supernatant counted separately in a gamma counter (Packard).

Specific binding (cpm) is determined as total binding in the absence of a competitor (mean of duplicates) minus non-specific binding. The non-specific binding is measured for each of the cell types used. Experiments are run on separate days using the same preparation of $^{125}$I-(modified) non-natural amino acid polypeptide and should display internal consistency. $^{125}$I-(modified) non-natural amino acid polypeptide demonstrates binding to the receptor, binding protein, or ligand-producing cells. The binding is inhibited in a dose dependent manner by unlabeled natural amino acid polypeptide, but not by a negative control polypeptide.

Example 5

In Vivo Studies of Modified Therapeutically Active Non-Natural Amino Acid Polypeptide Modified therapeutically active non-natural amino acid polypeptide, therapeutically active natural amino acid polypeptide and buffer solution are administered to mice or rats. The results will show superior activity and prolonged half life of the modified therapeutically active non-natural amino acid polypeptide of in comparison to that for therapeutically active natural amino acid polypeptide.

Example 6

Measurement of the In Vivo Half-Life of Conjugated and Non-Conjugated Modified Therapeutically Active Non-Natural Amino Acid Polypeptide and Variants Thereof All animal experimentation is conducted in an AAALAC accredited facility and under protocols approved by the Institutional Animal Care and Use Committee of St. Louis University. Rats are housed individually in cages in rooms with a 12-hour light/dark cycle Animals are provided access to certified Purina rodent chow 5001 and water ad libitum.

Example 7

Pharmacokinetic Studies

The quality of each modified therapeutically active non-natural amino acid polypeptide are evaluated by three assays before entering animal experiments. The purity of the modified therapeutically active non-natural amino acid polypeptide are examined by running a 4-12% acrylamide NuPAGE Bis-Tris gel with MES SDS running buffer under non-reducing conditions (Invitrogen, Carlsbad, Calif.). The gels are stained with Coomassie blue. The modified therapeutically active non-natural amino acid polypeptide band is greater than 95% pure based on densitometry scan. The endotoxin level in each modified therapeutically active non-natural amino acid polypeptide is tested by a kinetic LAL assay using the KTA$^2$ kit from Charles River Laboratories (Wilmington, Mass.), and is less than 5 EU per dose. The biological activity of the modified therapeutically active non-natural amino acid polypeptide is assessed with the cell assays that characterize bioactivity of the polypeptide.

Pharmacokinetic properties of modified therapeutically active non-natural amino acid polypeptide compounds are compared to each other and to therapeutically active natural amino acid polypeptide in male Sprague-Dawley rats (261-425 g) obtained from Charles River Laboratories. Catheters are surgically installed into the carotid artery for blood collection. Following successful catheter installation, animals are assigned to treatment groups (three to six per group) prior to dosing. Animals are dosed subcutaneously with 1 mg/kg of compound in a dose volume of 0.41-0.55 ml/kg. Blood samples are collected at various time points via the indwelling catheter and into EDTA-coated microfuge tubes. Plasma is collected after centrifugation, and stored at −80° C. until analysis. Compound concentrations are measured using antibody sandwich ELISA kits from either BioSource International (Camarillo, Calif.) or Diagnostic Systems Laboratories (Webster, Tex.). Concentrations are calculated using standards corresponding to the analog that is dosed. Pharmacokinetic parameters are estimated using the modeling program WinNonlin (Pharsight, version 4.1). Noncompartmental analysis with linear-up/log-down trapezoidal integration is used, and concentration data is uniformly weighted. The data is then plotted to obtain Cmax: maximum concentration; terminal$_{t1/2}$: terminal half-life; $AUC_{0 \rightarrow inf}$: area under the concentration-time curve extrapolated to infinity; MRT: mean residence time; Cl/f: apparent total, plasma clearance; and Vz/f: apparent volume of distribution during terminal phase.

Example 8

Pharmacodynamic Studies

Male Sprague-Dawley rats are obtained from Charles River Laboratories. Animals are allowed to acclimate for a period of three weeks, during which time biological characteristics associated with the natural amino acid polypeptide are monitored. Animals with an acceptable level of change in these biological characteristics are randomized to treatment groups. Rats are administered either a bolus dose or daily dose subcutaneously of the modified non-natural amino acid polypeptide. Throughout the study rats are daily and sequentially anesthetized, bled, and dosed (when applicable) and the correlating biological characteristics are measured. Blood is collected from the orbital sinus using a heparinized capillary tube and placed into an EDTA coated microfuge tube. Plasma is isolated by centrifugation and stored at −80° C. until analysis. The plasma concentrations following a single subcutaneous dose in the rats are obtained.

Example 9

Human Clinical Trial of the Safety and/or Efficacy of Modified Therapeutically Active Non-Natural Amino Acid Polypeptide Objective To compare the safety and pharmacokinetics of subcutaneously administered a modified therapeutically active non-natural amino acid polypeptide to the safety and pharmacokinetics of a therapeutically active natural amino acid polypeptide.

Patients

Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to a therapeutically active natural amino acid polypeptide within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design

This will be a Phase I, single-center, open-label, randomized, two-period crossover study in healthy male volunteers. Eighteen subjects are randomly assigned to one of two treatment sequence groups (nine subjects/group). A therapeutically active natural amino acid polypeptide is administered over two separate dosing periods as a bolus s.c. injection in the upper thigh using equivalent doses of the modified therapeutically active non-natural amino acid polypeptide. Additional dosing, dosing frequency, or other parameter as desired, may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the modified therapeutically active non-natural amino acid polypeptide as well.

Blood Sampling

Serial blood is drawn by direct vein puncture before and after administration of modified therapeutically active non-natural amino acid polypeptide or therapeutically active natural amino acid polypeptide. Venous blood samples (5 mL) for determination of serum modified therapeutically active non-natural amino acid polypeptide or therapeutically active natural amino acid polypeptide concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods

An ELISA kit procedure (Diagnostic Systems Laboratory [DSL], Webster Tex.), is used for the determination of serum concentrations.

Safety Determinations

Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis

Post-dose serum concentration values are corrected for pre-dose baseline concentrations by subtracting from each of the post-dose values the mean baseline concentration determined from averaging the levels from the three samples collected at 30, 20, and 10 minutes before dosing. Pre-dose serum concentrations are not included in the calculation of the mean value if they are below the quantification level of the assay. Pharmacokinetic parameters are determined from serum concentration data corrected for baseline concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results

The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar Pharmacokinetic Results Mean serum modified therapeutically active non-natural amino acid polypeptide or therapeutically active natural amino acid polypeptide concentration-time profiles (uncorrected for baseline levels) in all 18 subjects after receiving a single dose of modified therapeutically active non-natural amino acid polypeptide or therapeutically active natural amino acid polypeptide are compared at each time point measured. All subjects should have pre-dose baseline concentrations within the normal physiologic range. Pharmacokinetic parameters are determined from serum data corrected for pre-dose mean baseline concentrations and the $C_{max}$ and $t_{max}$ are determined. The mean $t_{max}$ for the therapeutically active natural amino acid polypeptide is significantly shorter than the $t_{max}$ for the modified therapeutically active non-natural amino acid polypeptide. Terminal half-life values are significantly shorter for the therapeutically active natural amino acid polypeptide compared with the terminal half-life for the modified therapeutically active non-natural amino acid polypeptide.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of modified therapeutically active non-natural amino acid polypeptide will be safe and well tolerated by healthy male subjects. Based on a comparative incidence of adverse events, clinical laboratory values, vital signs, and physical examination results, the safety profiles of the modified therapeutically active non-natural amino acid polypeptide and the therapeutically active natural amino acid polypeptide will be equivalent. The modified therapeutically active non-natural amino acid polypeptide potentially provides large clinical utility to patients and health care providers.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

| SEQ ID | Sequence | Notes | Protein, nucleic acid, tRNA or RS |
|---|---|---|---|
| 1 | CCGGCGGTAGTTCAGCAGGGCAGAACGGCGGACTCTA AATCCGCATGGCGCTGGTTCAAATCCGGCCCGCCGGAC CA | *M. jannaschii* mtRNA$_{CUA}^{Tyr}$ | tRNA |
| 2 | CCCAGGGTAGCCAAGCTCGGCCAACGGCGACGGACTC TAAATCCGTTCTCGTAGGAGTTCGAGGGTTCGAATCCC TTCCC TGGGACCA | HLAD03; an optimized amber supressor tRNA | tRNA |
| 3 | GCGAGGGTAGCCAAGCTCGGCCAACGGCGACGGACTT CCTAATCCGTTCTCGTAGGAGTTCGAGGGTTCGAATCC CTCCCCTCGCACCA | HL325A; an optimized AGGA frameshift supressor tRNA | tRNA |

SEQUENCE LISTING

| SEQ ID | Sequence | Notes | Protein, nucleic acid, tRNA or RS |
|---|---|---|---|
| 4 | MDEFEMIKRNTSEIISEEELREVLKKDEKSAGIGFEPSGKIH LGHYLQIKKMIDLQNAGFDIIILLADLHAYLNQKGELDEIR KIGDYNKKVFEAMGLKAKYVYGSTFQLDKDYTLNVYRL ALKTTLKRARRSMELIAREDENPKVAEVIYPIMQVNTYYY LGVDVAVGGMEQRKIHMLARELLPKKVVCIHNPVLTGLD GEGKMSSSKGNFIAVDDSPEEIRAKIKKAYCPAGVVEGNP IMEIAKYFLEYPLTIKRPEKFGGDLTVNSYEELESLFKNKE LHPMDLKNAVAEELIKILEPIRKRL | Aminoacyl tRNA synthetase for the incorporation of p-azido-L-phenylalanine p-Az-PheRS(6) | RS |
| 5 | MDEFEMIKRNTSEIISEEELREVLKKDEKSAGIGFEPSGKIH LGHYLQIKKMIDLQNAGFDIIILLADLHAYLNQKGELDEIR KIGDYNKKVFEAMGLKAKYVYGSSFQLDKDYTLNVYRL ALKTTLKRARRSMELIAREDENPKVAEVIYPIMQVNTSHY LGVDVAVGGMEQRKIHMLARELLPKKVVCIHNPVLTGLD GEGKMSSSKGNFIAVDDSPEEIRAKIKKAYCPAGVVEGNP IMEIAKYFLEYPLTIKRPEKFGGDLTVNSYEELESLFKNKE LHPMDLKNAVAEELIKILEPIRKRL | Aminoacyl tRNA synthetase for the incorporation of p-benzoyl-L-phenylalanine p-BpaRS(1) | RS |
| 6 | MDEFEMIKRNTSEIISEEELREVLKKDEKAAIGFEPSGKIHL GHYLQIKKMIDL QNAGFDIIILLADLHAYLNQKGELDEIRKIGDYNKKVFEA MGLKAKYVYGSPFQLDKDYTLNVYRLALKTTLKRARRS MELIAREDENPKVAEVIYPIMQVNAIYLAVDVAVGGMEQ RKIHMLARELLPKKVVCIHNPVLTGLDGEGKMSSSKGNFI AVDDSPEEIRAKIKKAYCPAGVVEGNPIMEIAKYFLEYPLT IKRPEKFGGDLTVNSYEELESLFKNKELHPMDLKNAVAEE LIKILE PIRKR L | Aminoacyl tRNA synthetase for the incorporation of propargyl-phenylalanine Propargyl-PheRS | RS |
| 7 | MDEFE MIKRN TSEII SEEEL REVLK KDEKS AAIGF EPSGK IHLGH YLQIK KMIDL QNAGF DIIIL LADLH AYLNQ KGELD EIRKI GDYNK KVFEA MGLKA KYVYG SPFQL DKDYT LNVYR LALKT TLKRA RRSME LIARE DENPK VAEVI YPIMQ VNIPY LPVD VAVGG MEQRK IHMLA RELLP KKVVC IHNPV LTGLD GEGKM SSSKG NFIAV DDSPE EIRAK IKKAY CPAGV VEGNP IMEIA KYFLE YPLTI KRPEK FGGDL TVNSY EELES LFKNK ELHPM DLKNA VAEEL IKILE PIRKR L | Aminoacyl tRNA synthetase for the incorporation of propargyl-phenylalanine Propargyl-PheRS | RS |
| 8 | MDEFE MIKRN TSEII SEEEL REVLK KDEKS AAIGF EPSGK IHLGH YLQIK KMIDL QNAGF DIIIL LADLH AYLNQ KGELD EIRKI GDYNK KVFEA MGLKA KYVYG SKFQL DKDYT LNVYR LALKT TLKRA RRSME LIARE DENPK VAEVI YPIMQ VNAIY LAVD VAVGG MEQRK IHMLA RELLP KKVVC IHNPV LTGLD GEGKM SSSKG NFIAV DDSPE EIRAK IKKAY CPAGV VEGNP IMEIA KYFLE YPLTI KRPEK FGGDL TVNSY EELES LFKNK ELHPM DLKNA VAEEL IKILE PIRKR L | Aminoacyl tRNA synthetase for the incorporation of propargyl-phenylalanine Propargyl-PheRS | RS |
| 9 | MDEFEMIKRNTSEIISEEELREVLKKDEKSATIGFEPSGKIH LGHYLQIKKMIDLQNAGFDIIILLADLHAYLNQKGELDEIR KIGDYNKKVFEAMGLKAKYVYGSNFQLDKDYTLNVYRL ALKTTLKRARRSMELIAREDENPKVAEVIYPIMQVNPLHY QGVDVAVGGMEQRKIHMLARELLPKKVVCIHNPVLTGL DGEGKMSSSKGNFIAVDDSPEEIRAKIKKAYCPAGVVEGN PIMEIAKYFLEYPLTIKRPEKFGGDLTVNSYEELESLFKNK ELHPMDLKNAVAEELIKILEPIRKRL | Aminoacyl tRNA synthetase for the incorporation of p-azido-phenylalanine p-Az-PheRS(1) | RS |
| 10 | MDEFEMIKRNTSEIISEEELREVLKKDEKSATIGFEPSGKIH LGHYLQIKKMIDLQNAGFDIIILLADLHAYLNQKGELDEIR KIGDYNKKVFEAMGLKAKYVYGSSFQLDKDYTLNVYRL ALKTTLKRARRSMELIAREDENPKVAEVIYPIMQVNPLHY QGVDVAVGGMEQRKIHMLARELLPKKVVCIHNPVLTGL DGEGKMSSSKGNFIAVDDSPEEIRAKIKKAYCPAGVVEGN PIMEIAKYFLEYPLTIKRPEKFGGDLTVNSYEELESLFKNK ELHPMDLKNAVAEELIKILEPIRKRL | Aminoacyl tRNA synthetase for the incorporation of p-azido-phenylalanine p-Az-PheRS(3) | RS |
| 11 | MDEFEMIKRNTSEIISEEELREVLKKDEKSALIGFEPSGKIH LGHYLQIKKMIDLQNAGFDIIILLADLHAYLNQKGELDEIR KIGDYNKKVFEAMGLKAKYVYGSTFQLDKDYTLNVYRL ALKTTLKRARRSMELIAREDENPKVAEVIYPIMQVNPVHY | Aminoacyl tRNA synthetase for the incorporation of p-azido- | RS |

| SEQ ID | Sequence | Notes | Protein, nucleic acid, tRNA or RS |
|---|---|---|---|
| | QGVDVAVGGMEQRKIHMLARELLPKKVVCIHNPVLTGL<br>DGEGKMSSSKGNFIAVDDSPEEIRAKIKKAYCPAGVVEGN<br>PIMEIAKYFLEYPLTIKRPEKFGGDLTVNSYEELESLFKNK<br>ELHPMDLKNAVAEELIKILEPIRKRL | phenylalanine<br>p-Az-PheRS(4) | |
| 12 | MDEFEMIKRNTSEIISEEELREVLKKDEKSATIGFEPSGKIH<br>LGHYLQIKKMIDLQNAGFDIIILLADLHAYLNQKGELDEIR<br>KIGDYNKKVFEAMGLKAKYVYGSSFQLDKDYTLNVYRL<br>ALKTTLKRARRSMELIAREDENPKVAEVIYPIMQVNPSHY<br>QGVDVAVGGMEQRKIHMLARELLPKKVVCIHNPVLTGL<br>DGEGKMSSSKGNFIAVDDSPEEIRAKIKKAYCPAGVVEGN<br>PIMEIAKYFLEYPLTIKRPEKFGGDLTVNSYEELESLFKNK<br>ELHPMDLKNAVAEELIKILEPIRKRL | Aminoacyl tRNA<br>synthetase for<br>the incorporation<br>of p-azido-<br>phenylalanine<br>p-Az-PheRS(2) | RS |
| 13 | MDEFEMIKRNTSEIISEEELREVLKKDEKSALIGFEPSGKIH<br>LGHYLQIKKMIDLQNAGFDIIILLADLHAYLNQKGELDEIR<br>KIGDYNKKVFEAMGLKAKYVYGSEFQLDKDYTLNVYRL<br>ALKTTLKRARRSMELIAREDENPKVAEVIYPIMQVNGCH<br>YRGVDVAVGGMEQRKIHMLARELLPKKVVCIHNPVLTG<br>LDGEGKMSSSKGNFIAVDDSPEEIRAKIKKAYCPAGVVEG<br>NPIMEIAKYFLEYPLTIKRPEKFGGDLTVNSYEELESLFKN<br>KELHPMDLKNAVAEELIKILEPIRKRL | Aminoacyl tRNA<br>synthetase for<br>the incorporation<br>of p-azido-<br>phenylalanine<br>(LW1) | RS |
| 14 | MDEFEMIKRNTSEIISEEELREVLKKDEKSALIGFEPSGKIH<br>LGHYLQIKKMIDLQNAGFDIIILLADLHAYLNQKGELDEIR<br>KIGDYNKKVFEAMGLKAKYVYGSEFQLDKDYTLNVYRL<br>ALKTTLKRARRSMELIAREDENPKVAEVIYPIMQVNGTHY<br>RGVDVAVGGMEQRKIHMLARELLPKKVVCIHNPVLTGL<br>DGEGKMSSSKGNFIAVDDSPEEIRAKIKKAYCPAGVVEGN<br>PIMEIAKYFLEYPLTIKRPEKFGGDLTVNSYEELESLFKNK<br>ELHPMDLKNAVAEELIKILEPIRKRL | Aminoacyl tRNA<br>synthetase for<br>the incorporation<br>of p-azido-<br>phenylalanine<br>(LW5) | RS |
| 15 | MDEFEMIKRNTSEIISEEELREVLKKDEKSAAIGFEPSGKIH<br>LGHYLQIKKMIDLQNAGFDIIILLADLHAYLNQKGELDEIR<br>KIGDYNKKVFEAMGLKAKYVYGSEFQLDKDYTLNVYRL<br>ALKTTLKRARRSMELIAREDENPKVAEVIYPIMQVNGGH<br>YLGVDVIVGGMEQRKIHMLARELLPKKVVCIHNPVLTGL<br>DGEGKMSSSKGNFIAVDDSPEEIRAKIKKAYCPAGVVEGN<br>PIMEIAKYFLEYPLTIKRPEKFGGDLTVNSYEELESLFKNK<br>ELHPMDLKNAVAEELIKILEPIRKRL | Aminoacyl tRNA<br>synthetase for<br>the incorporation<br>of p-azido-<br>phenylalanine<br>(LW6) | RS |
| 16 | MDEFEMIKRNTSEIISEEELREVLKKDEKSAAIGFEPSGKIH<br>LGHYLQIKKMIDLQNAGFDIIILLADLHAYLNQKGELDEIR<br>KIGDYNKKVFEAMGLKAKYVYGSRFQLDKDYTLNVYRL<br>ALKTTLKRARRSMELIAREDENPKVAEVIYPIMQVNVIHY<br>DGVDVAVGGMEQRKIHMLARELLPKKVVCIHNPVLTGL<br>DGEGKMSSSKGNFIAVDDSPEEIRAKIKKAYCPAGVVEGN<br>PIMEIAKYFLEYPLTIKRPEKFGGDLTVNSYEELESLFKNK<br>ELHPMDLKNAVAEELIKILEPIRKRL | Aminoacyl tRNA<br>synthetase for<br>the incorporation<br>of p-azido-<br>phenylalanine<br>(AzPheRS-5) | RS |
| 17 | MDEFEMIKRNTSEIISEEELREVLKKDEKSAGIGFEPSGKIH<br>LGHYLQIKKMIDLQNAGFDIIILLADLHAYLNQKGELDEIR<br>KIGDYNKKVFEAMGLKAKYVYGSTFQLDKDYTLNVYRL<br>ALKTTLKRARRSMELIAREDENPKVAEVIYPIMQVNTYYY<br>LGVDVAVGGMEQRKIHMLARELLPKKVVCIHNPVLTGLD<br>GEGKMSSSKGNFIAVDDSPEEIRAKIKKAYCPAGVVEGNP<br>IMEIAKYFLEYPLTIKRPEKFGGDLTVNSYEELESLFKNKE<br>LHPMDLKNAVAEELIKILEPIRKRL | Aminoacyl tRNA<br>synthetase for<br>the incorporation<br>of p-azido-<br>phenylalanine<br>(AzPheRS-6) | RS |

What is claimed is:

1. A compound or salt thereof having the structure of:

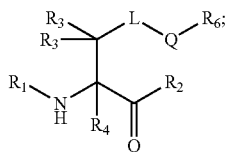

wherein L is optional, and when present is lower alkylene, substituted lower alkylene, lower cycloalkylene, substituted lower cycloalkylene, lower alkenylene, substituted lower alkenylene, alkynylene, lower heteroalkylene, substituted lower heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

Q is optional, and when present is a linker selected from the group consisting of lower alkylene, substituted lower alkylene, lower alkenylene, substituted lower alkenylene, lower heteroalkylene, substituted lower heteroalkylene, —O-(alkylene or substituted alkylene)-, —S-(alkylene or substituted alkylene)-, where k is 1, 2, or 3, —S(O)$_k$(alkylene or substituted alkylene)-, —C(O)-(alkylene or substituted alkylene)-, —C(S)-(alkylene or substituted alkylene)-, —NR'-(alkylene or substituted alkylene)-, —CON(R")-(alkylene or substituted alkylene)-, —CSN(R')-(alkylene or substituted alkylene)-, —N(R')CO-(alkylene or substituted alkylene)-, and where each R' is independently H, alkyl, or substituted alkyl;

$R_1$ is H, an amino protecting group, resin, amino acid, polypeptide, or polynucleotide; and R₂ is OH, an ester protecting group, resin, amino acid, polypeptide, or polynucleotide;

each of R₃ and R₄ is independently H, halogen, lower alkyl, or substituted lower alkyl, or R₃ and R₄ or two R₃ groups optionally form a cycloalkyl or a heterocycloalkyl;

each $R_a$ is independently selected from the group consisting of H, halogen, alkyl, —NO₂, —CN, substituted alkyl, —N(R')₂, —C(O)$_k$R', —C(O)N(R')₂, —OR', and —S(O)$_k$R', where k is 1, 2, or 3;

R₆ is a protected aldehyde or a masked aldehyde, wherein the protecting group includes, but is not limited to,

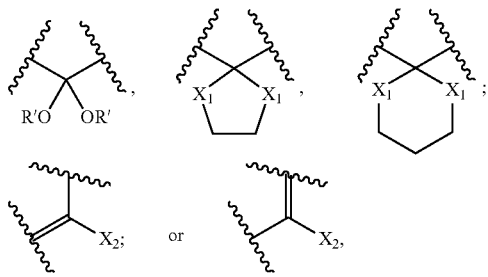

where each X₁ is independently selected from the group consisting of —O—, —S—, —N(H)—, —N(R)—, —N(Ac)—, and N(OMe)-; X₂ is OR, —OAc, —SR, —N(R)₂, —N(R)(Ac), —N(R)(OMe), or N₃, and where each R' and R is independently H, alkyl, or substituted alkyl.

2. The compound of claim 1 wherein X₁ is O.

3. The compound of claim 1 wherein both R₁ and R₂ are polypeptides.

4. A polypeptide containing at least one compound of claim 1 selected from the group:

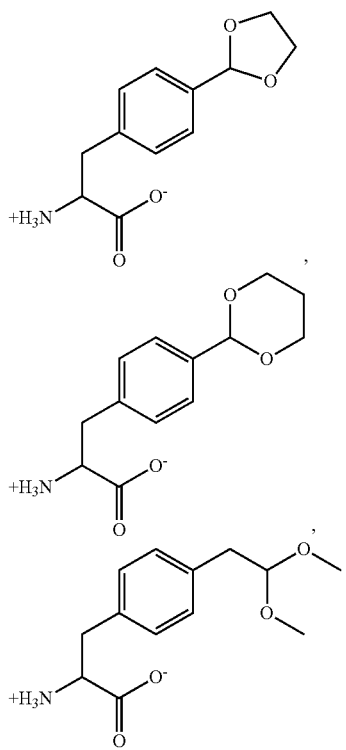

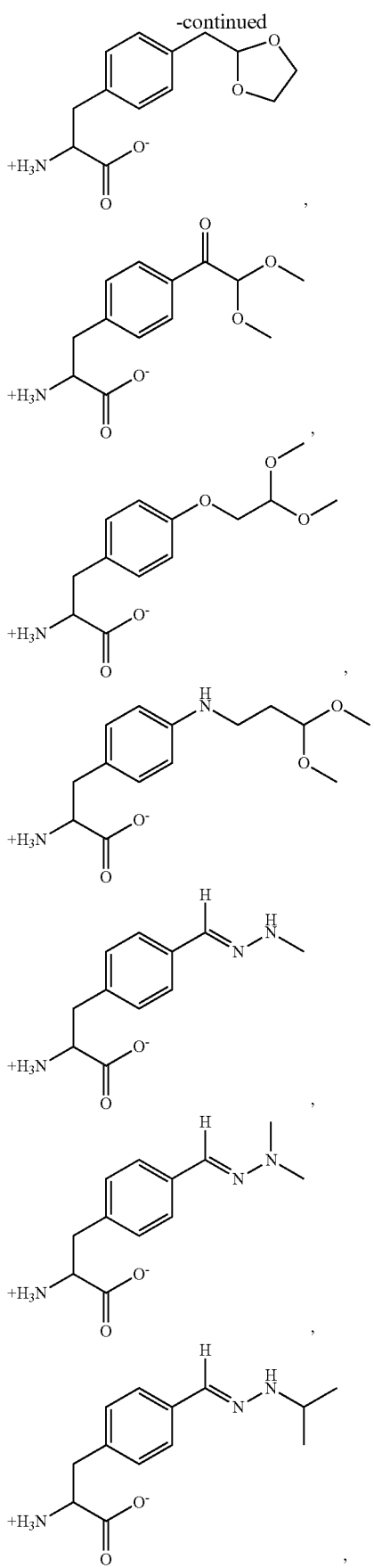

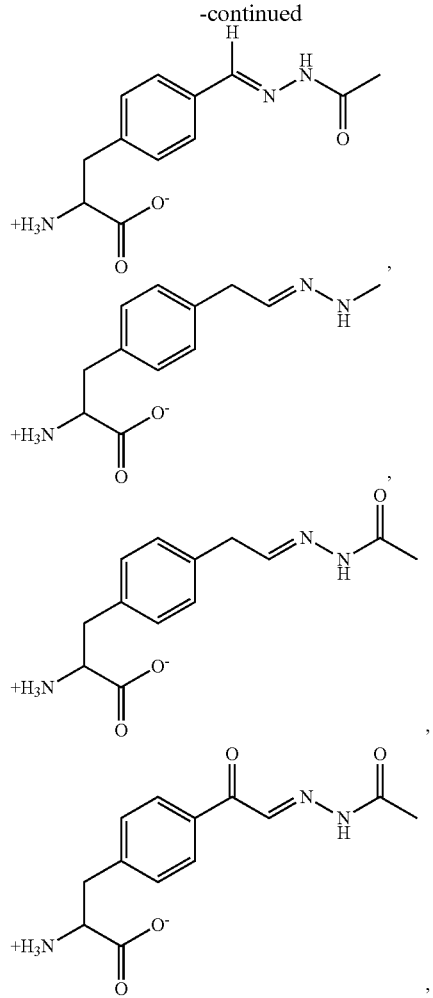
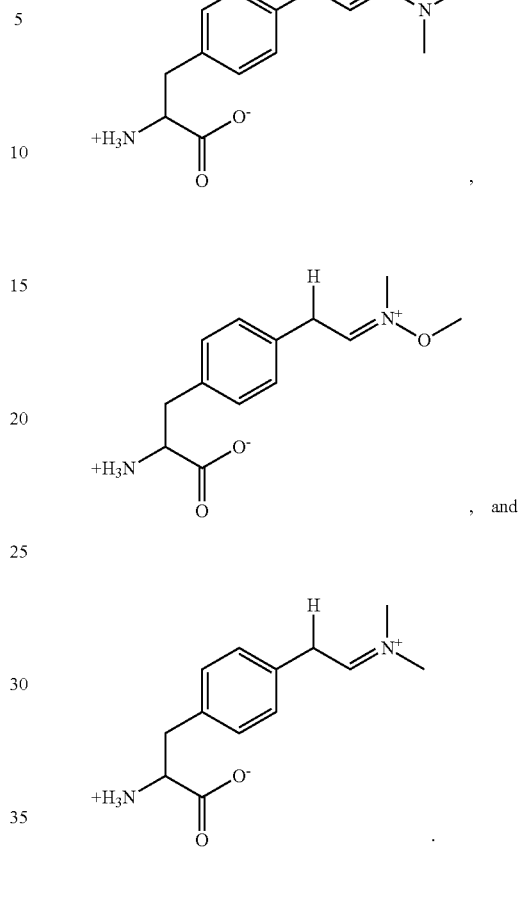
, and
* * * * *